US012421558B2

(12) United States Patent
Hamel et al.

(10) Patent No.: US 12,421,558 B2
(45) Date of Patent: *Sep. 23, 2025

(54) SYSTEMS AND METHODS FOR JOINT INTERACTIVE VISUALIZATION OF GENE EXPRESSION AND DNA CHROMATIN ACCESSIBILITY

(71) Applicant: 10X Genomics, Inc., Pleasanton, CA (US)

(72) Inventors: Jessica Hamel, Santa Cruz, CA (US); Vijay Kumar Sreenivasa Gopalan, San Diego, CA (US); Li Wang, Pleasanton, CA (US); Arundhati Shamoni Maheshwari, Oakland, CA (US); Jasper Staab, Honolulu, HI (US)

(73) Assignee: 10X GENOMICS, INC., Pleasanton, CA (US)

( * ) Notice: Subject to any disclaimer, the term of this patent is extended or adjusted under 35 U.S.C. 154(b) by 580 days.

This patent is subject to a terminal disclaimer.

(21) Appl. No.: 17/175,577

(22) Filed: Feb. 12, 2021

(65) Prior Publication Data

US 2021/0381056 A1  Dec. 9, 2021

Related U.S. Application Data

(60) Provisional application No. 63/061,952, filed on Aug. 6, 2020, provisional application No. 62/976,270, filed on Feb. 13, 2020.

(51) Int. Cl.
*G16B 40/00* (2019.01)
*C12Q 1/6886* (2018.01)
*G16B 5/20* (2019.01)
*G16B 15/00* (2019.01)
*G16B 20/30* (2019.01)
*G16B 45/00* (2019.01)

(52) U.S. Cl.
CPC ........... *C12Q 1/6886* (2013.01); *G16B 5/20* (2019.02); *G16B 15/00* (2019.02); *G16B 20/30* (2019.02); *G16B 40/00* (2019.02); *G16B 45/00* (2019.02); *C12Q 2600/158* (2013.01)

(58) Field of Classification Search
CPC .......... G16B 5/20; G16B 15/00; G16B 20/30; G16B 40/00; G16B 45/00
See application file for complete search history.

(56) References Cited

U.S. PATENT DOCUMENTS

| | | |
|---|---|---|
| 5,149,625 A | 9/1992 | Church et al. |
| 5,202,231 A | 4/1993 | Drmanac et al. |
| 5,413,924 A | 5/1995 | Kosak et al. |
| 5,436,130 A | 7/1995 | Mathies et al. |
| 5,472,881 A | 12/1995 | Beebe et al. |
| 5,512,131 A | 4/1996 | Kumar et al. |
| 5,587,128 A | 12/1996 | Wilding et al. |
| 5,599,675 A | 2/1997 | Brenner |
| 5,605,793 A | 2/1997 | Stemmer |
| 5,610,287 A | 3/1997 | Nikiforov et al. |
| 5,618,711 A | 4/1997 | Gelfand et al. |
| 5,695,940 A | 12/1997 | Drmanac et al. |
| 5,736,330 A | 4/1998 | Fulton |
| 5,750,341 A | 5/1998 | Macevicz |
| 5,807,522 A | 9/1998 | Brown et al. |
| 5,834,197 A | 11/1998 | Parton |
| 5,837,860 A | 11/1998 | Anderson et al. |
| 5,851,769 A | 12/1998 | Gray et al. |
| 5,856,174 A | 1/1999 | Lipshutz et al. |
| 5,958,703 A | 9/1999 | Dower et al. |
| 5,994,056 A | 11/1999 | Higuchi |
| 6,046,003 A | 4/2000 | Mandecki |
| 6,051,377 A | 4/2000 | Mandecki |
| 6,057,107 A | 5/2000 | Fulton |
| 6,103,537 A | 8/2000 | Ullman et al. |

(Continued)

FOREIGN PATENT DOCUMENTS

| | | |
|---|---|---|
| EP | 0249007 A2 | 12/1987 |
| EP | 0637996 B1 | 7/1997 |

(Continued)

OTHER PUBLICATIONS

Stuart, T., Butler, A., Hoffman, P., Hafemeister, C., Papalexi, E., Mauck, W.M., Hao, Y., Stoeckius, M., Smibert, P. and Satija, R.. Comprehensive integration of single-cell data. Cell, 177(7), pp. 1888-1902. (Year: 2019).*
Li, G., Ruan, X., Auerbach, R.K., Sandhu, K.S., Zheng, M., Wang, P., Poh, H.M., Goh, Y., Lim, J., Zhang, J. and Sim, H.S. Extensive promoter-centered chromatin interactions provide a topological basis for transcription regulation. Cell, 148(1), pp. 84-98. (Year: 2012).*
Waldispühl, J., Zhang, E., Butyaev, A., Nazarova, E. and Cyr, Y. Storage, visualization, and navigation of 3D genomics data. Methods, 142, pp. 74-80. (Year: 2018).*
Stuart, T. and Satija, R. Integrative single-cell analysis. Nature Reviews Genetics, 20(5), pp. 257-272. (Year: 2019).*
Anders et al., "Differential expression analysis for sequence count data," Genome Biology, Nov. 10, 2010, 12 pgs.

(Continued)

*Primary Examiner* — Olivia M. Wise
*Assistant Examiner* — Janna Nicole Schultzhaus

(57) ABSTRACT

Systems and methods for visualizing patterns in discrete attribute value datasets are provided. A dataset comprises a discrete attribute value for each gene in a plurality of genes, for each cell in a plurality of cells. The dataset further comprises ATAC counts for each ATAC peak in a plurality of peaks, for each of the cells. Cells are assigned cluster groups in a first plurality of cluster groups based on a first clustering of discrete attribute values for the genes across the cells. Cell are also assigned cluster groups in a second plurality of cluster groups based on a second clustering of ATAC fragment count values for the ATAC peaks across the cells. A projection of the cells uses one of the first or second cluster group assignments. There is indicated, for each cell within the projection, membership in the other of the first or second cluster group assignments.

20 Claims, 63 Drawing Sheets

(51 of 63 Drawing Sheet(s) Filed in Color)

(56) References Cited

U.S. PATENT DOCUMENTS

| | | |
|---|---|---|
| 6,143,496 A | 11/2000 | Brown et al. |
| 6,143,498 A | 11/2000 | Brown et al. |
| 6,172,218 B1 | 1/2001 | Brenner |
| 6,210,891 B1 | 4/2001 | Nyren et al. |
| 6,258,568 B1 | 7/2001 | Nyren |
| 6,266,459 B1 | 7/2001 | Walt et al. |
| 6,274,320 B1 | 8/2001 | Rothberg et al. |
| 6,278,794 B1 | 8/2001 | Parekh ............ G01N 27/44739 382/129 |
| 6,297,006 B1 | 10/2001 | Drmanac et al. |
| 6,297,017 B1 | 10/2001 | Thompson |
| 6,306,597 B1 | 10/2001 | Macevicz |
| 6,327,410 B1 | 12/2001 | Walt et al. |
| 6,355,198 B1 | 3/2002 | Kim et al. |
| 6,355,431 B1 | 3/2002 | Chee et al. |
| 6,361,950 B1 | 3/2002 | Mandecki |
| 6,372,813 B1 | 4/2002 | Johnson et al. |
| 6,391,937 B1 | 5/2002 | Beuhler et al. |
| 6,406,848 B1 | 6/2002 | Bridgham et al. |
| 6,432,360 B1 | 8/2002 | Church |
| 6,485,944 B1 | 11/2002 | Church et al. |
| 6,511,803 B1 | 1/2003 | Church et al. |
| 6,524,456 B1 | 2/2003 | Ramsey et al. |
| 6,586,176 B1 | 7/2003 | Trovsky et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,737,236 B1 | 5/2004 | Pieken et al. |
| 6,767,731 B2 | 7/2004 | Hannah |
| 6,770,441 B2 | 8/2004 | Dickinson |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,913,935 B1 | 7/2005 | Thomas |
| 6,929,859 B2 | 8/2005 | Chandler et al. |
| 6,969,488 B2 | 11/2005 | Bridham et al. |
| 6,974,669 B2 | 12/2005 | Mirkin et al. |
| 7,001,792 B2 | 2/2006 | Sauer et al. |
| 7,041,481 B2 | 5/2006 | Anderson et al. |
| 7,057,026 B2 | 6/2006 | Barnes et al. |
| 7,115,400 B1 | 10/2006 | Adessi et al. |
| 7,129,091 B2 | 10/2006 | Ismagilov et al. |
| 7,259,258 B2 | 8/2007 | Kozlov et al. |
| 7,268,167 B2 | 9/2007 | Higuchi et al. |
| 7,282,370 B2 | 10/2007 | Bridgham et al. |
| 7,323,305 B2 | 1/2008 | Leamon et al. |
| 7,375,234 B2 | 5/2008 | Sharpless et al. |
| 7,425,431 B2 | 9/2008 | Church et al. |
| 7,427,678 B2 | 9/2008 | Pieken et al. |
| 7,536,928 B2 | 5/2009 | Kazuno |
| 7,604,938 B2 | 10/2009 | Takahashi et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,708,949 B2 | 5/2010 | Stone et al. |
| 7,709,197 B2 | 5/2010 | Drmanac |
| 7,709,198 B2 | 5/2010 | Luo et al. |
| 7,745,178 B2 | 6/2010 | Dong |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,877,213 B2 | 1/2011 | Ghosh .................... G16B 25/00 702/19 |
| 7,901,891 B2 | 3/2011 | Drmanac |
| 7,910,354 B2 | 3/2011 | Drmanac et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,067,159 B2 | 11/2011 | Brown et al. |
| 8,133,719 B2 | 3/2012 | Drmanac et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,304,193 B2 | 11/2012 | Ismagilov et al. |
| 8,329,407 B2 | 12/2012 | Ismagilov et al. |
| 8,337,778 B2 | 12/2012 | Stone et al. |
| 8,460,865 B2 | 6/2013 | Chee et al. |
| 8,592,150 B2 | 11/2013 | Drmanac et al. |
| 8,603,749 B2 | 12/2013 | Gillevet |
| 8,748,094 B2 | 6/2014 | Weitz et al. |
| 8,748,102 B2 | 6/2014 | Berka et al. |
| 8,765,380 B2 | 7/2014 | Berka et al. |
| 8,774,494 B2 | 7/2014 | Staker .................... G06T 7/0012 382/151 |
| 8,804,182 B2 | 8/2014 | Kawasaki et al. |
| 8,822,148 B2 | 9/2014 | Ismagliov et al. |
| 8,871,444 B2 | 10/2014 | Griffiths et al. |
| 8,889,083 B2 | 11/2014 | Ismagilov et al. |
| 8,951,726 B2 | 2/2015 | Luo et al. |
| 9,012,370 B2 | 4/2015 | Hong |
| 9,017,948 B2 | 4/2015 | Agresti et al. |
| 9,029,083 B2 | 5/2015 | Griffiths et al. |
| 9,347,059 B2 | 5/2016 | Saxonov |
| 9,359,641 B2 | 6/2016 | Staker ........................ G06T 7/74 |
| 9,388,465 B2 | 7/2016 | Hindson et al. |
| 9,410,201 B2 | 8/2016 | Hindson et al. |
| 9,512,422 B2 | 12/2016 | Barnard et al. |
| 9,593,365 B2 | 3/2017 | Frisen et al. |
| 9,694,361 B2 | 7/2017 | Bharadwaj et al. |
| 9,695,468 B2 | 7/2017 | Hindson et al. |
| 9,727,810 B2 | 8/2017 | Fodor et al. |
| 9,783,841 B2 | 10/2017 | Nolan et al. |
| 9,824,068 B2 | 11/2017 | Wong |
| 9,889,422 B2 | 2/2018 | Smith et al. |
| 10,002,316 B2 | 6/2018 | Fodor et al. |
| 10,041,949 B2 | 8/2018 | Bendall et al. |
| 10,059,990 B2 | 8/2018 | Boyden et al. |
| 10,119,167 B2 | 11/2018 | Srinivasan et al. |
| 10,138,509 B2 | 11/2018 | Church et al. |
| 10,179,932 B2 | 1/2019 | Church et al. |
| 10,221,442 B2 | 3/2019 | Hindson et al. |
| 10,347,365 B2 | 7/2019 | Wong ................. G16B 6840/30 |
| 10,366,777 B2 | 7/2019 | Kyriazopoulou-Panagiotopoulou .... C40B 40/06 |
| 10,395,758 B2 | 8/2019 | Schnall-Levin |
| 10,832,796 B2 | 11/2020 | Hubbell ................ G16B 40/30 |
| 2001/0020588 A1 | 9/2001 | Adourian et al. |
| 2001/0044109 A1 | 11/2001 | Mandecki |
| 2002/0034737 A1 | 3/2002 | Drmanac |
| 2002/0051992 A1 | 5/2002 | Bridgham et al. |
| 2002/0089100 A1 | 7/2002 | Kawasaki |
| 2002/0092767 A1 | 7/2002 | Bjomson et al. |
| 2002/0179849 A1 | 12/2002 | Maher et al. |
| 2003/0008285 A1 | 1/2003 | Fi |
| 2003/0008323 A1 | 1/2003 | Ravki et al. |
| 2003/0027221 A1 | 2/2003 | Scott et al. |
| 2003/0028981 A1 | 2/2003 | Chandler et al. |
| 2003/0039978 A1 | 2/2003 | Hannah |
| 2003/0044777 A1 | 3/2003 | Beattie |
| 2003/0044836 A1 | 3/2003 | Levi |
| 2003/0104466 A1 | 6/2003 | Knapp et al. |
| 2003/0108897 A1 | 6/2003 | Drmanac |
| 2003/0149307 A1 | 8/2003 | Hai |
| 2003/0170698 A1 | 9/2003 | Gascoyne et al. |
| 2003/0182068 A1 | 9/2003 | Batt |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0132122 A1 | 7/2004 | Banerjee et al. |
| 2004/0258701 A1 | 12/2004 | Dominowski |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0100900 A1 | 5/2005 | Kawashima et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |

(56) References Cited

U.S. PATENT DOCUMENTS

| | | |
|---|---|---|
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0020371 A1 | 1/2006 | Ham et al. |
| 2006/0073487 A1 | 4/2006 | Ol et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0188901 A1 | 8/2006 | Barnes et al. |
| 2006/0199193 A1 | 9/2006 | Koo et al. |
| 2006/0240439 A1 | 10/2006 | Smith et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0281109 A1 | 12/2006 | Ost et al. |
| 2006/0292583 A1 | 12/2006 | Schnei |
| 2007/0003442 A1 | 1/2007 | Link et al. |
| 2007/0020617 A1 | 1/2007 | Trnovsky et al. |
| 2007/0054119 A1 | 3/2007 | Garstecki et al. |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0111241 A1 | 5/2007 | Cereb et al. |
| 2007/0154903 A1 | 7/2007 | Marla et al. |
| 2007/0166705 A1 | 7/2007 | Milton et al. |
| 2007/0172873 A1 | 7/2007 | Brenner et al. |
| 2007/0174007 A1 | 7/2007 | Ghosh ............... G16B 6825/30 702/19 |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0213766 A1 | 9/2008 | Brown et al. |
| 2008/0241820 A1 | 10/2008 | Krutzik et al. |
| 2008/0268431 A1 | 10/2008 | Choy et al. |
| 2008/0280773 A1 | 11/2008 | Fedurco |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0026082 A1 | 1/2009 | Rothberg et al. |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0118488 A1 | 5/2009 | Drmanac et al. |
| 2009/0127589 A1 | 5/2009 | Rothberg et al. |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | F. et al. |
| 2010/0022414 A1 | 1/2010 | Link et al. |
| 2010/0069263 A1 | 3/2010 | Shendure et al. |
| 2010/0105112 A1 | 4/2010 | Holtze et al. |
| 2010/0130369 A1 | 5/2010 | Shenderov et al. |
| 2010/0136544 A1 | 6/2010 | Agresti et al. |
| 2010/0137143 A1 | 6/2010 | Rothberg et al. |
| 2010/0137163 A1 | 6/2010 | Link et al. |
| 2010/0173394 A1 | 7/2010 | Colston et al. |
| 2010/0210479 A1 | 8/2010 | Griffiths et al. |
| 2010/0216153 A1 | 8/2010 | Lapidus et al. |
| 2010/0282617 A1 | 11/2010 | Rothberg et al. |
| 2011/0033854 A1 | 2/2011 | Drmanac et al. |
| 2011/0053798 A1 | 3/2011 | Hindson et al. |
| 2011/0059865 A1 | 3/2011 | Smith et al. |
| 2011/0071053 A1 | 3/2011 | Drmanac et al. |
| 2011/0086780 A1 | 4/2011 | Colston et al. |
| 2011/0092376 A1 | 4/2011 | Colston et al. |
| 2011/0092392 A1 | 4/2011 | Colston et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0257889 A1 | 10/2011 | Klammer et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0305761 A1 | 12/2011 | Shum et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0041727 A1 | 2/2012 | Mishra et al. |
| 2012/0071331 A1 | 3/2012 | Casbon et al. |
| 2012/0121481 A1 | 5/2012 | Romanow et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0196288 A1 | 8/2012 | Beer |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0230338 A1 | 9/2012 | Ganeshalingam et al. |
| 2012/0270305 A1 | 10/2012 | Reed et al. |
| 2012/0309002 A1 | 12/2012 | Link |
| 2012/0316074 A1 | 12/2012 | Saxonov |
| 2013/0028812 A1 | 1/2013 | Prieto et al. |
| 2013/0046030 A1 | 2/2013 | Rotem et al. |
| 2013/0078638 A1 | 3/2013 | Berka et al. |
| 2013/0079231 A1 | 3/2013 | Pushkarev et al. |
| 2013/0109575 A1 | 5/2013 | Kleinschmidt et al. |
| 2013/0130919 A1 | 5/2013 | Chen et al. |
| 2013/0157870 A1 | 6/2013 | Pushkarev et al. |
| 2013/0157899 A1 | 6/2013 | Adler et al. |
| 2013/0178368 A1 | 7/2013 | Griffiths et al. |
| 2013/0185096 A1 | 7/2013 | Giusti |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0225418 A1 | 8/2013 | Watson |
| 2013/0260372 A1 | 10/2013 | Buemann et al. |
| 2013/0268206 A1 | 10/2013 | Porreca et al. |
| 2013/0274117 A1 | 10/2013 | Church et al. |
| 2013/0311106 A1 | 11/2013 | White et al. |
| 2013/0317755 A1 | 11/2013 | Mishra et al. |
| 2014/0037514 A1 | 2/2014 | Stone et al. |
| 2014/0057799 A1 | 2/2014 | Johnson et al. |
| 2014/0065234 A1 | 3/2014 | Shum et al. |
| 2014/0079923 A1 | 3/2014 | George et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0200166 A1 | 7/2014 | Rooyen et al. |
| 2014/0206554 A1 | 7/2014 | Hi et al. |
| 2014/0214334 A1 | 7/2014 | Platt et al. |
| 2014/0227684 A1 | 8/2014 | Hi et al. |
| 2014/0227706 A1 | 8/2014 | Kato et al. |
| 2014/0228255 A1 | 8/2014 | Hi et al. |
| 2014/0235506 A1 | 8/2014 | Hi et al. |
| 2014/0287963 A1 | 9/2014 | Hi et al. |
| 2014/0302503 A1 | 10/2014 | Lowe et al. |
| 2014/0323316 A1 | 10/2014 | Drmanac et al. |
| 2014/0378322 A1 | 12/2014 | Hi et al. |
| 2014/0378345 A1 | 12/2014 | Hindson et al. |

(56) References Cited

U.S. PATENT DOCUMENTS

| | | |
|---|---|---|
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0066385 A1 | 3/2015 | Schnall-Levin et al. |
| 2015/0111256 A1 | 4/2015 | Church et al. |
| 2015/0133344 A1 | 5/2015 | Shendure et al. |
| 2015/0218633 A1 | 8/2015 | Hindson et al. |
| 2015/0220532 A1 | 8/2015 | Wong |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0232291 A1 | 8/2016 | Kyriazopoulou-Panagiotopoulou |
| 2016/0289760 A1 | 10/2016 | Suzuki et al. |
| 2016/0304860 A1 | 10/2016 | Hindson et al. |
| 2016/0350478 A1 | 12/2016 | Chin et al. |
| 2017/0016053 A1 | 1/2017 | Beechem et al. |
| 2017/0235876 A1 | 8/2017 | Jaffe et al. |
| 2017/0253918 A1 | 9/2017 | Kphman |
| 2018/0052081 A1 | 2/2018 | Kohman |
| 2018/0105808 A1 | 4/2018 | Mikkelsen et al. |
| 2018/0156784 A1 | 6/2018 | Usmani et al. |
| 2018/0196781 A1 | 7/2018 | Wong |
| 2018/0225416 A1 | 8/2018 | Wong et al. |
| 2018/0245142 A1 | 8/2018 | So et al. |
| 2018/0265928 A1 | 9/2018 | Schnall-Levin et al. |
| 2018/0340169 A1 | 11/2018 | Belhocine et al. |
| 2019/0032121 A1 | 1/2019 | Daugharthy et al. |
| 2019/0203275 A1 | 7/2019 | Frisen et al. |
| 2019/0332963 A1 | 10/2019 | Wong et al. |
| 2021/0097684 A1 | 4/2021 | Mellen ............... G01N 1/30 |
| 2021/0155982 A1 | 5/2021 | Yin ................. G06T 7/155 |

FOREIGN PATENT DOCUMENTS

| | | | |
|---|---|---|---|
| EP | 1336662 A2 | 8/2003 | ......... B01J 19/0046 |
| EP | 1019496 B1 | 9/2004 | |
| EP | 1482036 B1 | 10/2007 | |
| EP | 1594980 B1 | 11/2009 | |
| EP | 1967592 B1 | 4/2010 | |
| EP | 2258846 A2 | 12/2010 | |
| EP | 2145955 B1 | 2/2012 | |
| EP | 1905828 B1 | 8/2012 | |
| EP | 2136786 B1 | 10/2012 | |
| EP | 2136788 B1 | 10/2012 | |
| EP | 1908832 B1 | 12/2012 | |
| EP | 11908832 B1 | 12/2012 | |
| EP | 2540389 A1 | 1/2013 | |
| GB | 2485850 A | 5/2012 | |
| JP | 5949832 A | 3/1984 | |
| JP | 2006507921 A | 3/2006 | |
| JP | 2006289250 A | 10/2006 | |
| JP | 2007-193708 A | 8/2007 | |
| JP | 2007268350 A | 10/2007 | |
| JP | 2009208074 | 9/2009 | |
| RU | 2321638 C2 | 4/2008 | |
| WO | 1996029629 A2 | 9/1996 | |
| WO | 1996041011 A1 | 12/1996 | |
| WO | 1999009217 A1 | 2/1999 | |
| WO | 1999052708 A1 | 10/1999 | |
| WO | 2000008212 A1 | 2/2000 | |
| WO | 2000026412 A1 | 5/2000 | |
| WO | WO 2000/063437 A2 | 10/2000 | |
| WO | 2001014589 A2 | 3/2001 | |
| WO | 2001089787 A2 | 11/2001 | |
| WO | 2002031203 A2 | 4/2002 | |
| WO | 2002086148 A1 | 10/2002 | |
| WO | 2004002627 A2 | 1/2004 | |
| WO | 2004010106 A2 | 1/2004 | |
| WO | 2004069849 A2 | 8/2004 | |
| WO | 2004091763 A2 | 10/2004 | |
| WO | 2004102204 A1 | 11/2004 | |
| WO | 2004103565 A2 | 12/2004 | |
| WO | 2004105734 A1 | 12/2004 | |
| WO | 2005002730 A1 | 1/2005 | |
| WO | 2005021151 A1 | 3/2005 | |
| WO | 2005023331 A2 | 3/2005 | |
| WO | WO 2005/036451 A1 | 4/2005 | |
| WO | 2005040406 A1 | 5/2005 | |
| WO | 2005049787 A9 | 6/2005 | |
| WO | WO 2005/065814 A1 | 7/2005 | |
| WO | WO-2005082098 A2 | 9/2005 | |
| WO | WO-2006030993 A1 | 3/2006 | |
| WO | WO 2006/064199 A1 | 6/2006 | |
| WO | WO-2006078841 A1 | 7/2006 | |
| WO | WO-2006098571 A2 | 9/2006 | |
| WO | WO 2007/010251 A2 | 1/2007 | |
| WO | WO-2007001448 A2 | 1/2007 | |
| WO | WO-2007002490 A2 | 1/2007 | |
| WO | WO-2007024840 A2 | 3/2007 | |
| WO | WO-2007081385 A2 | 7/2007 | |
| WO | WO-2007081387 A1 | 7/2007 | |
| WO | 2007089541 A2 | 8/2007 | |
| WO | 2007114794 A1 | 10/2007 | |
| WO | 2007121489 A2 | 10/2007 | |
| WO | WO-2007114784 A1 | 10/2007 | |
| WO | 2007133710 A2 | 11/2007 | |
| WO | 2007138178 A2 | 12/2007 | |
| WO | 2007140015 A2 | 12/2007 | |
| WO | 2007149432 A2 | 12/2007 | |
| WO | WO-2007139766 A2 | 12/2007 | |
| WO | 2008021123 A1 | 2/2008 | |
| WO | 2008091792 A2 | 7/2008 | |
| WO | 2008102057 A1 | 8/2008 | |
| WO | 2008109176 A2 | 9/2008 | |
| WO | 2008121342 A2 | 10/2008 | |
| WO | 2008134153 A2 | 11/2008 | |
| WO | WO-2008134153 A1 | 11/2008 | |
| WO | 2007139766 A3 | 12/2008 | |
| WO | 2009005680 A1 | 1/2009 | |
| WO | 2009011808 A1 | 1/2009 | |
| WO | 2009023821 A1 | 2/2009 | |
| WO | 2009061372 A1 | 5/2009 | |
| WO | 2009085215 A1 | 7/2009 | |
| WO | 2010004018 A2 | 1/2010 | |
| WO | 2010033200 A2 | 3/2010 | |
| WO | 2010115154 A1 | 10/2010 | |
| WO | 2010126614 A2 | 11/2010 | |
| WO | 2010126814 A2 | 11/2010 | |
| WO | 2010127304 A2 | 11/2010 | |
| WO | 2010148039 A2 | 12/2010 | |
| WO | 2010151776 A2 | 12/2010 | |
| WO | 2011047870 A1 | 4/2011 | |
| WO | 2011056546 A1 | 5/2011 | |
| WO | 2011066476 A1 | 6/2011 | |
| WO | 2011074960 A1 | 6/2011 | |
| WO | WO 2011/094669 A1 | 8/2011 | |
| WO | WO 2011/127099 A1 | 10/2011 | |
| WO | 2012012037 A1 | 1/2012 | |
| WO | 2012048341 A1 | 4/2012 | |
| WO | 2012055929 A1 | 5/2012 | |
| WO | 2012061832 A1 | 5/2012 | |
| WO | 2012100216 A2 | 7/2012 | |
| WO | 2012083225 A3 | 8/2012 | |
| WO | 2012106546 A2 | 8/2012 | |
| WO | 2012112804 A1 | 8/2012 | |
| WO | 2012116331 A2 | 8/2012 | |
| WO | WO-2012083225 A2 | 9/2012 | |
| WO | 2012142531 A2 | 10/2012 | |
| WO | 2012142611 A2 | 10/2012 | |
| WO | WO 2012/140224 A1 | 10/2012 | |
| WO | 2012149042 A2 | 11/2012 | |
| WO | 2012166425 A2 | 12/2012 | |
| WO | 2013035114 A1 | 3/2013 | |
| WO | 2013055955 A1 | 4/2013 | |

(56) References Cited

FOREIGN PATENT DOCUMENTS

| | | |
|---|---|---|
| WO | 2013123125 A1 | 8/2013 |
| WO | 2013177220 A1 | 11/2013 |
| WO | 2014028537 A1 | 2/2014 |
| WO | WO 2014/060483 A1 | 4/2014 |
| WO | 2014093676 A1 | 6/2014 |
| WO | WO 2014/163886 A1 | 10/2014 |
| WO | WO 2014/210225 A1 | 12/2014 |
| WO | WO 2014/210233 A1 | 12/2014 |
| WO | 2015002908 A1 | 1/2015 |
| WO | 2015157567 A1 | 10/2015 |
| WO | WO 2015/157587 A1 | 10/2015 |
| WO | WO 2015/161173 A1 | 10/2015 |
| WO | 2015200891 A1 | 12/2015 |
| WO | WO 2016/007839 A1 | 1/2016 |
| WO | 2016130578 A1 | 8/2016 |
| WO | WO 2016/162309 A1 | 10/2016 |
| WO | WO 2016/166128 A1 | 10/2016 |
| WO | WO 2017/019456 A2 | 2/2017 |
| WO | WO 2017/027368 A1 | 2/2017 |
| WO | WO 2017/144338 A1 | 8/2017 |
| WO | WO 2017/222453 A1 | 12/2017 |
| WO | WO 2018/045181 A1 | 3/2018 |
| WO | WO 2018/045186 A1 | 3/2018 |
| WO | WO 2018/057999 A1 | 3/2018 |
| WO | WO 2018/075693 A1 | 4/2018 |
| WO | WO 2018/091676 A1 | 5/2018 |
| WO | WO 2018/107054 A1 | 6/2018 |
| WO | WO 2018/136856 A1 | 7/2018 |
| WO | WO 2019/068880 A1 | 4/2019 |
| WO | WO 2019/075091 A1 | 4/2019 |
| WO | WO 2019/113533 A1 | 6/2019 |
| WO | WO 2019204560 A1 | 10/2019 |
| WO | WO 2020/123316 A2 | 6/2020 |

OTHER PUBLICATIONS

Blondel et al., "Fast unfolding of communities in large networks," J. Stat. Mech., Jul. 25, 2008, 12 pgs.

Bluthmann et al., "T-cell-specific deletion of T-cell receptor transgenes allows functional rearrangement of endogenous α- and β-genes", Nature 334, 156-159 (1988).

Buenrostro et al., "ATAC-seq: A Method for Assaying Chromatin Accessibility Genome-Wide", Curr. Protoc. Mol. Biol. 109:21.29. 1-21.29.9.

Chen et al., "Clustering-based identification of clonally-related immunoglobulin gene sequence sets," Immunology Research, Sep. 27, 2010, 6(Suppl 1): S4. 7 pgs.

Duda et al., "Pattern Classification," 2010, pp. 115-116.

Ganusov et al., "Do most lymphocytes in humans really reside in the gut?" Trends in Immunology, vol. 28, Issue 12, p. 514-518, Dec. 1, 2007.

Goharian et al., "Comparative analysis of sparse matrix algorithms for information retrieval", Computer 2, 0.4, 2003.

Hastie et al., "The Elements of Statistical Learning", Springer, New York, pp. 55-57; 59-66; 59-64; ; 64-65, 69-72; 330-331.

Hershberg et al., "The analysis of clonal expansions in normal and autoimmune B cell repertoires," Philosophical Transactions B, Sep. 5, 2015, 16 pgs.

Li et al., "Utilization of IIg heavy chain variable, diversity, and joining gene segments in children with B-lineage acute lymphoblastic leukemia: implications for the mechanisms of VDJ recombination and for pathogenesis," Blood, Jun. 15, 2004, vol. 103, No. 12, pp. 4602-4609.

Li, "Tabix: fast retrieval of sequence features from generic TAB-delimited files", Bioinformatics. Mar. 1, 2011;27(5):718-9.

Matsuda et al., "The Complete Nucleotide Sequence of the Humabe Immunoglobulin Heavy Chain Variable Region Locus," J. Exp. Med., Dec. 7, 1998, vol. 188, No. 11, pp. 2151-2162.

Mostovoy et al., "A hybrid approach for de novo human genome sequence assembly and phasing", Nat Methods. Jul. 2016;13(7):587-90.

Narasimhan et al., "Health and population effects of rare gene knockouts in adult humans with related parents," Science 352, Apr. 22, 2016, 11 pgs.

Rudolph et al., "How TCRs Bind MHCs, Peptides, and Coreceptors", Annu Rev Immunol 24: pp. 419-466.

Uematsu et al., "In transgenic mice the introduced functional T cell receptor beta gene prevents expression of endogenous beta genes", Cell, Mar. 25, 1988;52(6):831-41.

Van der Maaten et al., "Visualizing Data using t-SNE," Journal of Machine Learning Research 9, Nov. 2008, pp. 2579-2605.

Vijayakumar et al., "Locally Weighted Projection Regression: An O(n) Algorithm for Incremental Real Time Learning in High Dimensional Space", Proc. of Seventeenth International Conference on Machine Learning (ICML2000) , pp. 1079-1086 (2000).

Yaari et al., "Practical guidelines for B-cell receptor repertoire sequencing analysis," Genomics Medicine, 2015, 7:121, 12 pgs.

Yassai et al., "A clonotype nomenclature for T cell receptors", Immunogenetics (2009) 61, pp. 493-502.

Yu et al., "Shrinkage estimation of dispersion in Negative Binomial models for RNA-seq experiments with small sample size," Bioinformatics, Apr. 14, 2013, vol. 29 No. 10 2013, pp. 1275-1282.

Zheng et al., "Halotyping germline and cancer genomes using high-throughput linked-read sequencing," Nat Biotechnol., Mar. 2016, 34(3): 303-311, 28 pgs.

Greiff et al., "Bioinformatic and Statistical Analysis of Adaptive Immune Repertoires," Trends in Immunology, Nov. 2015, vol. 36 No. 11, pp. 738-749.

Turchaninova et al., "High-quality full-length immunoglobulin profiling with unique molecular barcoding," Nature Protocols, Aug. 4, 2016, vol. 11 No. 9, pp. 1599-1616.

Zhang et al., "IMonitor: A Robust Pipeline for TCR and BCR Repertoire Analysis," Genetics, Aug. 21, 2015, vol. 201 No. 2, pp. 459-472.

Bluthmann et al., 1988, "T-cell-specific deletion of T-cell receptor transgenes allows functional rearrangement of endogenous alpha- and beta-genes," Nature 334, pp. 156-159.

Ganusov et al., 2007, "Do most lymphocytes in humans really reside in the gut?," Trends Immunol, 208(12), pp. 514-518.

Mostovoy et al., 2016, "A hybrid approach for de novo human genome sequence assembly and phasing," Nat. Methods 13, 587-590.

Narasimhan et al., 2016, "Health and population effects of rare gene knockouts in adult humans with related parents," Science 352, pp. 474-477 (2016).

Rudolph et al., 2006, "How TCRs bind MHCs, peptides, and coreceptors," Annu Rev Immunol 24:pp. 419-466, doi:10.1146/annurev.immunol.23.021704.115658.

Uematsu et al., 1988, "In transgenic mice the introduced functional T-cell receptor beta gene prevents expression of endogenous beta genes," Cell 52, pp. 831-841.

Yassai et al., 2009, "A clonotype nomenclature for T-cell receptors," Immunogenetics 61, pp. 493-502.

Yaari and Kleinstein, 2015, "Practical guidelines for B-cell repertoire sequencing analysis," Genome Medicine 7:121.

Matsuda et al., 1998, "The complete nucleotide sequence of the human immunoglobulin heavy chain variable region locus," The Journal of Experimental Medicine. 188 (11):2151-62, doi:10.1084/jem.188.11.2151.

Li et al., 2004, "Utilization of Ig heavy chain variable, diversity, and joining gene segments in children with B-lineage acute lymphoblastic leukemia: implications for the mechanisms of VDJ recombination and for pathogenesis," Blood. 103 (12): 4602-9, doi:10.1182/blood-2003-11-3857.

McLaren, 2016, et al., "The Ensembl Variant Effect Predictor," Genome Biology 17, p. 122, doi: 10.1186/s13059-016-0974-4.

Fisher, S. et al. "A Scalable, fully automated process for construction of sequence-ready human exome targeted capture libraries" Genome Biology (2011) 2:R1-R15. doi: 10.1186/gb-2011-12-1-r1. Epub Jan. 4, 2011.

Freiberg, et al. "Polymer microspheres for controlled drug release" Int J Pharm. Sep. 10, 2004;282(1-2):1-18.

Fu. A.Y. et al. "A microfabricated fluorescence-activated cell sorter" Nature Biotech (Nov. 1999) 17:1109-1111.

(56) References Cited

OTHER PUBLICATIONS

Fulton et al., "Advanced multiplexed analysis with the FlowMetrix system" Clin Chem. Sep. 1997;43(9): 1749-56.
Garstecki, P. et al. "Formation of monodisperse bubbles in a microfluidic flow-focusing device" Appl. Phys. Lett (2004) 85(13):2659-2651. DOI: 10.1063/1.1796526.
Ghadessy, et al. Directed evolution of polymerase function by compartmentalized self-replication. Proc Natl Acad Sci USA. Apr. 10, 2001;98(8):4552-7. Epub Mar. 27, 2001.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Gordon et al. "Consed: A Graphical Tool for Sequence Finishing," Genome Research (1998) 8:198-202.
Granieri, Lucia "Droplet-based microfluidics and engineering of tissue plasminogen activator for biomedical applications" Ph.D. Thesis, Nov. 13, 2009 (131 pages).
Guo, M.T. et al., "Droplet microfluidics for high-throughput biological assays" Lab Chip (2012) 12:2146-2155.
Gyarmati et al., "Reversible Disulphide Formation in Polymer Networks: A Versitile Functional Group from Synthesis to Application," European Polymer Journal, 2013, 49, 1268-1286.
Hashimshony, T. et al. "CEL-Seq: Single-Cell RNa-Seq by Multiplexed Linear Amplification" Cell Rep. Sep. 27, 2012;2(3):666-73. doi: 10.1016/j.celrep.2012.08.003. Epub Aug. 30, 2012.
He "Selective Encapsulation of Single Cells and Subcellular Organelles into Picoliter- and Femtoliter-Volume Droplets" Anal. Chem 77: 1539-1544 (2005).
Heng et al. "Fast and accurate long-read alignment with Burrows-Wheeler transform," Bioinformatics (2010) 25(14): 1754-1760.
Holtze, C. et al. Biocompatible surfactants for water-in-fluorocarbon emulsions. Lab Chip. Oct. 2008;8(10):1632-9. doi: 10.1039/b806706f. Epub Sep. 2, 2008.
Huang et al. "EagleView. A genome assembly viewer for next-generationsequencing technologies," Genome Research (2008) 18:1538-1543.
Huebner, "Quantitative detection of protein expression in single cells using droplet microfluidics", Chem. Commun. 1218-1220 (2007).
Hug, H. et al. "Measurement of the number of molecules of a single mRNA species in a complex mRNA preparation" J Theor Biol. Apr. 21, 2003;221(4):615-24.
Jena et al., "Cyclic olefin copolymer based microfluidic devices for biochip applications: Ultraviolet surface grafting using 2-methacryloyloxyethyl phosphorylcholine" Biomicrofluidics (Mar. 15, 2012) 6:012822 (12 pages).
Jung, W-C et al., "Micromachining of injection mold inserts for fluidic channel of polymeric biochips" Sensors (2007) 7:1643-1654.
Kanehisa et al. "KEGG: Kyoto Encyclopedia of Genes and Genomes," Nucleic Acids Research (2000) 28:27-30.
Khomiakov A et al., "Analysis of perfect and mismatched DNA duplexes by a generic hexanucleotide microchip". Mol Biol (Mosk). Jul.-Aug. 2003;37(4):726-41. Russian. Abstract only.
Kim et al. "HapEdit: an accuracy assessment viewer for haplotype assembly using massively parallel DNA-sequencing technologies," Nucleic Acids Research (2011) pp. 1-5.
Kim, et al. Albumin loaded microsphere of amphiphilic poly(ethylene glycol)/ poly(alpha-ester) multiblock copolymer. Eur J Pharm Sci. Nov. 2004;23(3):245-51.
Kim, et al. Fabrication of monodisperse gel shells and functioNal microgels in microfluidic devices. Angew Chem Int Ed Engl. 2007;46(11):1819-22.
Kim, J et al., "Rapid prototyping of microfluidic systems using a PDMS/polymer tape composite" Lab Chip (2009) 9:1290-1293.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Klein, et al. Droplet barcoding for single-cell transcriptomics applied to embryonic stem cells. Cell. May 21, 2015; 161:1187-1201.
Knight, et al. Subtle chromosomal rearrangements in children with unexplained mental retardation. Lancet. Nov. 13, 1999;354(9191):1676-81.
Koster et al., "Drop-based microfluidic devices for encapsulation of single cells", Lab on a Chip the Royal Soc. of Chem. 8: 1110-1115 (2008).
Kutyavin, et al. Oligonucleotides containing 2-aminoadenine and 2-thiothymine act as selectively binding complementary agents. Biochemistry. Aug. 27, 1996;35(34):11170-6.
Lagus, T.P. et al., "A review of the theory, methods and recent applications of high-throughput single-cell droplet microfluidics" J. Phys. D: Appl. Phys. (2013) 46:114005 (21 pages).
Li, Y., et al., "PEGylated PLGA Nanoparticles as protein carriers: synthesis, preparation and biodistribution in rats." Journal of Controlled Release, vol. 71, pp. 203-211 (2001).
Lippert et al. "Algorithmic strategies for the single nucleotide polymorphism haplotype assembly problem," Brief. Bionform (2002) 3:23-31.
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24(6):703-707 (Jun. 2006).
Lowe, Adam J."Norbornenes and [n]polynorbornanes as molecular scaffolds for anion recognition" Ph.D. Thesis (May 2010). (361 pages).
Lupski. Genomic rearrangements and sporadic disease. Nat Genet. Jul. 2007;39(7 Suppl):S43-7.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, D.A. et al., "Injection molded microfluidic chips featuring integrated interconnects" Lab Chip (2006) 6:1346-1354.
Makino, K. et al. "Preparation of hydrogel microcapsules Effects of preparation conditions upon membrane properties" Colloids and Surfaces: B Biointerfaces (1998) 12:97-104.
Margulies et al. "Genome sequencing in microfabricated high-density picoliter reactors," Nature (2005) 437:376-380.
Matochko, W.L. et al., "Uniform amplification of phage display libraries in monodisperse emulsions," Methods (2012) 58:18-27.
Mazutis, et al. Selective droplet coalescence using microfluidic systems. Lab Chip. Apr. 24, 2012;12(10):1800-6. doi: 10.1039/c2lc40121e. Epub Mar. 27, 2012.
McKenna et al. "The Genome Analysis Toolkit: A MapReduce framework for anayizing nextgeneration DNA sequencing data," Genome Research (2010) pp. 1297-1303.
Merriman, et al. Progress in ion torrent semiconductor chip based sequencing. Electrophoresis. Dec. 2012;33(23):3397-3417. doi: 10.1002/elps.201200424.
Miller et al. "Assembly Algorithms for next-generation sequencing data," Genomics, 95 (2010), pp. 315-327.
Mirzabekov, "DNA Sequencing by Hybridization- a Megasequencing Method and A Diagnostic Tool?" Trends in Biotechnology 12(1): 27-32 (1994).
Moore, J.L. et al., "Behavior of capillary valves in centrifugal microfluidic devices prepared by three-dimensional printing" Microfluid Nanofluid (2011) 10:877-888.
Mouritzen et al., Single nucleotide polymorphism genotyping using locked nucleic acid (LNa). Expert Rev Mol Diagn. Jan. 2003;3(1):27-38.
Myllykangas et al. "Efficient targeted resequencing of human germline and cancer genomes by oligonucleotide-selective sequencing," Nat Biotechnol, (2011) 29:1024-1027.
Nagashima, S. et al. "Preparation of monodisperse poly(acrylamide-co acrylic acid) hydrogel microspheres by a membrane emulsification technique and their size dependent surface properties" Colloids and Surfaces: B Biointerfaces (1998) 11:47-56.

(56) References Cited

OTHER PUBLICATIONS

Navin, N.E. "The first five years of single-cell cancer genomics and beyond" Genome Res. (2015) 25:1499-1507.
Nguyen, et al. In situ hybridization to chromosomes stabilized in gel microdrops. Cytometry. 1995; 21:111-119.
Novak, R. et al., "Single cell multiplex gene detection and sequencing using microfluidicallygenerated agarose emulsions" Angew. Chem. Int. Ed. Engl. (2011) 50(2):390-395.
Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, "Controlled production of monodisperse double emulsions by two-step droplet breakup in microfluidic devices", Langmuir, 20:9905-9908 (2004).
Perez, C., et al., "Poly(lactic acid)-poly(ethylene glycol) Nanoparticles as new carriers for the delivery ofplasmid DNa," Journal of Controlled Release, vol. 75, pp. 211-224 (2001).
Peters et al., "Accurate whole-genome sequencing and haplotyping from 10 to 20 human cells," Nature, Jul. 12, 2012, vol. 487, pp. 190-195.
Pinto, et al. Functional impact of global rare copy number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Pushkarev et al. "Single-molecule sequencing of an individual human genome," Nature Biotech (2009) 17:847-850.
Ritz, A. et al. "Characterization of structural variants with single molecule and hybrid sequencing approaches" Bioinformatics (2014) 30(24):3458-3466.
Ropers. New perspectives for the elucidation of genetic disorders. Am J Hum Genet. Aug. 2007;81(2):199-207. Epub Jun. 29, 2007.
Rotem, A. et al. "High-throughput single-cell labeling (Hi-SCL) for RNA-Seq using drop-based microfluidics" PLOS One (May 22, 2015) 0116328 (14 pages).
Ryan, et al. Rapid assay for mycobacterial growth and antibiotic susceptibility using gel microdrop encapsulation. J Clin Microbiol. Jul. 1995;33(7):1720-6.
Schirinzi et al., Combinatorial sequencing-by-hybridization: analysis of the NFI gene. Genet Test. 2006 Spring;10(1):8-17.
Schmitt, "Bead-based multiplex genotyping of human papillomaviruses", J. Clinical Microbiol., 44:2 504-512 (2006).
Sebat, et al. Strong association of de novo copy number mutations with autism. Science. Apr. 20, 2007;316 (5823):445-9. Epub Mar. 15, 2007.
Seiffert, S. et al., "Smart microgel capsules from macromolecular precursors" J. Am. Chem. Soc. (2010) 132:6606-6609.
Shah, "Fabrication of mono disperse thermosensitive microgels and gel capsules in micro fluidic devices", Soft Matter, 4:2303-2309 (2008).
Shendure et al. "Accurate Multiplex Polony Sequencing of an Evolved bacterial Genome" Science (2005) 809:1728-1732.
Shimkus et al. "A chemically cleavable biotinylated nucleotide: Usefulness in the recovery of protein-DNA complexes from avidin affinity columns" PNAS (1985) 82:2593-2597.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.
Sorokin et al., Discrimination between perfect and mismatched duplexes with oligonucleotide gel microchips: role of ThermodyNamic and kinetic effects during hybridization. J Biomol Struct Dyn. Jun. 2005;22(6):725-34.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Tawfik, D.S. et al. "Man-made cell-like compartments for molecular evolution" Nature Biotech (Jul. 1998) 16:652-656.
Tewhey et al. "The importance of phase information for human genomics," Nat Rev Genet (2011) 12:215-223.
Tewhey, R. et al., "Microdroplet-based PCR enrichment for large-scale targeted sequencing" Nature Biotech. (2009) 27(11):1025-1031 and Online Methods (11 pages).
Theberge, A.B, et al. Microdropelts in microfluidics: an evolving platform for discoveries in chemsitry and biology. Angew Chem Int Ed Engl. Aug. 9, 2010:49(34):5846-68. doi: 10.1002/anie.200906653.
Tonelli, C. et al., "Perfluoropolyether functional oligomers: unusual reactivity in organic chemistry" J. Fluorine Chem. (2002) 118:107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. "Methods for genomic partitioning" Annu Rev Genomics Human Genet. (2009) 10:263-284. doi: 10.1146/annurev-genom-082908-150112. Review.
Wang et al., Single nucleotide polymorphism discrimination assisted by improved base stacking hybridization using oligonucleotide microarrays. Biotechniques. 2003;35:300-08.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Weaver, J.C. et al. "Rapid clonal growth measurements at the single-cell level: gel microdroplets and flow cytometry", Biotechnology, 9:873-877 (1991).
Wheeler et al., "Database resources of the National Center for Biotechnology Information," Nucleic Acids Res. (2007) 35 (Database issue): D5-12.
Whitesides, "Soft lithography in biology and biochemistry", Annual Review of Biomedical Engineering, 3:335-373 2001).
Williams, R. et al. "Amplification of complex gene libraries by emulsion PCR" Nature Methods (Jul. 2006) 3(7):545-550.
Woo, et al. G/C-modified oligodeoxynucleotides with selective complementarity: synthesis and hybridization properties. Nucleic Acids Res. Jul. 1, 1996;24(13):2470-5.
Zerbino et al. "Velvet: Algorithms for de novo short read assembly using de Bruijn graphs," Genome Research (2008) 18:821-829.
Zerbino, D.R. "Using the Velvet de novo assembler for short-read sequencing technologies" Curr Protoc Bioinformatics (Sep. 1, 2010) 31:11.5:11.5.1-11.5.12.
Zerbino, Daniel, "Velvet Manual—version 1.1," Aug. 15, 2008, pp. 1-22.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/ bm800867n. Epub Oct. 9, 2008.
Zhao, J., et al., "Preparation of hemoglobin-loaded Nano-sized particles with porous structure as oxygen carriers," Biomaterials, vol. 28, pp. 1414-1422 (2007).
Zheng, X.Y. et al. "Haplotyping germline and cancer genomes with high-throughput linked-read sequencing" Nature Biotech (Feb. 1, 2016) 34(3):303-311 and Supplemental Material.
Zhu, S. et al., "Synthesis and self-assembly of highly incompatible polybutadienepoly(hexafluoropropoylene oxide) diblock copolymers" J. Polym. Sci. (2005) 43:3685-3694.
Zimmermann et at., Microscale production of hybridomas by hypo-osmolar electrofusion. Human Antibodies Hybridomas. Jan. 1992;3(1): 14-8.

(56) References Cited

OTHER PUBLICATIONS

Zong, C. et al. "Genome-wide detection of single-nucleotide and copy-number variations of a single human cell" Science. Dec. 21, 2012;338(6114):1622-6. doi: 10.1126/science.1229164.

International Search Report and Written Opinion for International Patent Application No. PCT/US2018/033499, mailed Sep. 6, 2018, 9 pages.

Freeman et al., "Profiling the T-cell receptor beta-chain repertoire by massively parallel sequencing", Genome Research, Dec. 31, 2009, 9 pages.

Bischof et al., "bcRep: R Package for Comprehensive Analysis of B Cell Receptor Repertoire Data", PLOS One, Aug. 23, 2016, 15 pages.

Abate et al., Valve-based flow focusing for drop formation. Appl Phys Lett. 2009;94. 3 pages.

Abate, A.R. et al. "Beating Poisson encapsulation statistics using close-packed ordering" Lab on a Chip (Sep. 21, 2009) 9(18):2628-2631.

Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.

Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.

Aitman, et al. Copy Number polymorphism in Fcgr3 predisposes to glomerulonephritis in rats and humans. Nature. Feb. 16, 2006;439(7078):851-5.

Akselband, "Enrichment of slow-growing marine microorganisms from mixed cultures using gel microdrop (GMD) growth assay and fluorescence-activated cell sorting", J. Exp. Marine Biol., 329:196-205 (2006).

Akselband, "Rapid mycobacteria drug susceptibility testing using gel microdrop (GMD) growth assay and flow cytometry", J. Microbiol. Methods, 62:181-197 (2005).

Anna et al., "Formation of dispersions using 'flow focusing' in microchannels", Appln. Phys. Letts. 82:3 364 (2003).

Attia, U.M et al., "Micro-injection moulding of polymer microfluidic devices" Microfluidics and nanofluidics (2009) 7(1):1-28.

Balikova, et al. Autosomal dominant microtia linked to five tandem copies of a copy-number-variable region at chromosome 4p16. Am J Hum Genet. Jan. 2008;82(1):181-7. doi: 10.1016/j.ajhg.2007.08.001.

Bansal et al. "An MCMC algorithm for haplotype assembly from whole-genome sequence data," (2008) Genome Res 18:1336-1346.

Bansal et al. "HapCUT: an efficient and accurate algorithm for the haplotype assembly problem," Bioinformatics (2008) 24:1153-1159.

Baret et al. "Fluorescence-activated droplet sorting (FADS): efficient microfluidic cell sorting based on enzymatic activity" Lab on a Chip (2009) 9(13):1850-1858.

Bentley et al. "Accurate whole human genome sequencing using reversible terminator chemistry," (2008) Nature 456:53-59.

Boone, et al. Plastic advances microfluidic devices. The devices debuted in silicon and glass, but plastic fabrication may make them hugely successful in biotechnology application. Analytical Chemistry. Feb. 2002; 78A-86A.

Braeckmans et al., Scanning the Code. Modern Drug Discovery. 2003:28-32.

Bransky, et al. A microfluidic droplet generator based on a piezoelectric actuator. Lab Chip. Feb. 21, 2009;9(4):516-20. doi: 10.1039/b814810d. Epub Nov. 20, 2008.

Brouzes, E et al., "Droplet microfluidic technology for single-cell high-throughput screening" PNAS (2009) 106(34):14195-14200.

Browning, S.R. et al. "Haplotype Phasing: Existing Methods and New Developments" NaRevGenet (Sep. 16, 2011) 12(10):703-714.

Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.

Carroll, "The selection of high-producing cell lines using flow cytometry and cell sorting", Exp. Op. Bioi. Therp., 4:11 1821-1829 (2004).

Chaudhary "A rapid method of cloning functional variable-region antibody genes in *Escherichia coli* as single-chain immunotoxins" Proc. Natl. Acad. Sci USA 87: 1066-1070 (Feb. 1990).

Chechetkin et al., Sequencing by hybridization with the generic 6-mer oligonucleotide microarray: an advanced scheme for data processing. J Biomol Struct Dyn. Aug. 2000;18(1):83-101.

Chen et al. "BreakDancer. an algorithm for high-resolution mapping of genomic structural variation," Nature Methods (2009) 6(9):677-681.

Chen, F. et al. "Chemical transfection of cells in picoliter aqueous droplets in fluorocarbon oil" Anal Chem (2011) 83(22):8816-8820.

Choi et al. "Identification of novel isoforms of the EML4-ALK transforming gene in non-small cell lung cancer," Cancer Res (2008) 68:4971-4976.

Chokkalingam, V et al., "Probing cellular heterogeneity in cytokine-secreting immune cells using droplet-based microfluidics" Lab Chip (2013) 13:4740-4744.

Chou, H-P. et al. "Disposable Microdevices for DNA Analysis and Cell Sorting" Proc. Solid-State Sensor and Actuator Workshop Hilton Head, SC Jun. 8-11, 1998, pp. 11-14.

Chu, L-Y. et al., "Controllable monodisperse multiple emulsions" Angew. Chem. Int. Ed. (2007) 46:8970-8974.

Clausell-Tormos et al., "Droplet-based microfluidic platforms for the encapsulation and screening of mammalian cells and multicellular organisms", Chem. Biol. 15:427-437 (2008).

Cleary et al. "Joint variant and de novo mutation identification on pedigrees from highthroughput sequencing data," J Comput Biol (2014) 21:405-419.

Cook, et al. Copy-Number variations associated with neuropsychiatric conditions. Nature. Oct. 16, 2008;455(7215):919-23. doi: 10.1038/nature07458.

Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.

De Bruin et al., UBS Investment Research. Q-Series?: DNa Sequencing. UBS Securities LLC. Jul. 12, 2007. 15 pages.

Demirci, et al. "Single cell epitaxy by acoustic picolitre droplets" Lab Chip. Sep. 2007;7(9):1139-45. Epub Jul. 10, 2007.

Doerr, "The smallest bioreactor", Nature Methods, 2:5 326 (2005).

Dowding, et al. "Oil core/polymer shell microcapsules by internal phase separation from emulsion droplets. II: controlling the release profile of active molecules" Langmuir. Jun. 7, 2005;21(12):5278-84.

Draper, M.C. et al., "Compartmentalization of electrophoretically separated analytes in a multiphase microfluidic platform" Anal. Chem. (2012) 84:5801-5808.

Dressler, O.J. et al., "Droplet-based microfluidics enabling impact on drug discovery" J. Biomol. Screen (2014) 19 (4):483-496.

Drmanac et al., Sequencing by hybridization (SBH): advantages, achievements, and opportunities. Adv Biochem Eng Biotechnol. 2002;77 :75-101.

Eastburn, D.J. et al., "Ultrahigh-throughput mammalian single-cell reverse-transcriptase polymerase chain reaction in microfluidic droplets" Anal. Chem. (2013) 85:8016-8021.

Eid et al. "Real-time sequencing form single polymerase molecules," Science (2009) 323:133-138.

Ekblom, R. et al. "A field guide to whole-genome sequencing, assembly and annotation" Evolutionary Apps (Jun. 24, 2014) 7(9):1026-1042.

Esser-Kahn, et al. Triggered release from polymer capsules. Macromolecules. 2011; 44:5539-5553.

Beattie et al., "Advances in Genosensor Research", (1995) Clin. Chem. 45, 700-706.

Beier et al., "Versatile derivatisation of solid support media for covalent bonding on DNA- microchips", (1999) Nucleic Acids Research 27, 1970-1977.

Canzar and Stazberg, 2018, "Short Read Mapping: An Algorithmic Tour," Proc IEEE Inst. Electr Electron Eng., 105(3), 436-458.

(56) References Cited

OTHER PUBLICATIONS

Carter et al., "Stabilization of an optical microscope to 0.1 nm in three dimensions", Applied Optics 46:421-427, 2007. $35.
Chen et al., "Nanoscale imaging of RNA with expansion microscopy", Nat. Methods 13:679-684, 2016.
Chrisey et al., "Covalent attachment of synthetic DNA to self-assembled monolayer films", (1996) Nucleic Acid Research 24, 3031-3039.
Cockroft et al., "A Single-Molecule Nanopore Device Detects DNA Polymerase Activity With Single-Nucleotide Resolution", J. Am. Chem. Soc. 130, 818-820 (2008).
Deamer et al., "Nanopores and nucleic acids: prospects for ultrarapid sequencing", Trends Biotechnol. 18, 147-151 (2000) $35.95.
Deamer et al., "Characterization of nucleic acids by nanopore analysis", Acc. Chem. Res. 35:817-825 (2002) $40.
Eagen, "Principles of Chromosome Architecture Revealed by Hi-C", Trends Biochem. Sci. (2018) 43(6): 469-478.
Fahy et al. "Design and synthesis of polyacrylamide-based oligonucleotide supports for use in nucleic acid diagnostics", (1993) Nucleic Acid Research 21, 1819-1826.
Gunderson et al., "Decoding randomly ordered DNA arrays", Genome Research 14:870- 877 (2004).
Guo et al. "Direct fluorescence analysis of genetic polymorphisms by hybridization with oligonucleotide arrays on glass supports", (1994) Nucleic Acid Research 22, 5456-5465.
Gupta et al., "Single-cell isoform RNA sequencing characterizes isoforms in thousands of cerebellar cells", Nature Biotechnol. 36:1197-1202, 2018.
Huang and Miller, "A Time-Efficient, Linear-Space Local Similarity Algorithm", Adv. Appl. Math, 12:337-57 (1991).
Jamur et al., "Permeabilization of cell membranes", Method Mol. Biol. 588:63-66, 2010.
Joos et al., "Covalent attachment of hybridizable oligonucleotides to glass supports", (1997) Analitical Biochemistry 247, 96-101. $35.95.
Koch et al., "Photochemical immobilization of anthraquinone conjugated oligonucleotides and PCR amplicons on solid surfaces", (2000) Bioconjugate Chem. 11, 474-483. $40.
Korlach et al., "Selective aluminum passivation for targeted immobilization of single DNA polymerase molecules in zero-mode waveguide nanostructures", Proc. Natl. Acad. Sci. USA (2008), 105, 1176-1181.
Lamture et al., "Direct detection of nucleic acid hybridization on the surface of a charge coupled device", (1994) Nucleic Acids Research 22, 2121-2125.
Lee et al., "Highly multiplexed subcellular RNA sequencing in situ" (2014) Science, 343(6177), 1360-1363.
Lee et al., "Fluorescent in situ sequencing (FISSEQ) of RNA for gene expression profiling in intact cells and tissues", Nat. Protoc. 10(3):442-458, 2015.
Levene et al., "Zero-mode waveguides for single-molecule analysis at high concentrations", Science (2003), 299, 682-686.
Li et al., "DNA molecules and configurations in a solid-state nanopore microscope", Nat. Mater. 2:611-615 (2003).
Liu et al., "Surface and interface control on photochemically initiated immobilization", (2006) Journal of the American Chemical Society 128, 14067-14072.
Lundquist et al., "Parallel confocal detection of single molecules in real time", Opt. Lett. (2008), vol. 33, No. 9, 1026-1028.
Ma B. et al., "PathHunter: faster and more sensitive homology search", Bioinformatics, Mar. 2002, vol. 18, Issue 3, pp. 440-445.
Macosko et al., "Highly Parallel Genome-wide Expression Profiling of Individual Cells Using Nanoliter Droplets", (2015) Cell 161, 1202-1214.
Miele et al., "Mapping cis- and trans-chromatin interaction networks using Chromosome Conformation Capture (3C)", Methods Mol Biol. (2009), 464.
Miller et al., "Basic concepts of microarrays and potential applications in clinical microbiology." Clinical microbiology reviews 22.4 (2009): 611-633.
Mitra et al., "Fluorescent in situ sequencing on polymerase colonies", (2003) Anal. Biochem., 320, 55-65.
Moffitt, "RNA Imaging with Multiplexed Error-Robust Fluorescence In Situ Hybridization (MERFISH)", (2016) Methods in Enzymology, 572, 1-49.
Nikforov et al., "The use of 96-well polystyrene plates for DNA hybridization-based assays: an evaluation of different approaches to oligonucleotide immobilization", (1995) Analytical Biochemistry 227, 201-209.
Raab et al., "Human tRNA genes function as chromatin insulators", EMBO. J. (2012), 31(2): 330-350.
Rao, N. "Discover the genes that matter while preserving spatial information: The Visium Gene Expression Solution", Webinar presented at Cell Biology 2019 Sep. 26, 2019 (Sep. 26, 2019), p. 1 pp. , Retrieved from the Internet: URL:https://www.labroots.com/webinar/discover-genes-matter-preserving-spatial-information-visium-gene-expression-solution XP054981474.
Rodrigues et al., "Slide-seq: A scalable technology for measuring genome-wide expression at high spatial resolution", Science 363(6434):1463-1467, 2019.
Rogers et al., "Use of a novel cross-linking method to modify adenovirus tropism", (1997) Gene Therapy 4, 1387-1392.
Rogers et al., "Immobilization of Oligonucleotides onto a Glass Support via Disulfide Bonds: A Method for Preparation of DNA Microarrays", (1999) Analytical Biochemistry 266, 23-30.
Ronaghi et al., "A sequencing method based on real-time pyrophosphate", Science 281 (5375), 363 (1998).
Ronaghi, "Pyrosequencing sheds light on DNA sequencing", Genome Res. 11(1), 3-11 (2001).
Ronaghi et al., "Real-time DNA sequencing using detection of pyrophosphate release", Anal. Biochem. 242(1), 84-9 (1996).
Running and Urdea, "A procedure for productive coupling of synthetic oligonucleotides to polystyrene microtiter wells for hybridization capture", (1990) BioTechnique 8, 276-279.
Shalon et al., "A DNA microarray system for analyzing complex DNA samples using two-color fluorescent probe hybridization", (1996) Genome Research, 639-645.
Shendure et al., "Accurate Multiplex Polony Sequencing of an Evolved Bacterial Genome", Science (2005), 309: 1728-1732.
Simonis et al., "Nuclear organization of active and inactive chromatin domains uncovered by chromosome conformation capture-on-chip (4C)", Nat. Genet. (2006), 38(11): 1348-1354.
Smith and Waterman, "Identification of Common Molecular Subsequences", J Mol. Biol., 147(1):195-97 (1981).
Söderberg et al., "Characterizing proteins and their interactions in cells and tissues using the in situ proximity ligation assay", Methods. (2008), 45(3): 227-32.
Soni et al., "Progress toward Ultrafast DNA Sequencing Using Solid-State Nanopores", Clin. Chem. 53, 1996-2001 (2007).
Stimpson et al., "Real-time detection of DNA hybridization and melting on oligonucleotide arrays by using optical wave guides", (1995) Proc. Natl. Acad. Sci. USA 92, 6379-6383.
Timofeev et al., "Regioselective immobilization of short oligonucleotides to acrylic copolymer gels", (1996) Nucleic Acids Research 24, 3142-3148.
Uchida, 2013, "Image processing and recognition for biological images," Develop. Growth Differ. 55, 523-549, doi:10.1111/dgd.12054.
Wang et al., "Three-dimensional intact-tissue sequencing of single-cell transcriptional states", (2018) Science, 361(6499) 5691.
Zhang et al., "Single-base mutational analysis of cancer and genetic diseases using membrane bound modified oligonucleotides", (1991) Nucleic Acids Research, 19, 3929-3933.
Jarosz, M. et al. "Using 1ng of DNA to detect haplotype phasing and gene fusions from whole exome sequencing of cancer cell lines" Cancer Res (2015) 75(suppl5):4742.
Extended European Search Report for EP Application No. 16737834.8, dated Jul. 27, 2018, 10 pages.
U.S. Appl. No. 15/019,928, filed Feb. 9, 2016, 10X Genomics, Inc.
International Search Report for International Patent Application No. PCT/US2016/013290, mailed May 19, 2016, 11 pages.
International Search Report for International Patent Application No. PCT/US2016/017196, mailed May 29, 2016, 14 pages.

(56) References Cited

OTHER PUBLICATIONS

Bansal et al., "HapCUT: an efficient and accurate algorithm for the haplotype assembly problem," Bioinformatics, vol. 24, 2008, pp. 153-1159.
Bansal et al., 2008, "An MCMC algorithm for haplotype assembly from whole-genome sequence data," Genome Res, 18:1336-1346.
Bentley et al., 2008, Accurate whole human genome sequencing using reversible terminator chemistry, Nature 456:53-59.
Browning et al., "Haplotype phasing: Existing methods and new developments," Nat Rev Genet., 12(10), Apr. 1, 2012, pp. 703-714.
Chen et al., 2009, "BreakDancer: an algorithm for high-resolution mapping of genomic structural variation," Nature Methods 6(9), pp. 677-681.
Choi et al., 2008, "Identification of novel isoforms of the EML4-ALK transforming gene in non-small cell lung cancer," Cancer Res, 68:4971-4976.
Cleary et al., 2014, "Joint variant and de novo mutation identification on pedigrees from high-throughput sequencing data," J Comput Biol, 21:405-419.
Eid et al., "Real-time sequencing form single polymerase molecules," Science 323:133-138.
Gordon et al., 1998, "Consed: A Graphical Tool for Sequence Finishing," Genome Research 8:198-202.
Heng and Durbin, 2010, "Fast and accurate long-read alignment with Burrows-Wheeler transform," Bioinformatics, 25(14): 1754-1760.
Huang and Marth, 2008, "EagleView: A genome assembly viewer for next-generation sequencing technologies," Genome Research 18:1538-1543.
Kanehisa and Goto, 2000, "KEGG: Kyoto Encyclopedia of Genes and Genomes," Nucleic Acids Research 28, 27-30.
Kirkness et al., 2013, "Sequencing of isolated sperm cells for direct haplotyping of a human genome," Genome Res, 23:826-832.
Kitzman et al., 2011, "Haplotype-resolved genome sequencing of a Gujarati Indian individual." Nat Biotechnol, 29:59-63.
Lippert et al., 2002, "Algorithmic strategies for the single nucleotide polymorphism haplotype assembly problem," Brief. Bionform 3:23-31.
Margulies et al., 2005, "Genome sequencing in microfabricated high-density picoliter reactors," Nature 437:376-380.
Myllykangas et al., 2011, "Efficient targeted resequencing of human germline and cancer genomes by oligonucleotide-selective sequencing," Nat Biotechnol, 29:1024-1027.
Pushkarev et al., 2009, "Single-molecule sequencing of an individual human genome," Nature Biotech 17:847-850.
Shendure et al., 2005, "Accurate Multiplex Polony Sequencing of an Evolved bacterial Genome" Science 309:1728-1732.
Tewhey et al., 2011, "The importance of phase information for human genomics," Nat Rev Genet, 12:215-223.
Wheeler et al., 2007, "Database resources of the National Center for Biotechnology Information, " Nucleic Acids Res. 35 (Database issue): D5-12.
Zerbino et al., "Velvet: Algorithms for de novo short read assembly using de Bruijn graphs," Genome Research 18, 2008, pp. 821-829.
Chen, F et al., "Chemical transfection of cells in picoliter aqueous droplets in fluorocarbon oil" Anal. Chem. (2011) 83:8816-8820.
U.S. Appl. No. 14/995,090, filed Jan. 13, 2016, now U.S. Pat. No. 10,650,912.
U.S. Appl. No. 16/854,754, filed Apr. 21, 2020.
U.S. Appl. No. 14/752,773, filed Jun. 26, 2015, now U.S. Pat. No. 10,839,939.
U.S. Appl. No. 15/801,868, filed Nov. 2, 2017, now U.S. Pat. No. 11,133,084.
U.S. Appl. No. 17/411,889, filed Aug. 25, 2021.
U.S. Appl. No. 15/891,607, filed Feb. 8, 2018, now U.S. Pat. No. 10,347,365.
U.S. Appl. No. 16/442,800, filed Jun. 17, 2019.
U.S. Appl. No. 15/984,324, filed May 19, 2018.
U.S. Appl. No. 17/039,935, filed Sep. 30, 2020, now U.S. Pat. No. 11,514,575.
10X Genomics Announces the Addition of Unbiased Gene Expression and B-cell Repertoire to the Chromium Single Cell V(D)J Solution, Oct. 18, 2018, https://www.businesswire.com/news/home/20171018005362/en/10x-Genomics-Announces-the-Addition-of-Unbiased-Gene-Expression-and-B-cell-Repertoire-to-the-Chromium-Single-Cell-V-D-J-Solution.
10X Genomics, 2019, "Chromium Next GEM Single Cell 3' Reagent Kits v3.1 User Guide", Document No. CG0000205 Rev D.
10X Genomics, 2017, "Chromium Single Cell 3' Reagent Kits v2 User Guide," Document No. CG00052 Rev B.
10X Genomics, 2018, "Chromium Single Cell V(D)J Reagents Kits User Guide," Document No. CG00086 Rev J.
10X Genomics, 2019. "Visium Spatial Gene Expression Solution." LITQQQ054 RevC Visium Spatial Gene Expression Product Flyer.
10X Genomics, "What is the difference between Single Cell 3' and 5' Gene Expression libraries?", downloaded from the Internet on Jan. 21, 2021.
"Bedtools: General Usage," http://bedtools.readthedocs.io/en/latest/content/general-usage.html ; Retrieved from the Internet Jul. 8, 2016.
Aken et al., 2015, "The Ensemble gene annotation system Database," baw093 doi 10.1093/database/baw093.
Bray, "The JavaScript Object Notation (JSON) Data Interchange Format," Mar. 2014, retrieved from the Internet Feb. 15, 2015; https://tools.ietf.org/html/rfc7159.
Chen et al., "RNA imaging. Spatially resolved, highly multiplexed RNA profiling in single cells," Science 348(6233), 2015.
Droplet Based Sequencing (slides) dated (Mar. 12, 2008).
Gao et al., "Q&A Expansion microscopy," BMC Biol 15:50, 2017.
Gartner, et al. The Microfluidic Toolbox: examples for fluidic interfaces and standardization concepts. Proc. SPIE 4982, Microfluidics, BioMEMS, and Medical Microsystems, (Jan. 17, 2003); doi: 10.1117-12.479566.
Illumina, "Multiplexed Sequencing with the Illumina Genome Analyzer System", Illumina Sequencing, 2008.
Illumina, Inc. An Introduction to Next-Generation Sequencing Technology. Feb. 28, 2012.
Kitzman, et al. Noninvasive whole-genome sequencing of a human fetus. Sci Transl Med. Jun. 6, 2012;4(137):137ra76.
Layer et al., 2014, "LUMPY: A probabilistic framework for structural variant discovery," Genome Biology 15(6):R84.
Lo, et al. "On the design of clone-based haplotyping", Genome Biol. 2013;14(9):R100.
Marcus, "Gene method offers diagnostic hope", The Wall Street Journal. Jul. 11, 2012.
Margulies, et al., "Genome Sequencing in Microfabricated High-Density Picolitre Reactors", Nature, v. 435, No. 15 (Year: 2005).
McCoy, R. et al. "Illumina TruSeq Synthetic Long-Reads Empower De Novo Assembly and Resolve Complex, Highly-Repetitive Transposable Elements" PLOS (2014) 9(9).
Microfluidic Chipshop. Microfluidic product catalogue. Mar. 2005.
Microfluidic Chipshop. Microfluidic product catalogue. Oct. 2009.
Rao, N. et al., "Envision New Dimensions Introducing the Visium Spatial Gene Expression Solution", Sep. 19, 2019 (Sep. 19, 2019).
Rotem, A. et al. "Single Cell Chip-Seq Using Drop-Based Microfluidics" Abstract #50. Frontiers of Single Cell Analysis, Stanford University Sep. 5-7, 2013.
Shlien, et al., "Copy number variations and cancer", Genome Med. Jun. 16, 2009;1(6):62. doi: 10.1186-gm62.
Simeonov et al., "Single nucleotide polymorphism genotyping using short, fluorescently labeled locked nucleic acid (LNa) probes and fluorescence polarization detection", Nucleic Acids Res. Sep. 1, 2002;30(17):e91.
The SAM/BAM Format Specification Working Group, "Sequence Alignment/ Map Format Specification," Dec. 28, 2014.
Trackets Blog, "SSH Tunnel-Local and Remote Port Forwarding Explained With Examples,", http://blog.trackets.com/2014/05/17/ssh-tunnel-local-and-remote-port-forwarding-explained-with-examples.html ; Retrieved from the Internet Jul. 7, 2016.
Voskoboynik, A. et al., "The genome sequence of the colonial chordate, Botryllus schlosseri." eLife Jul. 2, 2013, 2: e00569.

(56) References Cited

OTHER PUBLICATIONS

Wagner, O et al., "Biocompatible fluorinated polyglycerols for droplet microfluidics as an alternative to PEG-based copolymer surfactants" Lab Chip DOI:10.1039-C5LC00823A. 2015.

Wang, C., "Integrative Analysis of Multi-Modality Data in Cancer", Jan. 1, 2015 (Jan. 1, 2015), Dissertation, The Ohio State University, Graduate Program n Electrical and Computer Engineering.

Yamamoto, et al. "Chemical modification of Ce(IV)-EDTA-base artificial restriction DNa cutter for versatile manipulation of double-stranded DNA", Nucleic Acids Research. 2007; 35(7):e53.

Zheng, X., "SeqArray: an R/Bioconductor Package for Big Data Management of Genome-Wide Sequencing Variants", Department of Biostatistics, University of Washington-Seattle, Dec. 28, 2014.

Zheng, et al., "Massively parallel digital transcriptional profiling of single cells," Nature Communications, DOI: 101038/ncomms140949, (2017).

Triola, Elementary Statistics with multimedia guide, Tenth Edition, p. 520, 2007, Pearson / Addison Wesley New York.

Xia, "Soft lithography", Annual Review of Material Science, 28: 153-184 (1998).

Fredrickson, C.K. et al., "Macro-to-micro interfaces for microfluidic devices" Lab Chip (2004) 4:526-533.

Guo, M.T. et al., "Droplet microfluidics for high-throughput biological assyas" Lab Chip (2102) 12:2146-2155.

\* cited by examiner

| | |
|---|---|
| Discrete attribute value dataset | 120-1 |
|   Feature-barcode matrix | 121-1 |
|     Cell 1 | 126-1 |
|       Gene 1 for cell 1 | 122-1-1 |
|         (GEX) Discrete attribute value for gene 1 | 124-1-1 |
|       Gene 2 for Cell 1 | 122-2-1 |
|         (GEX) Discrete attribute value for gene 2 | 124-2-1 |
|       ⋮ | |
|       Gene M for Cell 1 | 122-M-1 |
|         (GEX) Discrete attribute value for Cell M | 125-M-1 |
|       ATAC Peak 1 for cell 1 | 123-1-1 |
|         ATAC Fragment count for peak 1 | 125-1-1 |
|       ATAC Peak 2 for Cell 1 | 123-2-1 |
|         ATAC Fragment count for peak 2 | 125-2-1 |
|       ⋮ | |
|       ATAC Peak L for Cell 1 | 123-L-1 |
|         ATAC Fragment count for peak L | 125-L-1 |
|       GEX Principal component value 1 for cell 1 | 164-1-1 |
|       ⋮ | |
|       GEX Principal component value N for cell 1 | 164-1-N |
|       GEX Two-dimensional datapoint for cell 1 | 166-1 |
|       GEX Cluster assignment for cell 1 | 158-1 |
|       GEX Category assignment 1 for cell 1 | 170-1-1 |
|         Class 1 for GEX category 1 | 172-1-1-1 |
|         ⋮ | |
|         Class M for GEX category 1 | 172-1-1-M |
|       ⋮ | |
|       GEX Category assignment Q for cell 1 | 170-1-Q |
|         Class 1 for GEX category Q | 172-1-Q-1 |
|         ⋮ | |
|         Class Z for GEX category Q | 172-1-Q-Z |
|     Continued on Figure 1C... | |

Figure 1B

| | |
|---|---|
| Discrete attribute value dataset 1 - continued | 120-1 (continued) |
|   Feature-barcode matrix - continued | 121-1 (continued) |
|     Cell 1 | 126-1 (continued) |
|       ATAC Principal component value 1 | 165-1-1 |
|       ⋮ | |
|       ATAC Principal component value P | 165-1-P |
|       ATAC Two-dimensional datapoint for cell 1 | 167-1 |
|       ATAC Cluster assignment for cell 1 | 159-1 |
|       ATAC Category assignment 1 for cell 1 | 171-1-1 |
|         Class 1 for ATAC category 1 | 173-1-1-1 |
|         ⋮ | |
|         Class M for ATAC category 1 | 173-1-1-M |
|       ⋮ | |
|       ATAC Category assignment P for cell 1 | 171-1-P |
|         Class 1 for ATAC category P | 173-1-P-1 |
|         ⋮ | |
|         Class W for ATAC category P | 173-1-P-W |
|     ⋮ | |
|     Cell Y | 126-Y |
|     Gene 1 | 193-1-1 |
|       Nearby gene inferred ATAC count (for each cell) | 194-1-1 |
|       Promoter sum inferred count (for each cell) | 195-1-1 |
|     ⋮ | |
|     Gene M | 193-1-M |
|       Nearby gene inferred ATAC count (for each cell) | 194-1-M |
|       Promoter sum inferred count (for each cell) | 195-1-M |
|   GEX t-SNE projection | 196 |
|   GEX UMAP projection | 197 |
|   ATAC t-SNE projection | 198 |
|   ATAC UMAP projection | 199 |

Figure 1C

| | |
|---|---|
| Discrete attribute value dataset 1 - continued | 120-1 (continued) |
|   Array of chromosome indices | 180-1 |
|     Chromosome index 1 | 182-1-1 |
|     ⋮ | |
|     Chromosome index L+M | 182-1-L+M |
|   Array of starting positions | 183-1 |
|     Starting position 1 | 184-1-1 |
|     ⋮ | |
|     Starting position L+M | 184-1-L+M |
|   Array of ending positions | 185-1 |
|     Ending position 1 | 186-1-1 |
|     ⋮ | |
|     Ending position L+M | 186-1-L+M |
|   Feature-linkage matrix | 187-1 |
|     Pointer array (P) | 188-1 |
|       Index 1 | 189-1-1 |
|       ⋮ | |
|       Index L | 189-1-L |
|     Index array (X) | 190-1 |
|       ATAC peak identity 1 | 190-1-1 |
|       ⋮ | |
|       ATAC peak identity K | 190-1-K |
|     Correlation array (C) | 191-1 |
|       Correlation 1 | 191-1-1 |
|       ⋮ | |
|       Correlation K | 191-1-K |
|     Significance array (S) | 192-1 |
|       Significance 1 | 192-1-1 |
|       ⋮ | |
|       Significance K | 192-1-K |
| ⋮ | |

Figure 1D

202 — A visualization system 100 comprising one or more processing cores, a persistent memory and a non-persistent memory, the persistent memory and the non-persistent memory collectively storing instructions for performing the following method.

204 — Store the dataset 120 in persistent memory. The dataset 120 comprises a corresponding GEX discrete attribute value 124 for each gene 122 in a plurality of genes for each respective cell 126 in a plurality of cells. The dataset 120 further comprises a corresponding ATAC fragment count 125 for each ATAC peak 123 in a plurality of ATAC peaks for each respective cell 126 in the plurality of cells. In some embodiments, the dataset 120 redundantly represents the corresponding discrete attribute value 124 for each gene in the plurality of genes for each respective cell in the plurality of cells in both a compressed sparse row format and a compressed sparse column format in which genes for a respective cell that have a null discrete attribute data value are discarded. In some embodiments the dataset 120 is compressed in accordance with a blocked compression algorithm.

205 — Each gene 122 in the plurality of genes is a respective gene in a plurality of genes. Each discrete attribute value 124 is a count of transcript reads within the cell that map to a respective gene in the plurality of genes. Each cell 126 is a single cell. The GEX data represents a whole transcriptome shotgun sequencing experiment that quantifies gene expression from a single cell in counts of transcript reads mapped to the genes.

206 — Cluster the dataset using the discrete attribute values for each gene in the plurality of genes for each respective cell in the plurality of cells thereby assigning each respective cell in the plurality of cells to a corresponding cluster in a first plurality of clusters. Each respective cluster in the first plurality of clusters consists of a unique different subset of the plurality of cells. The clustering loads less than the entirety of the dataset into the non-persistent memory at any given time during the clustering. Separately cluster the dataset using the ATAC fragment counts for each ATAC peak 123 in the plurality of ATAC peaks for each respective cell in the plurality of cells thereby assigning each respective cell in the plurality of cells to a corresponding cluster in a second plurality of clusters. Each respective cluster in the second plurality of clusters consists of a unique different subset of the plurality of cells.

208 — The clustering is performed on a computer system remote from the visualization system prior to storing the dataset in persistent memory.

210 — The clustering the dataset comprises hierarchical clustering, agglomerative clustering using a nearest-neighbor algorithm, agglomerative clustering using a farthest-neighbor algorithm, agglomerative clustering using an average linkage algorithm, agglomerative clustering using a centroid algorithm, or agglomerative clustering using a sum-of-squares algorithm.

212 — The clustering the dataset comprises k-means clustering, a fuzzy k-means clustering algorithm, or Jarvis-Patrick clustering.

Figure 2A (B)

230 — Display in a first panel a heat map that comprises a representation of the differential value for each respective gene in the plurality of genes for each cluster 158 in the first plurality of clusters.

232 — Derive a plurality of GEX principal component values 164 for each cell 126 in the plurality of cells based upon respective discrete attribute values 124 of each gene 122 for each cell 126 in the plurality of cells. Apply a dimension reduction technique to the plurality of GEX principal component values 164 for each cell 126 in the plurality of cells thereby determining a two-dimensional data point 166 for each cell 126 in the plurality of cells. Plot each respective cell 126 in the plurality of cells 126 in a second panel 420 (Figure 4A) based upon the two-dimensional data point 166 for the respective second entity (e.g., as a GEX t-SNE projection 196 or a GEX UMAP projection 197).

Derive a plurality of ATAC principal component values 165 for each cell 126 in the plurality of cells based upon respective ATAC fragment counts 125 of each ATAC peak 123 for each cell 126 in the plurality of cells. Apply a dimension reduction technique to the plurality of ATAC principal component values 165 for each cell 126 in the plurality of cells thereby determining a two-dimensional data point 167 for each cell 126 in the plurality of cells. Plot each respective cell 126 in the plurality of cells 126 in a second panel 420 (Figure 4B) based upon the two-dimensional data point 167 for the respective second entity (e.g., as an ATAC t-SNE projection 198 or an ATAC UMAP projection 199).

234 — Each cluster in the plurality of clusters is assigned a different graphic or color code. Each respective cell in the plurality of cells is coded in the second panel with the different graphic or color code for the cluster the respective cell has been assigned.

236 — The dimension reduction technique is t-distributed stochastic neighbor embedding.

238 — The dimension reduction technique is Sammon mapping, curvilinear components analysis, stochastic neighbor embedding, Isomap, maximum variance unfolding, locally linear embedding, or Laplacian Eigenmaps.

240 — Each said respective plurality of principal component value is derived from the discrete attribute values of each gene or ATAC peaks in a corresponding cell in the plurality of cells by principal component analysis that is performed on a computer system remote from the visualization system 100 prior to storing the dataset 120 in persistent memory, and the dataset includes each said respective plurality of principal component values.

SYSTEMS AND METHODS FOR JOINT INTERACTIVE VISUALIZATION OF GENE EXPRESSION AND DNA CHROMATIN ACCESSIBILITY

CROSS REFERENCE TO RELATED APPLICATIONS

This application claims priority to U.S. Provisional Patent Application No. 63/061,952, entitled "Systems and Methods for Joint Interactive Visualization of Gene Expression and DNA Chromatin Accessibility," filed Aug. 6, 2020, and to U.S. Provisional Patent Application No. 62/976,270, entitled "Methods For Characterizing Cells Using Gene Expression And Chromatin Accessibility," filed Feb. 13, 2020 each of which is hereby incorporated by reference in its entirety.

TECHNICAL FIELD

This specification describes technologies relating to visualizing RNA gene expression and DNA chromatin accessibility from the same cells.

BACKGROUND

The discovery of patterns in a dataset facilitates a number of technical applications such as the discovery of changes in discrete attribute values in genes between different classes (e.g., diseased state, non-diseased state, disease stage, etc.). For instance, in the biological arts, advances in RNA-extraction protocols and associated methodologies has led to the ability to perform whole transcriptome shotgun sequencing that quantifies gene expression in biological samples in counts of transcript reads mapped to genes. This has given rise to high throughput transcript identification and the quantification of gene expression for hundreds or even thousands of individual cells in a single dataset. Thus, in the art, datasets containing discrete attribute values (e.g., count of transcript reads mapped to individual genes in a particular cell) for each gene in a plurality of genes for each respective cell in a plurality of cells have been generated. While this is a significant advancement in the art, a number of technical problems need to be addressed to make such data more useful.

One drawback with such advances in the art the unsatisfactory way in which conventional methods find patterns in such datasets. For instance, such patterns may relate to the discovery of unknown classes among the members of the dataset. For example, the discovery that a dataset of what was thought to be homogenous cells turns out to include cells of two different classes. Such patterns may also relate to the discovery of variables that are statistically associated with known classes. For instance, the discovery that the transcript abundance of a subset of mRNA mapping to a core set of genes discriminates between cells that are in a diseased state versus cells that are not in a diseased state. The discovery of such patterns (e.g., the discovery of genes whose mRNA expression discriminates classes or that define classes) in datasets that are very large, are not amendable to classical statistics because of limited replicate information, and for which such patterns in many instances relate to biological processes that are not well understood remains a technical challenge for which improved tools are needed in the art in order to adequately address such drawbacks.

SUMMARY

Technical solutions (e.g., computing systems, methods, and non-transitory computer readable storage mediums) for addressing the above identified problems with discovery of patterns in datasets are provided in the present disclosure.

The following presents a summary of the present disclosure in order to provide a basic understanding of some of the aspects of the present disclosure. This summary is not an extensive overview of the present disclosure. It is not intended to identify key/critical elements of the present disclosure or to delineate the scope of the present disclosure. Its sole purpose is to present some of the concepts of the present disclosure in a simplified form as a prelude to the more detailed description that is presented later.

One aspect of the present disclosure provides a method for visualizing a pattern in a discrete attribute value dataset. The method is performed at a computer system comprising one or more processing cores and a memory, the memory storing instructions that use the one or more processing cores to perform the method. The method comprises storing the discrete attribute value dataset in the memory. The discrete attribute value dataset comprises a respective discrete attribute value for each corresponding gene in a plurality of genes, for each respective cell in a plurality of cells. The discrete attribute value dataset further comprises a respective ATAC fragment count for each corresponding ATAC peak in a plurality of ATAC peaks, for each respective cell in the plurality of cells.

In some embodiments, the plurality of cells comprises 100 cells, the plurality of genes comprises 100 genes, and the plurality of ATAC peaks comprises 50 ATAC peaks.

Each respective cell in the plurality of cells is assigned to a respective cluster group in a first plurality of cluster groups based on a first clustering of discrete attribute values for the plurality of genes across the plurality of cells. Each respective cell in the plurality of cells is also assigned to a respective cluster group in a second plurality of cluster groups based on a second clustering of ATAC fragment count values for the plurality of ATAC peaks across the plurality of cells.

The method further comprises displaying, in a first panel, a two-dimensional projection of the plurality of cells based on assignment of the plurality of cells to one of (i) the first plurality of cluster groups or (ii) the second plurality of cluster groups.

The method further comprises indicating within the two-dimensional projection, for each respective cell in the plurality of cells, membership in the other of (i) the first plurality of cluster groups or (ii) the second plurality of cluster groups, thereby visualizing the pattern in the discrete attribute value dataset.

In some embodiments membership of each respective cell in the plurality of cells in the other of (i) the first plurality of cluster groups or (ii) the second plurality of cluster groups is indicated by coloring the respective cell a color that is uniquely associated with a cluster group to which the respective cell has been assigned in the other of (i) the first plurality of cluster groups or (ii) the second plurality of cluster groups.

In some embodiments, the method further comprises computing, for each respective gene in the plurality of genes for each respective cluster in the first plurality of clusters or the second plurality of clusters, a difference in the discrete attribute value for the respective gene across the respective subset of cells in the respective cluster relative to the discrete attribute value for the respective gene across the first plurality of clusters or the second plurality of clusters other than the respective cluster, thereby deriving a differential value for each respective gene in the plurality of gene for each respective cluster in the first plurality of clusters or the second plurality of clusters. In such embodiments, there is displayed in a second panel, concurrently with the first panel, a heat map that comprises a representation of the differential value for each respective gene in the plurality of genes for each respective cluster in the first plurality of clusters or the second plurality of clusters thereby visualizing the pattern in the discrete attribute value dataset. In some such embodiments, the differential value for each respective gene in the plurality of genes for each respective cluster in the first plurality of clusters or the second plurality of clusters is a fold change (e.g., a $\log_2$ fold change or a $\log_{10}$ fold change) in (i) a first measure of central tendency of the discrete attribute value for the respective gene measured in each of the cells in the plurality of cells in the respective cluster and (ii) a second measure of central tendency of the discrete attribute value for the respective gene measured in each of the cells of all clusters in the first plurality of clusters or all clusters in the second plurality of clusters, other than the first respective cluster.

In some embodiments, the method further comprises normalizing the discrete attribute value prior for each respective gene in the plurality of genes prior to computing the differential value for each respective gene in the plurality of genes for each respective cluster in the first plurality of clusters or the second plurality of clusters. In some such embodiments, the normalizing comprises modeling the discrete attribute value of each gene associated with each cell in the plurality of cells with a negative binomial distribution having a consensus estimate of dispersion.

In some embodiments, the first clustering of discrete attribute values for the plurality of genes across the plurality of cells is a clustering of a first plurality of dimension reduction values for each respective cell in the plurality of cells, across the plurality of cells, where each respective dimensional reduction value in the first plurality of dimension reduction values for each respective cell in the plurality of cells is derived, using a first dimension reduction algorithm, from the discrete attribute values of each gene in the respective cell. In some such embodiments, the second clustering of ATAC fragment counts for the plurality of ATAC peaks across the plurality of cells is a clustering of a second plurality of dimension reduction values for each respective cell in the plurality of cells, across the plurality of cells, where each respective dimensional reduction value in the second plurality of dimension reduction values for each respective cell in the plurality of cells is derived, using the first dimension reduction algorithm (e.g., principal component analysis), from the ATAC fragment counts of each ATAC peak in the respective cell.

In some embodiments, the two-dimensional projection of the plurality of cells is based on the assignment of the plurality of cells to the first plurality of cluster groups, and the two-dimensional projection of the plurality of cells is obtained from t-distributed stochastic neighbor or UMAP embedding of the first plurality of dimension reduction values for each respective cell in the plurality of cells, across the plurality of cells.

In some embodiments, the two-dimensional projection of the plurality of cells is based on the assignment of the plurality of cells to the second plurality of cluster groups, and the two-dimensional projection of the plurality of cells is obtained from t-distributed stochastic neighbor or UMAP embedding of the second plurality of dimension reduction values for each respective cell in the plurality of cells, across the plurality of cells.

In some embodiments, the first clustering of discrete attribute values for the plurality of genes across the plurality of cells comprises application of a Louvain modularity algorithm, k-means clustering, a fuzzy k-means clustering algorithm, or Jarvis-Patrick clustering, and the second clustering of ATAC fragment count values for the plurality of ATAC peaks across the plurality of cells comprises application of a Louvain modularity algorithm, k-means clustering, a fuzzy k-means clustering algorithm, or Jarvis-Patrick clustering.

In some embodiments, the first clustering of discrete attribute values for the plurality of genes across the plurality of cells comprises k-means clustering into a first predetermined number of clusters, or the second clustering of ATAC fragment count values for the plurality of ATAC peaks across the plurality of cells comprises k-means clustering into a second predetermined number of clusters. In some such embodiments, the first or second predetermined number of clusters is an integer value between 2 and 50. In some such embodiments, the method further comprises obtaining the integer value from a user of the computer system.

In some embodiments, the respective discrete attribute value for each corresponding gene in a plurality of genes, for each respective cell in a plurality of cells represents a whole transcriptome shotgun sequencing experiment that quantifies gene expression from each respective single cell in the plurality of cells in counts of transcript reads mapped to the genes.

In some embodiments, each gene in a particular cell in the plurality of cells is uniquely represented within the discrete attribute value dataset with a first barcode that is unique to the particular cell.

In some embodiments, the discrete attribute value of each gene in a particular cell in the plurality of cells is determined after the particular cell has been separated from all the other cells in the plurality of cells into its own microfluidic partition.

In some embodiments, the plurality of cells comprises 1000 cells, 2000 cells, 5000 cells, 10,000 cells, 25,000 cells, 50,000 cells or 100,000 cells.

In some embodiments, the plurality of genes comprises 150 genes, 200 genes, 300 genes, 400 genes, 1000 genes, 2000 genes, 3000 genes, 4000 genes, or 5000 genes.

In some embodiments, the plurality of ATAC peaks comprises 100 ATAC peaks, 200 ATAC peaks, 500 ATAC peaks, 750 ATAC peaks, 1000 ATAC peaks, or 5000 ATAC peaks.

In some embodiments, the discrete attribute value dataset has a file size of at least 250 megabytes, 500 megabytes, one gigabyte, two gigabytes, or three gigabytes.

In some embodiments, the discrete attribute value dataset further comprises a feature-linkage matrix. The feature-linkage matrix stores, for each respective gene in the plurality of genes and, for each respective ATAC peak in the plurality of ATAC peaks, a collection of ATAC peaks and genes that are within a threshold distance of the respective gene or respective ATAC peak in a reference genome, and for each respective ATAC peak or respective gene in the collection: a correlation in an ATAC fragment count of the respective ATAC peak or a correlation in the discrete attribute value of the respective gene to the first ATAC peak or first gene across the plurality of cells. In such embodiments, the method further comprises receiving a selection of a first gene in the plurality of genes or a first ATAC peak in the plurality of ATAC peaks. In response to this selection, the feature-linkage matrix is used to obtain and provide a first plot comprising a graphical indicator for each gene in the plurality of genes or each peak in the plurality of peaks linked to the first gene or the first ATAC peak, by order of distance apart from the first gene or the first ATAC peak in the reference genome.

In some embodiments, the respective graphical indicator for each respective gene in the plurality of genes or each respective peak in the plurality of peaks linked to the first gene or the first ATAC peak is provided for each respective cluster group in the first plurality of cluster groups or each cluster group in the second plurality of cluster groups. The respective graphical indicator is dimensioned within the first plot to represent a proportion of cells in the respective cluster group that have a non-zero value for the discrete attribute value of the respective gene or a non-zero value for the ATAC fragment count of the respective ATAC peak.

In some embodiments, the feature-linkage matrix further stores, for each respective ATAC peak or respective gene in the collection: a significance in an ATAC fragment count of the respective ATAC peak or a significance in the discrete attribute value of the respective gene to the first ATAC peak or first gene across cells in the plurality of cells. In some such embodiments, method further comprises: limiting the first plot, to each gene in the plurality of genes or each peak in the plurality of peaks that have a threshold correlation or significance in an ATAC fragment count of the respective ATAC peak or discrete attribute value of the respective gene to the first ATAC fragment or first gene.

In some embodiments, the first plot is limited to each gene in the plurality of genes or each peak in the plurality of peaks that is within a threshold distance (e.g., 1 megabase, 2 megabases, or a value between 0.5 megabases and 10 megabases) of the first gene or first ATAC peak in a reference genome.

Another aspect of the present disclosure provides a method for characterizing cells, comprising partitioning a plurality of cells or cell nuclei and a plurality of barcode beads into a plurality of partitions, where at least a subset of the plurality of partitions each comprise a cell or cell nucleus of the plurality of cells or cell nuclei and a barcode bead of said plurality of barcode beads, and each bead in the subset of said plurality of partitions comprises a unique barcode sequence. The method further includes generating a plurality of barcoded nucleic acid molecules comprising barcode sequences, where a first subset of the plurality of barcoded nucleic acid molecules comprises a sequence corresponding to a ribonucleic acid (RNA) molecule and a second subset of said plurality of barcoded nucleic acid molecules comprises a sequence corresponding to a sequence corresponding to a region of accessible chromatin. The method further comprises sequencing the plurality of barcoded nucleic acid molecules, or derivatives generated therefrom, to generate sequencing information, and using the barcode sequence and the sequencing information to identify cell types in the sequencing information.

In some embodiments, the methods disclosed herein further comprise using said sequencing information to cluster cells by regions of accessible chromatin. In some embodiments, the methods further comprise using the sequencing information to cluster cells by gene expression. In some embodiments, the methods further comprise using the sequencing information and the cells clustered by gene expression to annotate, identify, or characterize cells clustered by regions of accessible chromatin. In some embodiments, the methods further comprise using the sequencing information and the cells clustered by regions of accessible chromatin to annotate, identify, or characterize cells clustered by gene expression. In some embodiments, the plurality of cells or cell nuclei are derived from a tumor sample or a sample suspected of comprising a tumor. In some embodiments, the methods further comprise using the sequencing information to identify a cell type, a cell state, a tumor-specific gene expression pattern, or a tumor-specific differentially accessible regions of chromatin in the tumor sample or the sample suspected of comprising said tumor. In some embodiments, the methods further comprise using the sequencing information to identify or confirm the presence of a tumor cell in the tumor sample or the sample suspected of comprising said tumor. In some embodiments, the methods further comprise administering a therapeutically effective amount of an agent targeting one or more targets identified in the tumor-specific gene expression pattern or the tumor-specific differentially accessible regions of chromatin. In some embodiments, the tumor is a B cell lymphoma.

Another aspect of the present disclosure provides a computer system comprising one or more processing cores and a memory, the memory storing instructions that use the one or more processing cores to perform any of the methods disclosed herein.

Another aspect of the present disclosure provides a non-transitory computer readable storage medium. The non-transitory computer readable storage medium stores instructions, which when executed by a computer system, cause the computer system to perform any of the methods disclosed herein.

As disclosed herein, any embodiment disclosed herein when applicable can be applied to any aspect.

Various embodiments of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The implementations disclosed herein are illustrated by way of example, and not by way of limitation, in the figures of the accompanying drawings. Like reference numerals refer to corresponding parts throughout the several views of the drawings.

FIGS. 1A, 1B, 1C and 1D are an example block diagram illustrating a computing device in accordance with some embodiments of the present disclosure.

FIGS. 2A, 2B and 2C collectively illustrate an example method in accordance with an embodiment of the present disclosure, in which optional steps are indicated by broken lines.

FIG. 3 illustrates a user interface for obtaining a dataset in accordance with some embodiments.

In FIG. 28A, populations of cells identified using open chromatin analysis alone would show as large clusters of cells (e.g., B cells (2508)). Such populations can be annotated using gene expression markers, such as those indicated in FIG. 28B. FIG. 28C illustrates the application of gene expression annotation in order to further stratify sub-populations of cells clustered by open chromatin (e.g., naïve/memory B cells (2722), IgM+IgD+ memory B cells (2724), and plasma B cells (2726)).

DETAILED DESCRIPTION

Figure 1A:
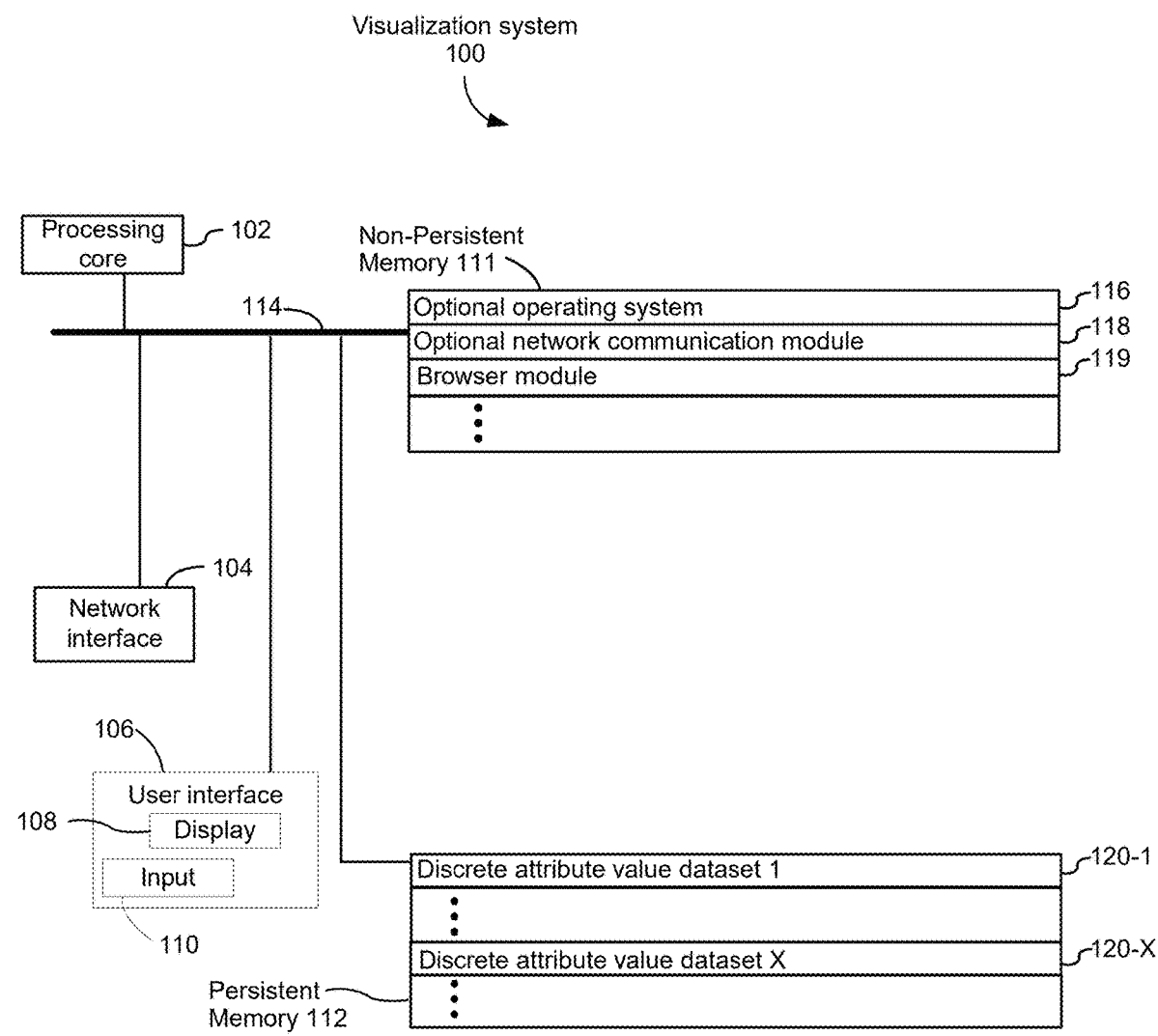

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions to detect a pattern in datasets. An example of such datasets are datasets arising from whole transcriptome shotgun sequencing pipelines that quantify gene expression in single cells in counts of transcript reads mapped to genes. Details of implementations are now described in conjunction with the Figures.

General Terminology

Specific terminology is used throughout this disclosure to explain various aspects of the apparatus, systems, methods, and compositions that are described. This sub-section includes explanations of certain terms that appear in later sections of the disclosure. To the extent that the descriptions in this section are in apparent conflict with usage in other sections of this disclosure, the definitions in this section will control.

(i) Subject

A "subject" is an animal, such as a mammal (e.g., human or a non-human simian), or avian (e.g., bird), or other organism, such as a plant. Examples of subjects include, but are not limited to, a mammal such as a rodent, mouse, rat, rabbit, guinea pig, ungulate, horse, sheep, pig, goat, cow, cat, dog, primate (e.g. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharomyces cerevisiae* or *Schizosaccharomyces pombe*; or a *Plasmodium falciparum*.

(ii) Nucleic acid and Nucleotide.

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g., found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

(iii) Barcode.

A "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. More details on barcodes and UMIs is disclosed in U.S. Provisional Patent Application No. 62/980,073, entitled "Pipeline for Analysis of Analytes," filed Feb. 21, 2020, which is hereby incorporated by reference.

(iv) Biological Samples.

As used herein, a "biological sample" is obtained from the subject for analysis using any of a variety of techniques including, but not limited to, biopsy, surgery, and laser capture microscopy (LCM), and generally includes tissues or organs and/or other biological material from the subject. Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells.

System.

FIG. 1A is a block diagram illustrating a visualization system 100 in accordance with some embodiments. The device 100 in some embodiments includes one or more processing units CPU(s) 102 (also referred to as processors), one or more network interfaces 104, a user interface 106 comprising a display 108 and an input module 110, a non-persistent 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium.

In some implementations, the non-persistent memory 111 or alternatively the non-transitory computer readable storage medium stores the following programs, modules and data structures, or a subset thereof, sometimes in conjunction with the persistent memory 112:

an optional operating system 116, which includes procedures for handling various basic system services and for performing hardware dependent tasks;

an optional network communication module (or instructions) 118 for connecting the visualization system 100 with other devices, or a communication network; and a browser module 119 for selecting a discrete attribute value dataset 120 from persistent memory and presenting information about the discrete attribute value dataset 120.

In some implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

Referring to FIGS. 1A, 1B, 1C, and 1D, persistent memory 112 stores one or more discrete attribute value datasets 120 (e.g., 120-1, . . . , 120-X). In some embodiments, a discrete attribute value dataset 120 comprises a feature-barcode matrix 121, an array of chromosome indices 180, an array of starting positions 183, an array of ending positions 185, and a feature-linkage matrix 187.

Feature-Barcode Matrix.

The feature-barcode matrix 121 comprises, for each respective cell 126 in a plurality of cells, (i) a discrete attribute value (gene expression value) 124 for each gene 122 in a plurality of genes, and (ii) assay for transposase accessible chromatin (ATAC) peaks values for each peak from a plurality of peaks. Typically, a discrete attribute value 124 for a given gene in a given cell is the amount of mRNA that was measured within the given cell for the given gene. Advantageously, the ATAC peak values and the discrete attribute values originate from the same cells.

As illustrated in FIGS. 1B and 1C, a feature-barcode matrix 121-1 (shown by way of example) includes information related to cell 1 (126-1), cell 2 (126-2) and other cells up to cell Y (126-Y). As shown for cell 1 (126-1), the cell 1 (126-1) includes discrete attribute value 124-1-1 for gene 1 of cell 1 (122-1-1), discrete attribute value for gene 2 of cell 1 (124-2-1), and other discrete attribute values up to discrete attribute value for gene M of cell 1 (124-M-1). In some embodiments, there are discrete attributes values for 10 or more, 100 or more, 1000 or more, or ten thousand or more genes in the feature-barcode matrix 121 for each cell in the plurality of cells represented in the feature-barcode matrix 121.

As shown for cell 1 (126-1), the cell 1 (126-1) further comprises ATAC peak fragment count 125-1-1 for ATAC peak 1 of cell 1 (123-1-1), ATAC peak fragment count 125-2-1 for ATAC peak 2 of cell 1 (123-2-1), and other ATAC peak fragment counts up to ATAC peak fragment count for ATAC peak L of cell 1 (125-L-1). In some embodiments, there are ATAC peak fragment counts for 10 or more, 100 or more, 1000 or more, or ten thousand or more ATAC peaks in the feature-barcode matrix 121 for each cell in the plurality of cells represented in the feature-barcode matrix 121.

For the ATAC data, in typical embodiments, there are no measures of gene expression. The metric for ATAC peak counts 125 is fragments (or UMIs) per called peak 123, where the peak 123 corresponds to a genomic region of accessible chromatin. Thus, for ATAC data, the feature-barcode matrix contains counts of fragments 125 in peaks 123 instead of gene expression.

In some embodiments, the feature-barcode matrix 121-1 includes ATAC peak data and gene expression discrete attribute values for 500 or more cells, 1000 or more cells, 10,000 or more cells, 15,000 or more cells, 20,000 or more cells, 25,000 or more cells, 30,000 or more cells, or 50,000 or more cells.

In some embodiments, the dataset further stores a plurality of GEX principal component values 164 and/or a two-dimensional GEX datapoint 166 and/or one or more GEX category 170 assignments for each respective cell 126 in the plurality of cells. FIG. 1B illustrates by way of example GEX principal component value 1 (164-1-1) through principal component value N (164-1-N) stored for cell 126-1 of the feature-barcode matrix 121-1 of the discrete attribute value dataset 120-1. The GEX principal components 164 are based upon the principal component analysis of the discrete attribute values 124 across the feature-barcode matrix and not the fragment counts 125.

In some embodiments, application of principal component analysis can drastically reduce (e.g., reduce by at least 5-fold, at least 10-fold, at least 20-fold, or at least 40-fold) the dimensionality of the GEX data (e.g. from approximately 20,000 dimensions to ten dimensions). That is, principal component analysis is used to assign each respective cell a plurality of GEX principal components that collectively describe the variation in the respective cell's mRNA expression levels with respect to expression levels of corresponding mRNA of other cells in the dataset. That is, each respective cell has the same set of GEX principal components, and the principal component analysis assigns different values to these GEX principal components for each respective cell in accordance with the variance in mRNA expression exhibited by the respective cell relative to the other cells.

FIG. 1B also illustrates the GEX cluster assignment for cell 1 (158-1), GEX category assignment 1 for cell 1 (170-1-1), including class 1 for GEX category assignment 1 (172-1-1-1) through class M for GEX category assignment 1 (172-1-1-M), through GEX category assignment Q for cell 1 (170-1-Q), including class 1 for GEX category assignment Q (172-1-Q-1) though class Z for GEX category assignment Q (172-1-Q-Z). These category and class assignments are based upon either (i) the principal component analysis of the discrete attribute values 124 across the plurality of cells represented by the feature-barcode matrix or (ii) the discrete attribute values 124 themselves, and not the ATAC fragment counts 125. In some embodiments each cell represented in the feature-barcode matrix 121-1 has five or more GEX principal component values, ten or more GEX principal component values, or twenty or more GEX principal component values. In some embodiments, the plurality of cells represented by the feature-barcode matrix are clustered into 3 or more, 4 or more, 5 or more, 6 or more, 7 or more, 8 or more, 9 or more, 10 or more, 15 or more or 20 or more GEX clusters.

In some alternative embodiments, the discrete attribute value dataset 120 stores a GEX two-dimensional datapoint 166 for each respective cell 126 in the plurality of cells (e.g., two-dimensional datapoint for cell 1 166-1 in FIG. 1B) based upon the discrete attribute values but not the fragment counts for peaks, but does not store the plurality of principal component values 164. In some embodiments, each discrete attribute value represents a number of mRNA measured in a respective cell that maps to a respective gene in the genome of the cell, and the discrete attribute value dataset further comprises the total RNA counts per cell.

In some embodiments, the dataset further stores a plurality of ATAC principal component values 165 and/or a two-dimensional ATAC datapoint 167 and/or one or more ATAC category 171 assignments for each respective cell 126 in the plurality of cells.

In some embodiments, application of principal component analysis can drastically reduce (e.g., reduce by at least 5-fold, at least 10-fold, at least 20-fold, or at least 40-fold) the dimensionality of the ATAC data (e.g. from approximately 20,000 dimensions to ten dimensions). That is, principal component analysis is used to assign each respective cell a plurality of ATAC principal components that collectively describe the variation in the respective cell's ATAC fragment counts of ATAC peaks with respect to ATAC fragment counts of corresponding ATAC peaks of other cells in the dataset. That is, each respective cell has the same set of ATAC principal components (e.g., ATAC components 1 through 10), and the principal component analysis assigns different values to these ATAC principal components for each respective cell in accordance with the variance in ATAC fragment count for ATAC peaks exhibited by the respective cell relative to the other cells.

FIG. 1C illustrates by way of example ATAC principal component value 1 (165-1-1) through principal component value P (165-1-P) stored for cell 126-1 of the feature-barcode matrix 121-1 of the discrete attribute value dataset 120-1. The ATAC principal components 165 are based upon the principal component analysis of the ATAC fragment counts 125 across the cells represented by the feature-barcode matrix and not the GEX discrete attribute values 124. FIG. 1C also illustrates the ATAC cluster assignment for cell 1 (159-1), ATAC category assignment 1 for cell 1 (171-1-1), including class 1 for category assignment 1 (173-1-1-1) through class M for category assignment 1 (173-1-1-M), through category assignment P for cell 1 (171-1-P), including class 1 for category assignment P (173-1-P-1) though class W for category assignment P 172-1-P-W. These category and class assignments are based upon either (i) the principal component analysis of the ATAC fragment counts 125 within the feature-barcode matrix or (ii) the ATAC fragment counts 125 themselves, and not the GEX discrete attribute values 125. In some embodiments each cell represented in the feature-barcode matrix 121-1 has five or more ATAC principal component values, ten or more ATAC principal component values, or twenty or more ATAC principal component values. In some embodiments, the plurality of cells represented by the feature-barcode matrix are clustered into 3 or more, 4 or more, 5 or more, 6 or more, 7 or more, 8 or more, 9 or more, 10 or more, 15 or more or 20 or more ATAC clusters. In some embodiments, the number of ATAC clusters represented by the plurality of cells of a given feature-barcode matrix is independent of (e.g. not the same as) the number of GEX clusters represented by the plurality of cells of the given feature-barcode matrix. As a nonlimiting example, in one instance the plurality of cells represented by the feature-barcode matrix are divided into 13 GEX clusters, and this same plurality of cells represented by the feature-barcode matrix are divided into 17 ATAC clusters. Of course, although number of ATAC clusters represented by the plurality of cells of a given feature-barcode matrix is independent of the number of GEX clusters represented by the plurality of cells of the given feature-barcode matrix, it is possible that the number of clusters is coincidentally the same. As a nonlimiting example of this, in another instance the plurality of cells represented by the feature-barcode matrix are divided into 10 GEX clusters, and this same plurality of cells represented by the feature-barcode matrix are divided into 10 ATAC clusters.

Figure 20:
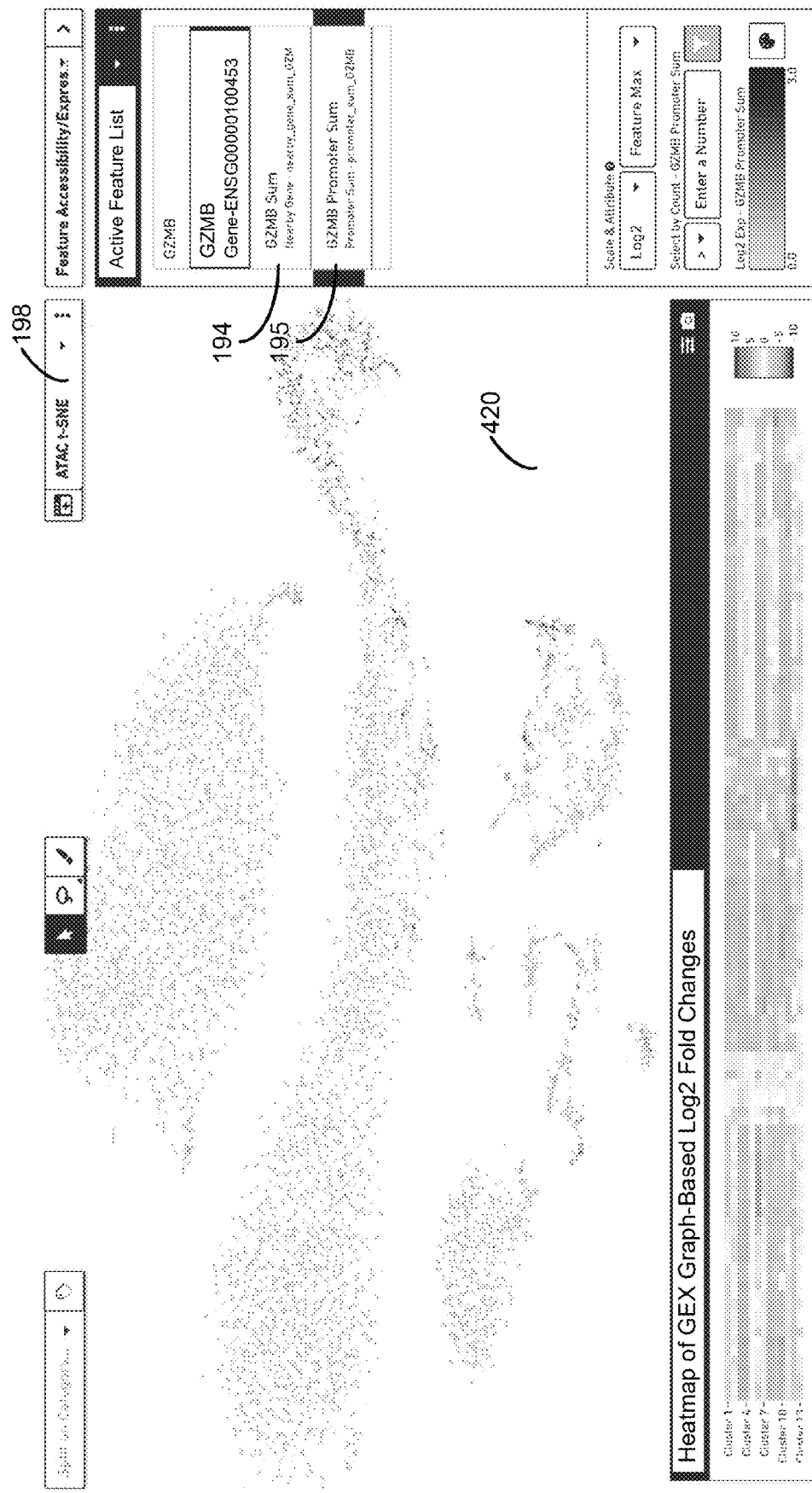
FIG. 20 illustrates an example of a user interface where the number of ATAC fragments near the promoter of the gene GZMB are quantified, on a cell by cell basis, in accordance with a scale (e.g., an intensity scale and/or a color scale), in accordance with some embodiments of the present disclosure.

In some embodiments, the feature-barcode matrix 121 also includes inferred counts 194/195 for each gene 193, for each cell, across the plurality of cells by the feature-barcode matrix 121 based on the ATAC data. In such embodiments, as illustrated in FIG. 20, the "Nearby Gene" aggregate count 194 sums single ATAC peaks within a given cell that are close to a given gene while the "Promoter Sum" aggregate count 195 sums ATAC peaks that overlap the gene's promoter region within a given cell. For example, if there are three called ATAC peaks in the dataset that are close to the GZMB gene, and two peaks that are close to the promoter, the GZMB Nearby Gene entry 194 will contain the sum of the fragment counts across those three ATAC peaks for each cell barcodes (e.g., for each cell represented by the feature-barcode matrix 121), and the GZMB Promoter Sum entry 195 will contain the sum of the fragment counts across the two ATAC peaks adjacent to the promoter for each cell barcode (e.g., for each cells represented by the feature-barcode matrix 121). As such, for GZMB there would be a plurality of entries 194 and 195, each such entry 194 and 195 representing a different cell in the plurality of cells. Projections.

In some embodiments, a 2-D t-Distributed Stochastic Neighboring Entities (t-SNE) projection 196 is computed based on the significant GEX principal component values 164 across the plurality of cells 126 represented by the feature-barcode matrix. t-SNE is a machine learning algorithm that is used for dimensionality reduction. See van der Maaten and Hinton, 2008, "Visualizing High-Dimensional Data Using t-SNE," Journal of Machine Learning Research 9, 2579-2605, which is hereby incorporated by reference. The nonlinear dimensionality reduction technique t-SNE is particularly well-suited for embedding high-dimensional data (here, the GEX principal components values 164 computed for each measured cell based upon the measured discrete attribute value 124 (e.g., expression level) of each gene 122 (e.g., expressed mRNA) in a respective cell 126 as determined by principal component analysis into a space of two, which can then be visualized as a two-dimensional visualization. In some embodiments, t-SNE is used to model each high-dimensional object (the GEX principal components 164 of each measured cell) as a two-dimensional point in such a way that similarly expressing cells are modeled as nearby two-dimensional datapoints and dissimilarly expressing cells are modeled as distant two-dimensional datapoints in the t-SNE projection. The t-SNE algorithm comprises two main stages. First, t-SNE constructs a probability distribution over pairs of high-dimensional cell vectors (vector of principal component values) in such a way that similar cell vectors (cells that have similar values for their GEX principal components 164 and thus presumably have similar discrete attribute values 124 across the plurality of genes) have a high probability of being picked, while dissimilarly dissimilar cell vectors (cells that have dissimilar values for their GEX principal components and thus presumably have dissimilar discrete attribute values 124 across the plurality of genes) have a small probability of being picked. Second, t-SNE defines a similar probability distribution over the plurality of cells 126 in the low-dimensional map, and it minimizes the Kullback-Leibler divergence between the two distributions with respect to the locations of the points in the map. In some embodiments the t-SNE algorithm uses the Euclidean distance between objects as the base of its similarity metric. In other embodiments, other distance metrics are used (e.g., Chebyshev distance, Mahalanobis distance, Manhattan distance, etc.).

In some embodiments, a t-SNE projection 198 is also computed based on the significant ATAC principal component values 165 across the plurality of cells 126 represented by the feature-barcode matrix. In such embodiments, t-SNE embeds the ATAC principal components values 165 computed for each measured cell 126 based upon the measured ATAC fragment counts 125 of each ATAC peak 123 in a respective cell 126 as determined by principal component analysis into a space of two, which can then be visualized as a two-dimensional visualization. In some such embodiments, t-SNE is used to model each high-dimensional object (the ATAC principal components 165 of each measured cell) as a two-dimensional point. As in the case of the GEX t-SNE calculations described above, the ATAC t-SNE algorithm comprises two main stages. First, the ATAC t-SNE constructs a probability distribution over pairs of high-dimensional cell vectors (vector of ATAC principal component values 165) in such a way that similar cell vectors (cells that have similar values for their ATAC principal components 165 and thus presumably have similar ATAC fragment counts 125 across the plurality of ATAC peaks 123) have a high probability of being picked, while dissimilarly dissimilar cell vectors (cells that have dissimilar values for their ATAC principal components and thus presumably have dissimilar ATAC fragment counts 125 across the plurality of ATAC peaks 123) have a small probability of being picked. Second, t-SNE defines a similar probability distribution over the plurality of cells 126 in the low-dimensional map, and it minimizes the Kullback-Leibler divergence between the two distributions with respect to the locations of the points in the map. In some embodiments the ATAC t-SNE algorithm uses the Euclidean distance between objects as the base of its similarity metric. In other embodiments, other distance metrics are used (e.g., Chebyshev distance, Mahalanobis distance, Manhattan distance, etc.).

In some embodiments, a GEX 2-D uniform manifold approximation and projection (UMAP) projection 197 is computed based on the significant GEX principal component values 164 across the plurality of cells 126 represented by the feature-barcode matrix. UMAP is described in McInnes and Healy, 2018, "UMAP: Uniform Manifold Approximation and Projection for Dimension Reduction," ArXiv e-prints 1802.03426, which is hereby incorporated by reference. Correspondingly, in some embodiments, an ATAC 2-D UMAP projection 199 is computed based on the significant ATAC principal component values 165 across the plurality of cells 126 represented by the feature-barcode matrix. As a result, users are able to explore classifications and scatter plots generated from the two separate analytes: ATAC and GEX.

Genomic Location of ATAC Peaks and GEX Genes.

In some embodiments, a discrete attribute dataset 120 further includes the genomic location of each ATAC peak and each gene. In some embodiments this information, for each such feature, is stored in each of three location arrays, namely, an array of chromosome indices 180, an array of starting positions 183, and an array of ending positions 185. Thus, the boundaries of a feature i (gene 122 or ATAC peak 123) in the feature-barcode matrix 121 are defined by the $i^{th}$ value of these three arrays. In this way, the location of these features in a genome plot can be determined, and also distances between linked features can be determined. For instance, the chromosome number of a given gene i is located at the $i^{th}$ entry 182 of array of chromosome index 180, the starting position of given gene i is located at the $i^{th}$ entry 184 of the array of starting positions 183, and the ending position of given gene i is located at the $i^{th}$ entry 186 of the array of ending positions 185. In this way, for a feature i, the chromosome, start position and end position of the feature can be found at location.chromosome[i], location.starts[i] and location.ends[i], where location.chromosome [i], location.starts[i], location.ends[i], are respectively the array of chromosome indices 180, array of starting positions 183, and array of ending positions 18. In some embodiments, the array of chromosome indices 180, array of staring positions 183, and array of ending positions 185 are integer arrays that can be stored as gzipped blocks.

Feature-Linkage Matrix.

Measurement of both gene expression and chromatin accessibility within the same cell provides for the opportunity to link correlated expression and accessibility patterns. Finding strong correlations between open DNA regions and mRNA transcribed from nearby sequences can reveal how the instructions encoded in our DNA trigger the cellular programs executed. For instance, given a feature (gene or peak) of interest, querying the linkage matrix and other structures in the discrete attribute value dataset 120 (e.g., in the form of a .cloupe file) efficiently provides (i) the chromosomal location of the gene or peak of interest, (ii) the identities and locations of the features linked to that gene or peak, and (iii) the correlations of those linkages, and the significance of those linkages. Accordingly, and referring to FIG. 1D, some embodiments of the discrete attribute value dataset 120 further include a feature-linkage matrix 187 between peak features, and between peak to gene features. Because linkages are symmetric (e.g., linkage(a, b)=linkage (b, a)), in preferred embodiments, such linkages are stored in triangular matrix form.

In some embodiments, there is a constraint that, in order to be included in the matrix, features (ATAC peaks 123 and genes 122) must be on the same chromosome and within some threshold distance from each other. In some embodiments, this threshold distance is 1 megabase. That is, the two peaks (or peak and gene) must map to within 1 megabase of each other on the same chromosome to be registered as linked within the feature linkage matrix 187. In alternative embodiments, the threshold distance is 1.5 megabases, 2.0 megabases, 2.5 megabases, 3.0 megabases, 3.5 megabases, 4.0 megabases, 4.5 megabases, 5.0 megabases, 5.5 megabases, 6.0 megabases, between 1.5 and 6.0 megabases, or some value greater than 6.0 megabases. Since the feature-barcode matrix 121 includes genes and ATAC peaks from across the gigabases of human and other genomes, this restriction ensures that the feature-linkage matrix 187 is extremely sparse. Thus, in some embodiments, the feature-linkage matrix is stored in persistent memory 112 as a sparse matrix, in compressed-sparse row (CSR) format. In some embodiments, there are four arrays in a feature-linkage matrix 187, a pointer array (P) (188), an index array (X) (190), a correlation array (C) (191), and a significance array (S) 192. In some embodiments, the pointer array (P) (188) may include one or more indexes such as Index 1 (189-1-1) and Index L (189-1-L).

The correlation array C (191) contains R-value correlations between linked features (from −1, indicating perfect opposites, to 1, indicating perfect alignment). The significance array S (192) contains the statistical significances of the linkages, defined as the negative log of the false discovery rate. A higher significance means the linkage is less likely to be due to random sampling.

The pointer array (P) 188 is of length L+M+1, where L+M is the total number of genes and ATAC peaks represented in the corresponding in the feature barcode matrix 121. For instance, if the feature-barcode matrix provides GEX discrete attribute values for a total of 21 different genes and a total of 30 different ATAC peaks across the plurality of cells 126 represented by the feature-barcode matrix 121, the pointer array has a length of 21+30+1=52. In some embodiments, the values P[i] and P[i+1] in the pointer array 188 define the minimum and maximum indices in the other three arrays (index array 190, correlation array 191, and significance array 192) to retrieve information about features linked to the feature i of the feature-barcode matrix. The subset X[P[i]]:X[P[i+1]] contains the row indices of the other features linked to feature i, C[P[i]]:C[P[i+1]] contains the respective correlations between feature i and the other features in X, and likewise S[P[i]]:S[P[i+1]] contains the respective significances between the linkages between feature i and the features over the same range in the index array X (190). For instance, for feature 20, the $20^{th}$ and the $(20+1)^{th}$ index in the pointer array 188 is consulted to retrieve two values (e.g., 1137 and 1530). These two values, 1137 and 1530, define the minimum and maximum indices that used within the index array 190 to learn the identity of each gene or peak that is linked to feature 20. These two values, 1137 and 1530, further define the minimum and maximum indices that used within the correlation array 191 to learn the correlation of each gene or peak that is linked to feature 20. Finally, these two values, 1137 and 1530, further define the minimum and maximum indices that are used within the significance array 192 to learn the significance of each gene or peak that is linked to feature 20. The sparse format of the index array 190, correlation array 191, and significance array 192 allows efficient storage in persistent memory 112 within a discrete attribute value dataset 120 (e.g., a cloupe file). Furthermore, in some embodiments, the index array 190, correlation array 191, and significance array 192 are stored in blocked gzip format with indices, such that lookups of the linkages of randomly selected features are efficient, and do not require loading the entire feature-linkage matrix into non-persistent memory 111.

Although FIGS. 1A, 1B, 1C, and 1D depict a "visualization system 100," the figures are intended more as functional description of the various features which may be present in computer systems than as a structural schematic of the implementations described herein. In practice, and as recognized by those of ordinary skill in the art, items shown separately could be combined and some items could be separated. Moreover, although FIG. 1A depicts certain data and modules in non-persistent memory 111, some or all of these data and modules may be in persistent memory 112. Further, while discrete attribute value dataset 120 is depicted as resident in persistent memory 112, a portion of discrete attribute value dataset 120 is, in fact, resident in non-persistent memory 111 at various stages of the disclosed methods.

Methods.

While a system in accordance with the present disclosure has been disclosed with reference to FIGS. 1A and 1i, a method in accordance with the present disclosure is now detailed with reference to FIGS. 2A, 2B, and 2C.

Block 202. One aspect of the present disclosure provides a visualization system 100. The visualization system 100 comprises one or more processing cores 102, a non-persistent memory 111 and a persistent memory 111, the persistent memory and the non-persistent memory collectively storing instructions for performing a method. A non-limiting example of a visualization system is collectively illustrated in FIGS. 1A, 1B, 1C, and 1D. As discussed above, it will be appreciated that the persistent memory and/or the non-persistent memory can be on a single computer, distributed across a network of computers, be represented by one or more virtual machines, or be part of a cloud computing architecture.

Figure 3:
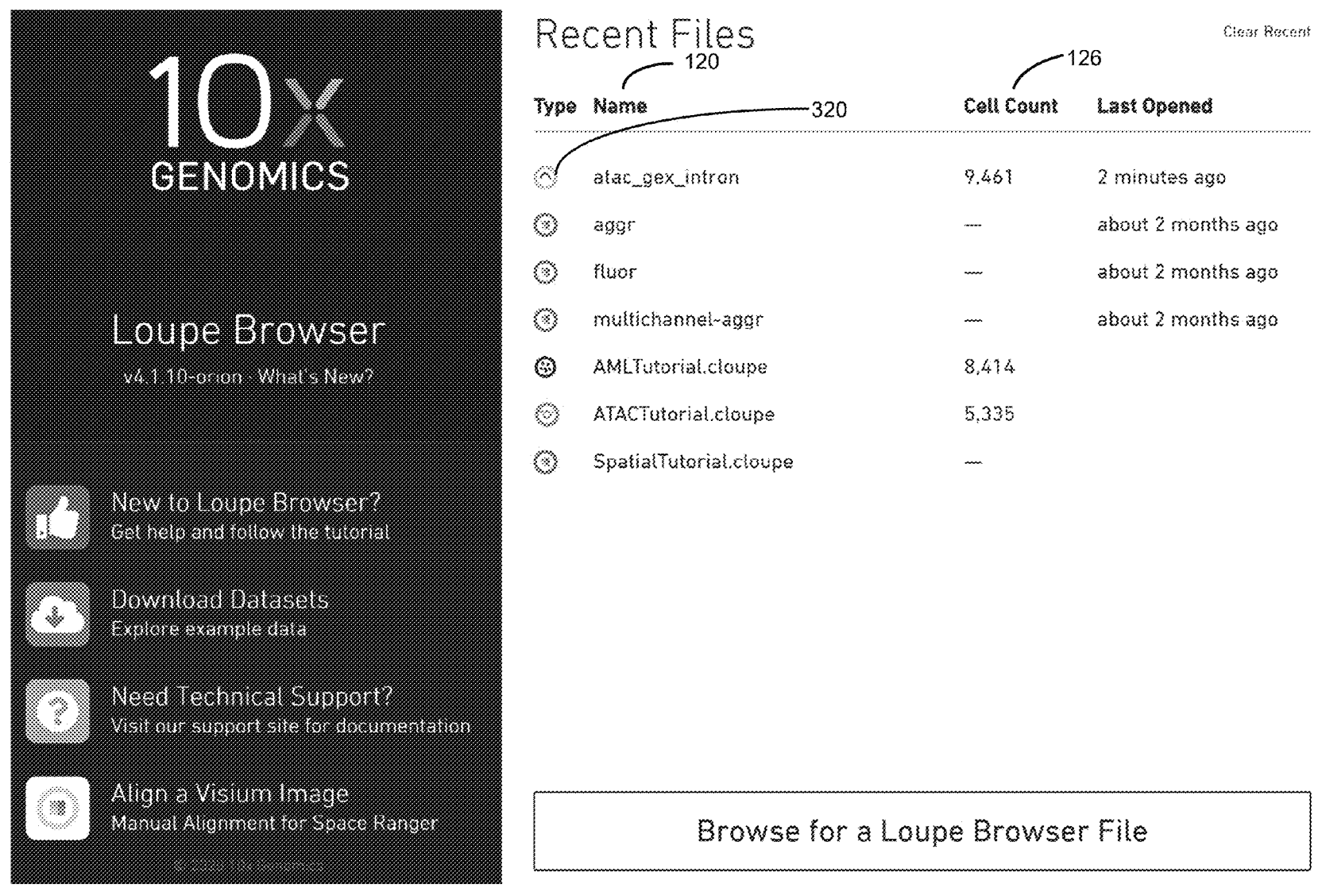

Block 204 and Block 205—Storing a discrete attribute value dataset 120 in persistent memory. The systems and methods of the present disclosure provide for storing a discrete attribute value dataset 120 in persistent memory 112. Referring to FIGS. 1B, 1C, and 1D, the discrete attribute value dataset 120 comprises a corresponding discrete attribute value 124 for each gene 122 in a plurality of genes for each respective cell 126 in a plurality of cells. The dataset 120 further comprises a corresponding ATAC fragment count 125 for each ATAC peak 123 in a plurality of ATAC peaks for each respective cell 126 in the plurality of cells. FIG. 3 illustrates the selection of a particular discrete attribute value dataset 120 using browser module 119. In particular, FIG. 3 illustrates how the browser module 119 provides some information regarding a given discrete attribute value dataset 120 such as its type, its name, the number of cells 126 represented by the discrete attribute value dataset 120 (if any), and the last time the discrete attribute value dataset was accessed.

In some embodiments, each discrete attribute value 124 is a count of transcript reads within the cell that map to a respective gene in the plurality of genes. In some embodiments, the discrete attribute values 124 of a discrete attribute value dataset 120 represents a whole transcriptome shotgun sequencing experiment that quantifies gene expression from a single cell in counts of transcript reads mapped to the genes. In some such embodiments, microfluidic partitions are used to partition very small numbers of mRNA molecules and to barcode those partitions. In some such embodiments, where discrete attribute values are measured from single cells, the microfluidic partitions are used to capture individual cells within each microfluidic droplet and then pools of single barcodes within each of those droplets are used to tag all of the contents (e.g., genes 122) of a given cell. For example, in some embodiments, a pool of ~750,000 barcodes is sampled to separately index each cells' transcriptome by partitioning thousands of cells into nanoliter-scale Gel Bead-In-EMulsions (GEMs), where all generated cDNA share a common barcode. Libraries are generated and sequenced from the cDNA and the barcodes are used to associate individual reads back to the individual partitions. In other words, each respective droplet (GEM) is assigned its own barcode and all the contents (e.g., mRNA for genes) in a respective droplet are tagged with the barcode unique to the respective droplet. In some embodiments, such droplets are formed as described in Zheng et al., 2016, Nat Biotchnol. 34(3): 303-311; or in See the Chromium™, Single Cell 3' Reagent Kits v2. User Guide, 2017, 10x Genomics®, Pleasanton, California, Rev. B, page, 2, each of which is hereby incorporated by reference. In some alternative embodiments, equivalent 5' chemistry is used rather than the 3' chemistry disclosed in these references.

In some embodiments there are tens, hundreds, thousands, tens of thousands, or one hundreds of thousands of such microfluidic droplets. In some such embodiments, at least seventy percent, at least eighty percent, at least ninety percent, at least ninety percent, at least ninety-five percent, at least ninety-eight percent, or at least ninety-nine percent of the respective microfluidic droplets contain either no cell 126 or a single cell 126 while the remainder of the microfluidic droplets contain two or more cells 126. In other words, to achieve single cell resolution, the cells are delivered at a limiting dilution, such that the majority (~90-99%) of generated nanoliter-scale gel bead-in-emulsions (GEMs) contains no cell, while the remainder largely contain a single cell. See the Chromium™, Single Cell 3' Reagent Kits v2. User Guide, 2017, 10x Genomics®, Pleasanton, California, Rev. B, page, 2, which is hereby incorporated by reference. In some alternative embodiments, equivalent 5' chemistry is used rather than the 3' chemistry disclosed in this reference.

Within an individual droplet, gel bead dissolution releases the amplification primer into the partitioned solution. In some embodiments, upon dissolution of the single cell 3' Gel Bead in a GEM, primers containing (i) an Illumina R1 sequence (read 1 sequencing primer), (ii) a 16 bp 10x Barcode, (iii) a 10 bp Unique Molecular Identifier (UMI) and (iv) a polydT primer sequence are released and mixed with cell lysate and Master Mix. Incubation of the GEMs then produces barcoded, full-length cDNA from poly-adenylated mRNA. After incubation, the GEMs are broken and the pooled fractions are recovered. See the Chromium™, Single Cell 3' Reagent Kits v2. User Guide, 2017, 10x Genomics®, Pleasanton, California, Rev. B, page, 2, which is hereby incorporated by reference. In some such embodiments, silane magnetic beads are used to remove leftover biochemical reagents and primers from the post GEM reaction mixture. Full-length, barcoded cDNA is then amplified by PCR to generate sufficient mass for library construction.

In this way, the genes 122 can be mapped to individual genes in the genome of a species and therefore they can be sequenced and, furthermore, the mRNA for genes 122 of a given cell 126 can be distinguished from the mRNA of genes of another cell 126 based on the unique barcode. This contrasts to bulk sequencing techniques in which all the cells are pooled together and the measurement profile is that of the genes of the whole collection of the cells without the ability to distinguish the measurement signal of genes by individual cells. An example of such measurement techniques is disclosed in United States Patent Publication No. 2015/0376609, which is hereby incorporated by reference. As such, in some embodiments, the sequence reads mapping to each gene in a particular cell in the plurality of cells is barcoded with a first barcode that is unique to the particular cell.

Figure 19:
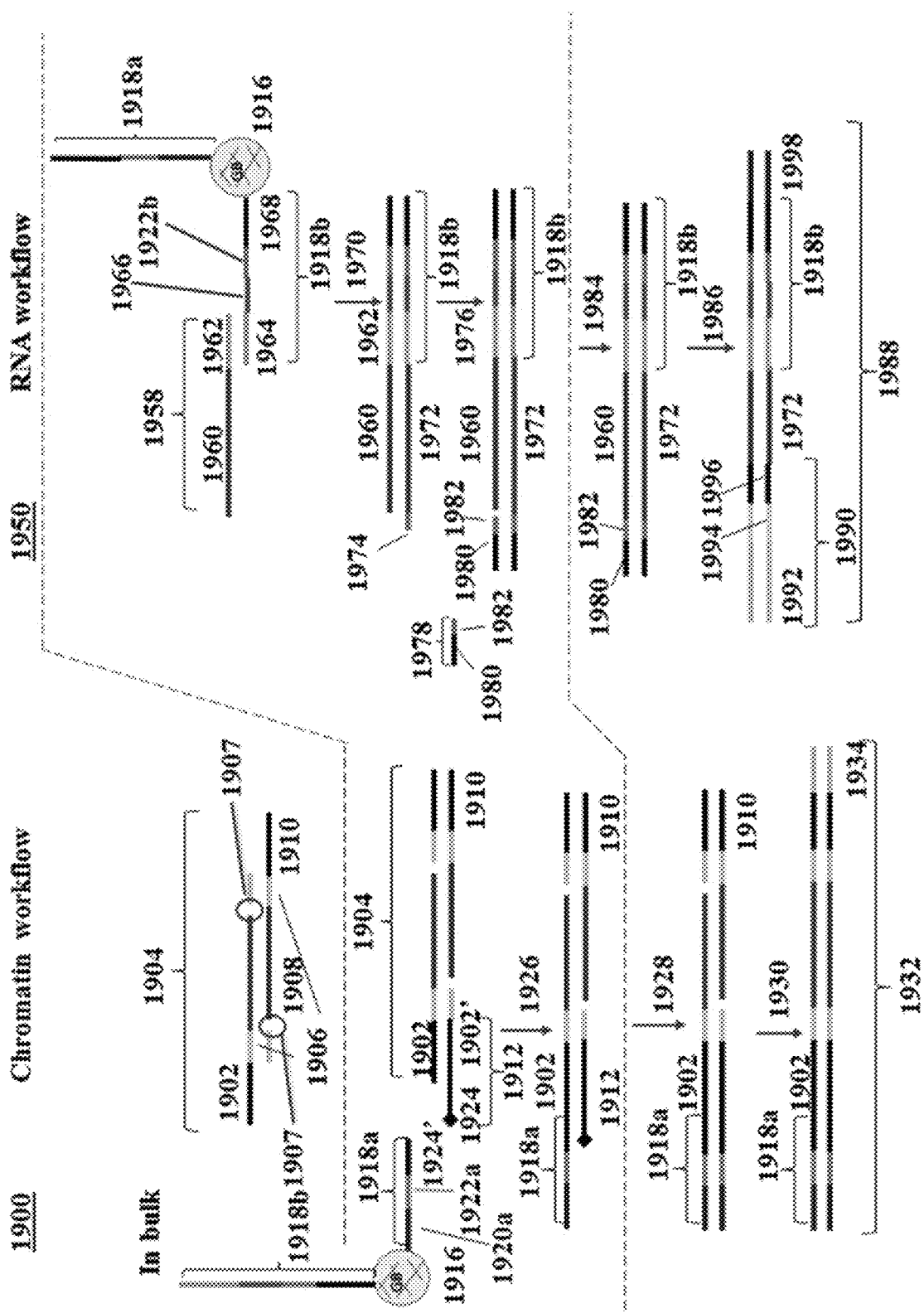
FIG. 19 illustrates an exemplary scheme for tandem ATAC ligation and RNA template switching in accordance with an embodiment of the present disclosure.

In some embodiments, physical measurement of RNA gene expression and DNA chromatin accessibility is from the same cells. That is, the assay measures both RNA and accessible chromatin from the same cell. FIG. 19 shows a non-limiting example schematic of such as assay. In particular, panel 1900 of FIG. 19 shows a workflow corresponding to processing of chromatin from a cell, cell bead, or cell nucleus, and panel 1950 of FIG. 19 shows a workflow corresponding to processing of an mRNA molecule from the cell, cell bead, or cell nucleus.

As shown in panel 1900, in bulk solution, chromatin included within a cell, cell bead, or cell nucleus is processed (e.g., as described herein) to provide a template nucleic acid fragment (e.g., tagmented fragment) 1904 comprising insert sequence 1908 (e.g., region of open chromatin) and a complement thereof, transposon end sequences 1906 and complements thereof, sequencing primer or portion thereof 1902 (e.g., an R1 sequence), sequencing primer or portion thereof 1910 (e.g., an R2 sequence), and gaps 1907. Template nucleic acid fragment 1904 may then be partitioned to a droplet or well, as described herein. Within the partition, the cell, cell bead, or cell nucleus comprising template nucleic acid fragment 1904 may be lysed, permeabilized, or otherwise processed to provide access to template nucleic acid fragment 1904 (and one or more RNA molecules) therein. The partition may comprise splint sequence 1912. In some embodiments, the splint sequence 1912 comprises a first sequence 1902' that is complementary to sequencing primer or portion thereof 1902 and a second sequence 1924. In some embodiments sequence 1924 comprises a blocking group (e.g., a 3' blocking group) that prevents extension by reverse transcription. The partition may also include a bead (e.g., gel bead) 1916 coupled to nucleic acid barcode molecules 1918a and 1918b. Nucleic acid barcode molecule 1918a may comprise a flow cell adapter sequence 1920a (e.g., a P5 sequence), a barcode sequence 1922a, and an overhang sequence 1924' that is complementary to sequence 1924 of the splint sequence. Sequence 1924 may hybridize to sequence 1924' to provide a partially double-stranded nucleic acid molecule comprising the sequences of nucleic acid barcode molecule 1918a and the template nucleic acid fragment 1904. In some embodiments, sequence 1924' of nucleic acid barcode molecule 1918a is ligated (e.g., using a ligase) 1926 to sequence 1902 of template nucleic acid fragment 1904. In some instances, 1904 is phosphorylated using a suitable kinase enzyme (e.g., polynucleotide kinase (PNK), such as T4 PNK). In some embodiments, PNK and ATP are added in bulk in the tagmentation reaction (e.g., ATAC) and/or prior to partitioning the cells, cell beads, or cell nuclei. 15 U of PNK with 1 mM of ATP may be spiked into the tagmentation reaction. For example, less than 95 U of PNK may be spiked into the tagmentation reaction. The contents of the partition may then be recovered in bulk solution (e.g., a droplet may be broken) to provide the partially double-stranded nucleic acid molecule comprising nucleic acid barcode molecule 1918a attached to template nucleic acid fragment 1904 in bulk solution. In bulk solution, gaps 1907 may be filled 1928 via a gap filling extension process (e.g., using a DNA polymerase) to provide a double-stranded nucleic acid molecule. This molecule may undergo amplification (e.g., PCR) 1930 to provide a double-stranded amplification product 1932 that includes sequences of the nucleic acid barcode molecule 1918a, the original chromatin molecule, and, optionally, an additional sequence 1934 that may be a flow cell adapter sequence (e.g., a P7 sequence). Gaps may be filled in the partition prior to bulk processing.

In parallel to the chromatin workflow of panel 1900, an RNA molecule deriving from the same cell, cell bead, or cell nucleus may be processed. As shown in panel 1950, RNA molecule 1958 comprising RNA sequence 1960 and polyA sequence 1962 and bead (e.g., gel bead) 1916 is provided within a partition. In some embodiments, bead (e.g., gel bead 1916, such as the same bead described in panel 1900) is included within the partition and is coupled to nucleic acid barcode molecule 1918b. Nucleic acid barcode molecule 1918b may comprise a flow cell adapter sequence 1968 (e.g., a P5 sequence), a barcode sequence 1922b (e.g., the same barcode sequence as barcode sequence 1922a), a UMI sequence 1966, and a polyT sequence 1964 complementary to polyA sequence 1962. In some instances, nucleic acid barcode molecule 1918b may comprise a sequencing primer sequence 1968 (e.g., an R1 sequence or partial R1 sequence), a barcode sequence 1922b (e.g., the same barcode sequence as barcode sequence 1922a), UMI sequence 1966, and a polyT sequence 1964 complementary to polyA sequence 1962. PolyT sequence 1964 may hybridize to polyA sequence 1962 of RNA molecule 1958. RNA molecule 1958 may be reverse transcribed 1970 off of the polyT sequence 1964 to provide a cDNA molecule comprising cDNA sequence 1972. The reverse transcription process may use a reverse transcriptase with terminal transferase activity that appends sequence 1974 to the resultant cDNA molecule comprising cDNA sequence 1972. In some embodiments sequence 1974 is a polyC sequence. A template switch oligonucleotide 1978 comprising a primer sequence 1980 and a sequence complementary 1982 to sequence 1974 (e.g., a polyG sequence) may hybridize to the cDNA molecule 1976. The contents of the partition are recovered in bulk solution (e.g., a droplet may be broken) to provide the cDNA molecule in bulk solution. The cDNA molecule undergoes amplification (e.g., PCR) 1984. Additional amplification (e.g., PCR) 1986 may to performed to provide a double-stranded amplification product 1988 that includes sequences of the nucleic acid barcode molecule 1918b, the original RNA molecule or cDNA corresponding thereto, a flow cell adapter sequence 1998 (e.g., a P7 sequence), and an additional sequence 1990 that may comprise a sequencing primer or portion thereof (e.g., an R2 sequence) 1996, a sample index sequence 1994, and a flow cell adapter sequence (e.g., a P5 sequence) 1992. The barcoded cDNA molecule may also or alternatively undergo fragmentation, end repair, dA tailing, ligation of one or more adapter sequences, and/or nucleic acid amplification. Additional schemes for collecting ATAC and GEX data for the discrete attribute value dataset 120 are described in U.S. patent application Ser. No. 16/789,287, entitled "Methods for Processing Nucleic Acid Molecules," filed Feb. 12, 2020, which is hereby incorporated by reference.

Consistent with the workflow of FIG. 19, in some embodiments, the discrete attribute value 124 of each gene 122 and the ATAC fragment count 125 of each region of open chromatin (ATAC peak 123) in a particular cell 126 in the plurality of cells is determined after the particular cell 126 has been separated from all the other cells in the plurality of cells into its own microfluidic partition. Such embodiments provide the ability to explore the heterogeneity between cells, which is one form of pattern analysis afforded by the systems and method of the present disclosure. In some such embodiments, because mRNA abundance and regiongs of open chromatin is being jointly measured, it is possible that the mRNA abundance and regions of open chromatin in each cell sample may vary vastly from cell to cell. As such, the disclosed systems and methods enable the profiling of which genes are being expressed and at what levels in each of the cells, as well as which regions of chromatin are open, and to use these gene profiles and open chromatin profiles (records of GEX discrete attribute values 124 and ATAC fragment counts 125), or principal components derived therefrom, to cluster cells and identify populations of related cells. As discussed above, the cells are clustered two different ways to form to sets of clusters, the GEX clusters 158 and the ATAC clusters 159. That is, the cells are clustered based on their GEX discrete attribute values 124 to form a first plurality of GEX clusters 158. Independent of this clustering, the cells are also clustered based on their ATAC fragment counts 125 to form a second plurality of ATAC clusters 159. This allows for the identification of cells with similar gene profiles and/or regions of open chromatin at different life cycle stages of the cell or different types of cells, different tissue, different organs, or other sources of cell heterogeneity. This further allows for the identification of any linkages between gene expression and open chromatin.

As such, in some embodiments, each cell 126 corresponds to a single cell, each gene 122 associated with a corresponding cell represents an mRNA (that maps to a gene that is in the genome of the single cell) and the discrete attribute value 124 is a number of copies of the mRNA that have been measured in the single cell. In some such embodiments, the discrete attribute value dataset 120 includes discrete attribute values 124 for 10 or more, 50 or more, 100 or more, 1000 or more, 3000 or more, 5000 or more, 10,000 or more, or 15,000 or more mRNAs in each cell represented by the dataset as well as ATAC fragment counts 125 for 10 or more, 50 or more, 100 or more, 1000 or more, 3000 or more, 5000 or more, 10,000 or more, or 15,000 or more ATAC peaks (open chromatin regions) in each cell represented by the dataset. In some such embodiments, the discrete attribute value dataset 120 includes discrete attribute values 124 for the mRNAs (genes 122) and ATAC fragment counts 125 for the ATAC peaks 123 of 500 or more cells, 5000 or more cells, 100,000 or more cells, 250,000 or more cells, 500,000 or more cells, 1,000,000 or more cells, 10 million or more cells or 50 million or more cells. In some embodiments, each single cell is a human cell. In some embodiments, each cell 126 represents a different human cell. In some embodiments, the discrete attribute value dataset 120 includes data for human cells of several different classes (e.g., representing different deceased states and/or wild type states). In such embodiments, the discrete attribute value 124 for a respective mRNA of a gene 122 in a given cell 126 is the number of mRNAs for the respective gene that were measured in the given cell. This will either be zero or some positive integer.

Moreover, the ATAC fragment count 125 for a respective ATAC peak 123 (open chromatin region) in a given cell 126 is the count of unique UMI for the respective ATAC peak 123 that were measured in the given cell. This will either be zero or some positive integer.

In some embodiments, the discrete attribute value 124 for a given gene 122 for a given cell 126 is a number in the set $\{0, 1, \ldots, 100\}$. In some embodiments, the discrete attribute value 124 for a given gene 122 for a given cell 126 is a number in the set $\{0, 1, \ldots, 50\}$. In some embodiments, the discrete attribute value 124 for a given gene 122 for a given cells 126 is a number in the set $\{0, 1, \ldots, 30\}$. In some embodiments, the discrete attribute value 124 for a given gene 122 for a given cell 126 is a number in the set $\{0, 1, \ldots, N\}$, where N is a positive integer, e.g, a number in the range of 30 to 10,000, etc.

In some embodiments, the ATAC fragment count 125 for a given ATAC peak 123 for a given cell 126 is a number in the set $\{0, 1, \ldots, 100\}$. In some embodiments, the ATAC fragment count 125 for a given ATAC peak 123 for a given cell 126 is a number in the set $\{0, 1, \ldots, 50\}$. In some embodiments, the ATAC fragment count 125 for a given ATAC peak 123 for a given cell 126 is a number in the set $\{0, 1, \ldots, 30\}$. In some embodiments, the ATAC fragment count 125 for a given ATAC peak 123 for a given cell 126 is a number in the set $\{0, 1, \ldots, M\}$, where M is a positive integer, e.g., a number in the range of 30 to 10,000, etc.

In some embodiments, the discrete attribute value dataset 120 includes discrete attribute values for 1000 or more, 3000 or more, 5000 or more, 10,000 or more, or 15,000 or more genes 122 in each cell 126 represented by the dataset. In some embodiments, the discrete attribute value dataset 120 includes ATAC fragment counts 125 for 1000 or more, 3000 or more, 5000 or more, 10,000 or more, or 15,000 or more ATAC peaks (e.g., open chromatin regions) in each cell 126 represented by the dataset. In some such embodiments, the discrete attribute value dataset 120 includes respective discrete attribute values 124 for the genes and ATAC fragment counts 125 for ATAC peaks 123 of 500 or more cells, 5000 or more cells, 100,000 or more cells, 250,000 or more cells, 500,000 or more cells, 1,000,000 or more cells, 10 million or more cells, or 50 million or more cells.

As the above ranges indicate, the systems and methods of the present disclosure support very large discrete attribute value datasets 120 that may have difficulty being stored in the persistent memory 112 of conventional devices due to persistent memory 112 size limitations in conventional devices. Moreover, the systems and methods of the present disclosure are designed for data in which the sparsity is significantly more than twenty percent. The number of zero-valued elements divided by the total number of elements (e.g., m×n for an m×n matrix) is called the sparsity of the matrix (which is equal to 1 minus the density of the matrix). While there are approximately twenty thousand genes in the human genome, most genes are not being expressed in a cell at any given time. Thus, it is expected that such data will have a sparsity approaching two percent in many instances. Thus, advantageously, to address the size constraints of the persistent memory (e.g., magnetic drives or solid state drives) 112 limitations of conventional computers, in some embodiments, the discrete attribute value dataset 120 is represented in a compressed sparse matrix representation that may be searched both on a feature basis (gene 122 basis or ATAC peak 123) and a cell 126 basis. To accomplish this, the discrete attribute value dataset 120 redundantly represents the corresponding discrete attribute value 124 for each gene 122 in a plurality of genes as well as the corresponding ATAC fragment count 125 for each ATAC peak 123 for each respective cell 126 in a plurality of cells in both a compressed sparse row format and a compressed sparse column format in which genes or ATAC peaks for a respective cell that have a null discrete attribute data value are optionally discarded.

In some embodiments, the average density of the feature-barcode matrices 121 that are used in the systems and methods of the present disclosure are on the order of two percent. Thus, if the features (genes and ATAC peaks) were viewed as a dense matrix, then only two percent of them would have data that is not zero. With a sparse matrix, all the zeroes are discarded. And so the sparse matrix allows for the dataset to fit in persistent memory 112. But with typical discrete attribute value datasets 120 of the present disclosure the memory footprint is still too high once the data for half a million cells 126 or more is used. For this reason, both the row-oriented and column-oriented spare-matrix representations of the data are stored in persistent memory 112 in some embodiments in compressed blocks (e.g., bgzf blocks) to support quick differential-expression analysis, which requires examination of the data (e.g. the discrete attribute values of genes) for individual cells. In the case of the gene "gene 3," access to the discrete attribute data for gene 3 works by looking at the address in the dataset for gene 3, which thereby identifies the block in which the data for gene 3 resides. As such, when doing differential expression for a subset of the cells in the discrete attribute value dataset 120, the address of the individual cell is first needed.

Accordingly, in some embodiments, the discrete attribute value dataset 120 is stored in compressed sparse row (CSR) format. Here the term "compressed sparse row" is used interchangeably with the term "compressed sparse column" (CSC) format. The CSR format stores a sparse m×n matrix M in row form using three (one-dimensional) arrays (A, IA, JA). Here, NNZ denotes the number of nonzero entries in M (note that zero-based indices shall be used here) and the array A is of length NNZ and holds all the nonzero entries of M in left-to-right top-to-bottom ("row-major") order. The array IA is of length m+1. It is defined by this recursive definition:

IA[0]=0;

IA[$i$]=IA[$i-1$]+(number of nonzero elements on the ($i-1$)$^{th}$ row in the original matrix).

Thus, the first m elements of IA store the index into A of the first nonzero element in each row of M, and the last element IA[m] stores NNZ, the number of elements in A, which can be also thought of as the index in A of first element of a phantom row just beyond the end of the matrix M. The values of the $i^{th}$ row of the original matrix is read from the elements A[IA[i]] to A[IA[i+1]−1] (inclusive on both ends), e.g. from the start of one row to the last index just before the start of the next.

The third array, JA, contains the column index in M of each element of A and hence is of length NNZ as well.

For example, the matrix M $$\begin{pmatrix} 0 & 0 & 0 & 0 \\ 5 & 8 & 0 & 0 \\ 0 & 0 & 3 & 0 \\ 0 & 6 & 0 & 0 \end{pmatrix}$$

is a 4×4 matrix with 4 nonzero elements, hence
A=[5 8 3 6]
IA=[0 0 2 3 4]
JA=[0 1 2 1]

In one implementation of the matrix M above, each row represents a different cell 126 and each element of a given row represents a different feature (gene 122 or ATAC peak 123) associated with the different cell. Further, the value at a given matrix element represents the discrete attribute value 124 if the feature is a gene 122 or the ATAC fragment count 125 if the feature is an ATAC peak 123. In some embodiments, the ATAC data is stored in CSR format in a first matrix and the GEX data is stored in CSR format in a second matrix. In some embodiments, the ATAC data and the GEX data are stored in CSR format in the same matrix.

In some embodiments, the discrete attribute value dataset 120 is also stored in compressed sparse column (CSC or CCS) format. A CSC is similar to CSR except that values are read first by column, a row index is stored for each value, and column pointers are stored. For instance, CSC is (val, row_ind, col_ptr), where val is an array of the (top-to-bottom, then left-to-right) non-zero values of the matrix; row_ind is the row indices corresponding to the values; and, col_ptr is the list of val indexes where each column starts. In some embodiments, the ATAC data is stored in compressed sparse column format in a first matrix and the GEX data is stored in compressed sparse column format in a second matrix. In some embodiments, the ATAC data and the GEX data are stored in compressed sparse column format in the same matrix.

Figure 4A:
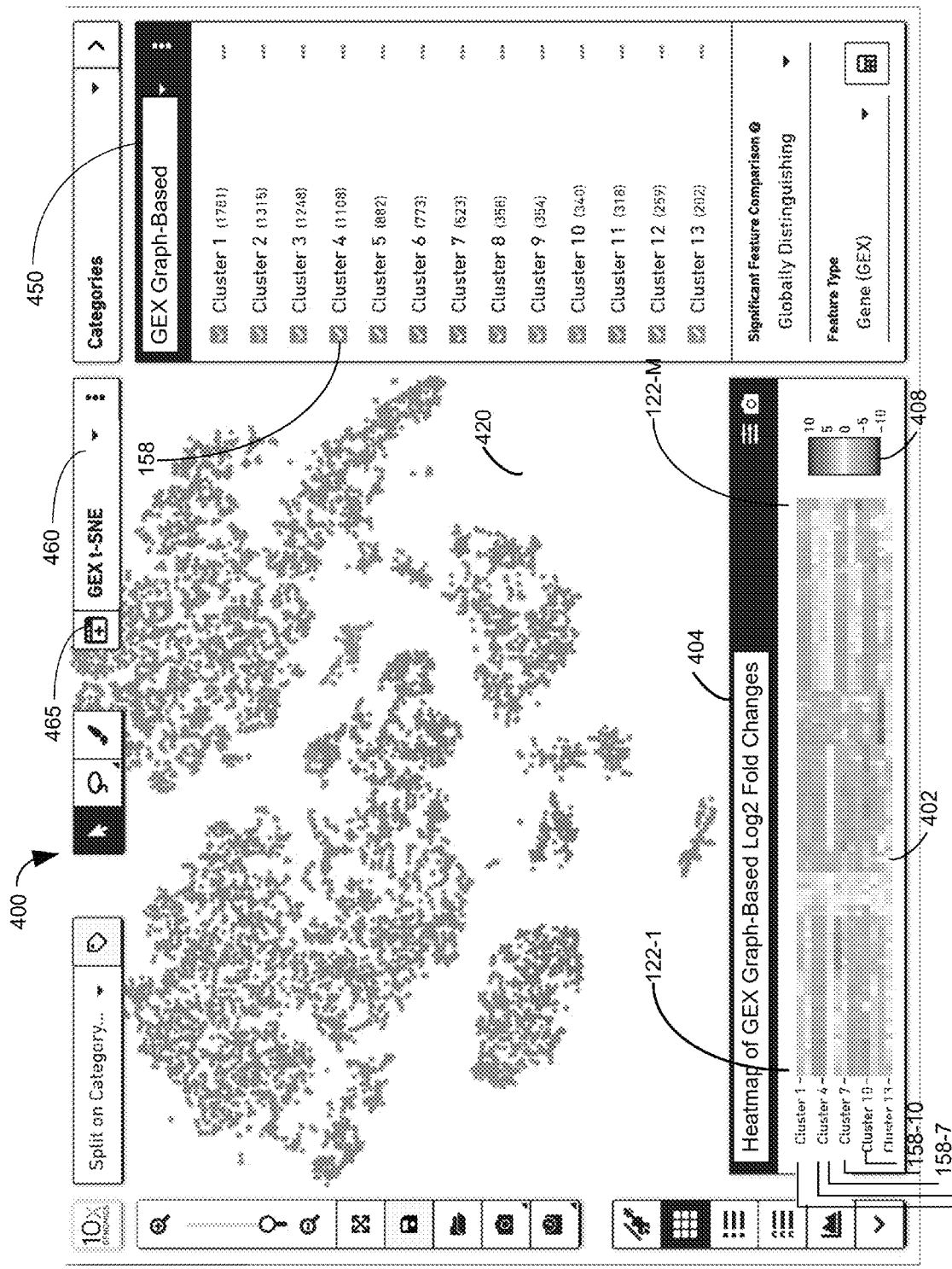
FIG. 4A illustrates an example display in which a heat map that comprises a representation of the differential value for each respective gene in a plurality of genes for each cluster in a first plurality of clusters is displayed in a first panel while each respective cell in a plurality of cells is displayed in a second panel based upon a dimension reduced two-dimensional GEX data point for the respective cells in accordance with some embodiments.

In addition to redundantly representing the corresponding discrete attribute value 124 for each gene 122 in a plurality of genes and the ATAC fragment count 125 for each ATAC peak 123 in a plurality of ATAC peaks for each respective cell 126 in a plurality of cells in both a compressed sparse row format and a compressed sparse column format, in some embodiments, the discrete attribute value dataset 120 is compressed in accordance with a blocked compression algorithm. In some such embodiments, this involves compressing the A and JA data structures but not the IA data structures using a block compression algorithm such as bgzf and storing this in persistent memory 112. Moreover, an index for compressed A and an index for compressed JA enable random seeks of the compressed data. In this way, although the discrete attribute value dataset 120 is compressed, it can be efficiently obtained and restored. All that needs to be done to obtain specific discrete attribute values 124 is seek to the correct block in persistent memory 112 and un-compress the block that contains the values and read them from within that block. Thus, certain operations, for example, like computing a differential heat map described below with reference to FIG. 4A, is advantageously fast with the systems and method of present disclosure because it is known ahead of time which block of compressed data the desired attribute values 124 are in. That is, the systems and methods of the present disclosure know which row that a particular sought after cell is from looking at the row address value of the sparse matrix, which is stored outside of the compressed values. So, all that is needed is to figure out which block has the sought after gene data and what their discrete attribute values are, the algorithm jumps to the spot in the correct block (e.g., bgzf block) that contains the data.

In some embodiments, in addition to the ATAC data, the discrete attribute value dataset 120 represents a whole transcriptome shotgun sequencing (RNA-seq) experiment that quantifies gene expression from a single cell in counts of transcript reads mapped to the genes.

Figure 24A:
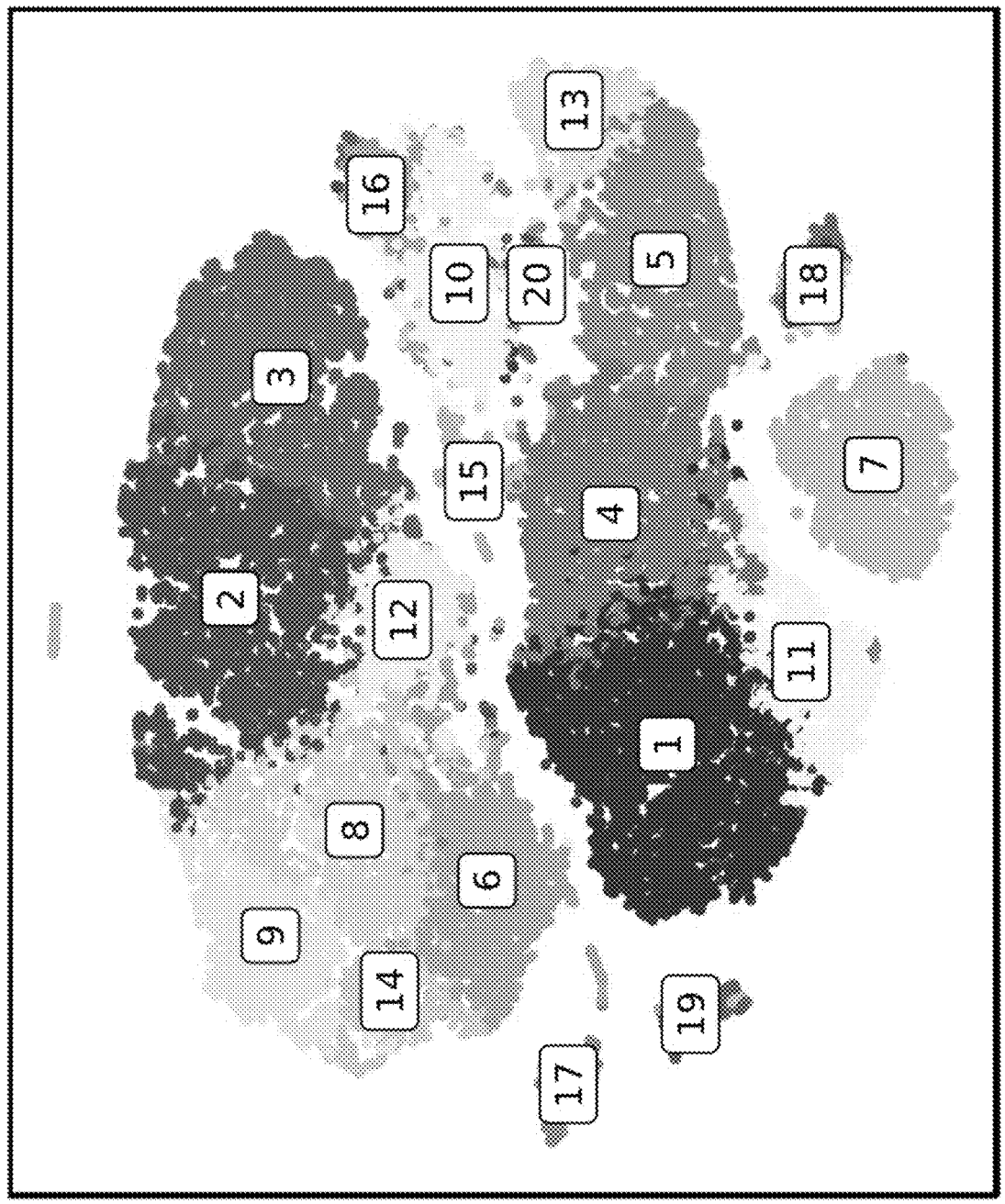
FIGS. 24A and 24B collectively illustrate cell clustering and annotation of cells using expressed markers, in accordance with an embodiment of the present disclosure. Gene expression (GEX) profiling was performed for 24,000 peripheral blood mononuclear cells (PBMCs) in a joint gene expression and open chromatin profiling assay, and gene expression annotations were obtained using expressed markers for 13 categories of cell types. Gene expression annotations were visualized using a t-distributed stochastic neighbor embedding (t-SNE) plot (2400).
Figure 24B:
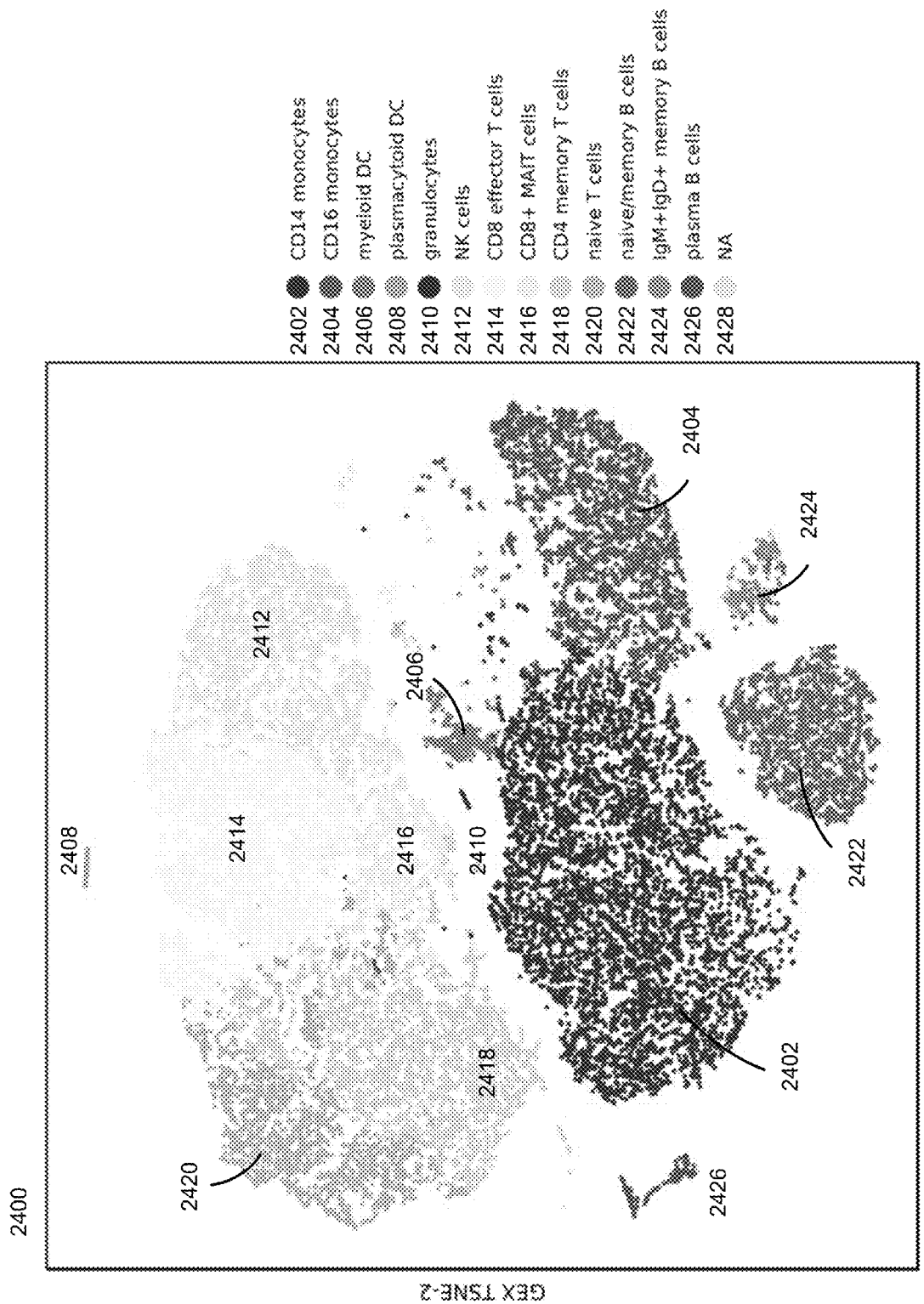

Block 206—clustering the dataset. In some embodiments, once a discrete attribute value dataset 120 is selected, e.g., using the interface illustrated in FIG. 3, the discrete attribute values 124 and/or the ATAC fragments counts 125 in the discrete attribute value dataset 120 are used by the browser module 119 to perform cluster visualization, as illustrated in FIG. 4A, FIG. 24 (e.g., discrete attribute values using gene expression), FIG. 25 (e.g., ATAC), and FIGS. 30A and 30B (e.g., gene expression and/or ATAC). In typical embodiments, either GEX principal component values 164 or ATAC principal component values 165 stored in the discrete attribute value dataset 120 that have been computed by the method of principal component analysis using the discrete attribute values 124 of the genes 122 or the ATAC fragment counts 125 of the ATAC peaks 123 across the plurality of cells 126 of the discrete attribute value dataset 120 are used to perform cluster visualization, as illustrated in FIG. 4A for the case of GEX principal component values 164.

Principal component analysis (PCA) is a mathematical procedure that reduces a number of correlated variables into a fewer uncorrelated variables called "principal components." The first principal component is selected such that it accounts for as much of the variability in the data as possible, and each succeeding component accounts for as much of the remaining variability as possible. The purpose of PCA is to discover or to reduce the dimensionality of the dataset, and to identify new meaningful underlying variables. PCA is accomplished by establishing actual data in a covariance matrix or a correlation matrix. The mathematical technique used in PCA is called Eigen analysis: one solves for the eigenvalues and eigenvectors of a square symmetric matrix with sums of squares and cross products. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows (or columns) of this matrix. See, for example, Duda, Hart, and Stork, *Pattern Classification*, Second Edition, John Wiley & Sons, Inc., NY, 2000, pp. 115-116, which is hereby incorporated by reference.

In some embodiments, principal component analysis, or other forms of data reduction, such as subset selection (e.g., as disclosed in Hastie, 2001, The *Elements of Statistical Learning*, Springer, New York, pp. 55-57), discrete methods (e.g., as disclosed in Furnival & Wilson, 1974, "Regression by Leaps and Bounds," Technometrics 16(4), 499-511), forward/backward stepwise selection (e.g., as disclosed in Berk, 1978, "Comparing Subset Regression Procedures," Technometrics 20:1, 1-6), shrinkage methods (e.g., as disclosed in Hastie, 2001, *The Elements of Statistical Learning*, Springer, New York, pp. 59-66), ridge regression (e.g., as disclosed in Hastie, 2001, *The Elements of Statistical Learning*, Springer, New York, pp. 59-64), lasso techniques (e.g., as disclosed in Hastie, 2001, *The Elements of Statistical Learning*, Springer, New York, pp. 64-65, 69-72, 330-331), derived input direction methods (e.g., principal component regression (PCR), partial least squares (PLS), etc. as disclosed, for example, in Viyayakurma and Schaal, 2000, "Locally Weighted Projection Regression: An O(n) Algorithm for Incremental Real Time Learning in High Dimensional Space, Proc. of Seventeenth International Conference on Machine Learning (ICML2000), pp. 1079-1086), or combinations thereof, are used to reduce the dimensionality of the GEX or ATAC data down to a certain number of dimensions (e.g., ten dimensions, or another number of dimensions) termed principal components or features (e.g., principal components 164 for GEX and principal component 165 for ATAC).

Referring to block 208, in some embodiments, such clustering is performed at a prior time on a remote computer system. That is, in some embodiments, the cluster assignment of each cell 126 was already performed prior to accessing the discrete attribute value dataset 120. In such embodiments, the discrete attribute value dataset 120 includes the GEX cluster assignment 158 and of each cell, as illustrated in FIG. 1B, as well as the ATAC cluster assignment 159 of each cell.

In some embodiments, the cluster assignment of each cell 126 is not performed prior to accessing the discrete attribute value dataset 120 but rather all the principal component analysis computation of the GEX principal component values 164 and the ATAC principal component values 165 is performed after accessing the discrete attribute value dataset 120.

For clustering in accordance with one embodiment of the systems and methods of the present disclosure, regardless at what stage it is performed, consider the case in which each cell 126 is associated with ten genes 122. In such instances, each cell 126 can be expressed as a vector:

$$\vec{X}_{10} = \{x_1, x_2, x_3, x_4, x_5, x_6, x_7, x_8, x_9, x_{10}\}$$

where $X_i$ is the discrete attribute value 124 for the gene i 124 associated with the cell 126. Thus, if there are one thousand cells 126, 1000 GEX vectors are defined. Those cells 126 that exhibit similar discrete attribute values across the set of genes 122 of the dataset 120 will tend to cluster together. For instance, in the case where each cell 126 is an individual cell, the genes 122 correspond to mRNA mapped to individual genes within such individual cells, and the discrete attribute values 124 are mRNA counts for such mRNA, it is the case in some embodiments that the discrete attribute value dataset 120 includes mRNA data from one or more cell types (e.g., diseased state and non-diseased state), two or more cell types, three or more cell types. In such instances, it is expected that cells of like type will tend to have like values for mRNA across the set of genes (mRNA) and therefor cluster together. For instance, if the discrete attribute value dataset 120 includes class a: cells from subjects that have a disease, and class b: cells from subjects that do not have a disease, an ideal clustering classifier will cluster the discrete attribute value dataset 120 into two groups, with one cluster group uniquely representing class a and the other cluster group uniquely representing class b. The same is true for ATAC data. Consider the case in which each cell 126 is associated with ten ATAC peaks 123. In such instances, each cell 126 can be expressed as a vector:

$$\vec{Y}_{10} = \{y_1, y_2, y_3, y_4, y_5, y_6, y_7, y_8, y_9, y_{10}\}$$

where $Y_i$ is the ATAC fragment count 125 for the ATAC peak i 123 associated with the cell 126. Thus, if there are one thousand cells 126, 1000 ATAC vectors are defined, one for each cell. Those cells 126 that exhibit similar ATAC fragment counts across the set of ATAC peaks (open chromatin regions) of the dataset 120 will tend to cluster together.

For GEX clustering in accordance with another embodiment of the systems and methods of the present disclosure, regardless at what stage it is performed, consider the case in which each cell 126 is associated with ten GEX principal component values 164 that collectively represent the variation in the discrete attribute values of a large number of genes 122 across the cells in the dataset. In such instances, each cell 126 can be expressed as a vector:

$$\vec{W}_{10} = \{w_1, w_2, w_3, w_4, w_5, w_6, w_7, w_8, w_9, w_{10}\}$$

where $W_i$ is the GEX principal component value 164 $i$ associated with the cell 126. Thus, if there are one thousand cells 126, one those vectors are defined. Those cells 126 that exhibit similar GEX principal component values 164 across the set of principal component values 164 will tend to cluster together. For instance, in the case where each cell 126 is an individual cell, the genes 122 correspond to mRNA mapped to individual genes within such individual cells, and the discrete attribute values 124 are mRNA counts for such mRNA, it is the case in some embodiments that the discrete attribute value dataset 120 includes mRNA data from one or more cell types (e.g., diseased state and non-diseased state), two or more cell types, three or more cell types, or more than four cell types. In such instances, it is expected that cells of like type will tend to have like principal component values 164 across the set of principal components and therefor cluster together. For instance, if the discrete attribute value dataset 120 includes class a: cells from subjects that have a disease, and class b: cells from subjects that have a disease, an ideal clustering classifier will cluster the discrete attribute value dataset 120 into two groups, with one cluster group uniquely representing class a and the other cluster group uniquely representing class b. In some embodiments, the ATAC principal component values 165 are likewise used to cluster the cells in the dataset into a plurality of ATAC clusters.

Clustering is described on pages 211-256 of Duda and Hart, *Pattern Classification and Scene Analysis*, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar." An example of a nonmetric similarity function s(x, x') is provided on page 216 of Duda 1973.

Once a method for measuring "similarity" or "dissimilarity" between points in a dataset has been selected, clustering requires a criterion function that measures the clustering quality of any partition of the data. Partitions of the dataset that extremize the criterion function are used to cluster the data. See page 217 of Duda 1973. Criterion functions are discussed in Section 6.8 of Duda 1973.

More recently, Duda et al., *Pattern Classification*, Second edition, John Wiley & Sons, Inc. New York, which is hereby incorporated by reference, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, Cluster analysis (Third Edition), Wiley, New York, N.Y.; and Backer, 1995, *Computer-Assisted Reasoning in Cluster Analysis*, Prentice Hall, Upper Saddle River, N.J. Referring to blocks 210-212, particular exemplary clustering techniques that can be used in the systems and methods of the present disclosure to cluster a plurality of vectors, (where each respective vector in the plurality of vectors comprises: (i) the discrete attribute values 124 of the genes 122 of a corresponding cell 126, (ii) the GEX principal components 164 of a corresponding cell 126, (iii) the ATAC fragment counts 125 of the ATAC peaks 123 of a corresponding cell 126, or (iv) the ATAC principal components 165 of a corresponding cell 126) includes, but is not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

Thus, in some embodiments, the discrete attribute values 124 for each gene 122 in the plurality of genes for each respective cell 126 in the plurality of cells, or principal component values 164 derived from the discrete attribute values 124, is clustered thereby assigning each respective cell 126 in the plurality of cell to a corresponding GEX cluster 158 in a first plurality of clusters and thereby assigning a cluster attribute value to each respective cell in the plurality of cells. Further, the ATAC fragment counts 125 for each ATAC peak 123 in the plurality of ATAC peaks for each respective cell 126 in the plurality of cells, or principal component values 165 derived from the ATAC fragment counts 125, is clustered thereby assigning each respective cell 126 in the plurality of cell to a ATAC corresponding cluster 159 in a second plurality of clusters and thereby assigning a cluster attribute value to each respective cell in the plurality of cells.

Referring to block 214, in one embodiment of the present disclosure k-means clustering is used for both the ATAC and GEX clustering. The goal of k-means clustering is to cluster the discrete attribute value dataset 120 based upon the principal components (or the discrete attribute values or ATAC fragment counts) of individual cells into K partitions. Referring to block 214, in some embodiments, K is a number between 2 and 50 inclusive for both the ATAC and the GEX clustering. In some embodiments, the number K is set to a predetermined number such as 10. In some embodiments, the number K is optimized for a particular discrete attribute value dataset 120. Referring to block 216, in some embodiments, a user sets the number K using browser module 119.

FIG. 4A illustrates an instance in which the atac_gex_intron dataset 120, constituting mRNA GEX data and ATAC data from 9,461 different cells, has been clustered, based on GEX principal components 164 into thirteen clusters 158. In some embodiments, for k-means clustering, the user selects in advance how many clusters the clustering algorithm will compute prior to clustering. In some embodiments, no predetermined number of clusters is selected. Instead, clustering is performed until predetermined convergence criteria are achieved. In embodiments where a predetermined number of clusters is determined, k-means clustering of the present disclosure is then initialized with K cluster centers $\mu_1, \ldots, \mu_K$ randomly initialized in two dimensional space. As discussed above, for each respective cell 126 $i$ in the dataset, a vector $X_i$ is constructed of each principal component value 164 associated with the respective cell 126. In the case where K is equal to 10, ten such vectors $\vec{X}$ are selected to be the centers of the ten clusters. Then, each remaining vector $\vec{X}_i$, corresponding to the cells 126 which were not selected to be cluster centers, is assigned to its closest cluster center:

$$C_k = \left\{ n: k = \arg\min_k \left\| \vec{X}_i - \mu_k \right\|^2 \right\}$$

where $C_k$ is the set of examples closest to $\mu_k$ using the objective function:

$$J(\mu, r) = \Sigma_{n=1}^N \Sigma_{k=1}^K r_{nk} \| \vec{X}_i - \mu_k \|^2$$

where $\mu_1, \ldots, \mu_K$ are the K cluster centers and $r_{nk} \in \{0, 1\}$ is an indicator denoting whether a cell 126 $\vec{X}_i$ belongs to a cluster k. Then, new cluster centers $\mu_k$ are recomputed (mean/centroid of the set $C_k$):

$$\mu_k = \frac{1}{|C_k|} \sum_{n \in C_k} \vec{X}_i$$

Then, all vectors $\vec{X}_i$, corresponding to the cells 126 are assigned to the closest updated cluster centers as before. This is repeated while not converged. Any one of a number of convergence criteria can be used. One possible convergence criteria is that the cluster centers do not change when recomputed. The k-means clustering computes a score for each respective cell 126 that takes into account the distance between the respective cell and the centroid of the cluster 158 that the respective cell has been assigned. In some embodiments this score is stored as a cluster attribute value for the cell 126.

Once the clusters are identified, as illustrated in FIG. 4A, individual clusters can be selected to display. For instance, referring to FIG. 4A, clusters 158 can be individually selected or deselected to display or remove them from panel 420. In FIG. 4A, each cluster 158 is assigned a different color. Each point in panel 420 represents one of the 9,461 cells in the atac_gex_intron dataset 120. Moreover, each cell in panel 420 is colored by its GEX cluster assignment 158.

Figure 4B:
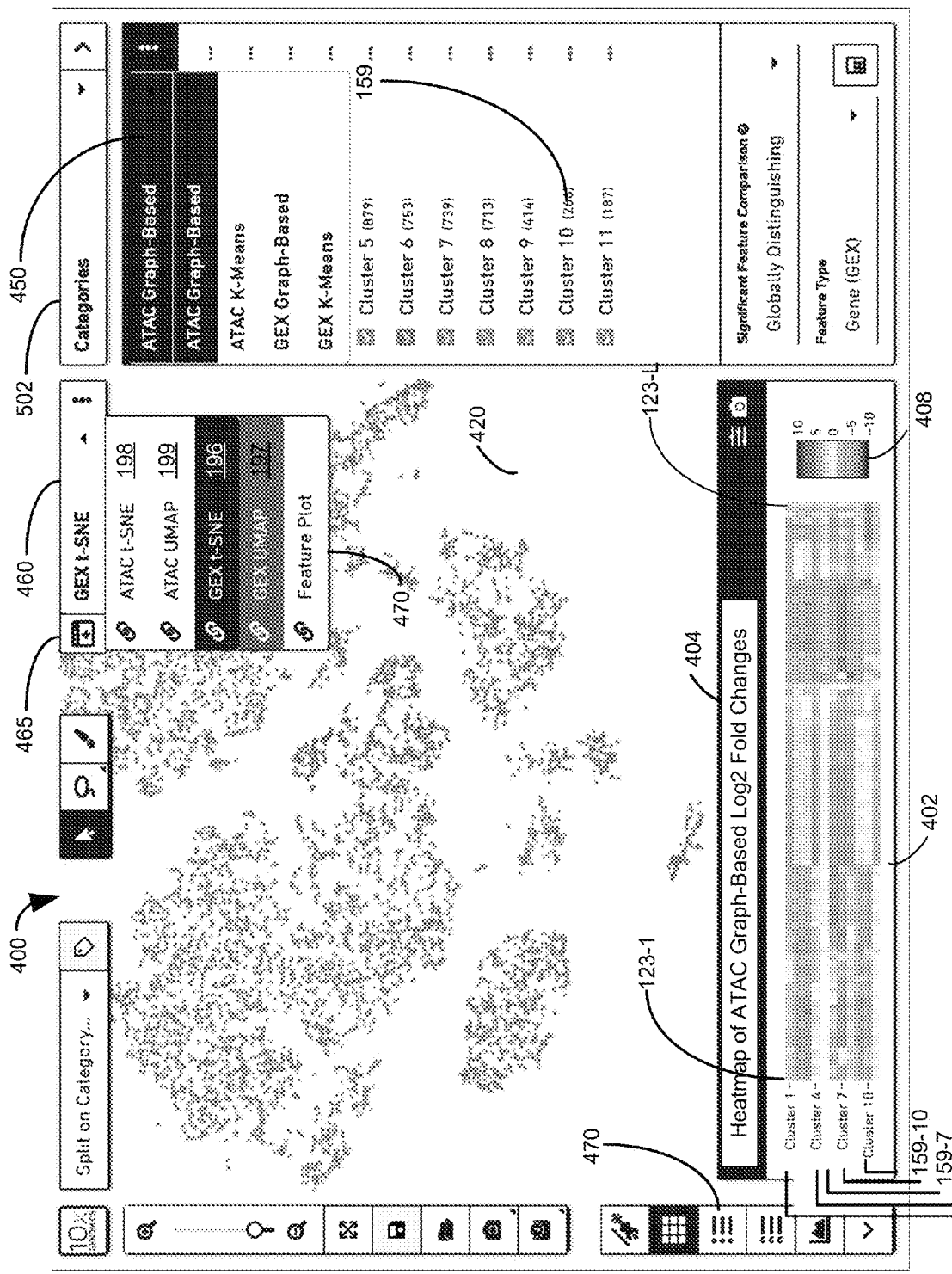
FIG. 4B illustrates an example display in which a heat map that comprises a representation of the differential value for each respective ATAC peak in a plurality of ATAC peaks for each cluster in a second plurality of clusters is displayed in a first panel while each respective cell in a plurality of cells is displayed in a second panel based upon a dimension reduced two-dimensional ATAC data point for the respective cells in accordance with some embodiments.
Figure 26A:
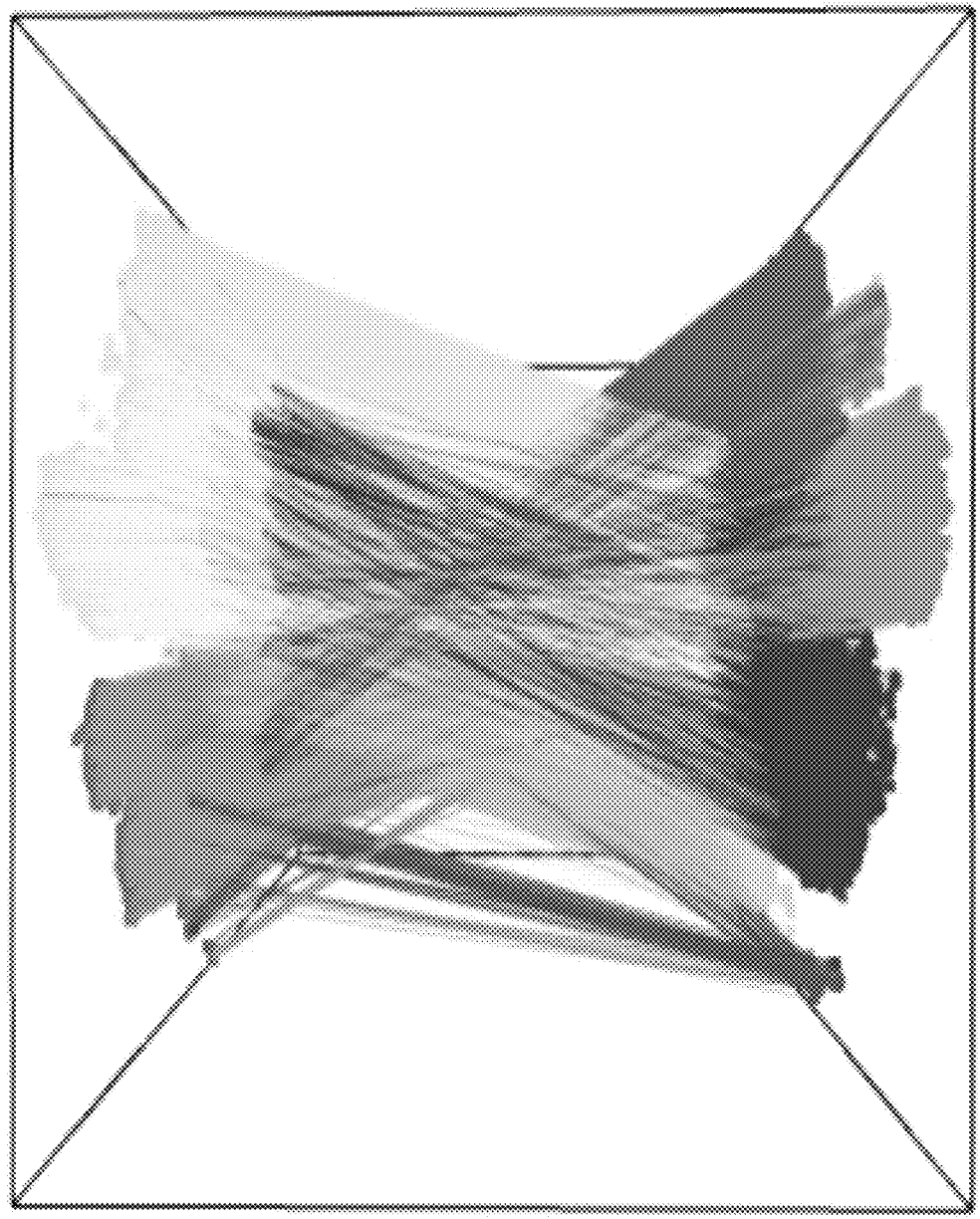
FIGS. 26A and 26B collectively illustrate concordance between the two read-outs of FIGS. 24 (2400) and 25 (2500), in accordance with an embodiment of the present disclosure.
Figure 26B:
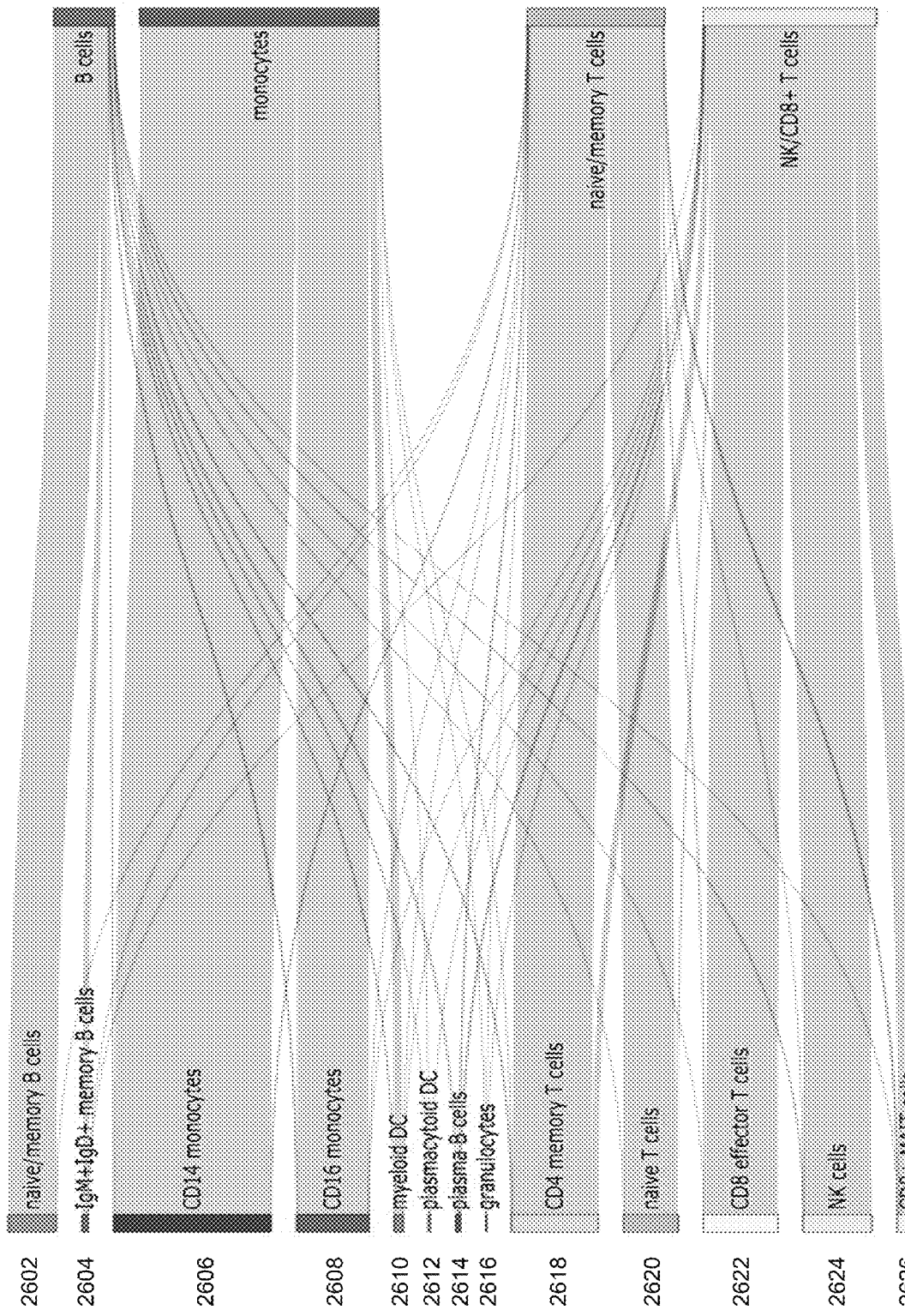

As discussed above, the cells of the discrete attribute value dataset are clustered in two different ways, GEX and ATAC. Affordance 450 can be used to recolor the cells in panel 420 in accordance with the ATAC cluster assignments 159. FIG. 4B illustrates the same view as FIG. 4A, only now the cells are colored using the 11 ATAC cluster assignment 159 instead of the 13 GEX cluster assignments. Moreover, in FIG. 4B, each cell in panel 420 is colored by its ATAC cluster assignment 159. As such, FIG. 4B illustrates displaying, in a first panel 420, a two-dimensional projection (GEX t-SNE) of the plurality of cells based on assignment of the plurality of cells to one of (i) the first plurality of cluster groups or (ii) the second plurality of cluster groups (in the case of FIG. 4B, the GEX cluster groups 158). FIG. 4B further illustrates indicating within the two-dimensional projection, for each respective cell in the plurality of cells, membership in the other of (i) the first plurality of cluster groups or (ii) the second plurality of cluster groups (in the case of FIG. 4B, the ATAC cluster groups 159) thereby visualizing the pattern in the discrete attribute value dataset. FIG. 4B further illustrates membership of each respective cell in the plurality of cells in the other of (i) the first plurality of cluster groups or (ii) the second plurality of cluster groups (in the case of FIG. 4B, the ATAC cluster groups 159) by coloring the respective cell a color that is uniquely associated with a cluster group to which the respective cell has been assigned in the other of (i) the first plurality of cluster groups or (ii) the second plurality of cluster groups (in the case of FIG. 4B, the ATAC cluster groups 159). For example, membership of cells in another plurality of cluster groups is illustrated in FIGS. 27, 28A-C, 29A-D, 32A-B, and 33A-D. Furthermore, in some embodiments, concordance between the first plurality of cluster groups and the second plurality of cluster groups is determined, as illustrated in FIGS. 26A-B.

Returning to FIG. 4A, in accordance with the systems and methods of the present disclosure, in typical embodiments each respective cluster 158 in the plurality of clusters consists of a unique different subset of the plurality of cells 126. Moreover, because in typical embodiments the discrete attribute value dataset 120 is too large to load into the non-persistent memory 111, in typical embodiments this clustering loads less than the entirety of the discrete attribute value dataset 120 into the non-persistent memory 111 at any given time during the clustering. For instance, in embodiments where the discrete attribute value dataset 120 has been compressed using bgzf, only a subset of the blocks of the discrete attribute value dataset 120 are loaded into non-persistent memory during the clustering of the discrete attribute value dataset 120. Once one subset of the blocks of the discrete attribute value dataset 120 have been loaded from persistent memory 112 into non-persistent memory 111 and processed in accordance with the clustering algorithm (e.g., k-means clustering), the subset of blocks of data is discarded from non-persistent memory 111 and a different subset of blocks of the discrete attribute value dataset 120 are loaded from persistent memory 112 into non-persistent memory 111 and processed in accordance with the clustering algorithm of the clustering module 152.

In some embodiments k-means clustering is used to assign cells 126 to clusters 158. In some such embodiments the k-means clustering uses as input the GEX principal component values 164 for each cell 126 as the basis for clustering the cells into cluster. Thus, the k-means algorithm computes like clusters of cells from the higher dimensional data (the set of GEX principal component values 164) and then after some resolution, the k-means clustering tries to minimize error. In this way, the k-means clustering provides cluster assignments 158, which are recorded in the discrete attribute value dataset 120. In some embodiments, with k-means clustering, the user decides in advance how many clusters 158 there will be. In some embodiments, the feature of k-means cluster is exploited by running a series of k-means clustering runs, with each different run having a different number of clusters (a different value for K). Thus, in some embodiments, a separate k-means clustering is performed on the GEX principal component data values 164 of each cell 122, ranging from two clusters to ten clusters, with each k-means clustering identifying a separability score (quality score) and all the results of each clustering embedded in the discrete attribute value dataset 120 from K=2 through K=10. In some such embodiments, such clustering is performed for K=2 through K=25. In some such embodiments, such clustering is performed for K=2 through K=100. The clustering that is displayed by default in such embodiments is the k-means clustering (1, . . . N) that has the highest separability score. In FIG. 4A, the cells of each cluster assignment 158 are displayed in panel 420 in a different color (e.g., the cells assigned to cluster 1 are displayed in red, the cells assigned to cluster 6 are displayed in green, etc.). In other embodiments, the cells of each cluster assignment 158 is displayed in panel 420 with a different dot pattern or hash pattern.

In some embodiments k-means clustering is also used to assign cells 126 to clusters 159. In some such embodiments the k-means clustering uses as input the ATAC principal component values 165 for each cell 126 as the basis for clustering the cells into cluster. Thus, the k-means algorithm computes like clusters of cells from the higher dimensional data (the set of ATAC principal component values 165) and then after some resolution, the k-means clustering tries to minimize error. In this way, the k-means clustering provides cluster assignments 159, which are recorded in the discrete attribute value dataset 120. In some embodiments, with k-means clustering, the user decides in advance how many clusters 159 there will be. In some embodiments, the feature of k-means cluster is exploited by running a series of k-means clustering runs, with each different run having a different number of clusters (a different value for K). Thus, in some embodiments, a separate k-means clustering is performed on the ATAC principal component data values 165 of each cell 122, ranging from two clusters to ten clusters, with each k-means clustering identifying a separability score (quality score) and all the results of each clustering embedded in the discrete attribute value dataset 120 from K=2 through K=10. In some such embodiments, such clustering is performed for K=2 through K=25. In some such embodiments, such clustering is performed for K=2 through K=100. The clustering that is displayed by default in such embodiments is the k-means clustering (1, . . . N) that has the highest separability score. In FIG. 4B, the cells assigned to each cluster assignment 159 is displayed in a different color. In other embodiments, the cells of each cluster assignment 159 is displayed in panel 420 with a different dot pattern or hash pattern.

The k-means clustering algorithm is an attempt to elucidate like clusters 158 (or clusters 159) within the data. There is no guarantee that the clusters 158 or clusters 159 represent physiologically significant events. In other words, a priori, it is not known what the clusters 158 or what cluster 159 mean. What is known is that the algorithm has determined that there are differences between the cells 126 that are being represented by different colors or different hash patterns or symbols. The systems and methods of the present disclosure provide tools for determining whether there is any meaning behind the differences between the clusters such as the heat map of panel 404.

Referring to block 214, in some embodiments of the present disclosure, rather than using k-means clustering for clustering ATAC or GEX data, a Louvain modularity algorithm is used. See, Blondel et al., Jul. 25, 2008, "Fast unfolding of communities in large networks," arXiv: 0803.0476v2 [physical.coc-ph], which is hereby incorporated by reference. In some embodiments, the user can choose a clustering algorithm. In some embodiments, the user can choose between at least K-means clustering and a Louvain modularity algorithm. In some embodiments, the clustering of the dataset comprises application of a Louvain modularity algorithm to a map, the map comprising a plurality of nodes and a plurality of edges. Each node in the plurality of nodes represents a cell in the plurality of cells. The coordinates in N-dimensional space of a respective node in the plurality of nodes are a set of principal components of the corresponding cell in the plurality of cells. The set of principal components is either derived from the corresponding discrete attribute values 124 of the plurality of genes for the corresponding cell or from the corresponding ATAC fragment counts 125 of the plurality of ATAC peaks 123 for the corresponding cell, where N is the number of principal components in each set of principal components. An edge exists in the plurality of edges between a first node and a second node in the plurality of nodes when the first node is among the k nearest neighboring nodes of the second node in the first plurality of node, where the k nearest neighboring nodes to the second node is determined by computing a distance in the N-dimensional space between each node in the plurality of nodes, other than the second node, and the second node. In some embodiments, the distance is a Euclidean distance. In other embodiments, other distance metrics are used (e.g., Chebyshev distance, Mahalanobis distance, Manhattan distance, etc.). In typical embodiments, the nodes and the edges are not weighted for the Louvain modularity algorithm. In other words, each node and each edge receives the same weight in such embodiments Block 218—Computing differential attribute values for each cluster. Once each cell 126 has been assigned to a respective cluster 158 based on GEX data, the systems and methods of the present disclosure are able to compute, for each respective gene 122 in the plurality of genes for each respective cluster 158 in a first plurality of clusters, a difference in the discrete attribute value 124 for the respective gene 122 across the respective subset of cells 126 in the respective cluster 158 relative to the discrete attribute value 124 for the respective gene 122 across the first plurality of clusters 158 other than the respective cluster, thereby deriving a differential value for each respective gene 122 in the plurality of genes for each cluster 158 in the first plurality of clusters. For instance, in some such embodiments, a differential expression algorithm is invoked to find the top expressing genes that are different between cell classes or other forms of cell labels. This is a form of the general differential expressional problem in which there is one set of expression data and another set of expression data and the question to be addressed is determining which genes are differentially expressed between the datasets.

In some embodiments differential expression is computed as the $\log_2$ fold change in (i) the average number of transcripts (discrete attribute value 124 for gene 122) measured in each of the cells of the subject cluster 158 that map to a particular gene and (ii) the average number of transcripts measured in each of the cells of all clusters other than the subject cluster that map to the particular gene. Thus, consider the case in which the subject cluster contains 50 cells and on average each of the 50 cells contain 100 transcripts for gene A. The remaining clusters in the first plurality of clusters (the GEX clusters) collectively contain 250 cells and on average each of the 250 cells contain 50 transcripts for gene A. Here, the fold change in expression for gene A is 100/50 and the $\log_2$ fold change is $\log_2(100/50)=1$. In FIG. 4A, lower panel, the $\log_2$ fold change is computed in this manner for each gene in represented in the discrete attribute set 120 and such values are presented in a color coded heat map.

Figure 2B:
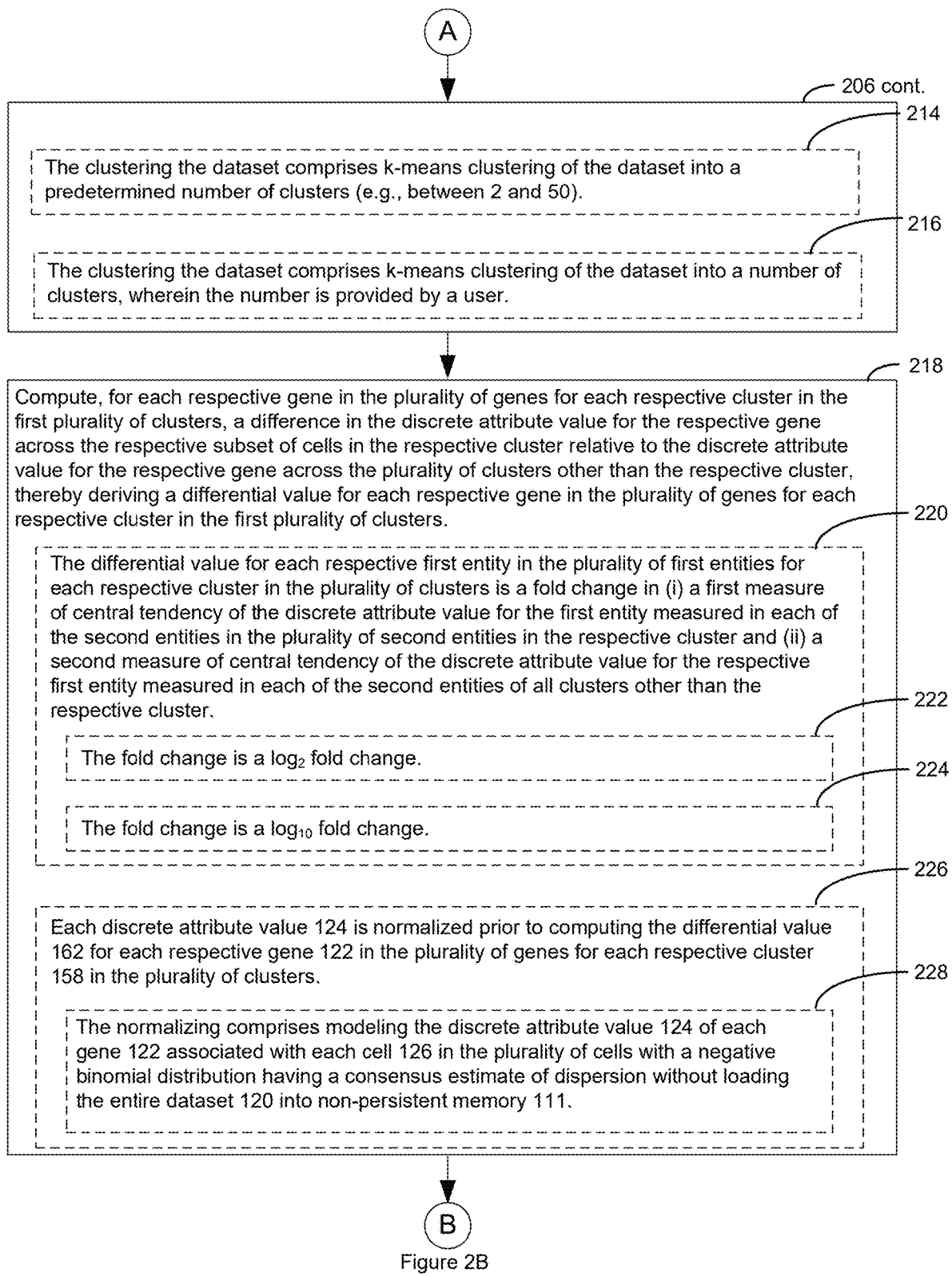

Referring to block 220 of FIG. 2B, in some embodiments, the differential value for each respective gene 122 in the plurality of genes for each respective cluster 158 in the first plurality of clusters (the GEX clusters) is a fold change in (i) a first measure of central tendency of the discrete attribute value 124 for the gene measured in each of the cells 126 in the plurality of cells in the respective cluster 158 and (ii) a second measure of central tendency of the discrete attribute value 124 for the respective gene 122 measured in each of the cells 126 of all clusters 158 in the first plurality of clusters other than the respective cluster. In some embodiments, the first measure of central tendency is an arithmetic mean, weighted mean, midrange, midhinge, trimean, Winsorized mean, median, or mode of all the discrete attribute value 124 for the gene measured in each of the cells 126 in the plurality of cells in the respective cluster 158. In some embodiments, the second measure of central tendency is an arithmetic mean, weighted mean, midrange, midhinge, trimean, Winsorized mean, median, or mode of all the discrete attribute values 124 for the gene 122 measured in each of the cells 126 in the plurality of cells 126 in all clusters of the first plurality of clusters other than the respective cluster. Referring to block 222, in some embodiments the fold change is a $\log_2$ fold change. Referring to block 224, in some embodiments the fold change is a $\log_{10}$ fold change.

Moreover, once each cell 126 has also been assigned to a respective cluster 159 based on ATAC data, the systems and methods of the present disclosure are able to compute, for each respective ATAC peak 123 in the plurality of ATAC peaks for each respective cluster 159 in a second plurality of clusters (the ATAC clusters), a difference in the ATAC fragment count 125 for the respective ATAC peak 123 across the respective subset of cells 126 in the respective cluster 159 relative to the ATAC fragment count 125 for the ATAC peak 123 across the second plurality of clusters 159 other than the respective cluster, thereby deriving a differential value for each respective ATAC peak 123 in the plurality of ATAC peaks for each cluster 159 in the second plurality of clusters (the ATAC clusters). For instance, in some such embodiments, a differential abundance algorithm is invoked to find the top ATAC peaks that are different between cell classes or other forms of cell labels. This is a form of the general differential abundance problem in which there is one set of abundance data and another set of abundance data and the question to be addressed is determining which peaks are differentially abundant between the datasets.

In some embodiments differential abundance is computed as the $\log_2$ fold change in (i) the average fragment count (ATAC fragment count for peak 123) measured in each of the cells of the subject cluster 159 that map to a particular ATAC peak 123 and (ii) the average number of fragments measured in each of the cells of all clusters other than the subject cluster that map to the particular ATAC peak 123. In FIG. 4B, lower panel, the $\log_2$ fold change is computed in this manner for each ATAC peak (123-1 through 123-L) represented in the discrete attribute set 120 and such values are presented in a color coded heat map.

In some embodiments, the differential value for each respective ATAC peak 123 in the plurality of ATAC peaks 123 for each respective cluster 159 in the second plurality of clusters is a fold change in (i) a first measure of central tendency of the ATAC fragment count 125 for the ATAC peak 123 measured in each of the cells 126 in the plurality of cells in the respective cluster 159 and (ii) a second measure of central tendency of the ATAC fragment count 125 for the respective ATAC peak 123 measured in each of the cells 126 of all clusters 159 in the second plurality of clusters (the ATAC clusters) other than the respective cluster. In some embodiments, the first measure of central tendency is an arithmetic mean, weighted mean, midrange, midhinge, trimean, Winsorized mean, median, or mode of all the ATAC fragment counts 125 for the ATAC peak 123 measured in each of the cells 126 in the plurality of cells in the respective cluster 159. In some embodiments, the second measure of central tendency is an arithmetic mean, weighted mean, midrange, midhinge, trimean, Winsorized mean, median, or mode of all the ATAC fragment count for the ATAC peak 123 measured in each of the cells 126 in the plurality of cells 126 in all clusters other than the respective cluster.

Given that measurement of discrete attribute values 124 for genes 122 (e.g., count of mRNA that maps to a given gene in a given cell) is typically noisy, the variance of the discrete attribute values 124 for genes 122 in each cell 126 (e.g., count of mRNA that maps to given gene in a given cell) in a given cluster 158 of such cells 126 is taken into account in some embodiments. This is analogous to the t-test which is a statistical way to measure the difference between two samples. Here, in some embodiments, statistical methods that take into account that a discrete number of genes 122 are being measured (as the discrete attribute values 124 for a given gene 122) for each cell 126 and that model the variance that is inherent in the system from which the measurements are made are implemented.

Thus, referring to block 226 of FIG. 2B, in some embodiments, each discrete attribute value 124 is normalized prior to computing the differential value 162 for each respective gene 122 in the plurality of first genes for each respective cluster 158 in the plurality of clusters. Referring to block 228 of FIG. 2B, in some embodiments, the normalizing comprises modeling the discrete attribute value 124 of each gene associated with each cell in the plurality of cells with a negative binomial distribution having a consensus estimate of dispersion without loading the entire dataset into non-persistent memory 111. Such embodiments are useful, for example, for RNA-seq experiments that produce discrete attribute values 124 for genes 122 (e.g., digital counts of mRNA reads that are affected by both biological and technical variation). To distinguish the systematic changes in expression between conditions from noise, the counts are frequently modeled by the Negative Binomial distribution. See Yu, 2013, "Shrinkage estimation of dispersion in Negative Binomial models for RNA-seq experiments with small sample size," Bioinformatics 29, pp. 1275-1282, which is hereby incorporated by reference.

The negative binomial distribution for a discrete attribute value 124 for a given gene 122 includes a dispersion parameter for the discrete attribute value 124 which tracks the extent to which the variance in the discrete attribute value 124 exceeds an expected value. See Yu, 2013, "Shrinkage estimation of dispersion in Negative Binomial models for RNA-seq experiments with small sample size," Bioinformatics 29, pp. 1275-1282, and Cameron and Trivedi, 1998, "Regression Analysis of Count Data," Econometric Society Monograph 30, Cambridge University Press, Cambridge, UK, each of which is hereby incorporated by reference. Rather than relying upon an independent dispersion parameter for the discrete attribute value 124 of each gene 122, some embodiments of the disclosed systems and methods advantageously use a consensus estimate across the discrete attribute values 124 of all the genes 122. This is termed herein the "consensus estimate of dispersion." The consensus estimate of dispersion is advantageous for RNA-seq experiments in which whole transcriptome shotgun sequencing (RNA-seq) technology quantifies gene expression in biological samples in counts of transcript reads mapped to the genes, which is one form of experiment used to acquire the disclosed dicreate attribute values 124 in some embodiments, thereby concurrently quantifying the expression of many genes. The genes share aspects of biological and technical variation, and therefore a combination of the gene-specific estimates and of consensus estimates can yield better estimates of variation. See Yu, 2013, "Shrinkage estimation of dispersion in Negative Binomial models for RNA-seq experiments with small sample size," Bioinformatics 29, pp. 1275-1282 and Anders and Huber, 2010, "Differential expression analysis for sequence count data," Genome Biol 11, R106, each of which are hereby incorporated by reference. For instance, in some such embodiments, sSeq is applied to the discrete attribute value 124 of each gene 122. sSeq is disclosed in Yu, 2013, "Shrinkage estimation of dispersion in Negative Binomial models for RNA-seq experiments with small sample size," Bioinformatics 29, pp. 1275-1282, which is hereby incorporated by reference. sSeq scales very well with the number of genes that are being compared. In typical experiments in accordance with the present disclosure, each cluster 158 may include hundreds, thousands, tens of thousands, hundreds of thousands, or more cells 126, and each respective cell 126 may contain mRNA expression data for hundreds, or thousands of different genes. As such, sSeq is particularly advantageous when testing for differential expression in such large discrete attribute value datasets 120. Of all the RNA-seq methods, sSeq is advantageously faster. Other single-cell differential expression methods exist and can be used in some embodiments, but they are designed for smaller-scale experiments. As such sSeq, and more generally techniques that normalize discrete attribute values by modeling the discrete attribute value 124 of each gene 122 associated with each cell 126 in the cells with a negative binomial distribution having a consensus estimate of dispersion without loading the entire discrete attribute value dataset 120 into non-persistent memory 111, are practiced in some embodiments of the present disclosure. In some embodiments, in the case where parameters for the sSeq calculations are calculated, the discrete attribute values for each of the genes is examined in order to get a dispersion value for all the genes. Here, although all the discrete attribute values for the genes are accessed to make the calculation, the discrete attribute values are not all read from persistent memory 112 at the same time. In some embodiments, discrete attribute values are obtained by traversing through blocks of compressed data, a few blocks at a time. That is, a set of blocks, consisting of the few compressed blocks, in the dataset are loaded into non-persistent memory from persistent memory and are analyzed to determine which genes the set of blocks represent. An array of discrete attribute values across the plurality of cells, for each of the genes encoded in the set of blocks, is determined and used calculate the variance, or other needed parameters, for these genes across the plurality of cells. This process is repeated in which new set of blocks is loaded into non-persistent memory from persistent memory, analyzed to determine which genes are encoded in the new set of blocks, and then used to compute the variance, or other needed parameters, for these genes across the plurality of cells for each of the genes encoded in the new set of blocks, before discarding the set of blocks from non-persistent memory. In this way, only a limited amount of the discrete attribute value dataset 120 is stored in non-persistent memory 111 at any given time (e.g., the data for a particular block that contain the discrete attribute values for a particular gene). Further, the systems and methods of the present disclosure are able to compute variance in discrete attribute values for a given gene because it has got all the discrete attribute values for that particular gene across the entire discrete attribute value dataset 120 stored in a single bgzf block, in some embodiments. Once the variance, or other needed parameter is computed for the genes (or discrete attribute values of the genes), the accessed set of bgzf blocks (which is a subset of the total number of bgzf blocks in the dataset), which had been loaded into non-persistent memory 111 to perform the computation, is dropped from non-persistent memory and another set of bgzf blocks for which such computations is to be performed is loaded into the non-persistent memory 111 from the persistent memory 112. In some embodiments, such processes run in parallel (e.g., one process for each gene) when there are multiple processing cores 102. That is, each processing core concurrently analyzes a different respective set of blocks in the dataset and computes statistics for those genes represented in the respective set of blocks.

Following such normalization, in some embodiments, for each respective gene 122, an average (or some other measure of central tendency) discrete attribute value 124 (e.g., count of the gene 122) for each gene 122 is calculated for each cluster 158 of cells 126. Thus, in the case where there is a first cluster 158-1 and second cluster 158-2 of cells 126, the average (or some other measure of central tendency) discrete attribute value 124 of the gene "A" across all the cells 126 of the first cluster 158-1, and the average (or some other measure of central tendency) discrete attribute value 124 of gene "A" across all the cells 126 of the second cluster 158-2 is calculated and, from this, the differential value for each gene with respect to the first cluster is calculated. This is repeated for each of the genes 122 in a given cluster. It is further repeated for each cluster 158 in the plurality of clusters. In some embodiments, there are other factors that are considered, like adjusting the initial estimate of the variance in the discrete attribute value 124 when the data proves to be noisy. In the case where there are more than two clusters, the average (or some other measure of central tendency) discrete attribute value 124 of gene A across all the cells 126 of the first cluster 158-1 and the average (or some other measure of central tendency) discrete attribute value 124 of gene A across all the cells 126 of the remaining cluster 158-2, is calculated and used to compute the differential value.

Moreover, in some embodiments, for each respective ATAC peak 123, an average (or some other measure of central tendency) ATAC fragment count 125 (e.g., count of the ATAC peak 123) for each ATAC peak 123 is calculated for each cluster 159 of cells 126. Thus, in the case where there is a first cluster 159-1 and a second cluster 159-2 of cells 126, the average (or some other measure of central tendency) ATAC fragment count 125 of the ATAC peak "A" across all the cells 126 of the first cluster 159-1, and the average (or some other measure of central tendency) ATAC fragment count 125 of ATAC peak "A" across all the cells 126 of the second cluster 159-2 is calculated and, from this, the differential value for each ATAC peak with respect to the first cluster 159-1 is calculated. This is repeated for each of the ATAC peaks 123 in a given cluster. It is further repeated for each cluster 159 in the second plurality of clusters. In some embodiments, there are other factors that are considered, like adjusting the initial estimate of the variance in the ATAC fragment count 125 when the data proves to be noisy. In the case where there are more than two clusters, the average (or some other measure of central tendency) ATAC fragment count 125 of ATAC peak A across all the cells 126 of the first cluster 159-1 and the average (or some other measure of central tendency) ATAC fragment count 125 of ATAC peak A across all the cells 126 of the remaining cluster 159-2, is calculated and used to compute the differential value.

Block 230—Display a heat map. With reference to FIG. 4A, once the differential value for each respective gene 122 in the plurality of genes for each respective cluster 158 in the first plurality of clusters has been computed or otherwise obtained, a heat map 402 of these differential values is displayed in a first panel 404 of an interface 400. In FIG. 4A, the heat map 402 comprises a representation of the differential value for each respective gene 122 in the plurality of genes for each cluster 158 in the first plurality of clusters. As illustrated in FIG. 4A, the differential value for each gene 122 in the plurality of genes (e.g., genes 122-1 to 122-M) for each cluster 158 (e.g., clusters 158-1, 158-4, 158-7, and 158-10) is illustrated in a color coded way to represent the $\log_2$ fold change in accordance with color key 408. In accordance with color key 408, those genes 122 that are upregulated in the cells 126 of a particular cluster 158 relative to all other clusters in the first plurality of clusters are assigned more positive values, whereas those genes 122 that are down-regulated in the cells 126 of a particular cluster 158 relative to all other clusters in the first plurality of clusters are assigned more negative values. In some embodiments, the heat map can be exported to persistent storage (e.g., as a PNG graphic, JPG graphic, or other file formats). Heat maps obtained using differential values for genes are further illustrated in FIGS. 29E and 32C.

With reference to FIG. 4B, once the differential value for each respective ATAC peak 123 in the plurality of ATAC peaks for each respective cluster 159 in the second plurality of clusters has been computed or otherwise obtained, a heat map 402 of these differential values is displayed in a first panel 404 of an interface 400. In FIG. 4B, the heat map 402 comprises a representation of the differential value for each ATAC peak 123 in the plurality of ATAC peaks 123 for each cluster 159 in the second plurality of clusters. As illustrated in FIG. 4B, the differential value for each ATAC peak 123 in the plurality of ATAC peaks (e.g., ATAC peaks 123-1 to 122-L) for each cluster 159 (e.g., clusters 158-1, 158-4, 158-7, and 158-9) is illustrated in a color coded way to represent the $\log_2$ fold change in accordance with color key 408. In accordance with color key 408, those ATAC peaks 123 that are upregulated in the cells 126 of a particular cluster 159 relative to all other clusters in the second plurality of clusters are assigned more positive values, whereas those ATAC peaks 123 that are down-regulated in the cells 126 of a particular cluster 159 relative to all other clusters in the second plurality of clusters are assigned more negative values. In some embodiments, the heat map is exported to persistent storage (e.g., as a PNG graphic, JPG graphic, or other file formats).

Figure 25A:
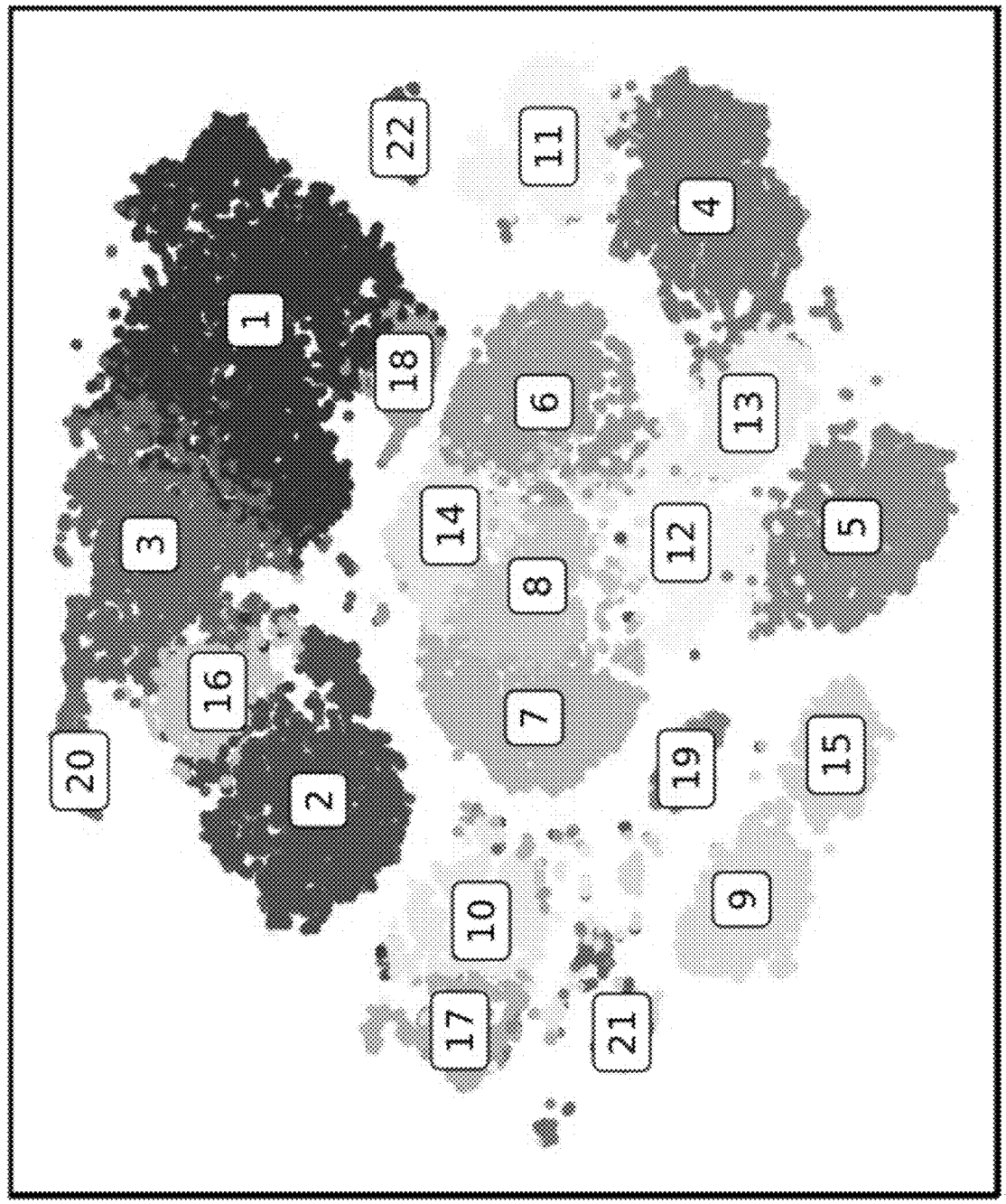
FIGS. 25A and 25B collectively illustrate cell clustering and annotation of cells using chromatin accessibility (open chromatin), in accordance with an embodiment of the present disclosure. An assay of transposase-accessible chromatin (ATAC) was performed for 24,000 peripheral blood mononuclear cells (PBMCs) in a joint gene expression and open chromatin profiling assay, and open chromatin annotations were obtained using transcription factor accessibility for 4 categories of cell types (monocytes, NK/CD8 T cells, naïve/memory T cells, and B cells) (2500).
Figure 25B:
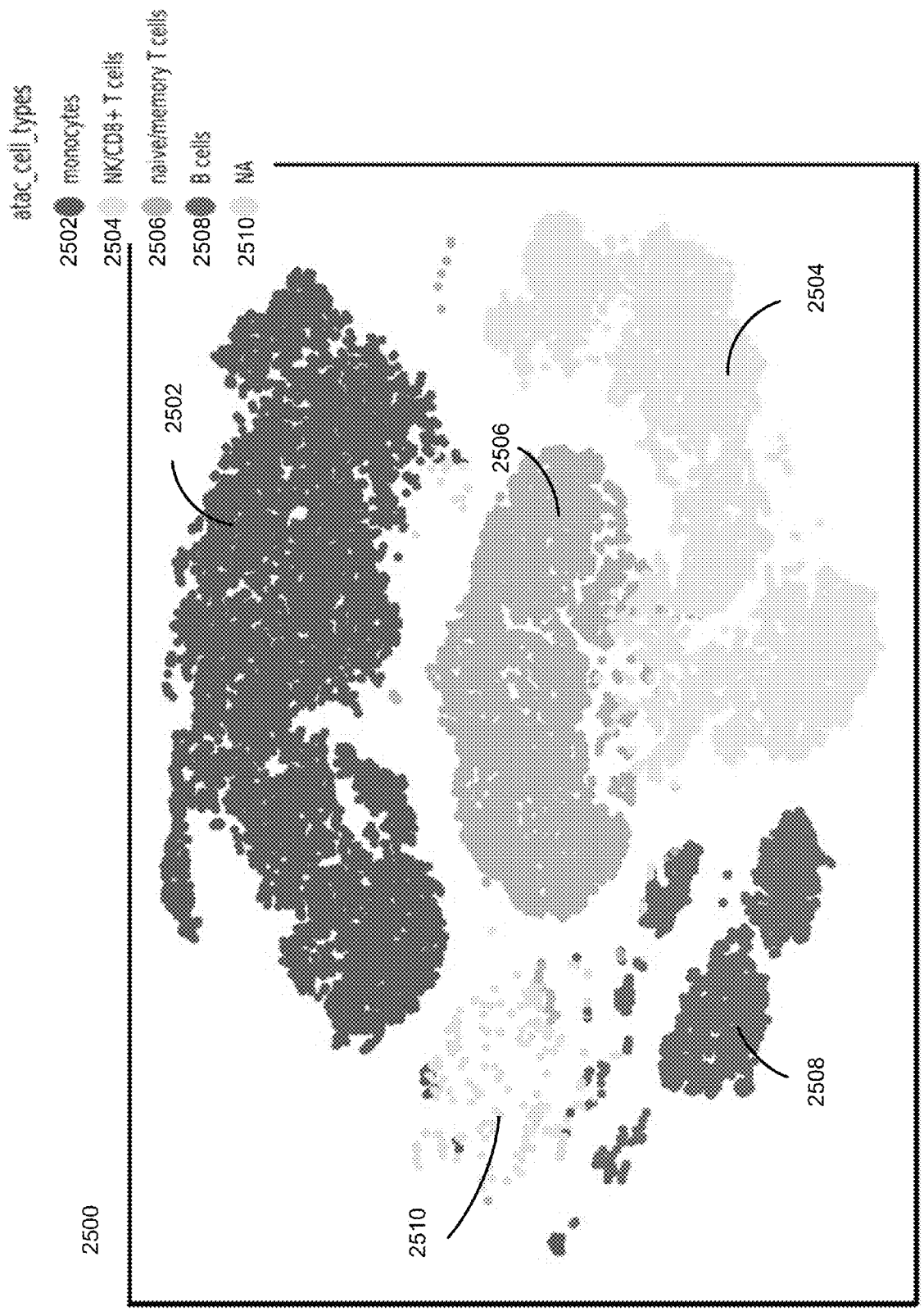

Block—232 plot a two dimensional plot of the cells in the dataset. With reference to FIGS. 4A and 4B, in some embodiments, a two-dimensional visualization (e.g., as illustrated in FIGS. 24, 25, and/or 30) of the discrete attribute value dataset 120 is also provided in a second panel 420. In some embodiments, the two-dimensional visualization in the second panel 420 is computed by a back end pipeline that is remote from visualization system 100 and is stored as two-dimensional datapoints 166 (FIG. 1B) and/or as projections 196 or 197 (FIG. 1C) in the discrete attribute value dataset 120. In some embodiments, the two-dimensional visualization 420 is computed by the visualization system 100 (FIG. 1A).

Because the initial data is sparse, in some embodiments, in the case of GEX data, the two-dimensional visualization 420 of FIG. 4A is prepared by computing a plurality of GEX principal component values 164 for each respective cell 126 in the plurality of cells based upon respective discrete attribute values 124 for each gene 122 in the respective cell 126. In some embodiments, the plurality of GEX principal component values is ten. In some embodiments, the plurality of GEX principal component values is between 5 and 100.

In some embodiments, the plurality of GEX principal component values is between 5 and 50. In some embodiments, the plurality of GEX principal component values is between 8 and 35. Then, a dimension reduction technique is applied to the plurality of GEX principal components values for each respective cell 126 in the plurality of cells thereby determining a two-dimensional data point 166 for each cell 126 in the plurality of cells. Each respective cell 126 in the plurality of cells is then plotted in the second panel of FIG. 4A based upon the two-dimensional data point for the respective cell.

Likewise, in some embodiments, in the case of ATAC data, the two-dimensional visualization 420 of FIG. 4B is prepared by computing a plurality of ATAC principal component values 165 for each respective cell 126 in the plurality of cells based upon respective ATAC fragment counts 125 for each ATAC peak 123 in the respective cell 126. In some embodiments, the plurality of ATAC principal component values is ten. In some embodiments, the plurality of principal component values is between 5 and 100. In some embodiments, the plurality of ATAC principal component values is between 5 and 50. In some embodiments, the plurality of ATAC principal component values is between 8 and 35. Then, a dimension reduction technique is applied to the plurality of ATAC principal components values for each respective cell 126 in the plurality of cells thereby determining a two-dimensional data point 167 for each cell 126 in the plurality of cells. Each respective cell 126 in the plurality of cells is then plotted in the second panel of FIG. 4B based upon the two-dimensional data point for the respective cell.

t-SNE.

In some embodiments, the dimension reduction technique that is applied to the GEX principal components or the ATAC principal components is t-Distributed Stochastic Neighboring Entities (t-SNE) (e.g., as illustrated in FIGS. 24, 25, and/or 30). In the case of GEX data, the collection of two-dimensional datapoints 166 upon application of t-SNE is stored as a GEX t-SNE projection 196. In the case of ATAC data, the collection of two-dimensional datapoints 167 upon application of t-SNE is stored as an ATAC t-SNE projection 198 (FIG. 1D). One embodiment of the present disclosure provides a back end pipeline for computing such t-SNE projections that is performed on a computer system other than the visualization system 100. In other embodiments, the visualization system 100 computes the t-SNE projections. t-SNE is particularly well-suited for embedding high-dimensional data (e.g., the GEX principal components values 164 or the ATAC principal components values 165) computed for each measured cell based upon the measured discrete attribute value (e.g., expression level) of each gene 122 (e.g., expressed mRNA) or the ATAC fragments counts for each ATAC peak in a respective cell as determined by principal component analysis into a space of two, which can then be visualized as a two-dimensional visualization (e.g. the scatter plot of second panel 420) of FIG. 4A (GEX t-SNE projection 196) or FIG. 4B (ATAC t-SNE projection 198). In some embodiments, t-SNE is used to model each high-dimensional object (the principal components of each measured cell) as a two-dimensional point in such a way that cells with similar principal component values are modeled as nearby two-dimensional datapoints 166/167 and cells with dissimilar principal component values are modeled as distant two-dimensional datapoints 166/167 in the two-dimensional plot.

UMAP.

In some embodiments, the dimension reduction technique that is applied to the GEX principal components or the ATAC principal components is a uniform manifold approximation and projection (UMAP). In the case of GEX data, the collection of two-dimensional datapoints 166 upon application of UMAP is stored as a GEX UMAP projection 197. In the case of ATAC data, the collection of two-dimensional datapoints 167 upon application of UMAP is stored as an ATAC UMAP projection 199 (FIG. 1D). One embodiment of the present disclosure provides a back end pipeline for computing such UMAP projections that is performed on a computer system other than the visualization system 100. In other embodiments, the visualization system 100 computes the UMAP projections. UMAP is particularly well-suited for embedding high-dimensional data (e.g., the GEX principal components values 164 or the ATAC principal components values 165) computed for each measured cell based upon the measured discrete attribute value (e.g., expression level) of each gene 122 (e.g., expressed mRNA) or the ATAC fragments counts for each ATAC peak in a respective cell as determined by principal component analysis into a space of two, which can then be visualized as a two-dimensional visualization. In some embodiments, UMAP is used to model each high-dimensional object (the principal components of each measured cell) as a two-dimensional point in such a way that cells with similar principal component values are modeled as nearby two-dimensional datapoints 166/167 and cells with dissimilar principal component values are modeled as distant two-dimensional datapoints 166/167 in the two-dimensional plot.

Affordance 460 of FIGS. 4A and 4B can be used to select among the GEX t-SNE projection 196, GEX UMAP projection 197, ATAC t-SNE projection 198, and ATAC UMAP projection 199 for the discrete attribute value dataset 120.

Other Dimension Reduction Methods.

In some embodiments, referring to block 236 and block 238 of FIG. 2C, rather than using t-SNE or UMAP, the dimension reduction technique used to reduce the principal component values 164 or 165 to a corresponding two-dimensional datapoint 166 or 167 is Sammon mapping, curvilinear components analysis, stochastic neighbor embedding, Isomap, maximum variance unfolding, locally linear embedding, or Laplacian Eigenmaps. These techniques are described in van der Maaten and Hinton, 2008, "Visualizing High-Dimensional Data Using t-SNE," Journal of Machine Learning Research 9, 2579-2605, which is hereby incorporated by reference. In some embodiments, the user has the option to select the dimension reduction technique. In some embodiments, the user has the option to select t-SNE, Sammon mapping, curvilinear components analysis, stochastic neighbor embedding, Isomap, maximum variance unfolding, locally linear embedding, or Laplacian Eigenmaps.

Referring to block 234 of FIG. 2C, and as illustrated in FIGS. 4A and 4B, in some embodiments each cluster 158 in the first plurality of clusters (GEX clusters) or the second plurality of clusters (ATAC clusters) is assigned a different graphic or color code. Further, each respective cell 126 in the plurality of entities is coded in the second panel 420 with the different graphic or color code for the cluster 158 the respective cell has been assigned.

Referring to block 240, in some embodiments, each of the respective plurality of principal component values is derived from the discrete attribute values of each gene or ATAC peak in a corresponding cell in the plurality of cells by principal component analysis. In some embodiments, such analysis is performed on a computer system remote from the visualization system 100 prior to storing the discrete attribute value dataset 120 in persistent memory. In such embodiments the dataset includes each respective plurality of principal component values.

Now that the overall functionality of the systems and methods of the present disclosure has been introduced, attention turns to additional features afforded by the present disclosure. As illustrated in FIG. 4A, for each cluster 158, there is a row in the lower panel 404 that illustrates the fold change (e.g. $\log_2$ fold change) of the average discrete attribute value 124 for each respective gene 122 across the cells 126 of the cluster 158 represented by the row compared to the average discrete attribute value 124 of the respective gene 122 in the remainder of the population of cells represented by the discrete attribute value dataset 120.

Correspondingly, as illustrated in FIG. 4B, for each cluster 159, there is a row in the lower panel 404 that illustrates the fold change (e.g. $\log_2$ fold change) of the average ATAC peak fragment count 125 for each ATAC peak 123 across the cells 126 of the cluster 159 represented by the row compared to the average ATAC peak fragment count 125 of the respective ATAC peak 123 in the remainder of the population of cells represented by the discrete attribute value dataset 120.

Referring back to FIG. 4A, legend 408 on the right of the lower panel 404 indicates the $\log_2$ fold change compared to the average expression in the population. For instance, in one color coding scheme, red means higher abundance (higher discrete attribute values 124), blue means lower abundance (lower discrete attribute values 124), in a given cluster 158 as compared to the average abundance in the population. In FIG. 4A, $\log_2$ fold change in expression refers to the $\log_2$ fold value of (i) the average number of transcripts (discrete attribute value) measured in each of the cells of the subject cluster that map to a particular gene 122 and (ii) the average number of transcripts measured in each of the cells of all clusters other than the subject cluster that map to the particular gene.

Referring to FIG. 4B, here legend 408 on the right of the lower panel 404 indicates the $\log_2$ fold change compared to the average fragment count in the population. For instance, in one color coding scheme, red means higher fragment counts (higher ATAC fragment counts 125), blue means lower fragment counts (lower ATAC fragment counts 125), in a given cluster 159 as compared to the average fragment count in the population. In FIG. 4B, $\log_2$ fold change in fragment counts refers to the $\log_2$ fold value of (i) the average number of ATAC fragment counts measured in each of the cells of the subject cluster that map to a particular ATAC fragment 123 and (ii) the average number of ATAC fragment counts measured in each of the cells of all clusters other than the subject cluster that map to the particular ATAC peak.

Linked windows. To allow users to see common characteristics or compare different images at once, one aspect of the present disclosure makes use of novel linked windows. Referring to FIG. 4B, clicking on the "Add Window" affordance 465 brings up a list of projections 470 for the discrete attribute value dataset 120 to open in a linked window. Thus, referring to FIG. 4B, the GEX t-SNE projection 196 is visible in panel 420 and the user has the option of adding a window for the ATAC t-SNE projection 198, ATAC UMAP projection 199, GEX UMAP projection 197, or another instance of the GEX t-SNE projection 196. In fact, the user can add multiple instances of any of these projections by successive use of the "Add Window" affordance. Clicking on one of the projections listed in panel 470 opens that projection in a smaller window within the operating system 116. Actions taken in the main window, such as changing the active category, or showing expression or accessibility for a particular feature, will propagate to the linked windows.

Figure 5:
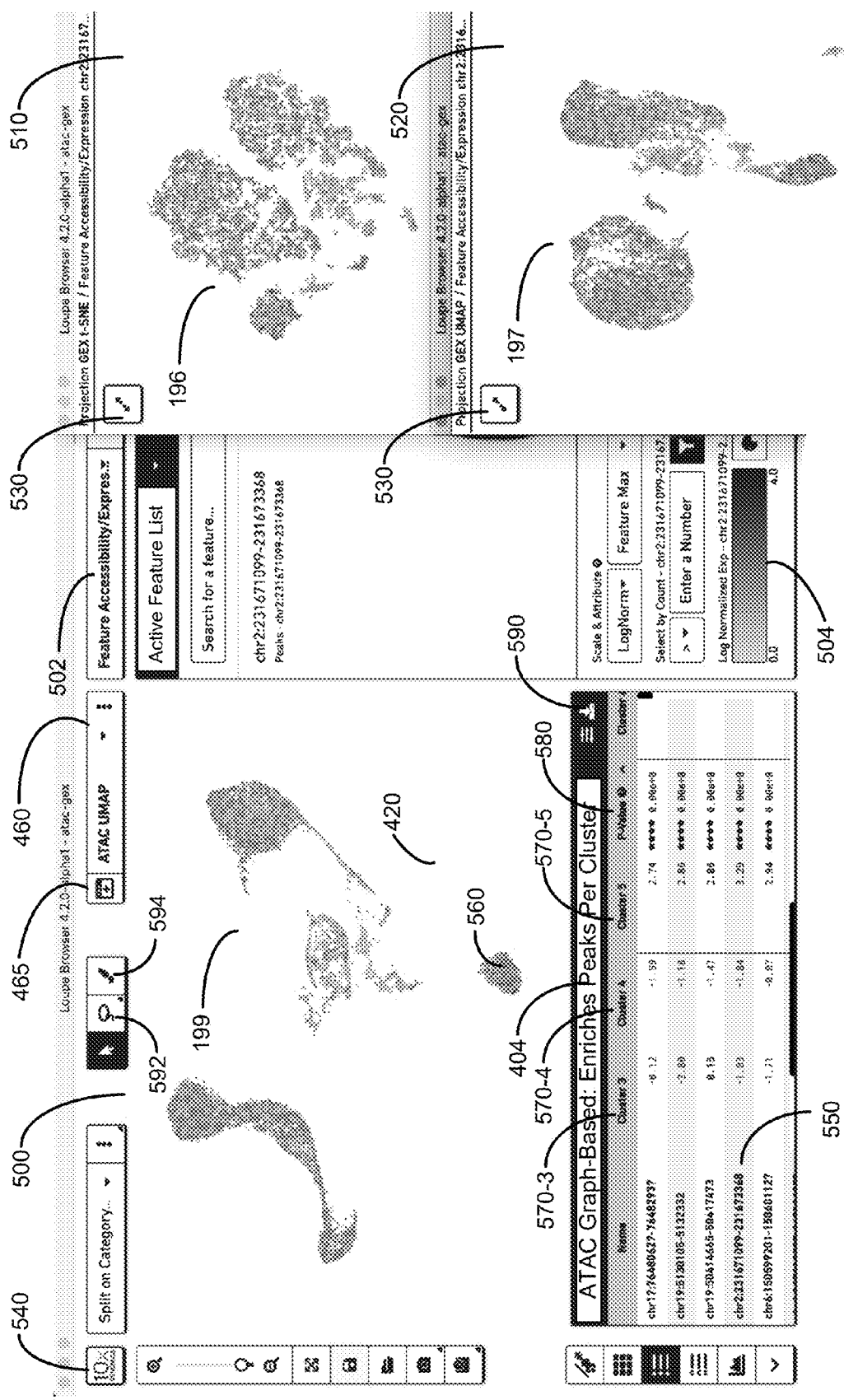
FIG. 5 illustrates the use of linked windows in accordance with some embodiments of the present disclosure.

FIG. 5 shows three concurrent views of the same discrete attribute value dataset 120: the ATAC UMAP projection 199, the GEX t-SNE projection 196 and the GEX UMAP projection 197, with the same feature, ATAC peak chr2: 2311671099-231673368 highlighted. In other words, for each projection, each respective cell in the plurality of cells represented by the discrete attribute dataset 120 are color coded in accordance with scale 504 by the ATAC fragment count 125 at ATAC peak chr2:2311671099-231673368. Zoom, pan and split operations are separate per window. In this manner, it is also easy to see whether there is coherence between gene expression-derived clusters 158 and ATAC-derived clusters 159.

Figure 6:
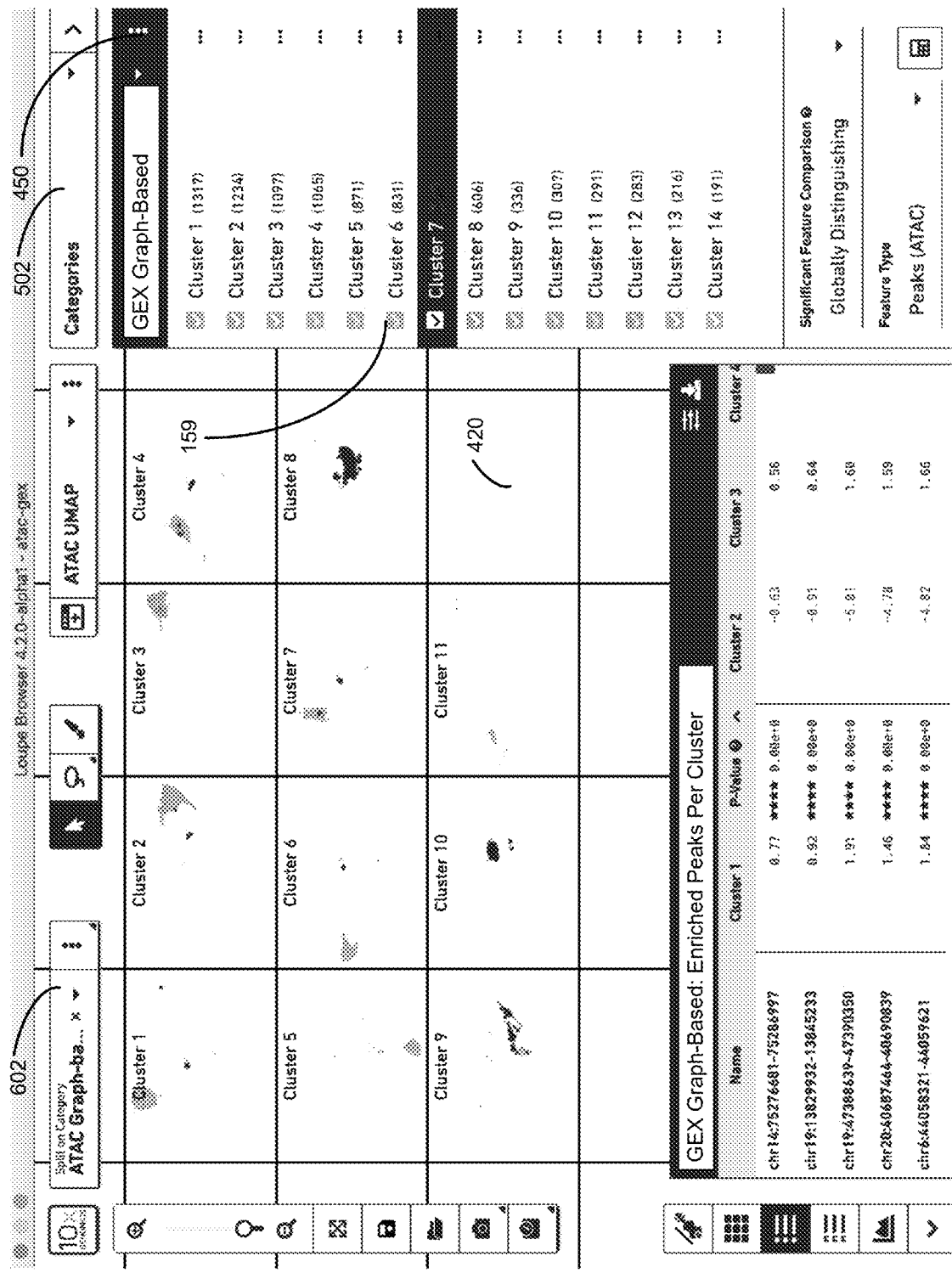
FIG. 6 illustrates splitting the view of a discrete attribute value dataset into component clusters in accordance with some embodiments of the present disclosure.

With both ATAC and GEX projections displayed, a user can toggle between the ATAC graph-based clusters 159 and the GEX graph-based clusters 158 using a combination of affordances 502 and 502. Specifically, affordance 502 can be used to toggle between "Feature Accessibility Expression" as illustrated in FIG. 5 and "Categories" as illustrated in FIGS. 4A and 6. When affordance 502 is in "Categories" mode, the user can then select between GEX clusters 158 and ATAC clusters 159 using affordance 450 as illustrated in FIGS. 4B and 6. In particular, FIG. 4B shows that the user can used panel 450 to select between ATAC graph-based clusters, ATAC K-means clusters, GEX graph-based clusters, and GEX K-means clusters. Such toggling between ATAC graph-based clusters and GEX graph-based clusters provides one basis for determining whether certain clusterings appear concordant between the GEX and ATAC data. Moreover, using the split view affordance 602 in the main window 420 allows for cross-projection overlap analysis in further detail. For instance, in FIG. 6 affordance 502 is toggled to "Categories," affordance 450 is used to select GEX graph-based clustering, and affordance 602 is used to select ATAC graph-based clusters. Thus, in FIG. 6, the cells in the plurality of cells in the discrete attribute dataset 120 for each ATAC graph based cluster 159 are shown in separate subpanels in the main panel 420 of FIG. 6. Moreover, each such cell is mapped into the subpanel based on its two-dimensional UMAP coordinates. Finally, each cell is uniquely colored not by which graph based ATAC cluster 159 it has been assigned, but rather, by which GEX based cluster 158 it have been assigned. Thus, from FIG. 6, it is apparent that there is a strong correlation between the GEX Graph-Based Cluster 7 and the ATAC Graph-Based Cluster 8 because almost all of the cells in ATAC Graph-Based Cluster 8 in the main panel 402 are colored with the color assigned to GEX Graph-Based Cluster 7.

Referring to FIG. 5, in some embodiments, linked windows (e.g., windows 510 and 520 open initially in miniaturized view as illustrated in FIG. 5, where only the projection and a button 530 to expand the window to a full panel is shown. However, when using a mouse cursor to hover over a linked window (e.g., window 510), more options are revealed that provide a subset of common actions, such as the ability to pan and zoom a linked window. However, the linked windows are still predominantly controlled by manipulating the original, or anchor window 500.

Referring to FIG. 5, changes to the anchor window 500 will propagate automatically to the other linked windows (e.g., windows 510 and 520), such as selection of active clusters (which clusters are displayed across all the linked windows), selecting an individual cluster, creating a new cluster or modifying a cluster, selecting one or more genes or ATAC peaks to show feature expression (gene, peak), changing cluster membership, changing individual cluster colors or the active expression color scale, and in selecting transcription factor motifs. However, features such as panning, zooming, and window sizes remain independent in the anchor and linked windows.

Referring to FIG. 5, it is possible to expand a linked window from mini-mode to access the full range of visualization options by clicking on the expand affordance 530. Clicking affordance 530 within the linked window again will shrink the linked window (e.g., 510, 520, etc.) back to mini-mode. In some embodiments, changes to the discrete attribute value dataset 120 in any window are saved through the anchor window. Thus, referring to FIG. 5, any change to the discrete attribute value dataset 120 in windows 510 or 520 must be saved through window 500 in such embodiments. As such, using linked windows avoids having to jump back and forth, making the investigation fluid and intuitive.

It is also possible to have other linked windows open to concurrently view additional discrete attribute value datasets 120. To avoid confusion, when multiple attribute value datasets are displayed, the color of the button 540 (FIG. 5) on the main window 500 and the affordances 530 of the windows linked to the main window of each discrete attribute value dataset will adopt its own common unique color that is different than that of any other discrete attribute value datasets 120 that are displayed. For instance, if an additional discrete attribute dataset 120 was displayed along with the one illustrated in FIG. 5, the logo 540 of main window 500, and the affordance 530 of windows 510 and 520 of the originally displayed discrete attribute value dataset would have a common first color while the logo 540 of the main window 500 of the additional discrete attribute dataset 120 along with the displayed affordances 530 of windows linked to it would have a common second color different from the first color.

Moreover, linked windows are not limited to spatial discrete attribute value datasets 120. Most gene expression datasets have both t-SNE and UMAP projections 121 (see U.S. patent application Ser. No. 16/442,800 entitled "Systems and Methods for Visualizing a Pattern in a Dataset," filed Jun. 17, 2019) that can be linked and viewed at the same time in a similar fashion.

While linked windows have been illustrated in conjunction with showing mRNA-based UMI abundance as well as ATAC peak count, they can also be used to illustrate the quantification of other analytes, arranged in two-dimensional space using dimension reduction algorithms such as t-SNE or UMAP, including any combination of intracellular proteins (e.g., transcription factors), cell methylation status, other forms of accessible chromatin (e.g., DNase-seq, and/or MNase-seq), metabolites, barcoded labelling agents (e.g., the oligonucleotide tagged antibodies) and V(D)J sequences of an immune cell receptor (e.g., T-cell receptor), perturbation agent (e.g., a CRISPR crRNA/sgRNA, TALEN, zinc finger nuclease, and/or antisense oligonucleotides. Any of these can be compared to each other or to mRNA-based UMI abundance and/or ATAC peak count.

Linkage Matrix Visualization and Analysis.

Figure 7:
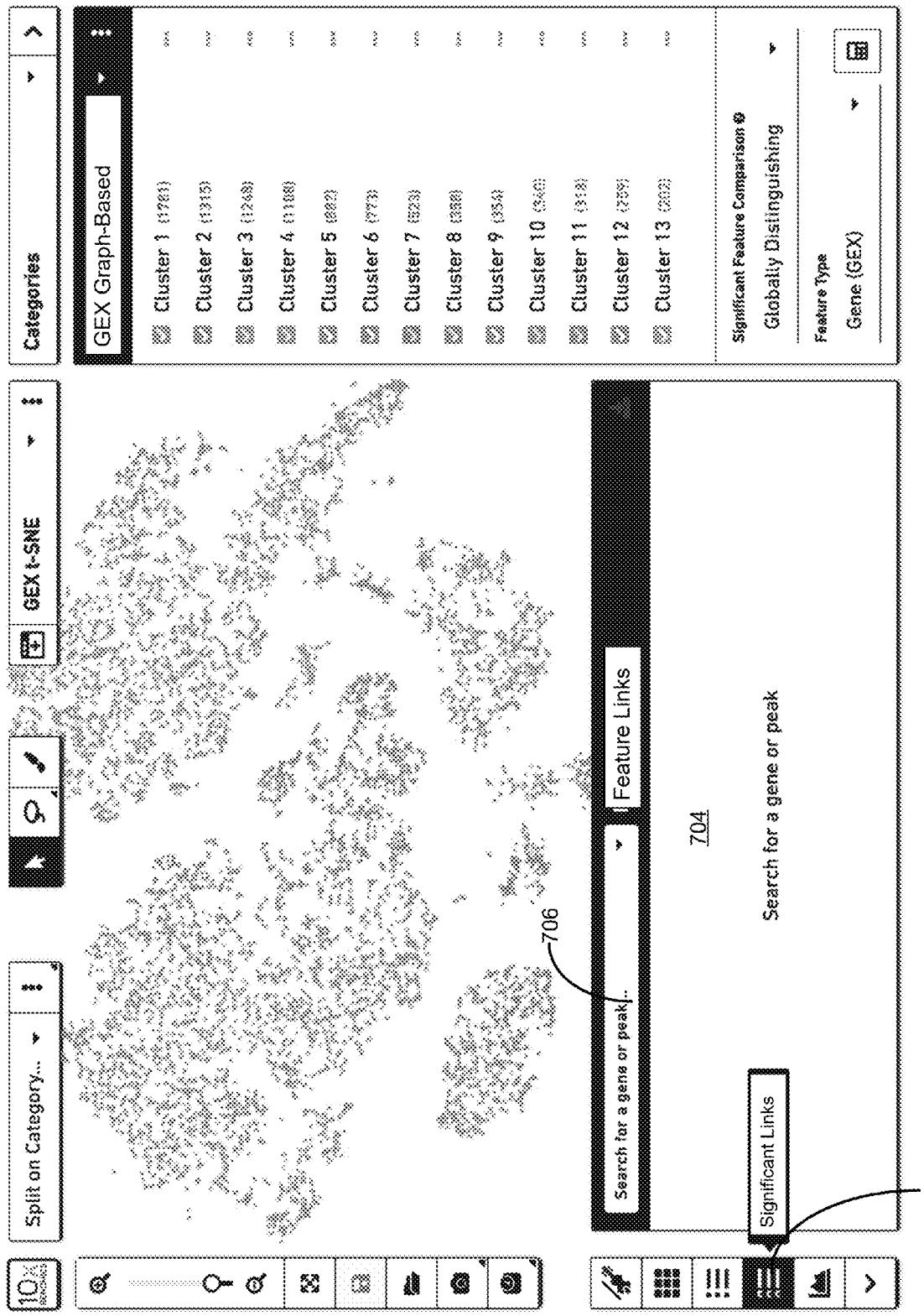
FIG. 7 illustrates selection of links to a gene or peak in accordance with some embodiments of the present disclosure.
Figure 8:
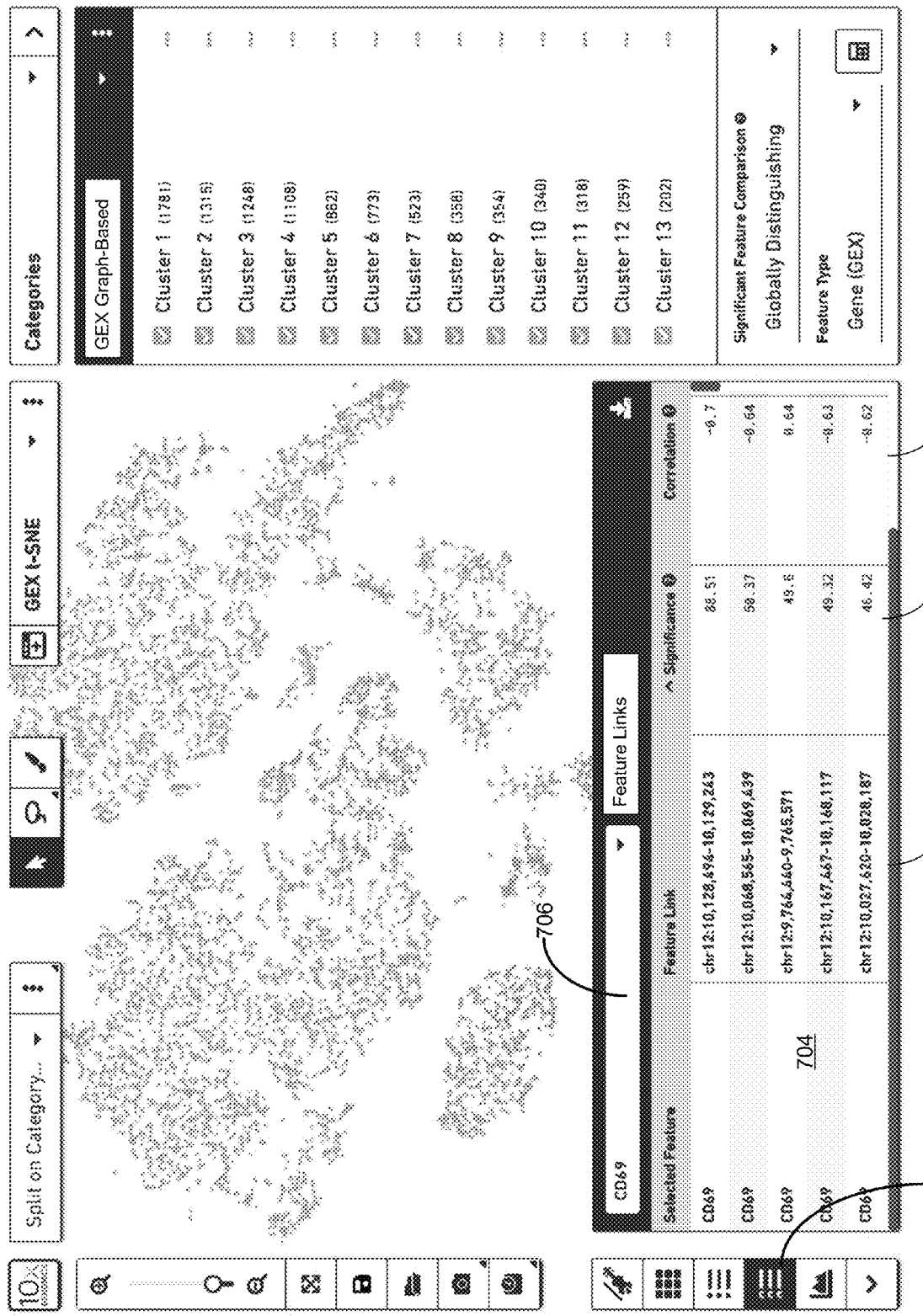
FIG. 8 illustrates a table of ATAC peaks that are linked to the gene CD69 in accordance with some embodiments of the present disclosure.

Linkage table. Advantageously, some embodiments of the present disclosure provide the ability to review linkages between features, such as ATAC peaks and genes that are in the above described feature-linkage matrix 187, in a tabular fashion or in an interactive graphical fashion. In some embodiments, the tabular view is accessed by clicking on the list-with-arcs affordance (e.g., icon) 702 of FIG. 7. This bring up a Feature Links table 704 which remained empty as illustrated in FIG. 7 until a search query is entered into search query box 706. A user may type a gene or peak of interest into search query box 706. The search query box will generate autocomplete options for both genes and ATAC peaks based on gene and ATAC peaks represented in the active discrete attribute value dataset 120. When a feature is autocompleted or otherwise entered into the search query box 706, a query will generate a table of linked features and display them in the Feature Links Table 704, as shown for gene CD69 in FIG. 8. This table contains the name of both the original feature of interest (CD69 in FIG. 8) and the linked features 802, the significance 192 of such linkages, and the correlation 191 and the distance between features. Clicking on any of column headers in table 704 will sort the table of linked features by the values of that column. For instance, clicking on the column header of significance 192 column a first time will sort the linked features of table 704 from highest to lowest significance to CD69. Then, clicking on the column header of significance 192 column a second time will sort the linked features from lowest to highest significance to CD69. In this manner, a user can rapidly get a picture of other features strongly linked to the source feature (CD69 in FIG. 8).

Figure 9:
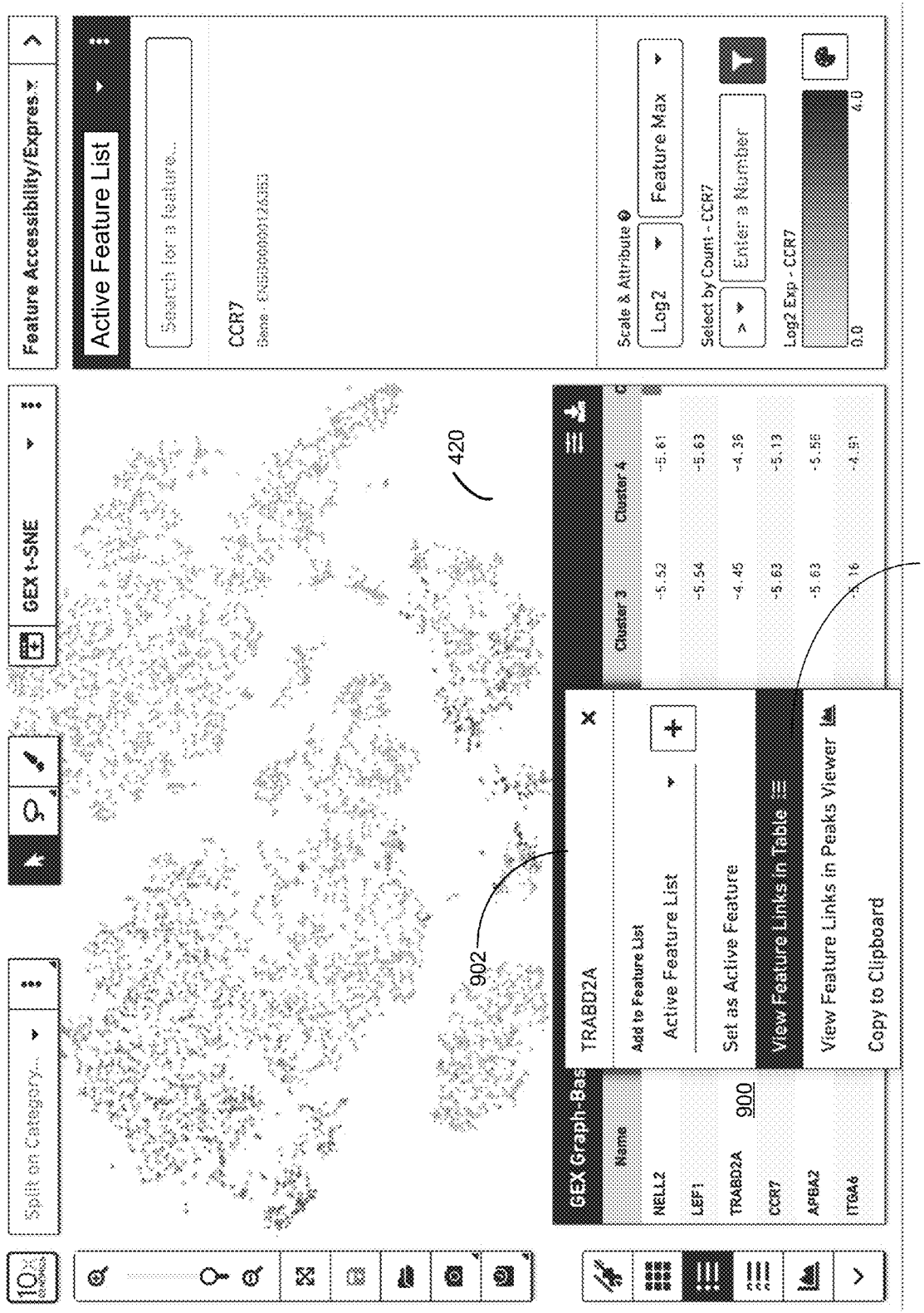
FIG. 9 illustrates details of a particular gene represented in a discrete attribute value dataset in accordance with some embodiments of the present disclosure.

Linkage table 704 can also be accessed from other locations. For instance, referring to FIG. 9, clicking on a gene in the significant genes table 900 brings up the menu of options 902. Option 904 of menu 902 is the option to view features linked to the selected gene, TRABD2A in FIG. 9, as the source feature in a linkage matrix table. In addition, referring back to FIG. 8, clicking on any one of the features in the 'Feature Link' column 802 brings up a menu similar to that of menu 902, through which the user can recenter the linkage matrix table around the selected new feature. A user may also use the menu to view expression or accessibility levels graphically over the 2-D projection, or add the feature to a list for later retrieval.

Linkage Viewer.

Figure 10:
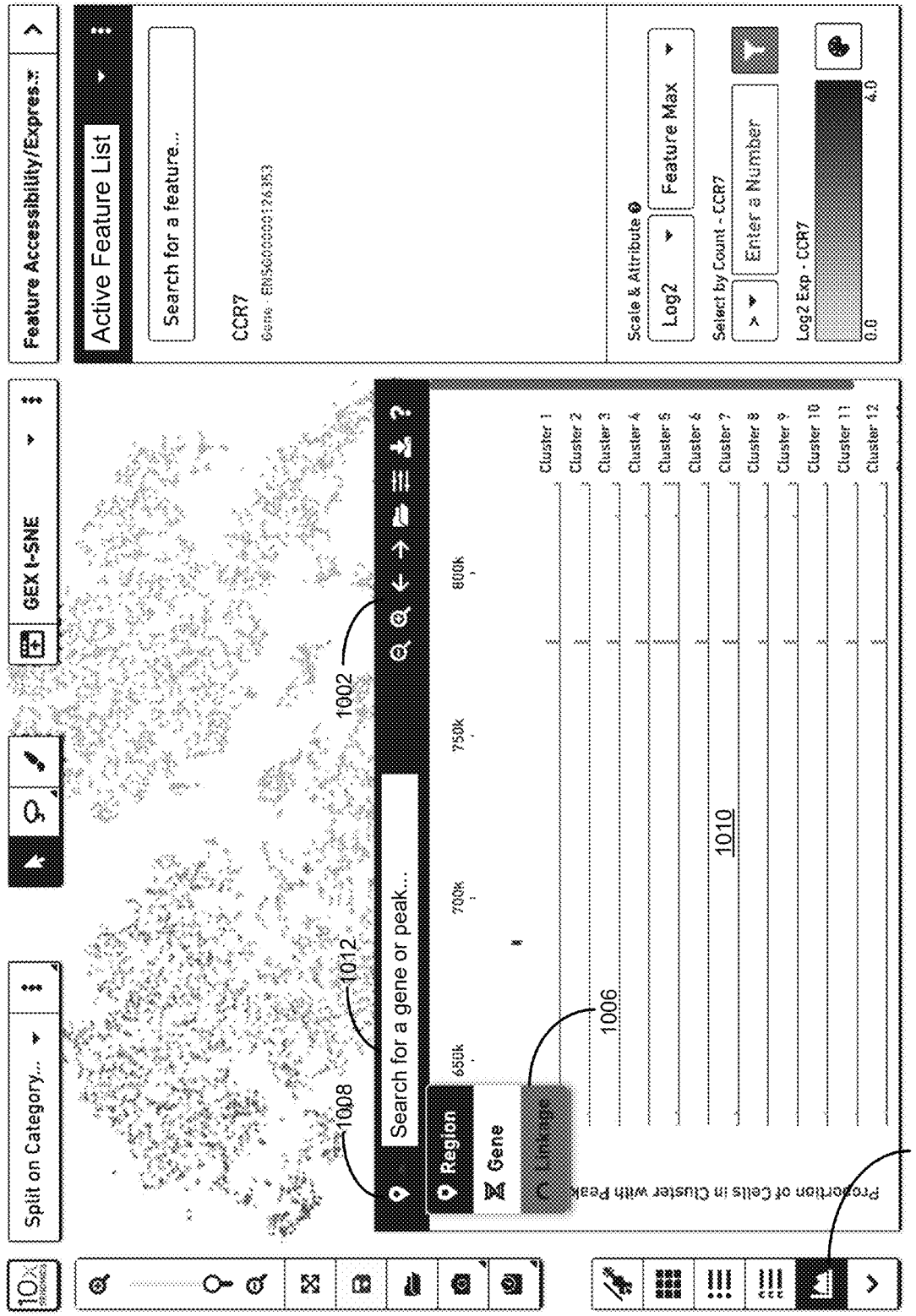
FIG. 10 illustrates a linkage map for each cluster in a plurality of clusters for the feature ENSG00000126353 in accordance with some embodiments of the present disclosure.

Referring to FIG. 10, the systems and methods of the present disclosure also provide a linkage mode (linkage viewer 1110) within an ATAC peak viewer 1002. The ATAC peak viewer 1002 is accessed by clicking on affordance 1004. From the Peak Viewer panel 1002, selecting "Linkage" 1006 from the mode selector 1008 loads the linkage viewer 1010. In a similar manner to the tabular view of FIG. 8, typing in the name of a feature at search query prompt 1012 will trigger an autocomplete menu.

Figure 11:
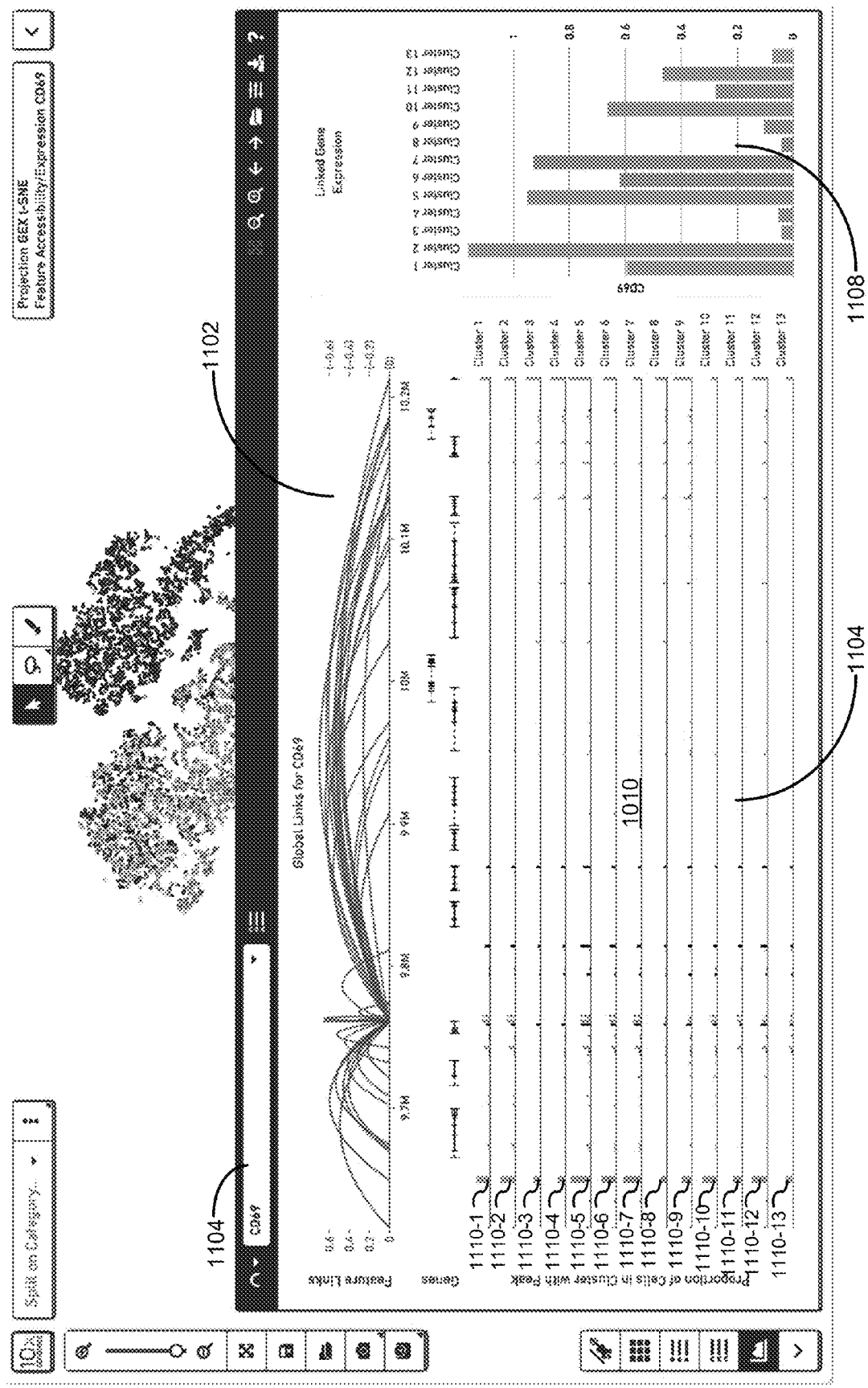
FIG. 11 illustrates ATAC peak linkages and gene linkages, on a cell cluster by cell cluster basis, to the gene CD69 in accordance with some embodiments of the present disclosure.

Entering CD69 into prompt 1012 of FIG. 10 will bring up a view like the one shown in FIG. 11, where the linkage viewer 1010 is now anchored to the selected feature of interest (in this case, gene CD69). In the linkage viewer, there are three plots. First, there is an arc plot 1102, which illustrates the locations and correlations of the features linked to the subject feature, here CD69. These locations and correlations are drawn from the feature-linkage matrix 187, as discussed above in conjunction with FIG. 1D. Second, there is a peak graph 1104, showing the positions and frequencies of peaks, on a cell cluster by cell cluster basis, that are linked to the subject feature. Third, there is a gene expression panel 1108, showing abundance, on a cell cluster by cell cluster basis, of either (i) all genes linked to the feature (gene or ATAC peak) anchoring the view or (ii) the gene anchoring the current view. In FIG. 10, gene expression panel 1108 shows, on a cell cluster by cell cluster basis, the abundance of the anchoring gene CD69. FIG. 11 thus illustrates how a feature-linkage matrix 187 is used to service the selection of a first gene 122 in the plurality of genes or a first ATAC peak 123 in the plurality of ATAC peaks at affordance 1105. In response to this selection at affordance 1105, the feature-linkage matrix 187 is used to obtain and provide a first plot 1010 comprising a graphical indicator for each gene in the plurality of genes and/or each peak in the plurality of peaks linked to the first gene or the first ATAC peak, by order of distance apart from the first gene or the first ATAC peak in the reference genome. In some embodiments, as illustrated in FIG. 11, the respective graphical indicator for each respective gene in the plurality of genes or each respective peak in the plurality of peaks linked to the first gene or the first ATAC peak is provided for each respective cluster group. FIG. 11, for instance, shows how a respective graphical indicator 1110 of a particular gene linked to CD69 is provided for each respective cluster group in the displayed plurality of cluster groups one through thirteen. In some embodiments, as illustrated for the graphical indicators 1110-1 through 1110-13 of FIG. 11, each respective graphical indicator is dimensioned within the first plot 1110 to represent a proportion of cells in the respective cluster group that have a non-zero value for the discrete attribute value of the respective linked gene or a non-zero value for the ATAC fragment count of the respective linked ATAC peak. Thus, in FIG. 11, each graphical indicator 1110-1 through 1110-13 is sized to reflect the proportion of cells in the respective cluster group that have a non-zero value for the discrete attribute value of the respective gene represented by the corresponding graphical indicator 1110.

By default, the genomic window represented by the linkage viewer 1010 will span all the features linked to the anchor feature. The arc plot 1102 and peak graph 1104 share the same genomic x-axis, which are physical locations on the genome. The features linked to CD69 roughly span chr12:9600000-10200000. In some embodiments, this window is 2 megabases wide as discussed above in conjunction with the feature-linkage matrix 187 illustrated in FIG. 1D. A user may zoom into a narrower region of the linkage view 1010 by dragging their mouse over a window in the arc plot 1102 or peak graph 1104.

The arc plot 1102 illustrates the direction and magnitude of the linkages between the anchor feature and linked features. In the embodiment illustrated in FIG. 11, blue arcs (left of the anchoring feature in plot 1102) represent positive correlations, implying that cells with higher levels of CD69 expression have open chromatin at those linked peak regions, and regions from cells not expressing CD69 may be inaccessible. Red arcs (right of the anchoring feature in arc plot 1102) are negative correlations, implying the opposite. The height of the peaks are proportional to the correlative R-value 191; the closer to −1 or 1, the higher the R value, and the stronger the correlation. Other embodiments of the present disclosure alter the color, width or transparency of the peak curves of FIG. 1102 in relation to the statistical significance of the linkage. For instance, more arcs representing more statically significant links are thicker than arc representing less statically significant arcs in some embodiments. The y-axis of the arc plot 1102 shows the absolute correlation of all the peaks, which is dynamic relative to the linked feature with the highest r-value.

The peak graph 1104 below the arc plot shows the location, size, and frequency of all peaks linked to the anchor feature within the active clustering. In FIG. 11, the active clustering is the precomputed Louvain graph-based method over the gene expression-derived clusters. Changing the active clustering will change the clusters within the peak graph. For instance, the clustering can be changed to k-means GEX clustering, Louvain graph-based ATAC clustering, or k-means ATAC clustering, to name some non-limiting examples of alternative clusterings. The heights of the peaks in each cluster track are proportional to the percentage of cells within that cluster where the chromatin is open within that peak region.

Figure 12:
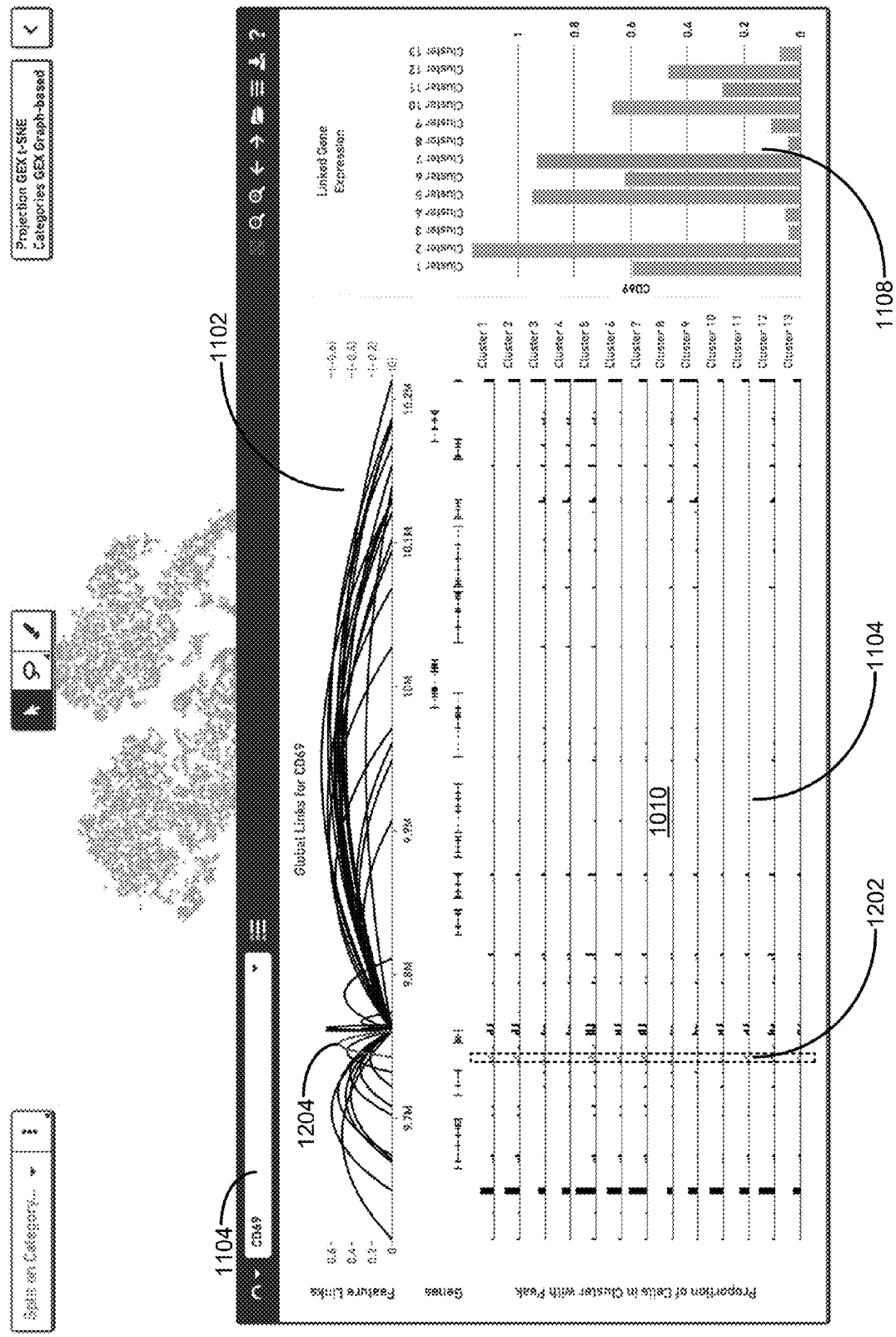
FIG. 12 illustrates selection of one arc in a linkage view in accordance with some embodiments of the present disclosure.

Clicking on an arc in the arc plot 1102 will highlight the arc in the arc plot, and the target peak within the peak graph 1104. FIG. 12 shows this. Arc 1204 has been selected in arc plot 1102 and so the linked peak 1202 corresponding to arc 1204 has been highlighted in the peak graph 1104. In this manner, the differences between clusters of open chromatin frequencies for the linked peak can be visualized.

In some embodiments, gene expression panel 1108 can show the differences in gene expression between clusters for all genes linked to the anchor feature. To show this more precisely, FIG. 13A re-anchors the linkage view around the feature with the highest positive correlative value to CD69: chr12:9760094-9761921. The gene expression panel 1108 now shows the distribution of expression among all genes 1302 linked to that peak, as determined by the feature-linkage matrix 187, within the currently selected cell clusters. For instance, in the case of chr12:9760094-9761921, there are a total of 10 linked genes 1302 (1302-1 through 1302-10), and the expression of each of these genes, on a cluster by cluster basis is now displayed in the gene expression panel 1108.

Figure 13A:
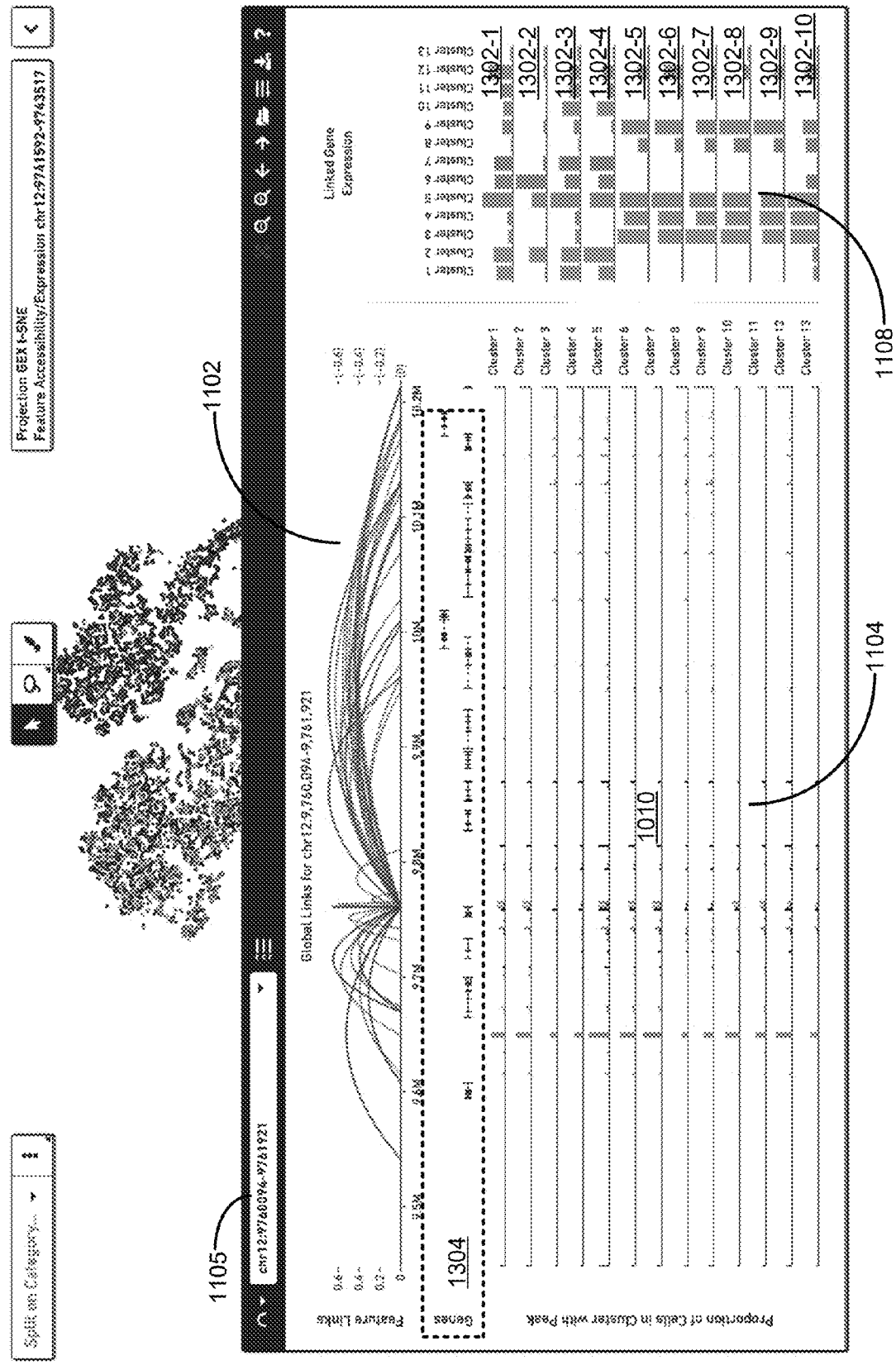
FIG. 13A illustrates re-anchoring a linkage view around the feature with the highest positive correlative value to CD69: chr12:9760094-9761921, in accordance with some embodiments of the present disclosure.

The order of display of genes 1302 in the gene expression panel 1108, from top to bottom, is in genomic order in FIG. 13A. In other embodiments, the genes 1302 are presented in order of highest to lowest significance 192. In other embodiments, the genes 1302 are presented in order of lowest to highest significance 192. In other embodiments, the genes 1302 are presented in order of highest to lowest correlative value 191. In other embodiments, the genes 1302 are presented in order of lowest to highest correlative value 192. In still other embodiments, the genes 1302 are presented in order of closest to furthest genetic distance to the anchoring feature. In still other embodiments, the genes 1302 are presented in order of furthest to closest genetic distance to the anchoring feature. In some embodiments, only the N genes closest to the anchoring feature are shown in panel 1108, where N is a positive integer between 1 and 20 (e.g., 1, 2, 3, 4, 5, 6, 7, 8, 9, 10, 11, 12, 13, 14, 15, 16, 17, 18, 19, or 20).

Hovering over a row 1302 in the gene expression panel 1108 shows the identity of the linked gene, as well as the average expression per cluster. In some embodiments, this is absolute expression (UMI/cell). In other embodiments this is relative (average log-normalized count per cell). The gene expression panel 1108 shows a clear correlative pattern and anti-pattern. Genes positively correlated to the specified peak (rows 1-4, including CD69 on row 1302-4) have higher levels of gene expression in clusters 1, 2, 6, and 7, whereas genes negatively correlated to the anchoring peak have higher levels of gene expression in clusters 3, 4, 8 and 9. Cluster 5, on the other hand, shows high level of expressions regardless throughout all the cell clusters. The y-axis of each gene expression plot is independent due to differences in overall abundance; the purpose of the panel is to show common patterns of relative expression.

In some embodiments (not shown in FIG. 13A), the accessibility or expression of the anchor feature is illustrated, on a cell cluster by cell cluster basis, above the gene expression panel 1108.

Figure 13B:
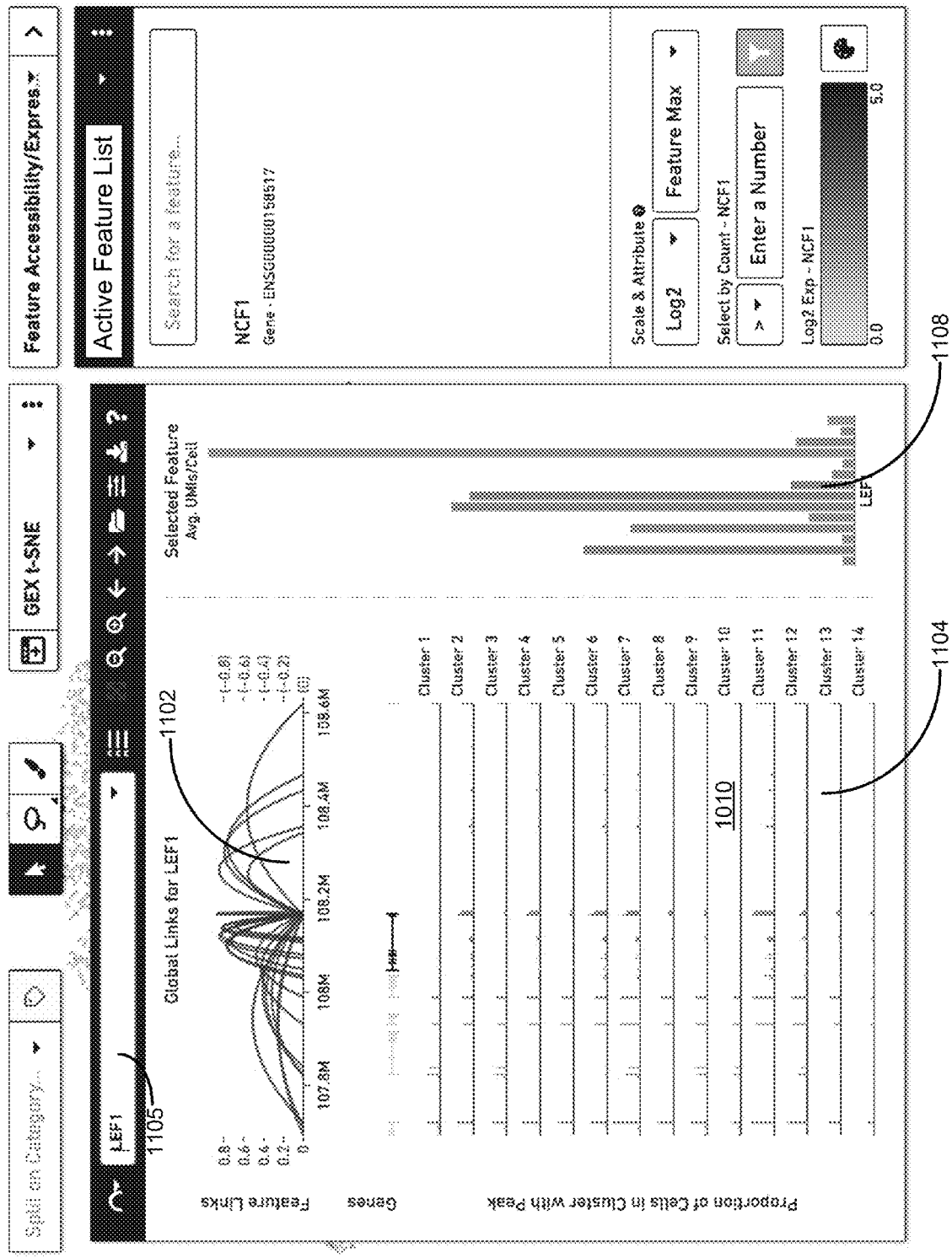
FIG. 13B illustrates linkages to the queried gene LEF1 and the average UMIs/cell per cell cluster for LEF1, in accordance with some embodiments of the present disclosure.
Figure 13C:
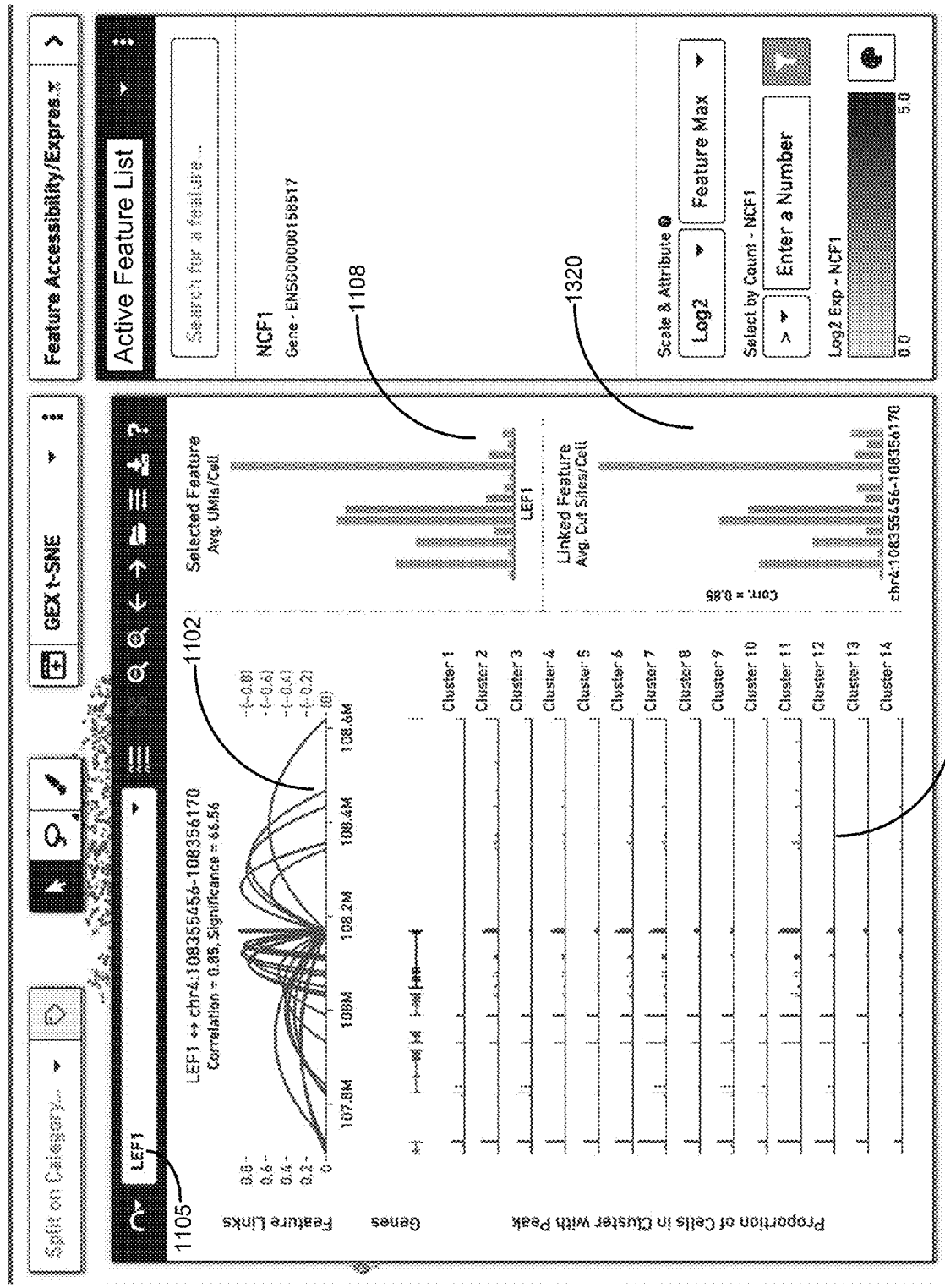
FIG. 13C illustrates selection of ATAC Peak chr4: 108355456-108356170 which is linked to LEF1 and the average cut sites/cell per cell cluster for ATAC Peak chr4: 108355456-108356170 as well as the average UMIs/cell per cell cluster for LEF1, in accordance with some embodiments of the present disclosure.
Figure 13D:
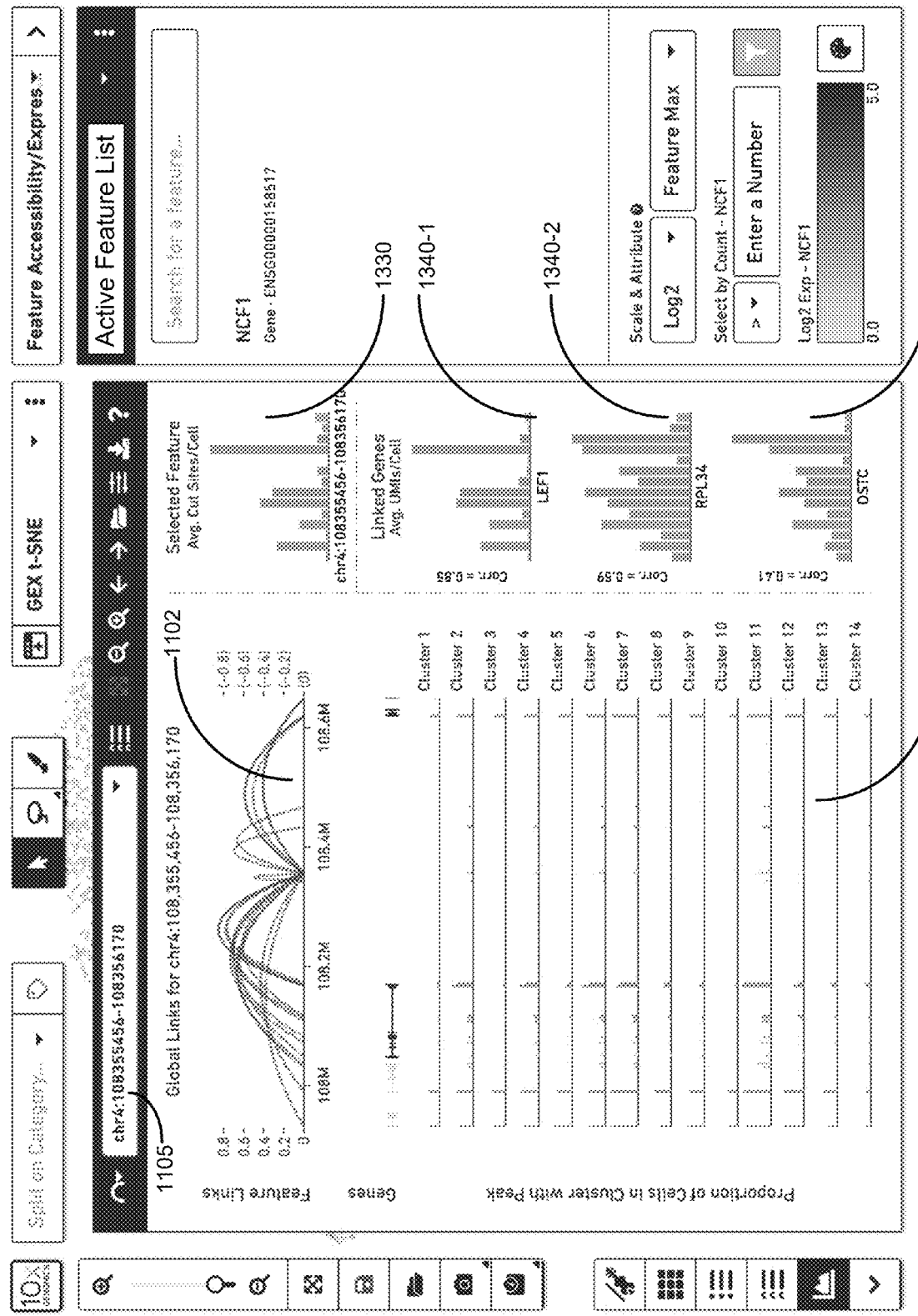
FIG. 13D illustrates a user query for features linked to the ATAC Peak chr4:108355456, along with the average cut sites/cell per cell cluster 1330 for the searched-for ATAC Peak chr4:108355456, as well as all the average UMIs/cell, per cell cluster, for each of three genes linked to ATAC Peak chr4:108355456, in accordance with some embodiments of the present disclosure.
Figure 13E:
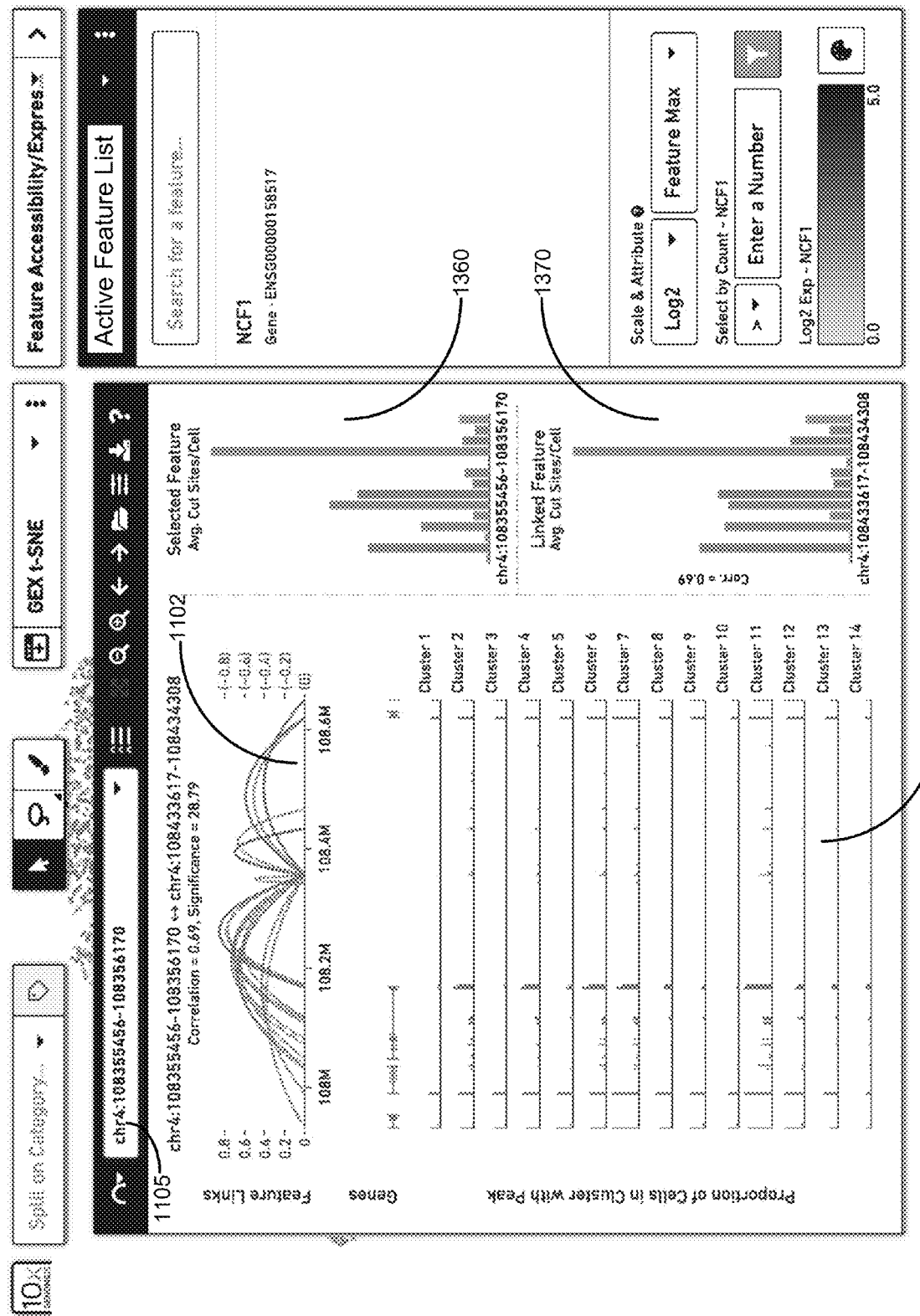
FIG. 13E illustrates, upon user selection of link chr4: 108355456-108356170-chr4:108433617-108434308 in the arc plot of FIG. 13D, the average cut sites/cell, per cell cluster, for the searched-for peak chr4:108355456-108356170 as a first graph and also the average Cut Sites/Cell, per cell cluster, for the linked feature chr4:108433617-108434308, as a second graph, in accordance with some embodiments of the present disclosure.

In some embodiments (not shown in FIG. 13A), a user clicks on a gene annotation in genes display 1304, a peak in peak graph 1104, or an arc in arc plot 1102. In response, a distribution (ATAC peak count or GEX data depending on the nature of the selected feature), on a cell cluster by cell cluster basis, of the selected feature is illustrated in gene expression panel 1108. In some such embodiments, the distribution, on a cell cluster by cell cluster basis, of the anchoring feature is also shown in gene expression panel 1108. In this way, a direct comparison of the distribution of the selected linked feature with the anchor feature, on a cell cluster by cluster basis, can be made. Referring to FIG. 13B, when a user is searching for a gene (e.g., LEF1 at affordance 1105 as illustrated in FIG. 13B), they will see the average UMIs/cell per cell cluster 158 or 159 for that gene in plot 1108. When a user clicks on a particular linked ATAC peak 123 (e.g., selection of ATAC Peak chr4:108355456-108356170) in the arc plot 1102, they will also see the average cut sites/cell per cell cluster 158 or 159 for the linked ATAC peak 123 (e.g. chr4:108355456-108356170) as illustrated in plot 1320 of FIG. 13C. Conversely, referring to FIG. 13D, when a user is searching for a peak (e.g., entry of ATAC Peak chr4:108355456-108356170 at affordance 1105), they will see the average cut sites/cell, per cell cluster 158 or 159 in plot 1330 for the searched-for ATAC peak 123 (ATAC Peak chr4:108355456-108356170) as well as all the average UMIs/cell per cell cluster 159 or 159 for all linked genes. In some embodiments, hovering over a column in panel 1330 of FIG. 13D shows the numerical average cut sites/cell of the ATAC peak 123 (chr4:108355456-108356170) across the cells in the cell cluster represented by the selected column. In the case of ATAC Peak chr4: 108355456-108356170, there three linked genes: LEF1 represented by plot 1340-1, RPL34 represented by plot 1340-2, and OSTC represented by plot 1340-3. Referring to FIG. 13D, when a user clicks on a link in arc plot 1102 (e.g., the chr4:108355456-108356170-chr4:108433617-108434308 link), the average cut sites/cell, per cell cluster 158 or 159, for the searched-for peak (chr4:108355456-108356170 in FIG. 13E) is displayed as graph 1360 and also the average UMIs/Cell or average Cut Sites/Cell, per cell cluster 158 or 159, for the linked feature, whether it be linked to a gene or another peak, is displayed as graph 1370 (as illustrated for the linked feature chr4:108433617-108434308 in FIG. 13E).

In some embodiments, as illustrated in FIG. 13A, when the linkage viewer 1010 is anchored on a peak instead of a gene, dashed arcs in the arc plot 1102 are peak-to-peak links, while solid arcs are peak-to gene links. In alternative embodiments, not shown, when the linkage viewer 1010 is anchored on a peak instead of a gene, arcs in the arc plot 1102 representing peak-to-peak links have a first linewidth and/or color and arcs in the arc plot 1102 representing peak-to-gene links have a second linewidth and/or color different from the first linewidth and/or color.

In addition, in some embodiments, the gene annotations 1304 between the arc plot 1102 and the peak graph 1104 highlight linked genes in black, while greying out genes in the genomic window that did not have strong linkage to the anchor peak.

Linkage Filter Options.

Figure 14:
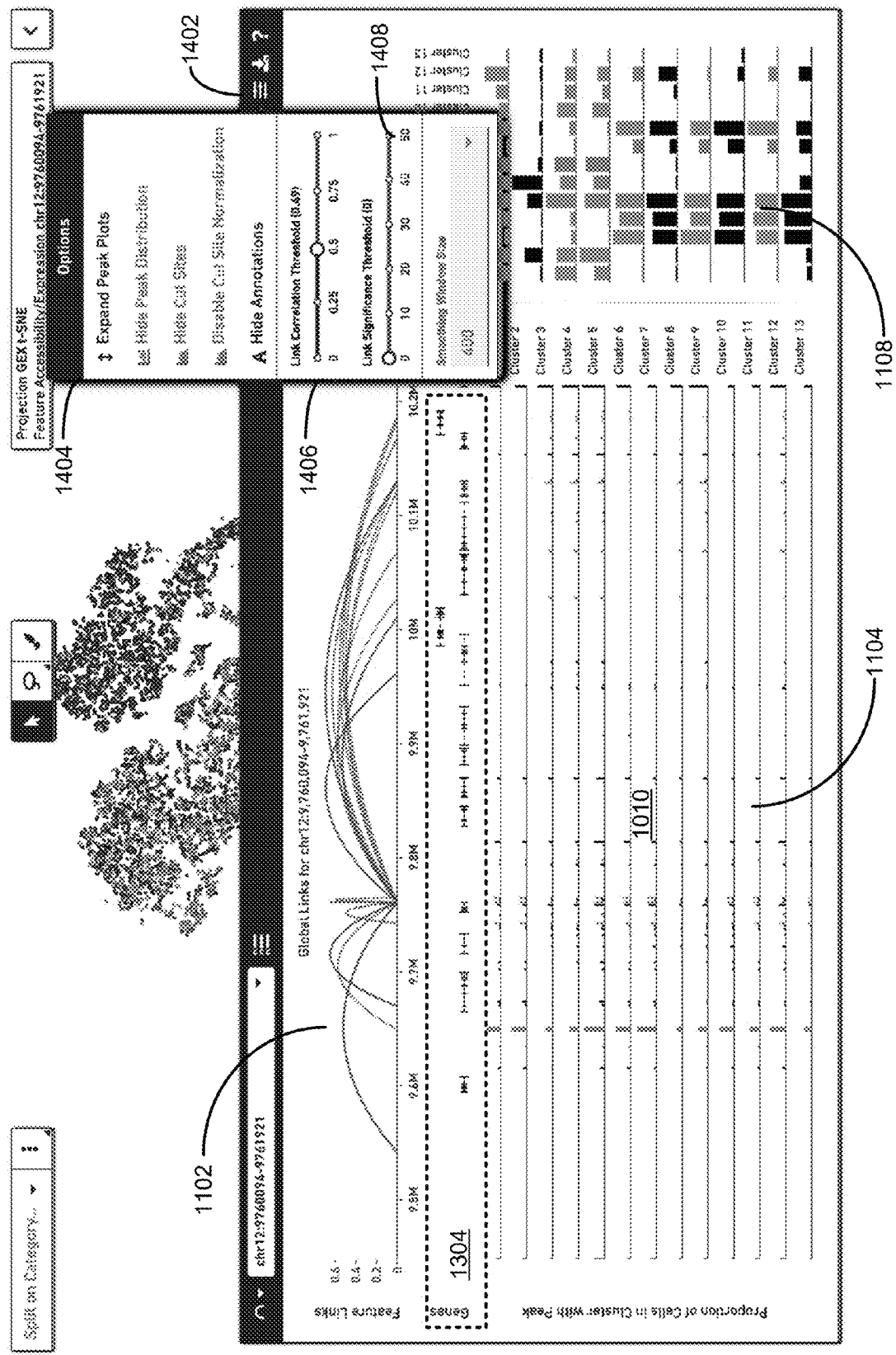
FIG. 14 illustrates a correlation slider, which filters linkages by absolute r-value, and a significance filter, which filters linkages by significance score (negative log false-discovery-rate) and that collectively provide linkage filters in accordance with some embodiments of the present disclosure.

In some embodiments, one or more tools for filtering linkages are provided. These one or more tools are useful, for example, when displaying a wide genomic region. These one or more tools are also useful, for example, when displaying an anchor feature linked to a large number of other features. Referring to FIG. 14, clicking on the options icon 1402 an options menu 1404. The options menu includes a correlation slider (filter) 1406 that filters linkages by absolute r-value 191 and, optionally, a significance slider (filter) 1408, which filters linkages by significance score (negative log false-discovery-rate) 192. Linkages that do not meet the filtering criterion or criteria will be hidden from the arc plot 1102, and linked genes that do not meet the filtering criterion or criteria are greyed out in the gene expression panel 1304.

In some embodiments, not shown in FIG. 14, options menu 1404 includes an additional filter that allows a user to limit the view within linkage viewer 1010 to gene-to-peak linkages. That is, only gene-to-peak linkages are displayed in the arc plot 1102 of linkage viewer 1010 when this filter is enforced, and when the filter is not enforced, both peak-to-peak and gene-to-peak linkages are displayed in the linkage viewer.

Additional Features.

Referring to FIG. 5, selection of a particular ATAC peak 123 in the lower panel 404 causes each respective cell 126 in the upper panel 420 to be colored on a color scale that represents the ATAC fragment count 125 of that respective ATAC peak 123 in each respective cell 126. So, for example, referring to FIG. 5, when a user clicks on the ATAC peak 550 entitled chr2:231671099-231673368 in the lower panel 404, each respective cell 126 in the upper panel 420 is colored to reflect the ATAC fragment count 125 for chr2:231671099-231673368 in the respective cell 126. From FIG. 5, upper panel, it is seen that high expression of chr2:231671099-231673368 is exhibited in portion 560 of the ATAC UMAP. In instances where the lower panel is showing genes rather than ATAC peaks, selection of such genes will cause the cells in the upper panel 420 to be colored to reflect the discrete attribute value for the selected gene. This is seen for example, in FIG. 9, where the cells in the upper panel 420 have been colored to reflect the CCR7 discrete attribute value of CCR7 in each cell.

In some embodiments, the user can select more than one gene 122 or ATAC peak 123 in the lower panel 404 and thereby cause the upper panel 420 to concurrently illustrate the discrete attribute value 124 or ATAC fragment count 125 of each of the more than one gene 122 or more than one ATAC fragment count 125 in each respective cell 126 in the discrete attribute value dataset 120 at the same time.

Referring to FIG. 4B, an alternate view to the bottom panel 404 of FIG. 4B is shown by clicking on affordance 470. Upon selection of affordance 470, a tabular representation of the $\log_2$ ATAC fragment counts 125 of the heat map of FIG. 4B is illustrated in column format in FIG. 5, whereas the heat map of FIG. 4B shows the $\log_2$ ATAC fragment counts 125 for ATAC peaks 123-1 through 123-L in a row for each cluster. For instance, in FIG. 4B, the average ATAC fragment count 125 in cluster 159-1 for each ATAC peaks 123-1 through 123-L is shown in the first row in panel 404. Turning to FIG. 5, the user can select any respective cluster 159 by selecting the column label for the respective cluster (column labels for clusters 3, 4 and 5 are marked as 570-3, 570-4, and 570-5, respectively in FIG. 5). This will re-rank all the ATAC peaks 123 such that those ATAC peaks 123 that are associated with the most significant ATAC fragment counts 125 in the selected cluster 159 are ranked first. Selecting the same cluster 159 by again selecting the column label for the respective cluster will re-rank all the ATAC peaks 123 such that those ATAC peaks 123 that are associated with the least significant ATAC fragment counts 125 in the selected cluster 159 are ranked first. Moreover, a p-value 580 is provided for the ATAC fragment count 125 of each ATAC peak 123 in the selected cluster to provide the statistical significance of the ATAC fragment count 125 in the selected cluster 159 relative to the ATAC fragment count 125 of the same ATAC peak 123 in all the other clusters 159. For instance, in FIG. 5, ATAC cluster 159-5 has been selected through column header 570-5 and thus the p-values 580 listed are the ATAC fragment count 125 of each ATAC peak 123 in the cluster 159-5 to provide the statistical significance of the ATAC fragment count 125 in cluster 159-5 relative to the ATAC fragment count 125 of the same ATAC peak 123 in all the other clusters 159. In some embodiments, these p-values are calculated based upon the ATAC fragment count 125, not the $\log_2$ values used for visualization in the heat map 402 of FIG. 5B. In some embodiments, p-values are annotated with a star system, in which four stars means there is a significant difference between the selected cluster (cluster 158-5 in FIG. 5) and the rest of the clusters for a given ATAC peak, whereas fewer stars means that there is a less significant difference in the ATAC fragment count 125 between the ATAC peak in the selected cluster relative to all the other clusters. While the above-discussion has been in relation to ATAC peaks 123, the same tools are provided when genes 122 and their discrete attribute values are displayed instead. Thus, the systems and methods of the present disclosure provide quantitative inspection of the difference in discrete attribute value 158 in any one cluster 158 or the ATAC fragment count 159 in any one cluster 158 (GEX clusters) or cluster 159 (ATAC clusters) relative to the rest of the clusters. The ranked table (e.g., 404 of FIG. 5) can be exported using affordance 590.

Moreover, a user can identify a set of cells of interest using the lasso selection tool 592 and the draw selection tool 594 provided in the upper panel of FIG. 5. Once identified, such cells can be assigned a custom classification and/or exported.

Referring again to FIG. 4A, the heatmap 402 provides a $\log_2$ differential that is optimal in instances where the cell 126 is a cell and the discrete attribute value 124 represents the number of transcripts that map to a given gene in the cell in order to provide a sufficient dynamic range over the number of transcripts seen per gene in the given cell. In some embodiments, $\log_{10}$ differential expression is used instead. However, it is expected that $\log_{10}$ does not provide sufficient dynamic range for appropriate visualization of the relative expression of gene data in the k-means clusters in some instances. This is because the distinction between zero and one count in the raw data is also fairly important. Because of this, it is not desirable to drown the difference between zero and one with the difference between nine and ten. The difference between zero and one in the discrete attribute value 124 differential (between one cluster and the other clusters) is a significant jump and so a log scale that is able to at least have that floor where "zero" is one color in the heat map 402 and "one" is something that is visually different from "zero." Hence the $\log_2$ scale is used in the heat map 402 illustrated in FIG. 4A.

FIGS. 4 through 14 illustrate the analysis of data that comes out of a cell analysis (e.g., single cell sequencing) pipeline. Another aspect of the present disclosure handles situations in which the pipeline consists of multiple GEX classes 172 and/or ATAC classes 173 of cells 126. That is, situations in which each such sample comprises first discrete attribute values 124 for each respective gene 122 (e.g., mRNA that map to a particular gene in a plurality of genes) and/or first ATAC fragment counts 125 for each respective ATAC peak 123 in each cell 126 in a first plurality of cells under a first condition (therefore representing first class 172 and/or first class 173), second discrete attribute values 124 for each respective gene 122 and/or second ATAC fragment counts 125 for each respective ATAC peak 123 in each cell in a second plurality of different cells under a second condition (therefore representing a second class 172 and/or second class 173), and so forth. In other situations, each such sample consists of first discrete attribute values 124 for each respective gene 122 (e.g., mRNA that map to a particular gene in a plurality of genes) and/or first ATAC fragment counts 125 for each respective ATAC peak 123 in each cell 126 in a first plurality of cells of a first type (first class 172 and/or first class 173), second discrete attribute values 124 for each respective gene 122 and/or second ATAC fragment counts 125 for each respective ATAC peak 123 in each cell in a second plurality of cells of a second type (second class 172 and/or second class 173), and so forth, where each such class 172 and/or 173 refers to a different cell type, a different disease state, a different tissue type, a different organ type, a different species, or different assay conditions or any of the forgoing. In some embodiments, the discrete attribute value dataset 120 contains data for cells from two or more such classes, three or more such classes, four or more such classes, five or more such classes, ten or more such classes 172, or 100 or more such classes 172 and/or classes 173.

Figure 15:
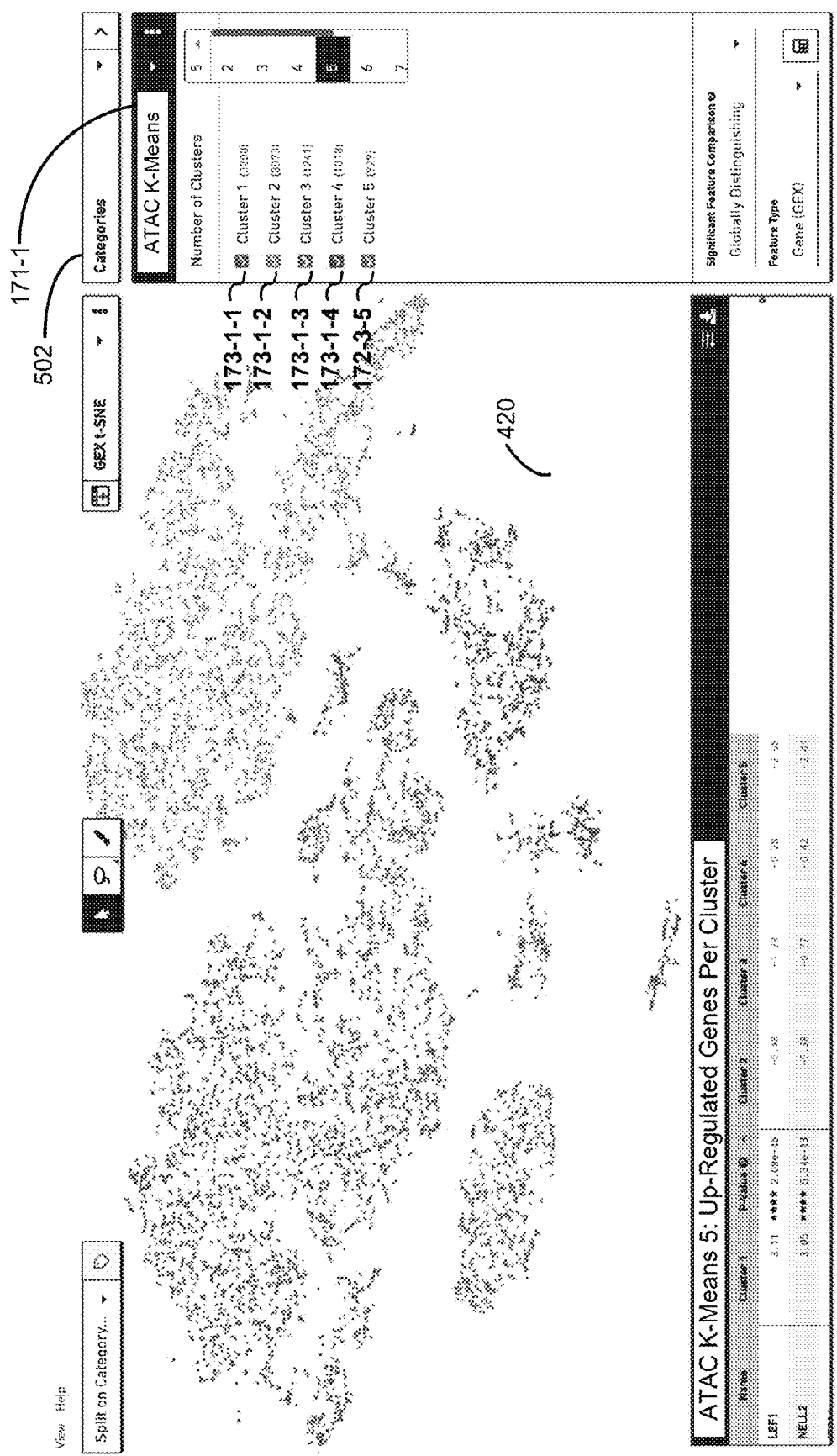
FIG. 15 illustrates the user selection of ATAC classes for an ATAC category in accordance with some embodiments of the present disclosure.

Referring to FIG. 15, in some embodiments, there are a plurality of ATAC categories 171 and each cell 126 is in each such category 171. In some such embodiments, each category 171 has one or more sub-categories, termed classes 173, which can be individually selected. In some embodiments, all such data is preloaded into a single discrete attribute value dataset 120. One example of a category 171 is ATAC K-means clustering (where the ATAC K-means clustering is the "category" 170 and each K-means cluster 159 is an example of a class 173).

Other non-limiting examples of categories not shown in FIG. 15 include "LibraryID" (where LibraryID is the category 171 and which library a cell originated from is the class 173), and "Cohort" (where Cohort is the category 171, and which patient sub-population a cell originated within the cohort is the class 173). Selection of such a category leads to a view in panel 420 in which each cell is color coded by a phenotypic status (e.g., acute myeloid leukemia status associated with the selected category). The spatial representation of the cells in the panel 420 does not change by selection of such categories, only the labeling for the cells changes.

Turning to FIG. 15, by selecting affordance 502, a drop-down menu is provided. The dropdown menu shows all the different categories 170 and/or categories 171 that are associated with each cell in the discrete attribute value dataset 120 as illustrated, for example, in FIG. 4B). Returning to FIG. 15, in the dataset illustrated in FIG. 15, the category is "ATAC K-means" 171-1, the selection of which will provide the view of FIG. 15 panel 420, in which each cell 126 is color coded by its K-means cluster 159 identity 173. As such, the K-means clustering itself is deemed a category 171 and the clusters 159 are each deemed a different class 173 of the category 171.

In some embodiments, where there is a category 171 in a discrete attribute value dataset 120 having ATAC classes 173, each respective cell in the discrete attribute value dataset 120 is a member of each respective ATAC category 171 and one of the ATAC classes 173 of each respective ATAC category 171. In some such embodiments, where the dataset 120 comprises a plurality of categories 171, each respective cell in the discrete attribute value dataset 120 is a member of each respective ATAC category 171, and a single class 173 of each respective ATAC category 171.

In some embodiments where there is a category 171 in a discrete attribute value dataset 120 that has no underlying classes 173, a subset of the cells in the dataset 120 are a member of the category 171. In some embodiments where there is a category 171 in a discrete attribute value dataset 120 having subclasses 173, only a portion of the respective cells in the dataset 120 are a member of the category 171. Moreover, each cell in the portion of the respective cells is independently in any one of the respective classes 173 of the category 171.

A user can select or deselect any category 171. Moreover, a user can select or deselect any combination of classes 173 in a selected category 171. Referring to FIG. 15, in some embodiments, the user is able to click on a single category 173 (the categories are labeled as 173-1-2, 173-1-3, 173-1-4, and 173-1-5, respectively, in FIG. 15) to highlight the cells belonging to that category (cluster) in the plot 420. In this way, by successively clicking on categories 173, the user is able to turn on or off the coloring of the cells corresponding to these categories in panel 410.

Because panel 420 is a GEX t-SNE projection, in two-dimensional space there is an appearance that the clusters 173 overlap each other. However, in the multi-dimensional space in which the clustering was performed, the clusters 173 do not overlap each other.

Figure 16:
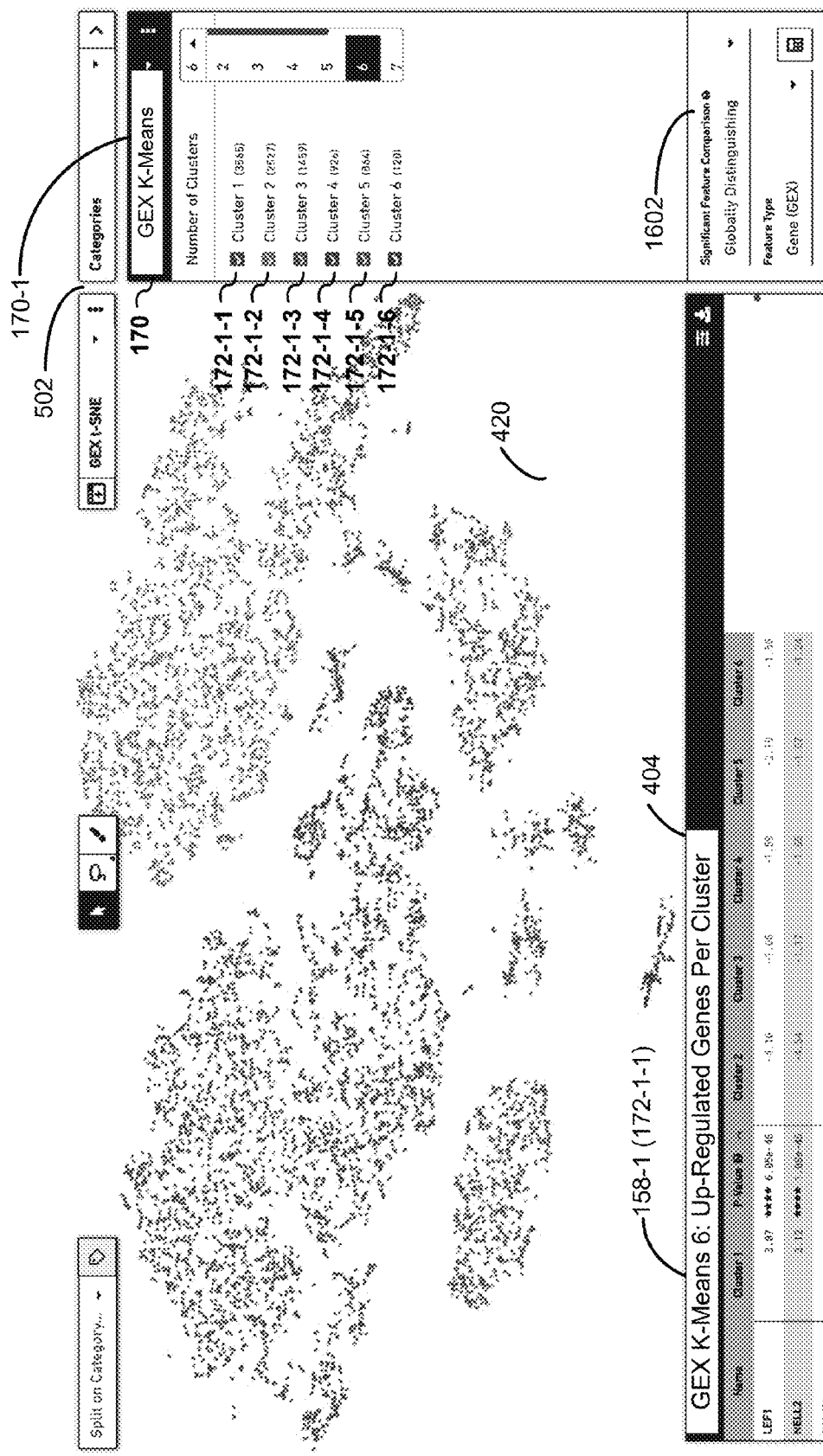
FIG. 16 illustrates the user selection of GEX classes for a GEX category in accordance with some embodiments of the present disclosure.

Referring to FIG. 16, in some embodiments, there are a plurality of GEX categories 170 and each cell 126 is in each such category 170. In such embodiments, each GEX category 170 has one or more sub-categories, termed GEX classes 172, which can be individually selected. In some embodiments, all such data is preloaded into a single discrete attribute value dataset 120. Examples of categories 170 are illustrated in FIG. 4B and include ATAC graph-based, ATAC K-means clustering, GEX graph-based clustering, and GEX K-means clustering. In FIG. 16 GEX K-means 170-1 is selected and GEX K-means is the category 170 and each GEX K-means cluster 158 is an example of a GEX class 172.

In the dataset illustrated in FIG. 16, selection of the category "GEX K-means" 170-1 provides the view of FIG. 16 panel 420, in which each cell 126 is color coded by its GEX K-means cluster 158 identity. As such, the GEX K-means clustering itself is deemed a category 170 and the GEX clusters 158 are each deemed a different GEX class 172 of the GEX category 170.

In some embodiments, where there is a category 170 in a discrete attribute value dataset 120 having classes 172, each respective cell in the discrete attribute value dataset 120 is a member of each respective category 170 and one of the classes 172 of each respective category 170. In some such embodiments, where the dataset comprises a plurality of categories 170, each respective cell in the discrete attribute value dataset 120 is a member of each respective category 170, and a single class of each respective category 170.

In some embodiments where there is a category 170 in a discrete attribute value dataset 120 that has no underlying classes 172, a subset of the cells in the dataset 120 are a member of the category 170.

In some embodiments where there is a category 170 in a discrete attribute value dataset 120 having subclasses 172, only a portion of the respective cells in the dataset 120 are a member of the category 170. Moreover, each cell in the portion of the respective cells is independently in any one of the respective classes 172 of the category 170.

A user can select or deselect any category 170. A user can also select or deselect any combination of classes 172 in a selected category 170. Thus, referring to FIG. 16, in some embodiments, the user is able to click on a single category 172 (the categories are labeled as 172-1-2, 172-1-3, 172-1-4, 172-1-5, and 172-1-6, respectively, in FIG. 16) to highlight the cells belong to that category (cluster) in the plot 420. Selection of a highlighted category causes the cells in panel 420 that belong to that category to no longer be colored by that category. Instead, they are greyed out. Because panel 420 is a t-SNE projection, in two-dimensional space there is an appearance that the clusters 172 overlap each other. However, in the multi-dimensional space in which the clustering was performed, the clusters 172 do not overlap each other.

The presentation of the data in the manner depicted for example in FIGS. 4-16 advantageously provides the ability to determine the genes 122 whose discrete attribute values 124 separates (discriminates) classes 172 within a selected category based upon their discrete attribute values. The presentation of the data in the manner depicted for example in FIGS. 4-16 advantageously also provides the ability to determine the ATAC peaks 123 whose ATAC fragment count 125 separates (discriminates) classes 173 within a selected category 172 based upon their ATAC fragment count 125. To further assist with this, the significant genes (e.g., Sig. genes) affordance 1602 is selected thereby providing two options "globally distinguishing" as illustrated in FIG. 16 and locally distinguishing (not shown in FIG. 16).

Figure 17:
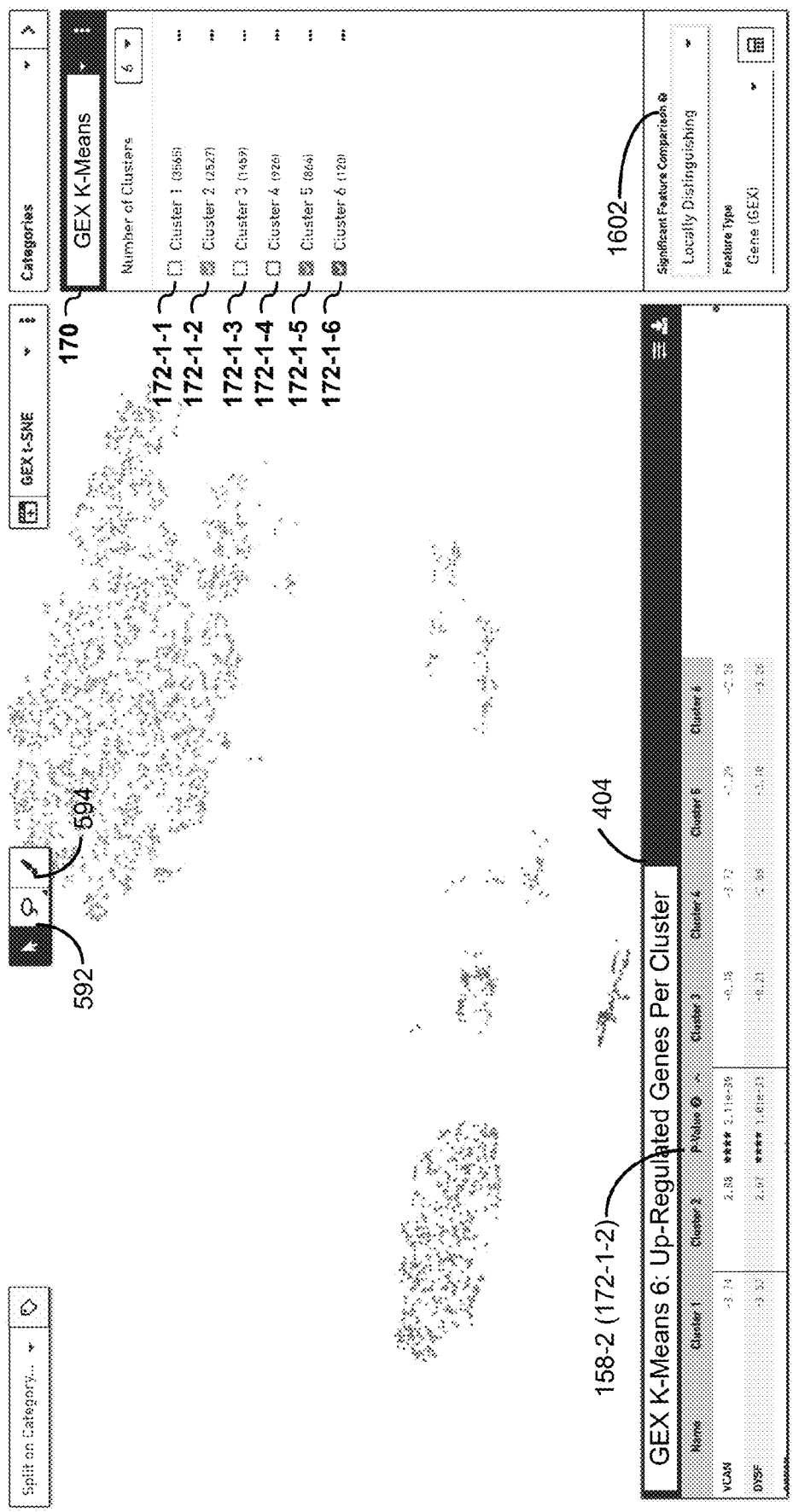
FIG. 17 illustrates a locally distinguishing significant feature comparison feature among selected classes (e.g., K-means clusters) of a category in accordance with some embodiments of the present disclosure.

Referring to FIG. 16, the significant feature comparison 1602 identifies the feature (genes 122 or ATAC peaks 123) whose values (discrete attribute values 124 or ATAC fragment counts 125) within the selected classes statistically discriminate with respect to the entire discrete attribute value dataset 120 (e.g., finds genes expressed highly within the selected categories 170, relative to all the categories in the dataset 120 or finds ATAC peaks that high counts within the selected categories, relative to all the categories in the dataset 120). Referring to FIG. 17, the locally distinguishing option identifies the features (genes or ATAC peaks) whose values (GEX discrete attribute values 124 or ATAC counts 125) discriminate the selected classes without considering the values (discrete attribute values 124 or ATAC counts) in classes of cells that have not been selected.

In some embodiments, visualization system 100 comprises a plurality of processing cores 102 and the identification of features (genes or ATAC peaks whose values (discrete attribute values 124 or ATAC fragment counts 125) discriminate classes under either the globally distinguishing or locally distinguishing algorithms makes use of the processing cores 102 to independently build up needed statistics (e.g., a measure of central tendency of the discrete attribute value) of individual features across a class and/or one or more categories of a class of cells (or the entire dataset).

To further illustrate, turning to FIG. 17 in which the "GEX K-Means" category 170 option has been selected and the data for the cells in the GEX K-Means classes 172-2-1, 172-2-3 and 172-2-4 have been deselected, the locally distinguishing affordance 1202 of FIG. 16 identifies the cells 126 whose discrete attribute values (e.g., mRNA counts) uniquely discriminate the selected cluster 158-2 (class 172-1-2) from cluster classes 172-1-5 and 172-1-6 in the discrete attribute value dataset 120 without considering the values (discrete attribute values 124 or ATAC counts) in classes 172-1-1, 172-1-3, and 1-172-4. Such discriminating genes are listed out in the lower panel 404 of FIG. 17. By contrast, as illustrated in FIG. 16, the globally distinguishing option identifies the genes 122 in lower panel 404 whose discrete attribute values 124 discriminate the difference between the class 172-1-1 (158-1) and all the remaining classes 172 of the GEX K-Means category 170.

Advantageously, the systems and method of the present disclosure allow for the creation of new categories using the upper panel 420 and any number of classes within such categories using lasso 592 or draw selection tool 594 of FIG. 17. So, for example, if a user would like to identify cell subtypes, this can be done by selecting a number of cells displayed in the upper panel 420 with the lasso tools. Moreover, they can also be selected from the lower panel 404 (e.g., the user can select a number of cells by their discrete attribute values or ATAC fragment counts). In this way, a user can drag and create a class within a category. The user is prompted to name the new category and the new class within the category. The user can create multiple classes of cells within a category. Once the classes of a category have been defined in this way, the user can compute the genes whose discrete attribute values discriminate between the identified user defined classes. In some such embodiments, such operations proceed faster than with categories that make use of all the cells in the discrete attribute value dataset 120 because fewer numbers of cells are involved in the computation. In some embodiments, the speed of the algorithm to identified genes that discriminate classes is proportional to the number of classes in the category times the number of cells that are in the analysis. For instance, in some embodiments identification of discriminating genes in the case where there are two classes and twenty-five cells takes about four to five seconds on a standard client device 100.

In some embodiments, a discrete attribute value dataset 120 can have data for up to 750,000 cells and still identify genes or ATAC peaks that discriminate between classes of a category in real time (e.g., less than 30 minutes, less than 10 minutes, less than 5 minutes, or less than 1 minute).

Discrete Attribute Value Pipeline.

As discussed above, methods for collecting ATAC and GEX data for discrete attribute value datasets 120 are described in U.S. patent application Ser. No. 16/789,287, entitled "Methods for Processing Nucleic Acid Molecules," filed Feb. 12, 2020, which is hereby incorporated by reference. In some embodiments, the Cell Ranger™ analysis pipelines perform secondary analysis and visualization of such data. In addition to performing standard analysis steps such as demultiplexing, alignment, and gene counting, Cell Ranger™ leverages the bar codes described in U.S. patent application Ser. No. 16/789,287, entitled "Methods for Processing Nucleic Acid Molecules," filed Feb. 12, 2020, which is hereby incorporated by reference to generate GEX expression data and ATAC fragment count data with single-cell resolution in the form of the discrete attribute value dataset 120. This data type enables applications including cell clustering, cell type classification, differential gene expression, and differential ATAC fragment count at a scale of hundreds to millions of cells. Moreover, as discussed above, because the pipeline delivers this information by indexing discrete attribute value 124 from cells on an individual cell basis using barcodes, the data from such single cells can be combined with the data from other pipelines that make use of barcodes to track data from single cells, such as the V(D)J Pipeline described in U.S. patent application Ser. No. 15/984,324, entitled "Methods for Clonotype Screening," filed May 19, 2019, which is hereby incorporated by reference, to provide unique biological insight into underlying molecular mechanisms associated with cell samples.

In the embodiments of the present disclosure, techniques for analyzing biological samples are provided. The techniques involve acquiring a sample (e.g., a tumor biopsy, a sample of any tissue, body fluid, etc.) and processing the sample to acquire data from each cell in the sample for computational analysis. Each cell in the sample is barcoded, at a minimum, as discussed above. The acquired data is stored in a certain manner, for example, in specific data structure(s), for consumption by one or more processors (or processing cores) that are configured to access the data structures and to perform computational analysis such that biologically meaningful patterns within the sample are detected. The computational analysis and associated computer-generated visualization of results of the computational analysis on a graphical user interface allow for the observation of properties of the sample that would not otherwise be detectable. In particular, in some embodiments, each cell of the sample is subjected to analysis and characteristics of each cell within the sample are obtained such that it becomes possible to characterize the sample based on differentiation among different types of cells in the sample. For example, the clustering analysis, as well as other techniques of data analysis described above, reveal distributions of cell populations and sub-populations within a sample that would not be otherwise discernable. This leads to the discovery of novel cell types, or to the novel discovery of relationships between (A) aspects of the cellular phenotypes, such as genome (e.g., genomic rearrangements, structural variants, copy number variants, single nucleotide polymorphisms, loss of heterozygosity, rare variants), epigenome (e.g., DNA methylation, histone modification, chromatin assembly, protein binding), transcriptome (e.g., gene expression, alternative splicing, non-coding RNAs, small RNAs), proteome (e.g., protein abundance, protein-protein interactions, cytokine screening), metabolome (e.g., absence, presence, or amount of small molecules, drugs, metabolites, and lipids), and/or phenome (e.g., functional genomics, genetics screens, morphology), and (B) particular phenotypic states, such as absence or presence of a marker, participation in a biological pathway, disease state, absence or presence of a disease state, to name a few non-limiting examples. The identification of different classes of cells within the sample allows for taking an action with respect to the sample or with respect to a source of the sample. For example, depending on a distribution of cell types within a biological sample that is a tumor biopsy obtained from a subject, a specific treatment can be selected and administered to the subject.

In the embodiments of the present disclosure, a sample can include multiple second cells, and the described techniques allow for the determination of feature (e.g., mRNA sequences that map to a particular gene in a plurality of genes and/or ATAC peaks) having values (e.g., certain discrete attribute values or ATAC fragment counts) within each cell in the sample. For example, in some embodiments, in the case of genes, each discrete attribute value is a count of transcript reads within a single cell that map to a respective gene in the plurality of genes. As another example, in some embodiments, in the case of ATAC peaks, each ATAC fragment count is a count of ATAC fragments within a single cell that map to a respective ATAC peak in the plurality of ATAC peaks. In the described embodiments, as discussed above, such counts can be in the form of a count of UMIs. In this way, gene expression or ATAC fragment count per cell is determined and a discrete attribute value dataset is generated that includes discrete attribute values for each gene in each cell as well as ATAC fragment counts for each ATAC peak in each cell.

Furthermore, the techniques in accordance with the described embodiments allow clustering and otherwise analyzing the discrete attribute value dataset so as to identify patterns within the dataset and thereby assign each cell to a type or class. As used in this context here, a class refers to a different cell type, a different disease state, a different tissue type, a different organ type, a different species, or different assay conditions or any other feature or factor that allows for the differentiation of cells (or groups of cells) from one another. The discrete attribute value dataset includes any suitable number of cell classes of any suitable type. Moreover, as discussed above, the described techniques (including barcoding and computational analysis and visualization) provide the basis for identifying relationships between cellular phenotype and overall phenotypic state of an organism that is the source of the biological sample from which the sample was obtained that would not otherwise be discernable.

Transposase Accessible Chromatin (ATAC) Pipeline.

An assay for transposase accessible chromatin (ATAC) has been described above and further details for such assays is provided in U.S. patent application Ser. No. 16/789,287, entitled "Methods for Processing Nucleic Acid Molecules," filed Feb. 12, 2020, which is hereby incorporated by reference. In such embodiments, a count 125 of each ATAC peak 123 in a plurality of ATAC peaks is acquired. In some embodiments, ATAC with high-throughput sequencing (ATAC-seq) maps chromatin accessibility by probing for DNA accessibility using hyperactive Tn5 transposase. Tn5 transposase inserts sequencing adapters into accessible regions of chromatin. See Buenrostro et al., 2015, "ATAC-seq: A Method for Assaying Chromatin Accessibility Genome-Wide," Curr Protoc Mol Biol. 109:21.29.1-9. In the systems and methods of the present disclosure, however, single cell ATAC techniques are provided that allow for the acquisition of ATAC data from each cell in a sample. The chromatin profiling of numerous cells (e.g., tens of thousands of single cells) in parallel allows workers to see how chromatin compaction and DNA-binding proteins regulate gene expression at high resolution.

For the ATAC portion of the discrete attribute value dataset 120, in typical embodiments, there are no measures of gene expression. The primary entity of rows in the matrix for ATAC data within the discrete attribute value dataset 120 is fragments (or UMIs) 125 per called ATAC peak 123, where the peak 123 corresponds to a genomic region of accessible chromatin. Referring to FIG. 1B, the ATAC matrix for discrete attribute value dataset 120-1 comprises ATAC peak elements 123-1-1 through 123-L-1, together with their measured ATAC fragment counts 125-1-1 through 125-L-1. For ATAC data, fragment counts 125 in peaks 123 instead of gene expression is recorded. In some embodiments, ATAC matrices will also contain aggregate rows as described below. As such, the ATAC pipeline generates a feature-barcode matrix, identifies clusters 159 based on the feature-barcode matrix, identifies significant features 165 (using, e.g., a principal component analysis or other forms of data reduction such as those disclosed herein), and computes a 2-D t-SNE projection 198 or 2-D UMAP 199 projection based on the significant elements of the matrix. Because the ATAC pipeline performs a type of analysis that is different from the GEX pipeline discussed above, different types of graphical user interface components are needed to display the results of the ATAC pipeline, as discussed below.

In some embodiments, an ATAC pipeline identifies distinct peak regions, which can be regions encompassing from hundreds to thousands of nucleotides. In these regions, fragments derived from open chromatin sites can be detected. A feature metadata module (a label class) can be used to associate ATAC peaks 123 with nearby promoter genes, to encode user-specified tags, such as, e.g., a gene target of CRISPR guide RNA, whether an antibody is a positive or negative control, a source reference genome of a gene feature in the feature data module (matrix), etc.

In some embodiments, a visualization system is provided that is configured to present a graphical user interface on a display of a computing device. In some embodiments, a graphical user interface, also referred to herein as browser module 119, is configured to receive a discrete attribute value dataset 120 that includes GEX data as well as ATAC data. In some embodiments, prior to being accessed by the browser module 119, the data for the discrete attribute value dataset 120 is transformed into a format suitable for representation of the data on the graphical user interface. The data is presented on the graphical user interface in the format that allows manipulating the data based on user input or in other manner. One or more patterns within the data can be detected by the computing hardware executing the browser module 119. The graphical user interface is configured to display the discrete attribute value dataset 120 and various patterns in the manner that allows for revealing previously unknown groups or patterns within the data (e.g., within cells from a biological sample). Moreover, the graphical user interface is configured to receive instructions (e.g., user input) in response to which new patterns can be defined within the data. In some embodiments, user-specific tags are not encoded into the discrete attribute value dataset 120. In alternative embodiments, user-specific tags are encoded into the discrete attribute value dataset 120. In some embodiments, rather than making use of user-specific tags, nearby promoters, nearby genes, peak region function, transcription factor motifs, and unique transcript IDs are encoded in the discrete attribute value dataset 120. As one nonlimiting example, FIG. 1C, discussed above, describes how ATAC nearby gene inferred count 194 and promoter sum inferred count 195 is stored for each gene 193 in the plurality of genes represented by the discrete attribute value dataset 120. In some embodiments, user-specific tags are encoded in the discrete attribute value dataset 120.

As discussed above, in some embodiments, a browser module 119 is executed in conjunction with display 108 of a visualization system 100. FIG. 4A illustrates an example of browser module 119. In some embodiments, for representation and manipulation of ATAC data, the user interface includes certain features specific to the ATAC peak data. In some embodiments, the discrete attribute value dataset 120 includes an identifier indicating whether the dataset 120 includes gene expression data (e.g. in the form of discrete attribute value dataset 120), ATAC peaks, or both. For example, in FIG. 3, icon 320 to the left of the "atac_gex_intron" discrete attribute value dataset 120 indicates that this dataset includes both GEX and ATAC data. Various other icons in FIG. 3 illustrate other forms of discrete attribute value datasets 120. It should be appreciated that the representations in FIG. 3 are shown by way of example only, as any other indicators can be used to differentiate between discrete attribute value datasets 120, including gene expression data and data sets including both gene expression and ATAC data.

Figure 18:
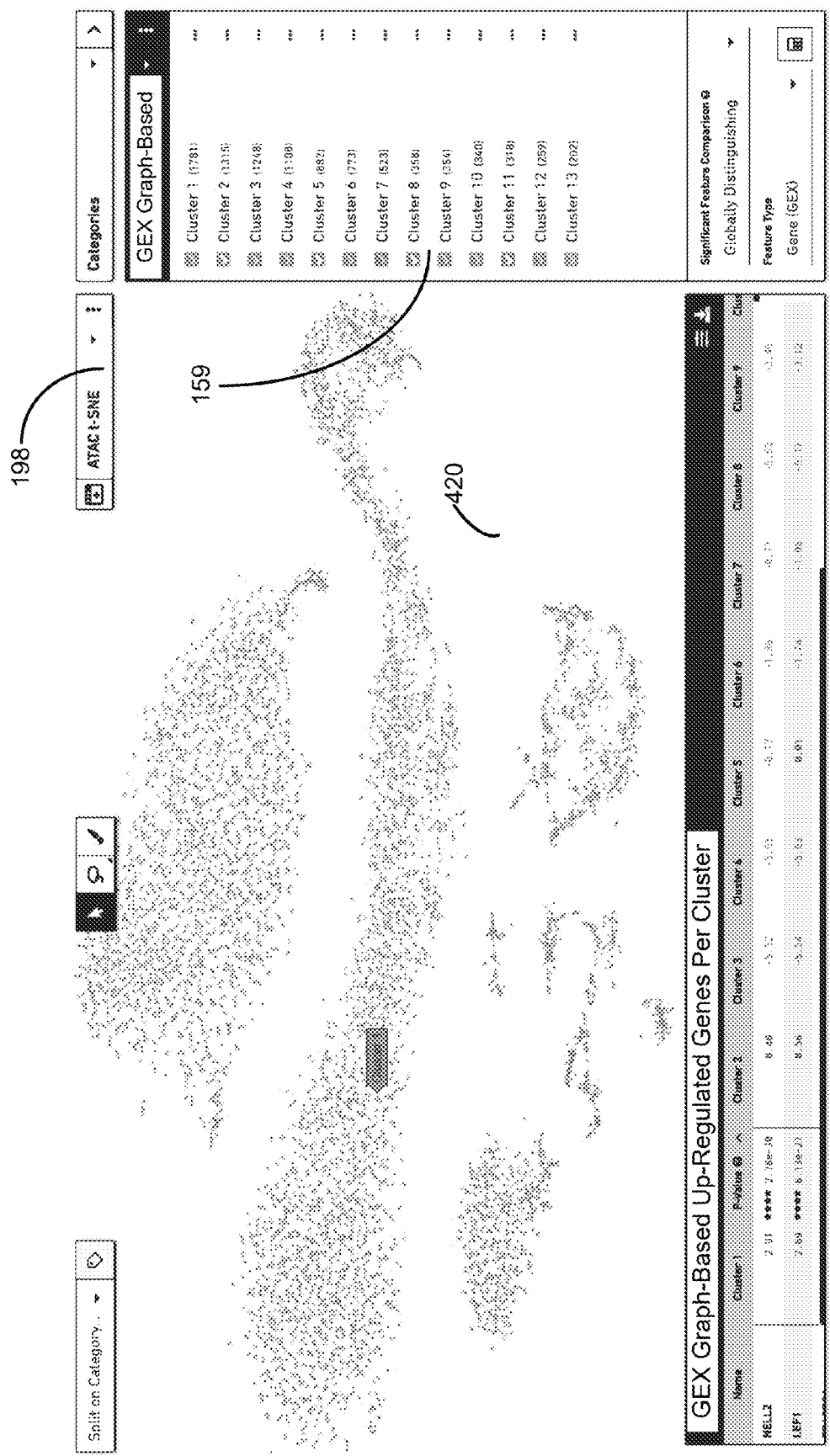
FIG. 18 illustrates an ATAC t-SNE plot, but with the cells clustered (e.g., visualized as colored cells) based on GEX clustering rather than ATAC clustering, in accordance with some embodiments of the present disclosure.

In some embodiments, the ATAC pipeline and the GEX pipeline are configured to generate clusters and/or t-SNE projections and/or UMAP projections based on subsets of features in the discrete attribute value dataset 120. For example, in one example embodiment, when the discrete attribute value dataset 120 comprises antibody data, discrete attribute values 124 related to genes 122 in the discrete attribute value dataset 120 are used to determine clusters 158 and create a GEX t-SNE projection 196 or GEX UMAP projection 197, and ATAC fragment counts 125 related to ATAC peaks are used to construct an ATAC t-SNE projection 196 or ATAC UMAP projection 199. As shown in FIG. 4B, in some embodiments, a projection selector affordance 460 receives input indicating selection of a GEX t-SNE projection 196, GEX UMAP projection 197, ATAC t-SNE projection 198, or ATAC UMAP projection 199 within the discrete attribute value dataset 120. For instance, to generate the ATAC t-SNE projection 198, the plurality of ATAC peaks 123 is dimension reduced using, for example, principal component analysis, across the cells of the discrete attribute dataset 120 to form reduction components (e.g., principal components) 165 and these reduction components are further reduced by t-SNE to generate the two dimensional plot of FIG. 18 in which cells with similar ATAC reduction components (e.g., principal components) 165 are clustered together into ATAC clusters 159 and cells with dissimilar reduction components (e.g., principal components) 165 lie further apart from each other in panel 420. Moreover, the plotted cells are color coded by which GEX cluster 159 they are in. In this way, FIG. 18 illustrates an ATAC t-SNE plot, but with the cells clustered (e.g., colored) based on GEX clustering rather than ATAC clustering.

As discussed above, in some embodiments the GEX t-SNE projection 196, GEX UMAP projection 197, ATAC t-SNE projection 198, and/or ATAC UMAP projection 199 for the discrete attribute value dataset 120 are computed in upstream processing rather than by browser module 119. In some embodiments, to generate additional projections, a configuration file is specified that identifies the barcode sequence corresponding to a feature barcode, its type, as well as additional metadata. In some embodiments, such feature barcodes are separate and apart from the barcodes for the GEX data. An example of a line from an antibody configuration file, which represents one form of feature, is as follows:

id, name, read, pattern, sequence, feature_type
CD3, CD3_UCHT1_TotalC, R2, ˆNNNNNNNNNN(BC)NNNNNNNNN, CTCATTGTAACTCCT, Antibody Capture The first two columns are the feature ID ("id") and display name "name" that will propagate to the browser module 119, the read and pattern columns indicate to the pipeline how to extract the barcode sequence from the raw sequencing read, the sequence column specifies the identifying sequence per feature, and the "feature_type" column specifies the feature type. For such a configuration file, all features of type "Antibody Capture" are combined to create an additional projection. If the configuration file had multiple feature types, the pipeline can generate a projection for each distinct feature type. The additional projections can be stored in the same format as the t-SNE projection from versions of browser module 119 discussed above.

Each ATAC peak 123 corresponds to an open area of the genome at a particular location. There can be multiple distinct ATAC peak 123 locations near a particular gene, or a particular gene transcription start site. Both ATAC peak types can be marked as being "nearby" that gene. Thus, in some embodiments the "nearby gene inferred count 194" is a representation of open sites of the genome per cell near that particular gene. FIG. 20 illustrates a representation (a $\log_2$ fold change) of ATAC peaks around the GZMB promoter that were combined, on an individual cell by cell basis, to form an aggregate feature ("GZMB Promoter Sum") for each cell in the plurality of cells of the discrete attribute value dataset 120. In this way, the combined number of ATAC fragments near each gene per cell is superimposed, in panel 420, on any supported projection of the plurality of cells of the discrete attribute value dataset 120. In FIG. 20, the projection that is displayed is an ATAC t-SNE projection. Thus, in FIG. 20, the individual cells are arranged in panel 420 by an ATAC t-SNE projection but are colored based on their individual GZMB Promoter Sum.

A discrete attribute value dataset can include features of multiple types, and differential expression/chromatin accessibility can be segmented by feature type. Accordingly, in some embodiments, the browser module 119 is configured to receive input indicating selection of a type of a feature with respect to which a differential expression/accessibility is desired to be performed.

In some embodiments, default options for a discrete attribute value dataset 120 are "peak," "motif," and either a "promoter" or "nearby gene" options.

Since multiple feature types are supported by the browser module 119 in the described embodiments, in some in embodiments, in any user interface element where a user is entering a feature name to be autocompleted, the feature type is displayed in the autocompletion entry. This allows a user to distinguish, e.g., between a CD4 gene and a CD4 protein.

In some embodiments, as discussed above, differential discrete attribute values for genes in each cluster 158 can be computed. Moreover, in some embodiments, as discussed above, differential ATAC fragment counts for ATAC fragments in each cluster 159 can be computed. For example, once each cell has been assigned to a respective cluster, the systems and methods of the present disclosure are able to compute, for each respective gene or ATAC peak, for each respective cluster, a difference in the discrete attribute value for the respective gene or the respective ATAC peak across the respective subset of cells in the respective cluster relative to the discrete attribute value or ATAC fragment count for the respective gene or ATAC peak across the plurality of clusters other than the respective cluster, thereby deriving a differential value for each respective gene or ATAC peak in the genes or ATAC peaks for each cluster. In this way, for example, the top most abundant genes or ATAC peaks that are different between cell classes or other forms of cell labels can be determined. This allows determining which genes or ATAC peaks discriminate between GEX or ATAC classes, GEX or ATAC categories, and/or GEX or ATAC clusters.

ATAC Peak Viewer.

In some embodiments of the present disclosure, browser module 119 is configured to display ATAC data in an intuitive manner. In some embodiments browser module 119 includes a set of tools that support representation and analysis of ATAC data and such tools are referred to herein as an ATAC Peak Viewer.

An ATAC peak 123 in accordance with the present disclosure is a representation of a region of open, accessible chromatin determined by analyzing fragments read between transposase cut sites. Unlike gene expression, where a gene is expected at the same location in a genome as per a reference genome, the location of ATAC peaks 123 can vary from run to run as different cells can have different regions of open chromatin accessible to regulatory elements. Accordingly, in the embodiments described herein, each ATAC peak 123 has a name associated therewith, with the name corresponding to the peak's genomic location (e.g., "chr2:237835-238281," in one example). The name of each ATAC peak 123 is stored in the feature-barcode matrix 121 of a discrete attribute dataset 120 similar to the manner in which gene names 122 are stored.

The described techniques provide computational visualization of ATAC peaks 123 in a manner that allows identifying each peak's genomic context, including nearby genes, exons, and untranslated regions (UTRs). In some embodiments, gene, exon and UTR information is stored in the discrete attribute value dataset in a manner similar to gene annotations. The gene, exon, and UTR transcripts can be derived from genomic reference information. In some embodiments, the discrete attribute value dataset 120 includes contig indexes, start positions, end positions, gene names, gene IDs, and strandedness. The discrete attribute value dataset also supports annotation of functional regions in a gene and includes a transcript annotation module. In one embodiment, the transcript annotation module includes the following data structures:

array (string) of transcript IDs of length T (distinct transcript IDs for all transcript annotations);

array (uint) of transcript object types of length U+E=A, the total number of annotations, which is made of U UTR annotations and E exon annotations (this indicates whether the information in all subsequent arrays pertains to an exon or a UTR);

array (int) of indices into the gene ID array, of length A (the gene ID of an annotation);

array (int) of indices into the transcript ID array, of length A (the transcript ID of an annotation);

contig index array (int) of length A;

start position array (int) of length A;

end position array (int) of length A;

strand array (int) of length A.

Following these notations, a single transcript annotation is formed from entries at position i for all arrays of length A. In this manner, a transcript annotation is formed from a gene ID, transcript ID, contig index, start position, end position, and strand. Moreover, the locations of multiple exons and UTRs per transcript and multiple transcripts per gene are encoded. Information on one, two, or more than two transcripts per gene can be stored in this way.

In some embodiments, the gene and transcript annotation information is sorted by respective genomic positions. In some embodiments, in response to a query, such as, e.g., a range query indicating an interval of interest, a server executing the browser module 119 can perform a binary search by position to find elements within the interval with performance O(log A). The performance is improved due to the fact that the annotations are grouped by chromosome/contig, such that the search for gene annotations can start within a smaller subset of the data.

ATAC peak locations are also sorted and stored in memory in a similar manner. The ATAC peaks are representations of open chromatin regions that can be determined by identifying an overlap between fragments exposed by two transposase cut sites. Furthermore, analyzing the fragments themselves can reveal additional information and structure. Accordingly, in some embodiments, the ATAC pipeline is configured to generate a fragments module (stored separately from the discrete attribute dataset) that includes the following columns: a cell barcode column storing a barcode of a cell on which the fragment was found, and a contig, start and end position columns storing the contig, start, and end positions of the fragment, respectively. The fragments module can be in the form of a tab delimited data structure, which can be optionally compressed (e.g. gzipped). In some embodiments, the ATAC pipeline is configured to compute a tabix index over the compressed (e.g., gzipped) tab-delimited information stored in the fragments module. A tabix index module stores the computed tabix index that allows for faster lookup of the on-disk chunks of fragments within a particular interval. The tabix index can be computed as described, for example, in Li, 2011, "Tabix: fast retrieval of sequence features from generic TAB-delimited files," Bioinformatics, 27(5): 718-719. Other techniques can be used additionally or alternatively. In some embodiments, the tabix file module is embedded into the attribute value dataset 120, whereas the fragments module, which may be hundreds of megabytes to gigabytes in size, is stored separately from the discrete attribute value dataset.

Referring to FIG. 10, visual representation of ATAC peaks and associated information is provided in the a user interface rendered by the browser 119 and in some embodiments includes an affordance 1004 that is configured to receive input indicating a selection of an option to display a peak viewer panel 1002. The peak viewer panel can be configured to display a relative distribution of ATAC peaks and occurrence of fragments between different clusters in a currently-selected category. As shown in FIG. 10, query box 102 is responsive to an input a gene or a genomic region (peak). For example, as shown in FIG. 10, when the user input includes "CD69," ATAC peaks per each GEX cluster 159 (13 clusters, in this example) near the CD69A gene are displayed. As another example (FIG. 13A), when the user input includes, e.g., "chr:12:9760094-9761921," all ATAC peaks and genes, and their respective quantities in cells on a cluster by cluster basis, within a base pair region (e.g., 1 megabase) of the selected (anchoring) peak are displayed.

As shown in FIG. 11 illustrating an example of a visual representation of ATAC peaks 123 identified near the CD69 gene in cells from a certain sample, each peak 123 can be represented as a corresponding rectangle that spans a certain genomic region within which the peak was detected. Each "active" (selected) cluster has a track (row) in the visualization. In this example, the height of the peak rectangle within each track is proportional to the percentage of cells within that cluster that have a fragment site within a particular peak for which the peak count for that cell at that peak in the feature dataset (e.g., a peak-barcode matrix) is non-zero. In this example, peak heights are normalized to the highest frequency among all clusters. However, it should be appreciated that the normalization is optional. If an input device (e.g., a computer mouse or another device, including user's finger if the display is a touch screen) is detected over a representation of a peak, information related to the peak, such as, e.g., the peak's position, frequency within the cluster, and whether the peak region either encloses or is near a functional region of the gene, can be displayed. Such annotation is illustrated at element 2104 in FIG. 21.

If a pointer of an input device (e.g., a computer mouse) is disposed over a peak (or otherwise positioned with respect to the peak, depending on the specific implementation) in FIG. 11, information on the peak's position, frequency within a cluster, and whether the peak region either encloses or is near a functional region of the gene can be displayed. In the example of FIG. 11, referring again to the example of the CD69 gene, when the mouse is positioned over a rectangle corresponding to a peak, the processor instructs the user interface to display the peak's location, the potential function of the peak's region if any (e.g., CD69 Promoter) and the relative frequency within that cluster (e.g., a number between 0 percent and 100 percent).

Figure 21:
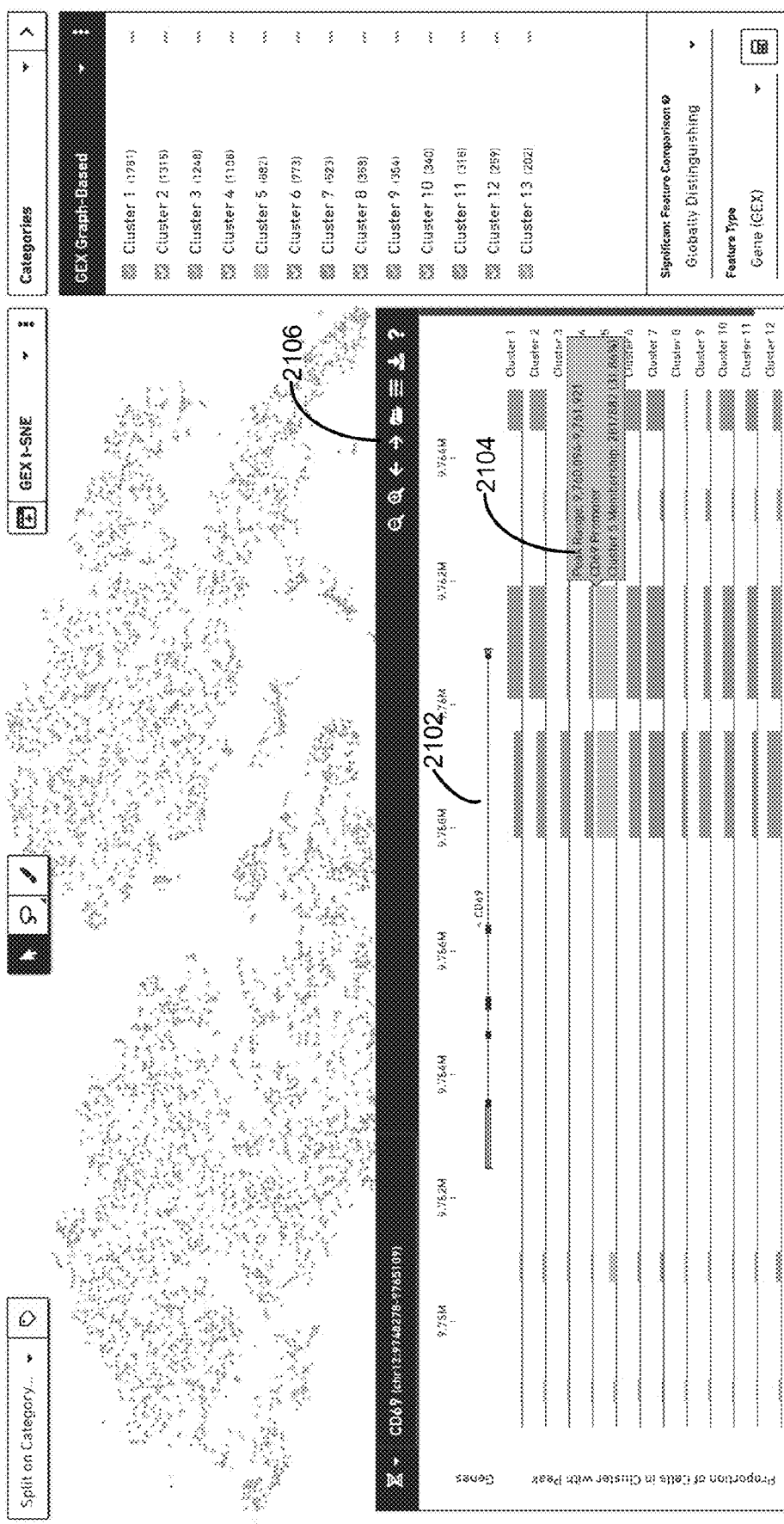
FIG. 21 illustrates an example of the user interface where information on a selected peak is displayed in accordance with some embodiments of the present disclosure.
Figure 22:
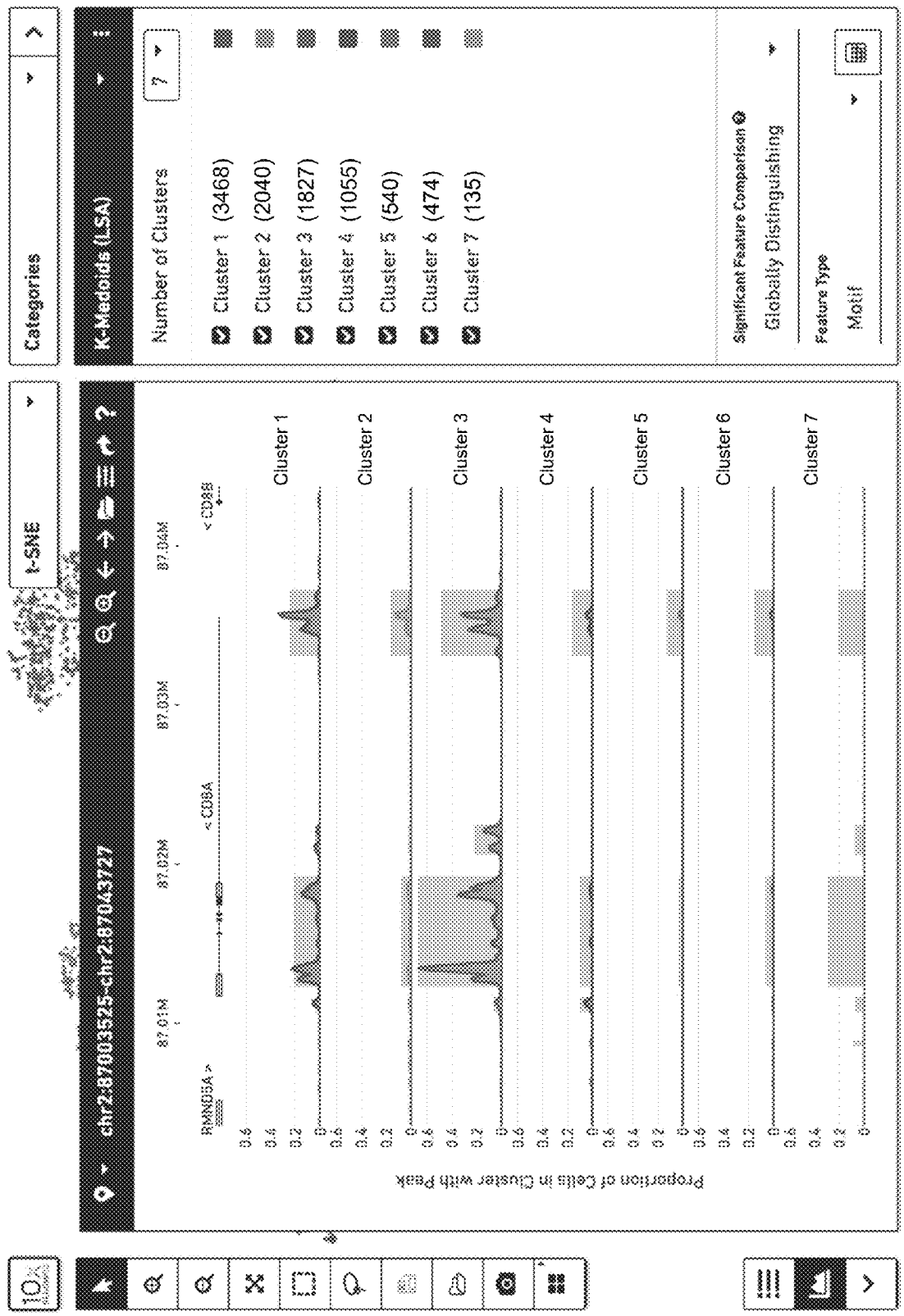
FIG. 22 illustrates an example of a user interface for selectively presenting information from a discrete attribute dataset 120, including information on fragments, in accordance with some embodiments of the present disclosure.

As discussed above, embodiments of the present disclosure store and employ gene and transcript annotations. In some implementations of the browser module 119, gene annotations for a genomic region are displayed as lines 2102, e.g., above the cluster peak tracks, as illustrated in FIG. 21. In some embodiments, the gene can be represented by a solid line. However, it should be appreciated that various other representations of a gene can be generated additionally or alternatively. For example, in some implementations, a gene boundary may be dashed, and a recorded transcript may be in the form of a solid line. Any other types of representations can be used, including, e.g., vertical lines that indicate gene boundaries. In some embodiments, the exons of the gene have thicker line widths, or are otherwise marked, relative to the introns of the gene. In some embodiments, exonic regions and untranslated regions (UTRs) can be represented in the user interface in any suitable manner. For example, in one implementation, exonic regions of the gene annotation are shown as solid rectangles (e.g., black or of any other color) adjacent to (e.g., atop) the gene annotation, and UTRs are in the form of unfilled rectangles. Visual representation(s) of one, two, or more than two transcripts per gene in a reference genome can be generated. In some implementations, a strand of a gene is shown by a backward (<) or forward (>) arrow next to the gene annotation. In response to detecting that an input device is positioned such that it hovers over the gene name, gene position, gene ID, and transcript ID (as found in the reference genome) may be displayed in some implementations.

The representation of ATAC peaks and associated information in accordance with embodiments of the present disclosure can be modified in various ways in response to user input. For example, user input can be received indicating an instruction to zoom out, zoom in, pan left and pan right using collective affordances 2106.

In some embodiments, the default representation of ATAC peaks displays the peaks, e.g., as shown in FIG. 21. Furthermore, the browser module 119 is configured to display representation of the overlap of open fragments. This information can be displayed in response to input specifying a location of a fragments module (or file) storing the fragment information associated with the ATAC dataset. For example, the fragment information can be acquired (e.g., from a fragments dataset in response to a user input (e.g., with response to a "folder" icon) including an instruction to load a ".tsv.gz" file. In some embodiments, a user input can indicate a URL indicating a location of the fragments module file. In some embodiments, a back-end server performs a "sanity check" to verify that the fragments module is correctly associated with the stored fragments tabix index. If the proper association is verified, the fragment information, together with peak information, can be employed for every range and gene query. On the back-end, the server interrogates the tabix index stored in the discrete attribute dataset 120, which will return the byte offset of the chunks within the block-gzipped fragments file containing fragments within the visible region. Since the beginning and ending chunks may also contain fragment locations outside the visible window, the server may apply overlap filtering to ensure that each fragment is within the visible window.

Figure 23:
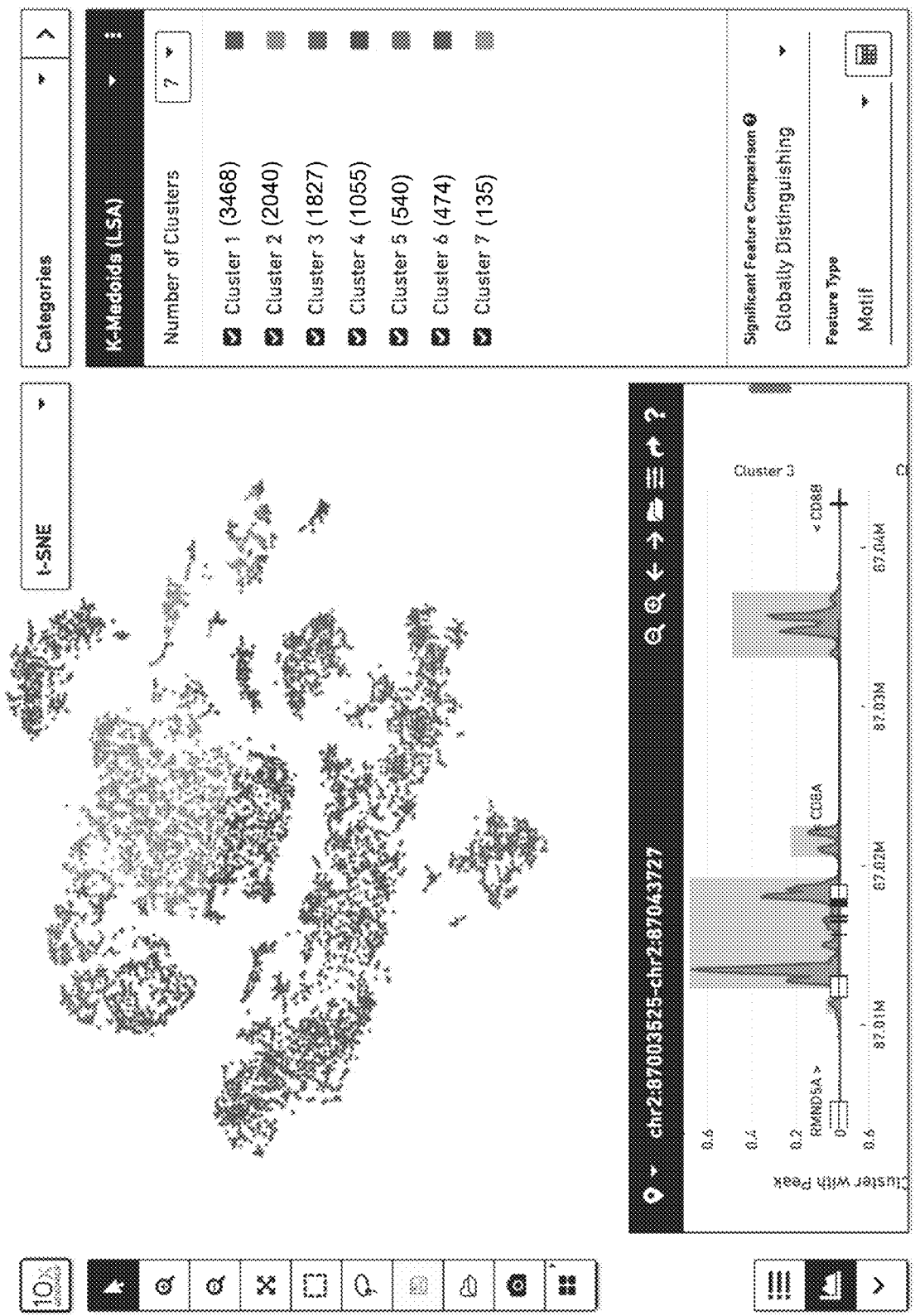
FIG. 23 illustrates an example of a user interface for selectively presenting information from an ATAC dataset, where the user interface present cluster information and ATAC peak information in accordance with some embodiments of the present disclosure.

In some embodiments, when fragments information is loaded into memory for use by processing core(s) executing the browser module 119, a user interface is instructed to present respective fragments information along with a representation of the peaks. For example, as shown in FIG. 23, the user interface can present fragments information in the form of grey (in this example) rectangles "behind" the peaks. This information is generated as rolling window sums of fragment cut sites within a certain distance (e.g., default may be 200 bp or a window of another size) from that spot in the genome. The y-value of each track is the total number of fragments found in cells among that cluster with a start or end position within n base pairs of the underlying genomic location on the x-axis, where n can be user-specified. In the example of the user interface in FIG. 23, heights of the grey rectangles representing fragments are normalized to the largest number of cut sites found at any point in any one cluster. In some embodiments, these may be further normalized by cell count per cluster. If a pointer of an input device is detected over the trace, the number of fragment cut sites (either the start or end of the fragment) within a certain distance of that point is displayed. This indicates accessibility of the chromatin of that point. The representation of the fragment peaks in relation to functional elements in the gene allows assessing biological context of those peaks.

The ATAC peaks and associated information can be displayed in an interactive manner, such that one or more elements in the user interface can be modified automatically or in response to user input. For example, in some embodiments, user input can be received instructing the server to modify the representation of the peaks. For example, a selection of a "disable auto height" option will result in a change in the allocation for each cluster from a percentage of the peak viewer height to a fixed number of pixels. In this view, the gene annotation track drops from above the clusters to an overlay atop it. As shown in FIG. 23, in response to user input (which can be, for example, moving the scroll bar up and down), cluster representation can be displayed underneath the gene annotation. A user can instruct the user interface to return to the auto height representation by selecting the "enable auto height" option. Furthermore, when peak distribution and fragment cut site location data is loaded, the user interface provides an option to "hide" fragment traces or peaks with the "show/hide peak distribution" and "show/hide cut sites" options displayed on the user interface. Similarly, gene annotations can be displayed or removed from the display.

Furthermore, as mentioned above, values of the fragment traces are functions of the windows around each position in the genome. The described techniques allow a user to vary the "openness" metric, based on the assumption that chromatin may be less accessible downstream from a particular cut site. Thus, the user interface can allow selecting the width of the window used to mark locations as being accessible by choosing, e.g., a value of a "smoothing window size" option. Smaller windows may reveal further nuances in the distribution of cut sites.

In some embodiments, underlying data and/or the graphical representation of the peak information can be stored in a suitable format. For example, in response to an indication that an "export" option is selected, the server hardware can instruct the browser module 119 to store the information. In this way, the frequency of each currently visible peak within each cluster can be stored, e.g., as a CSV file that is exported as a .bedgraph file representing the windowed cut site sums for each cluster. The graphical representation of the peaks can be stored in PNG, SVG, or any other suitable format. It should be noted that the embodiments of the present disclosure are not limited with respect to a format in which the peak data and peak's graphical representation can be stored.

Another aspect of the present disclosure provides a method for characterizing cells, comprising partitioning a plurality of cells or cell nuclei and a plurality of barcode beads into a plurality of partitions, where at least a subset of the plurality of partitions each comprise a cell or cell nucleus of the plurality of cells or cell nuclei and a barcode bead of said plurality of barcode beads, and each bead in the subset of said plurality of partitions comprises a unique barcode sequence. The method further includes generating a plurality of barcoded nucleic acid molecules comprising barcode sequences, where a first subset of the plurality of barcoded nucleic acid molecules comprises a sequence corresponding to a ribonucleic (RNA) molecule and a second subset of said plurality of barcoded nucleic acid molecules comprises a sequence corresponding to a sequence corresponding to a region of accessible chromatin. The method further comprises sequencing the plurality of barcoded nucleic acid molecules, or derivatives generated therefrom, to generate sequencing information, and using the barcode sequence and the sequencing information to identify cell types in the sequencing information.

In some embodiments, the methods disclosed herein further comprise using said sequencing information to cluster cells by regions of accessible chromatin. In some embodiments, the methods further comprise using the sequencing information to cluster cells by gene expression. In some embodiments, the methods further comprise using the sequencing information and the cells clustered by gene expression to annotate, identify, or characterize cells clustered by regions of accessible chromatin. In some embodiments, the methods further comprise using the sequencing information and the cells clustered by regions of accessible chromatin to annotate, identify, or characterize cells clustered by gene expression. In some embodiments, the plurality of cells or cell nuclei are derived from a tumor sample or a sample suspected of comprising a tumor. In some embodiments, the methods further comprise using the sequencing information to identify a cell type, a cell state, a tumor-specific gene expression pattern, or a tumor-specific differentially accessible regions of chromatin in the tumor sample or the sample suspected of comprising said tumor. In some embodiments, the methods further comprise using the sequencing information to identify or confirm the presence of a tumor cell in the tumor sample or the sample suspected of comprising said tumor. In some embodiments, the methods further comprise administering a therapeutically effective amount of an agent targeting one or more targets identified in the tumor-specific gene expression pattern or the tumor-specific differentially accessible regions of chromatin. In some embodiments, the tumor is a B cell lymphoma.

EXAMPLES

Example 1. Joint ATAC and Gene Expression Profiling of Peripheral Blood Mononuclear Cells As described herein, in some embodiments, complex biological systems can be better understood by profiling a plurality of different modalities within single cells. For example, in some instances, each cell in a plurality of cells can be assayed using gene expression analysis to obtain patterns in discrete attribute values for genes and/or differential values thereof (e.g., fold change and/or relative gene expression), as well as using open chromatin analysis (e.g., ATAC fragment count values) to obtain information on regions of chromatin accessibility and/or associated cell populations. Subsequently, analysis of these individual modalities (e.g., clustering based on discrete attribute values and/or clustering based on ATAC fragment count values) for the plurality of cells can be combined to obtain indications of membership in each of the respective modalities for each respective cell in the plurality of cells (e.g., membership in one or more of gene expression clusters and/or open chromatin clusters). Linkages obtained using assignment of single cells to multiple modality classes (e.g., a single population of cells, where each respective cell is analyzed for both gene expression and open chromatin profiling) are likely to be more robust than, for example, single modality analysis on each of separate sub-populations of cells (e.g., a first subset of cells analyzed for gene expression and a second subset of cells analyzed for open chromatin). For example, in some instances, comparisons drawn from a plurality of separate analyses of a respective plurality of sub-populations provide inferred linkages, in contrast to true linkages that can be obtained from a plurality of analyses performed on a single cell. Accordingly, a joint open chromatin (ATAC) and gene expression (GEX) profiling assay was performed for 24,000 peripheral blood mononuclear cells (PBMCs), in accordance with some embodiments of the present disclosure.

Each cell in the plurality of PBMCs was analyzed and clustered by gene expression (GEX) profiling using expressed markers (FIG. 24) and open chromatin analysis using an assay of transposase-accessible chromatin (ATAC) (FIG. 25). For each modality, the plurality of cells was visualized as a dimension reduced projection using t-distributed stochastic neighbor embedding (t-SNE) (plots 2400 and 2500). For the gene expression analysis, each cell in the plurality of cells was assigned to a respective cluster group (e.g., annotated) from 13 gene expression clusters (e.g., 2402, 2404, 2406, 2408, 2410, 2412, 2414, 2416, 2418, 2420, 2422, 2424, and/or 2426). In some embodiments, there is an additional group designed as "NA" 2428 (e.g., none of the above 13 gene expression clusters). For the open chromatin analysis, each cell in the plurality of cells was assigned to a respective cluster group (e.g., annotated) from 4 chromatin accessibility clusters (e.g., 2502, 2504, 2506, and/or 2508). In some embodiments, there is an additional group designed as "NA" 2510 (e.g., none of the above 4 chromatin accessibility clusters). Concordance observed between the two modalities (e.g., gene expression and open chromatin) is illustrated in FIGS. 26A and 26B. FIG. 26A shows concordance between gene expression annotations (RNA (2400)) and open chromatin annotations (ATAC (2500)) for each respective cell in the plurality of PBMCs used in the joint ATAC and GEX profiling assay. FIG. 26B maps the relationships between gene expression clusters and open chromatin clusters as indicated by the overlap of cells assigned to each cluster type (e.g., co-annotations of PBMCs shared between cell type annotations; indicated by gray). Clusters (e.g., 2602, 2604, 2606, 2608, 2610, 2612, 2614, 2616, 2618, 2620, 2622, 2624, and/or 2626) identified by gene expression profiling (RNA) are indicated to the left and cell type annotations identified by open chromatin profiling (ATAC) are indicated to the right of FIG. 26B.

Figure 27A:
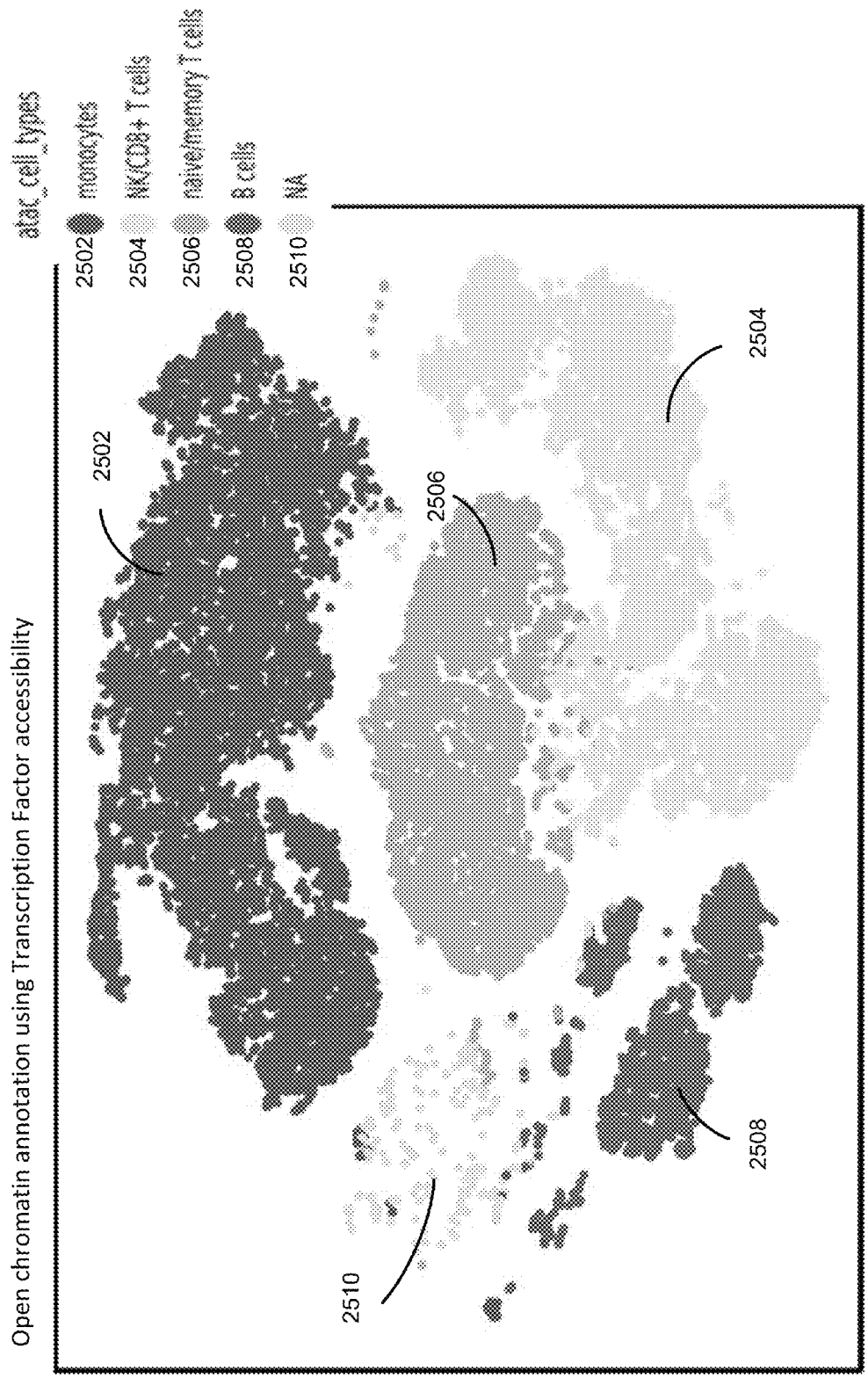
FIGS. 27A and 27B collectively illustrate the transfer of gene expression marker-derived annotation into accessible chromatin clustered populations, in accordance with an embodiment of the present disclosure. Top panel: cells were clustered and annotated with ATAC data using transcription factor accessibility (e.g., open chromatin), providing annotated cell clusters with limited specificity to differentiate additional, more precise cell types. Bottom panel: cells clustered using open chromatin (ATAC) clustering were further annotated using gene expression markers.
Figure 27B:
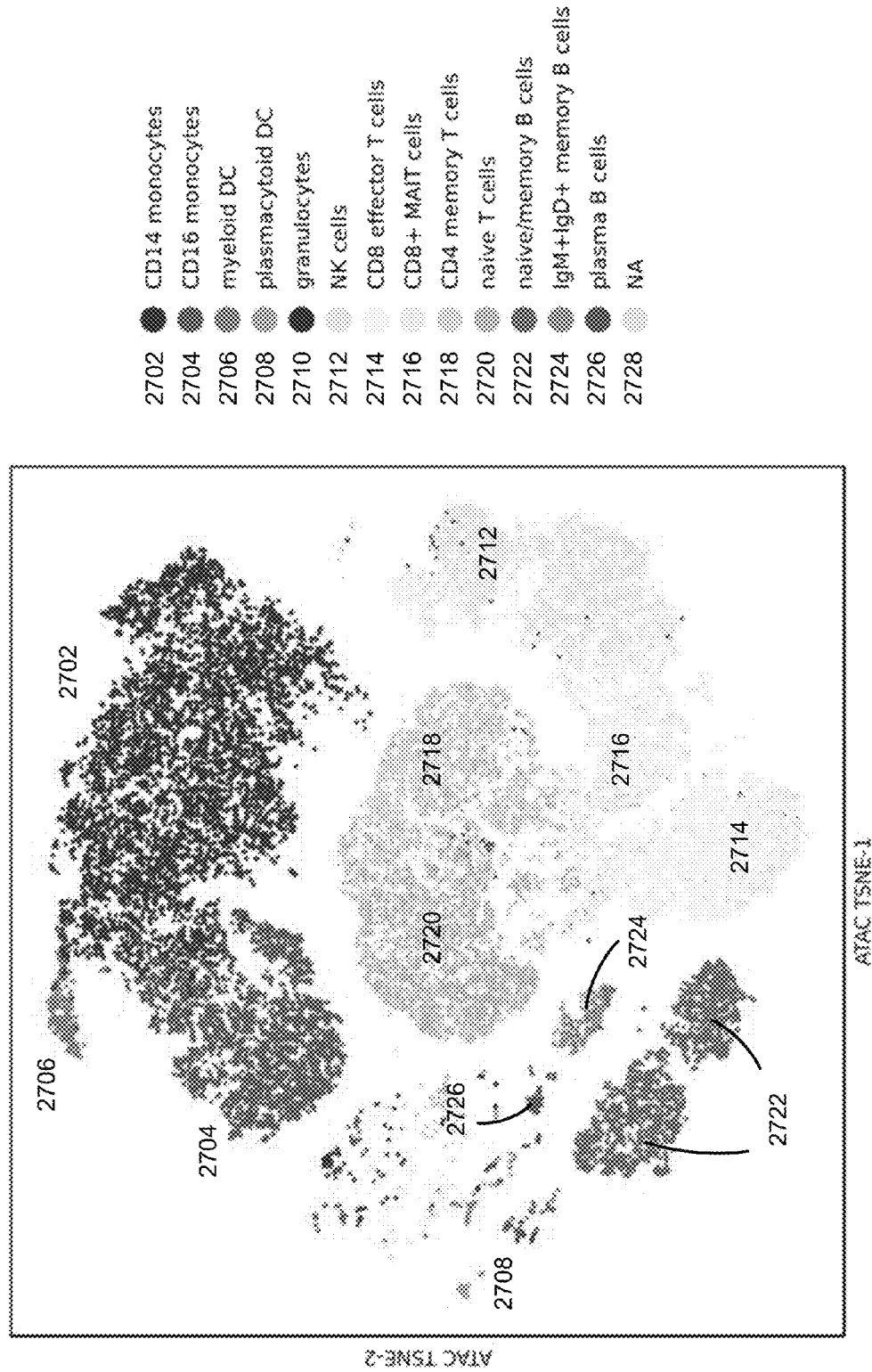

Gene expression marker-derived annotations were transferred onto cell populations clustered by accessible chromatin analysis, as illustrated in FIGS. 27A and 27B. In some embodiments, there are 13 clusters (e.g., 2702, 2704, 2706, 2708, 2710, 2712, 2714, 2716, 2718, 2720, 2722, 2724, and/or 2726). In some embodiments, there is an additional group designed as "NA" 2728 (e.g., none of the above 13 clusters). The top panel illustrates cells that were clustered and annotated with ATAC data using transcription factor accessibility (e.g., a two-dimensional projection of the plurality of cells based on assignment of the plurality of cells to open chromatin cluster groups), while the bottom panel shows these same clusters differentially annotated with the assignment of each cell to a respective gene expression cluster, obtained from gene expression clustering analysis (e.g., an indication of membership, for each cell in the plurality of cells, in a respective gene expression cluster group). Whereas single modality annotation of cell clusters (e.g., ATAC clustering only) results with limited specificity, FIGS. 27A and 27B show that additional annotation of such cell clusters with a second modality (e.g., gene expression markers and/or gene expression clustering annotation) can be used to differentiate additional, more precise cell types and provide further context around particular cell types.

Figure 28A:
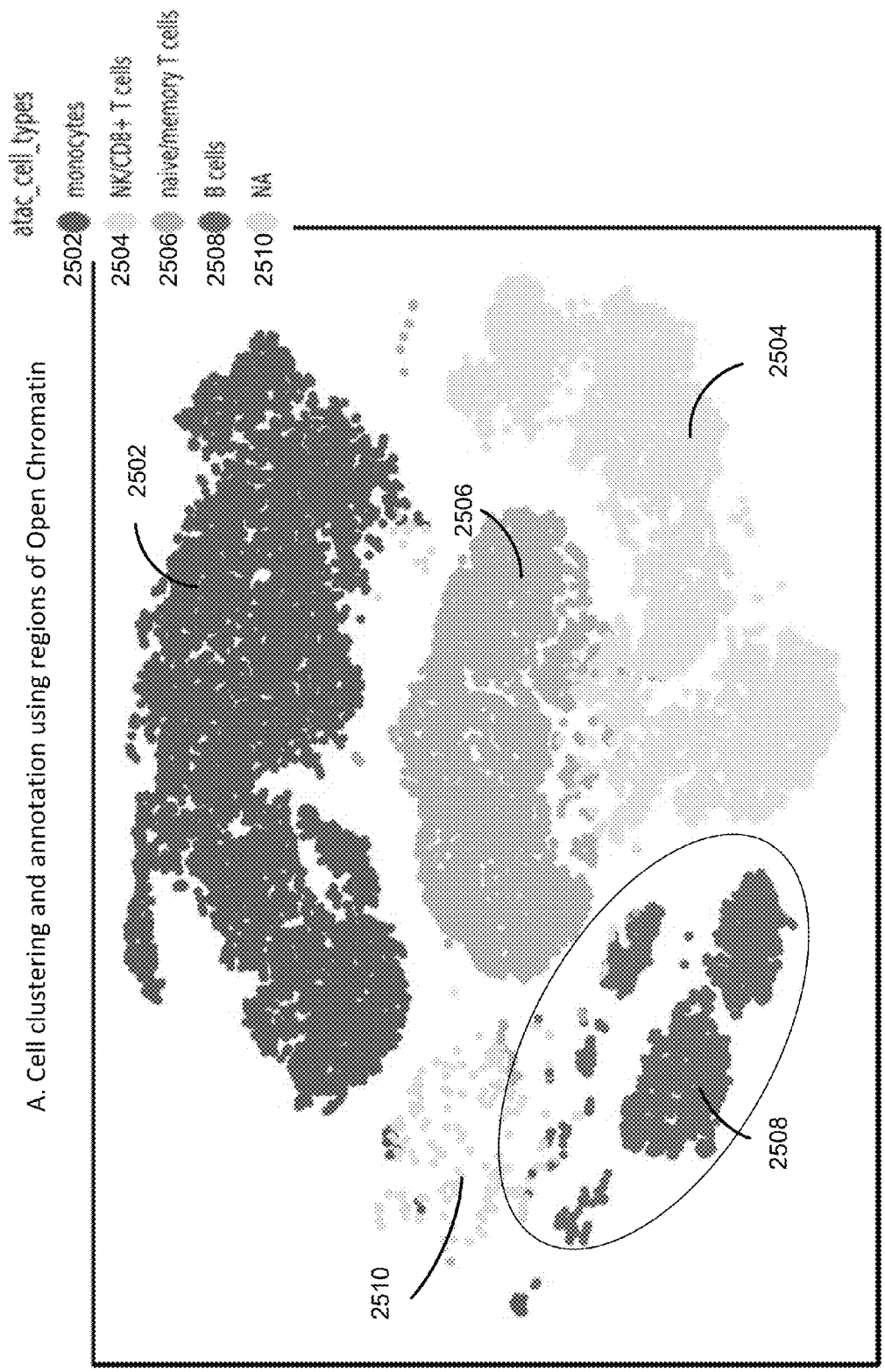
FIGS. 28A, 28B, and 28C collectively illustrate the identification of novel populations of cells that would otherwise be unidentified and/or unannotated when analyzing either gene expression or regions of open chromatin alone, in accordance with an embodiment of the present disclosure.
Figure 28B:
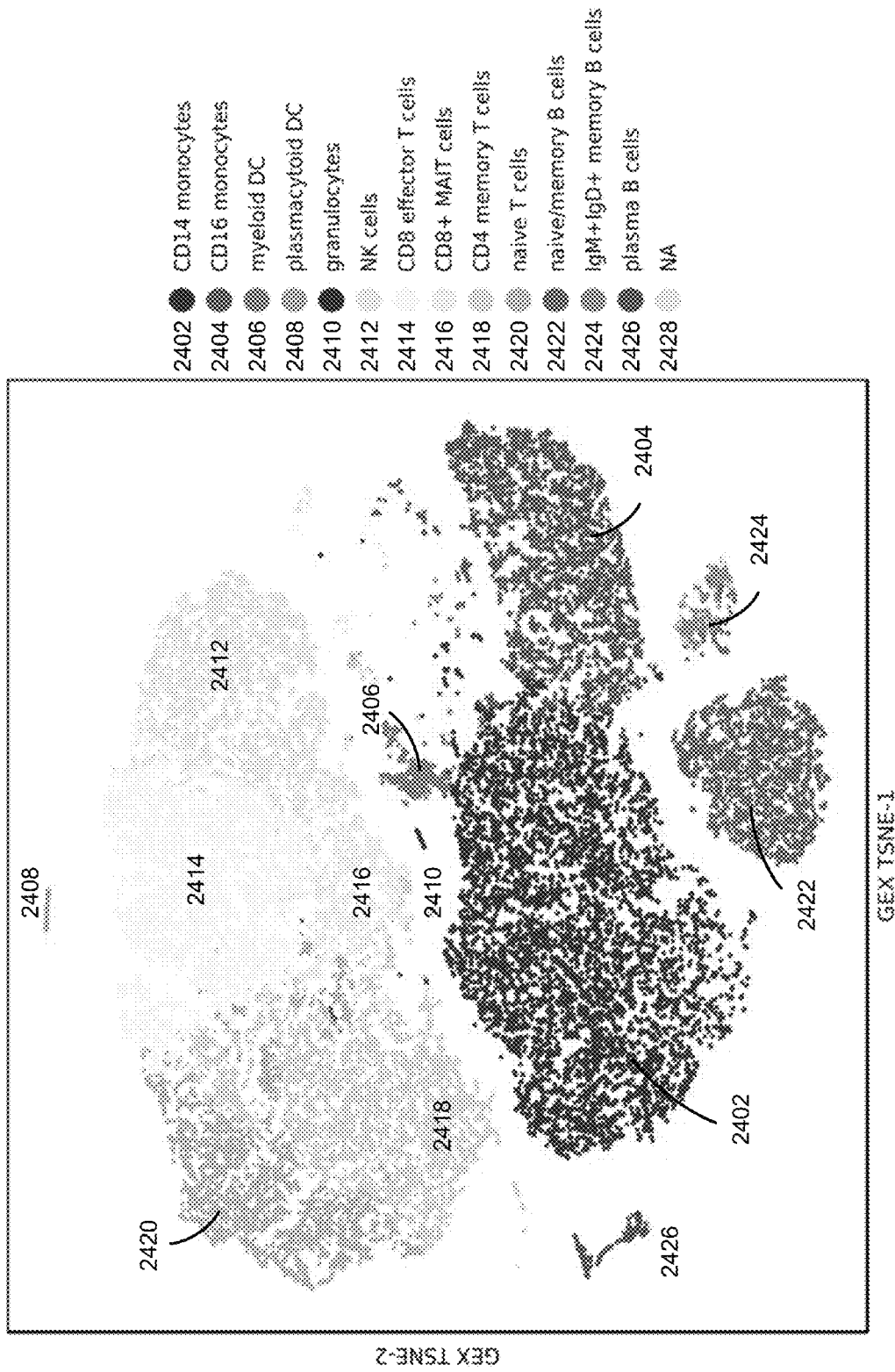
Figure 28C:
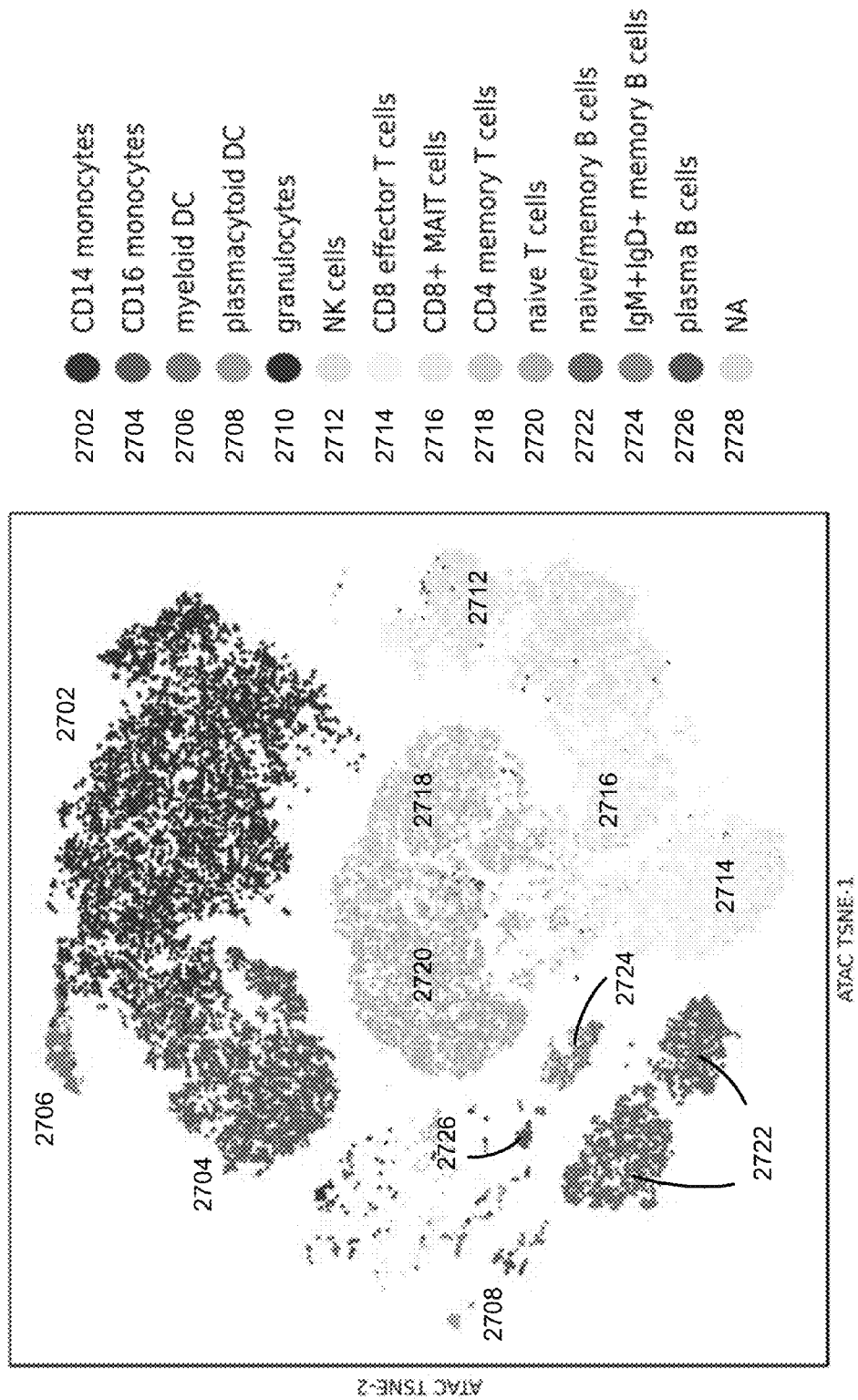

Additional gene expression analysis was performed to identify novel or stratified populations of cells otherwise undetected when using analysis of either gene expression or regions of open chromatin alone. For example, as illustrated in FIG. 28A, one or more populations of cells identified using open chromatin analysis alone may be visualized as large clusters or groups of clusters of cells. In particular, as illustrated in FIG. 28A, B cells are visualized as a plurality of large cluster groups comprising multiple smaller populations of cells. (2508). Similarly, populations of cells identified using gene expression markers alone may include mixed populations of cell subtypes, as illustrated in FIG. 28B. In particular, naïve and memory B cells are grouped together in a single cluster (2422). Whereas FIG. 28C shows that the combination of different modalities (e.g., open chromatin clustering and annotation using gene expression analysis) allows the stratification of the large B cell cluster (2508) into three separate sub-populations (e.g., naïve/memory B cells (2722), IgM+IgD+ memory B cells (2724), and plasma B cells (2726)), it further indicates the presence of two possible sub-populations of cells in the naïve/memory B cell ATAC/GEX-annotated cluster.

Figure 29A:
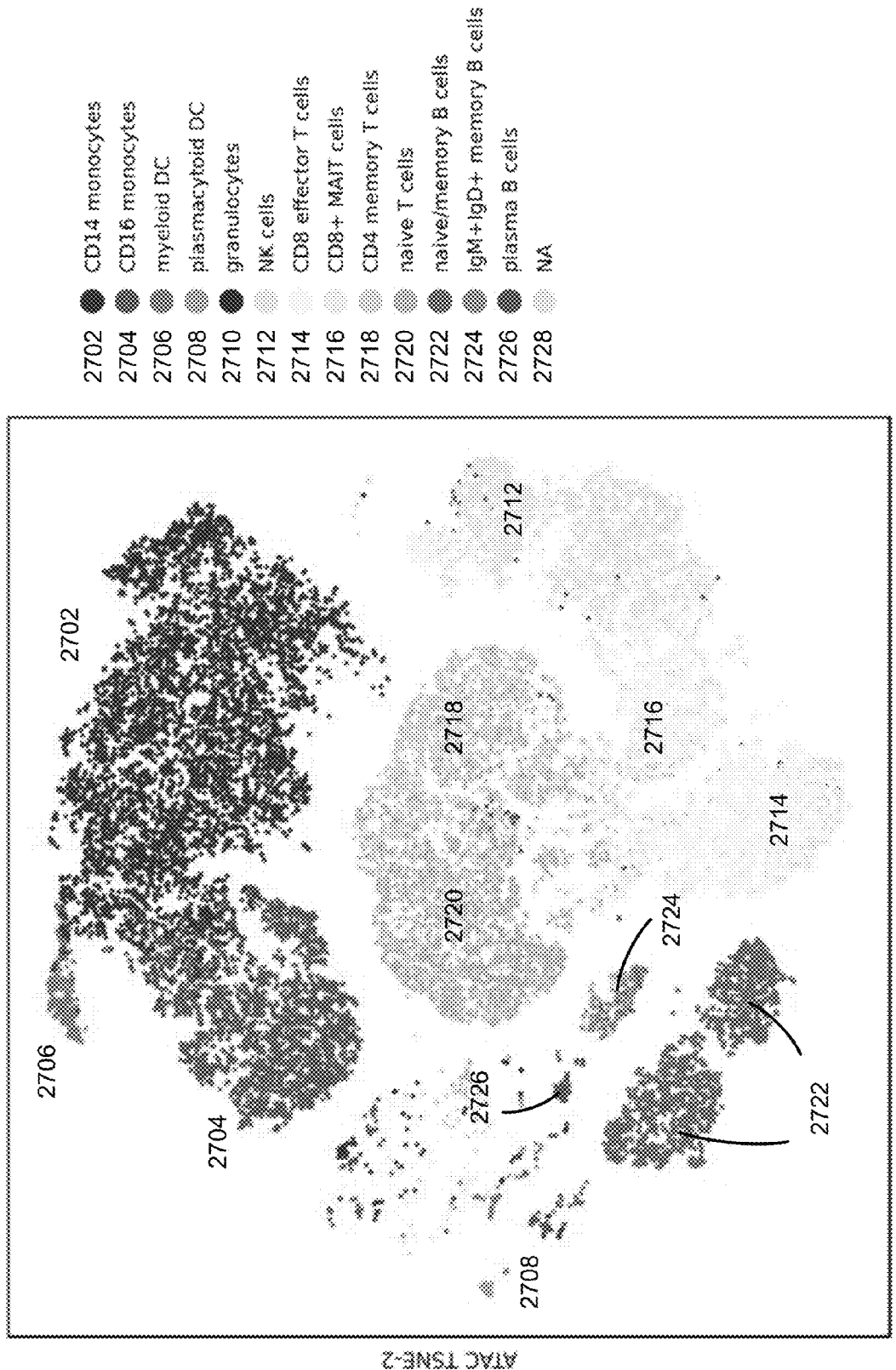
FIGS. 29A, 29B, 29C, 29D, and 29E collectively illustrate differential gene expression in the annotated cells shown in FIGS. 28A-C, and the identification and differentiation of prospective naïve vs. memory B cells, in accordance with an embodiment of the present disclosure. A population of cells identified by gene expression (GEX) analysis to be a single cluster of naïve/memory B cells (FIG. 29B (2422)), nevertheless appeared as two distinct clusters of naïve/memory B cells in the gene expression-annotated open chromatin clustering (FIG. 29A; 2722). Further analysis of the differential gene expression in the gene expression-annotated open chromatin clustering plot revealed two distinct populations of cells (subcluster 1 (2902) and subcluster 2 (2904)) that were visibly separated when using open chromatin clustering (FIG. 29C) but were obscured when viewing gene expression cluster analysis alone (FIG. 29D). Gene expression analysis of subcluster 1 and subcluster 2 identified subcluster 1 as prospective memory B cells (relatively higher Ig, relatively lower naïve B cell associated transcripts) and subcluster 2 as prospective naïve B cells (relatively lower Ig, relatively higher naïve B cell associated transcripts), as illustrated in FIG. 29E.
Figure 29B:
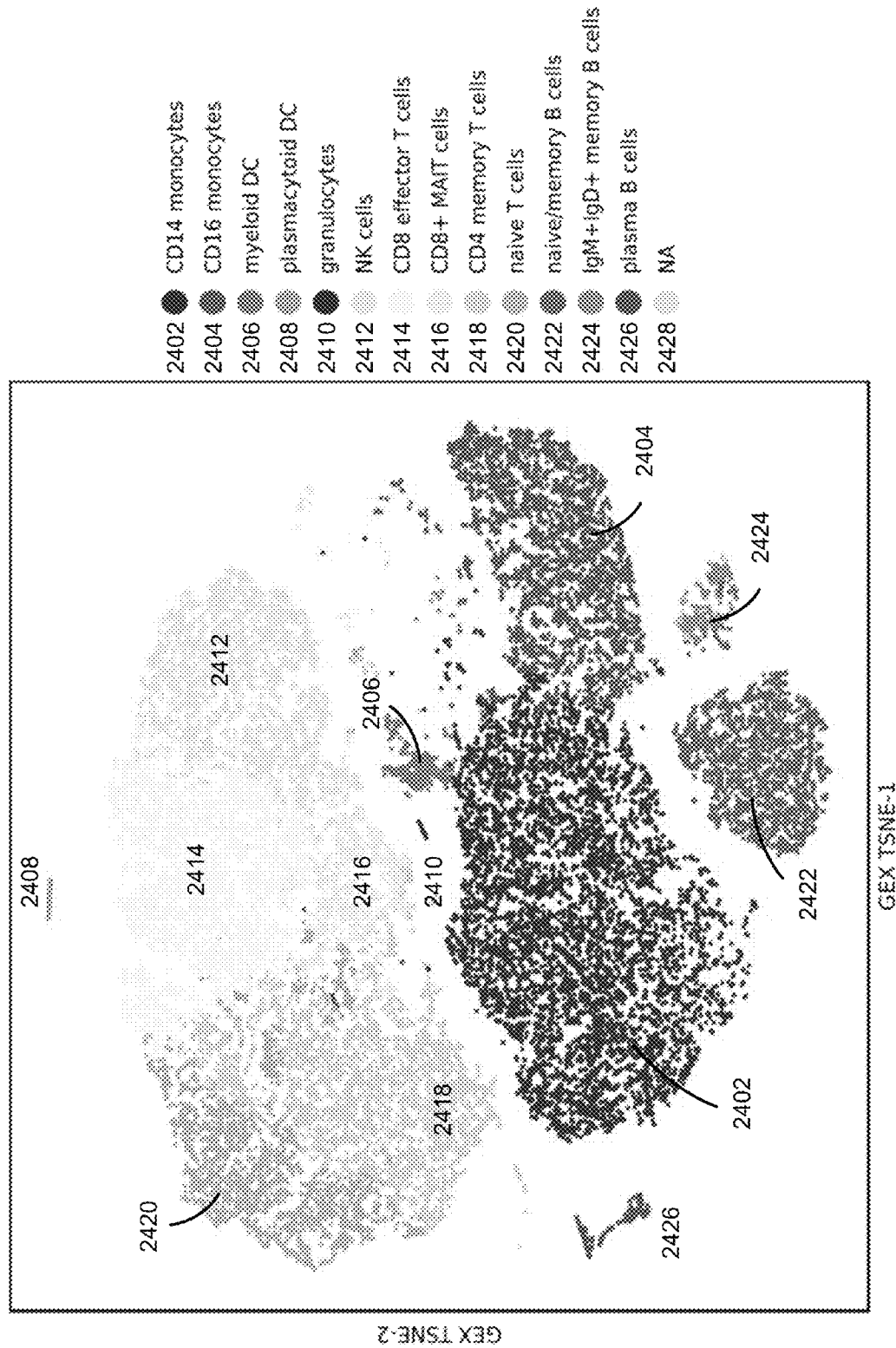
Figure 29C:
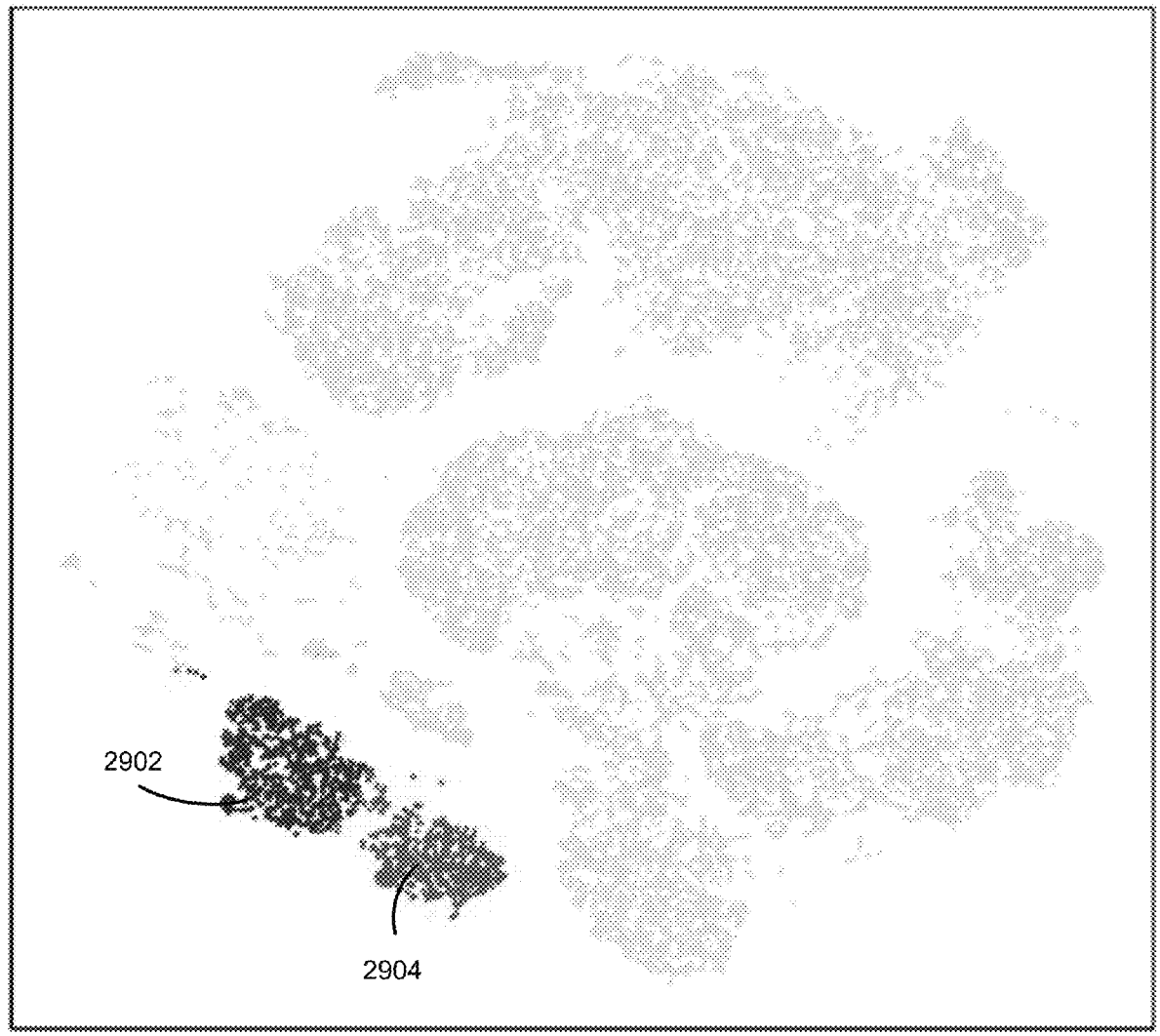
Figure 29D:
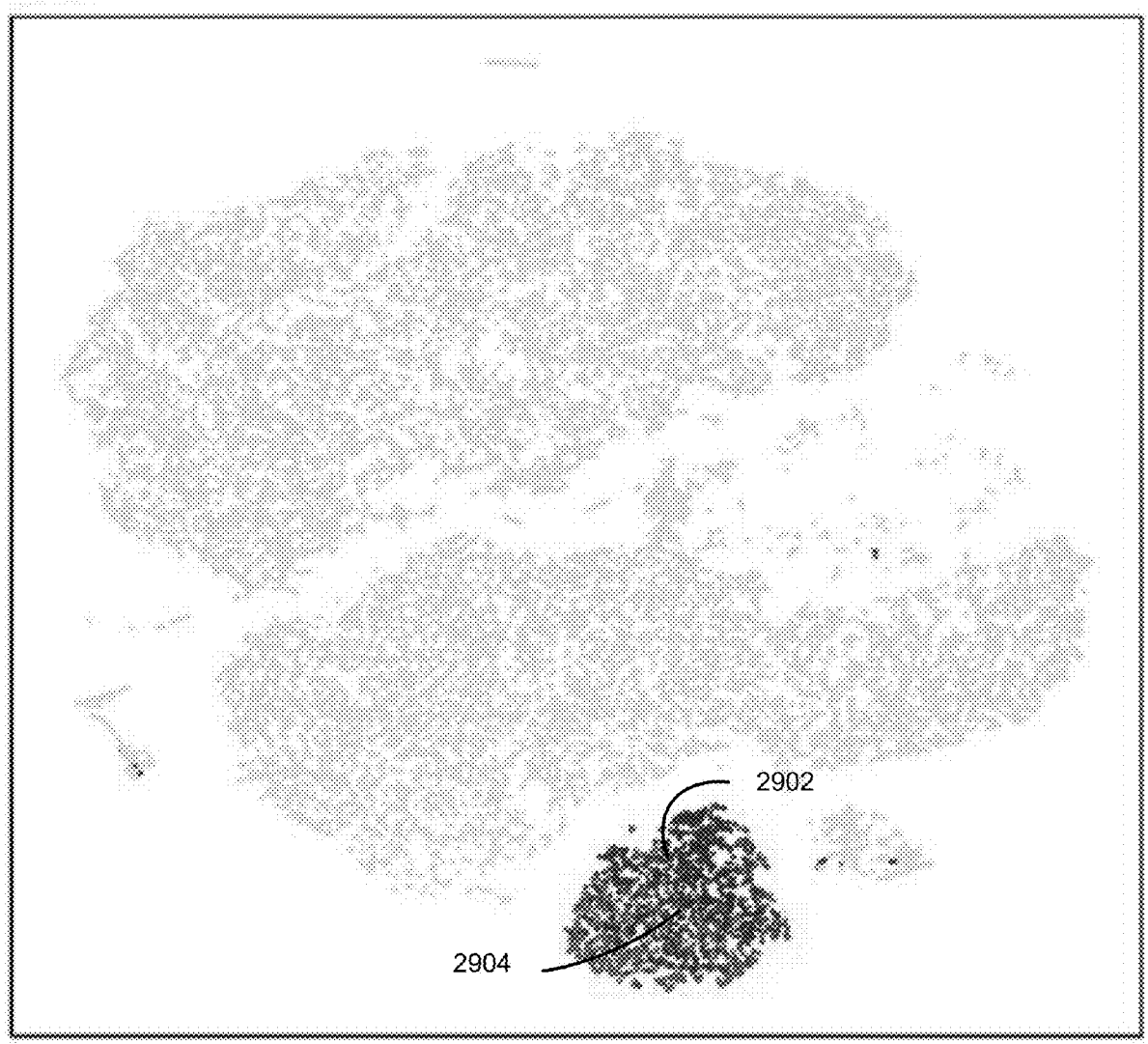
Figure 29E:
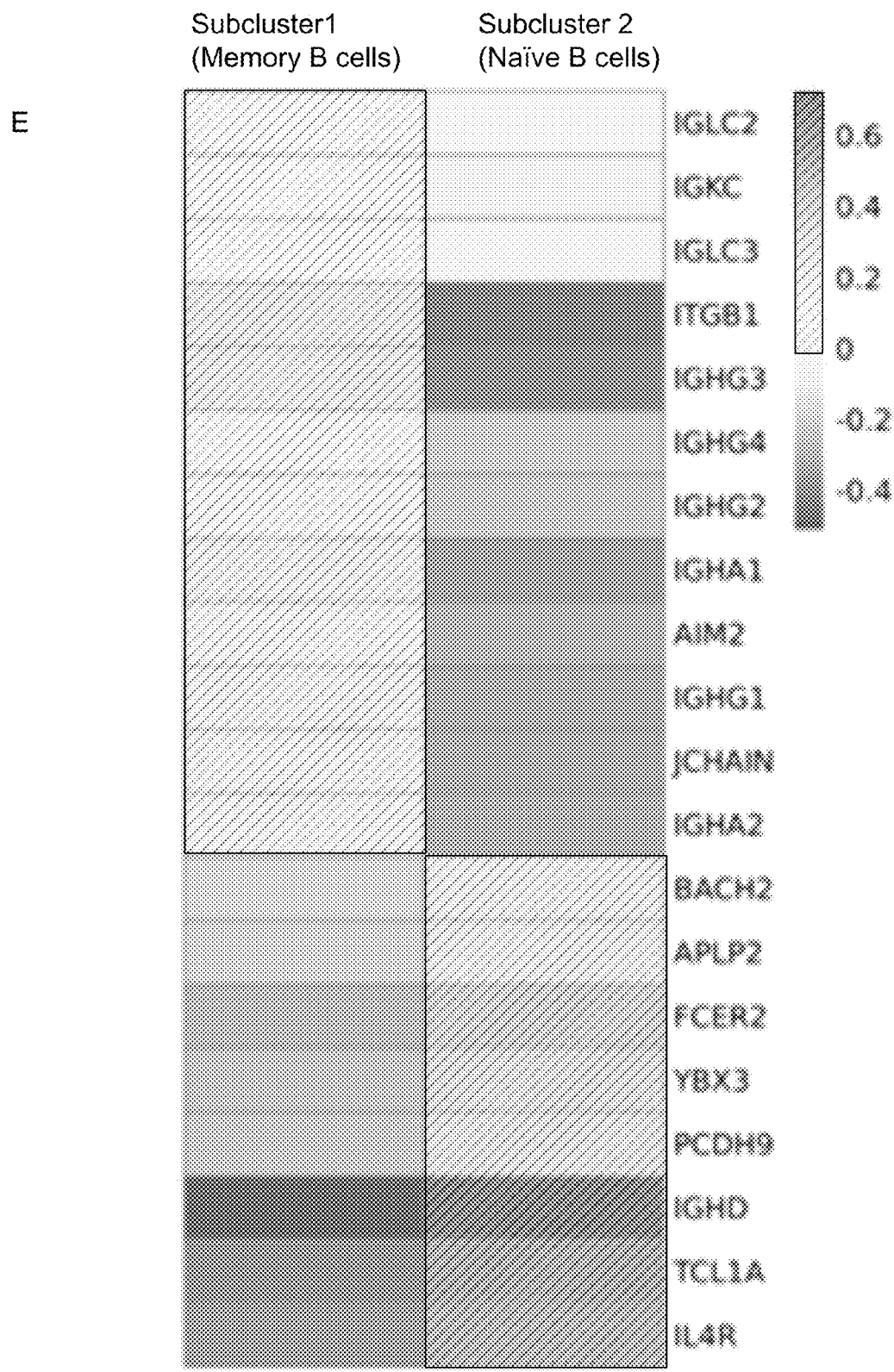

FIGS. 29A and 29B further show a comparison of the naïve/memory B cell cluster using two different methods of analysis. Whereas GEX-clustering and annotation alone indicate only a single population of naïve/memory B cells (FIG. 29B; 2422), ATAC-clustering coupled with GEX-annotation indicated two sub-populations (FIG. 29A; 2722). Further analysis of the differential gene expression in the gene expression-annotated open chromatin clustering plot revealed that the two distinct sub-populations of cells (sub-cluster 1 (2902) and subcluster 2 (2904)) that were visible when viewing open chromatin clustering (FIG. 29C) represented prospective memory B cells and naïve B cells, respectively. These sub-populations were indistinguishable when viewing gene expression clustering alone, with memory B cells and naïve B cells clustering together (FIG. 29D). Gene expression analysis of the memory B cells in subcluster 1 and the naïve B cells in subcluster 2 identified differential gene expression of representative markers, where prospective memory B cells expressed relatively higher Ig, relatively lower naïve B cell associated transcripts and prospective naïve B cells expressed relatively lower Ig, relatively higher naïve B cell associated transcripts, as illustrated in FIG. 29E. Together, the data indicate that additional annotation of open chromatin (ATAC) clusters with gene expression markers can provide additional context around particular cell types and subtypes that would be lacking not only when using only ATAC clustering and annotation, but also when using only gene expression clustering and annotation. Thus, in some embodiments, both gene expression analysis and open chromatin analysis are improved by the additional annotation of a second modality, for example, by facilitating the identification of novel populations of cells that would otherwise be unidentified and/or unannotated when analyzing either gene expression or regions of open chromatin alone.

Example 2. Functional Characterization of a Small B Cell Lymphoma

Figure 30A:
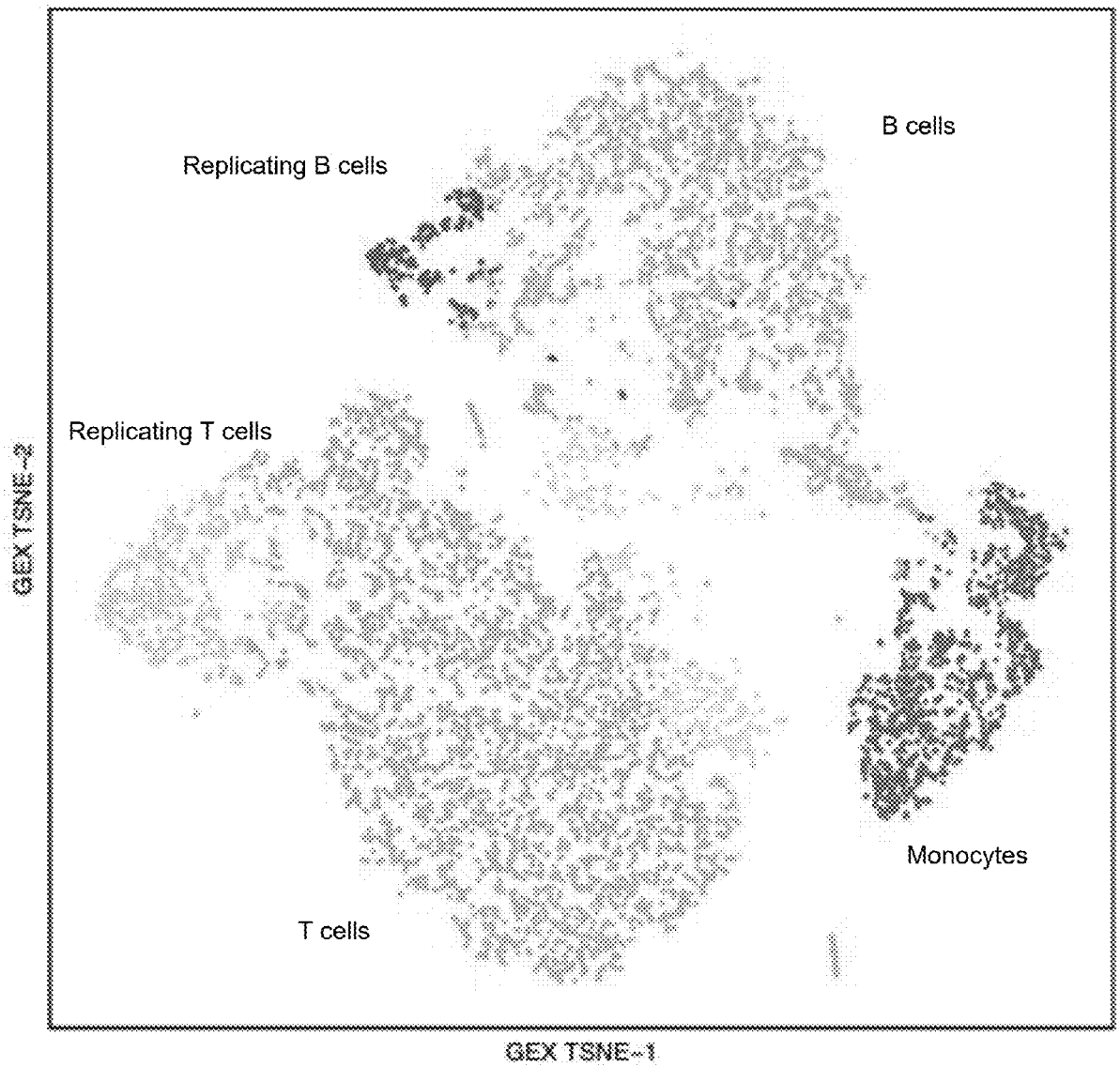
FIGS. 30A and 30B collectively illustrate cell type annotation of a tumor sample using gene expression (GEX) markers and transcription factor (ATAC) accessibility, in accordance with an embodiment of the present disclosure. Gene expression clustering identified five cell type categories (B cells, replicating B cells, monocytes, T cells, and replicating T cells) (FIG. 30A). Open chromatin clustering identified three cell type categories (B cells, monocytes, and T cells) (FIG. 30B).
Figure 30B:
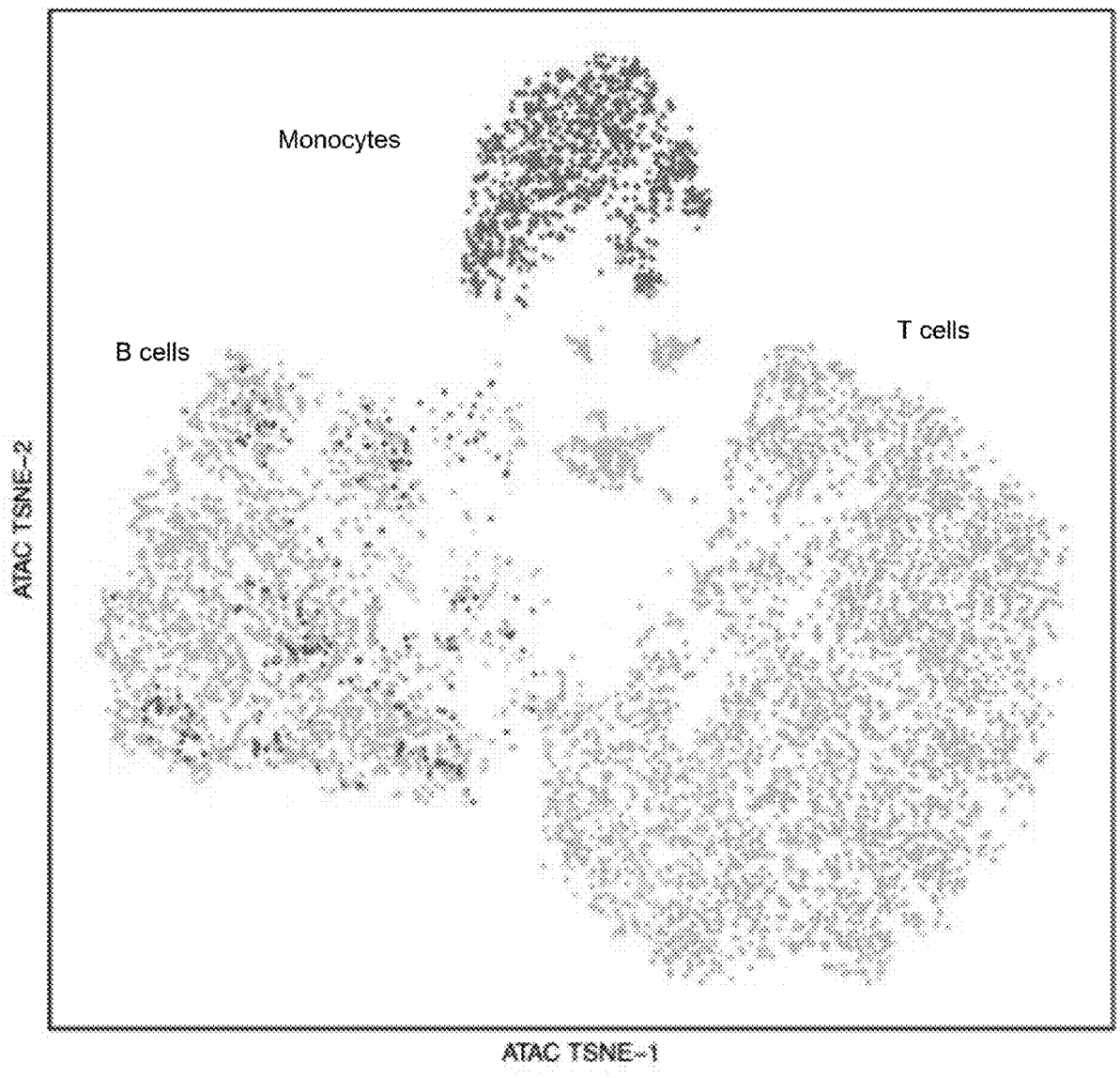

A sample of an intra-abdominal lymph node tumor was obtained from a subject in order to perform a functional characterization of a small B cell lymphoma and the signaling pathways thereof. A pathology report for the subject indicated a diagnosis of diffuse small lymphocytic lymphoma of the lymph node (e.g., malignant lymphoma, small B cell, diffuse type, IHC: CD20(+), CD3(−)). Approximately 9000 nuclei (e.g., cells) from the tumor sample were profiled using gene expression analysis and single cell open chromatin (ATAC-seq). For each modality (e.g., GEX analysis and ATAC-seq), the plurality of cells was visualized as a dimension reduced projection using t-distributed stochastic neighbor embedding (t-SNE). Gene expression clustering assigned tumor cells to one of five cell type categories (B cells, replicating B cells, monocytes, T cells, and replicating T cells), as illustrated in FIG. 30A. Open chromatin clustering assigned tumor cells to one of three cell type categories (B cells, monocytes, and T cells), as illustrated in FIG. 30B.

Figure 31A:
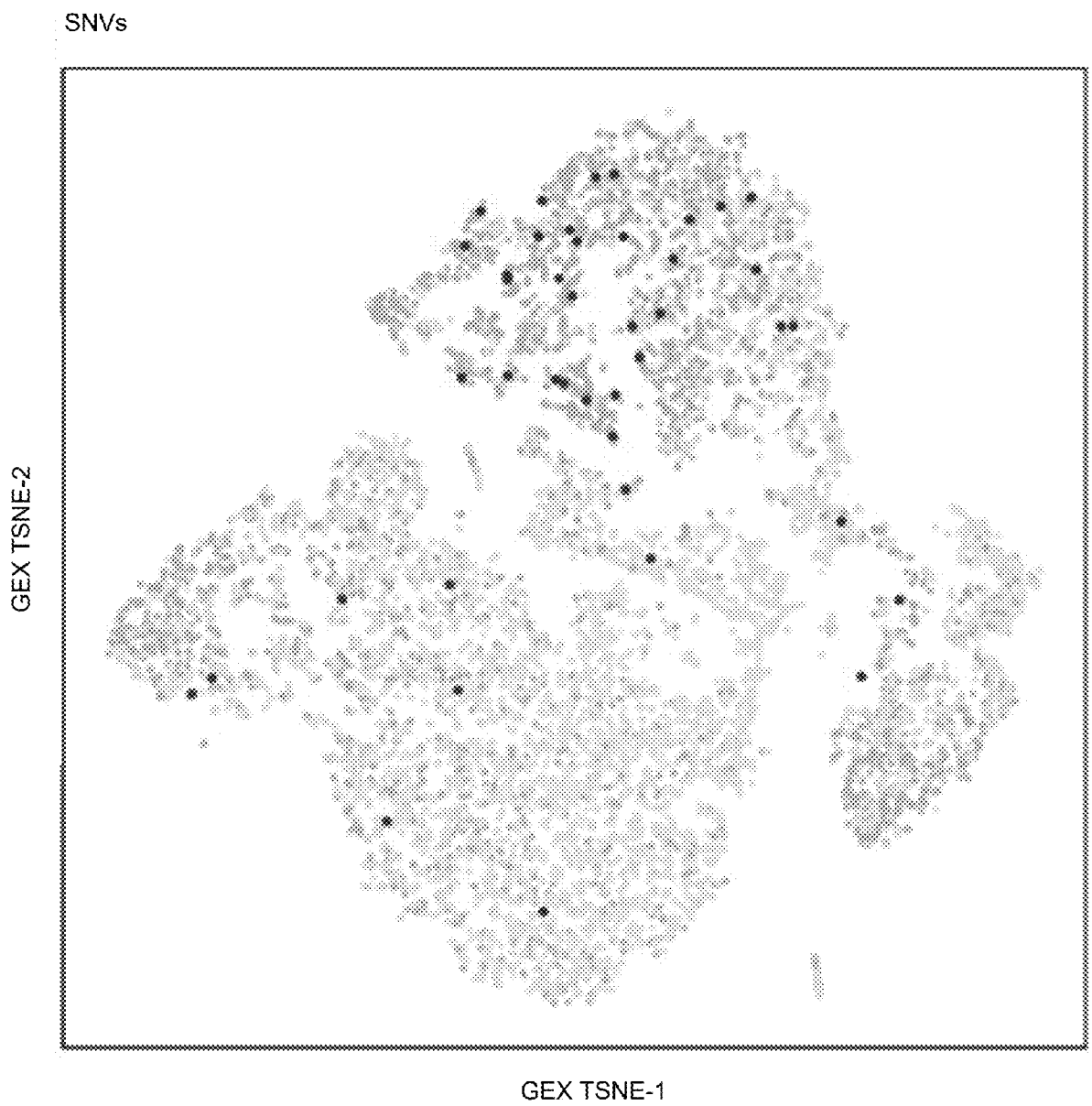
FIGS. 31A, 31B, and 31C collectively illustrate the identification of tumor from normal B cells using mutational load (SNVs) (FIG. 31A) and the BANK1 pathway (markers of B cell hyper-activation) (FIG. 31B), in gene expression data from the lymph node tumor sample, in accordance with an embodiment of the present disclosure. Two sub-populations of B cells (tumor B cells and normal B cells) in cell populations clustered by gene expression profiling are identified in FIG. 31C.
Figure 31B:
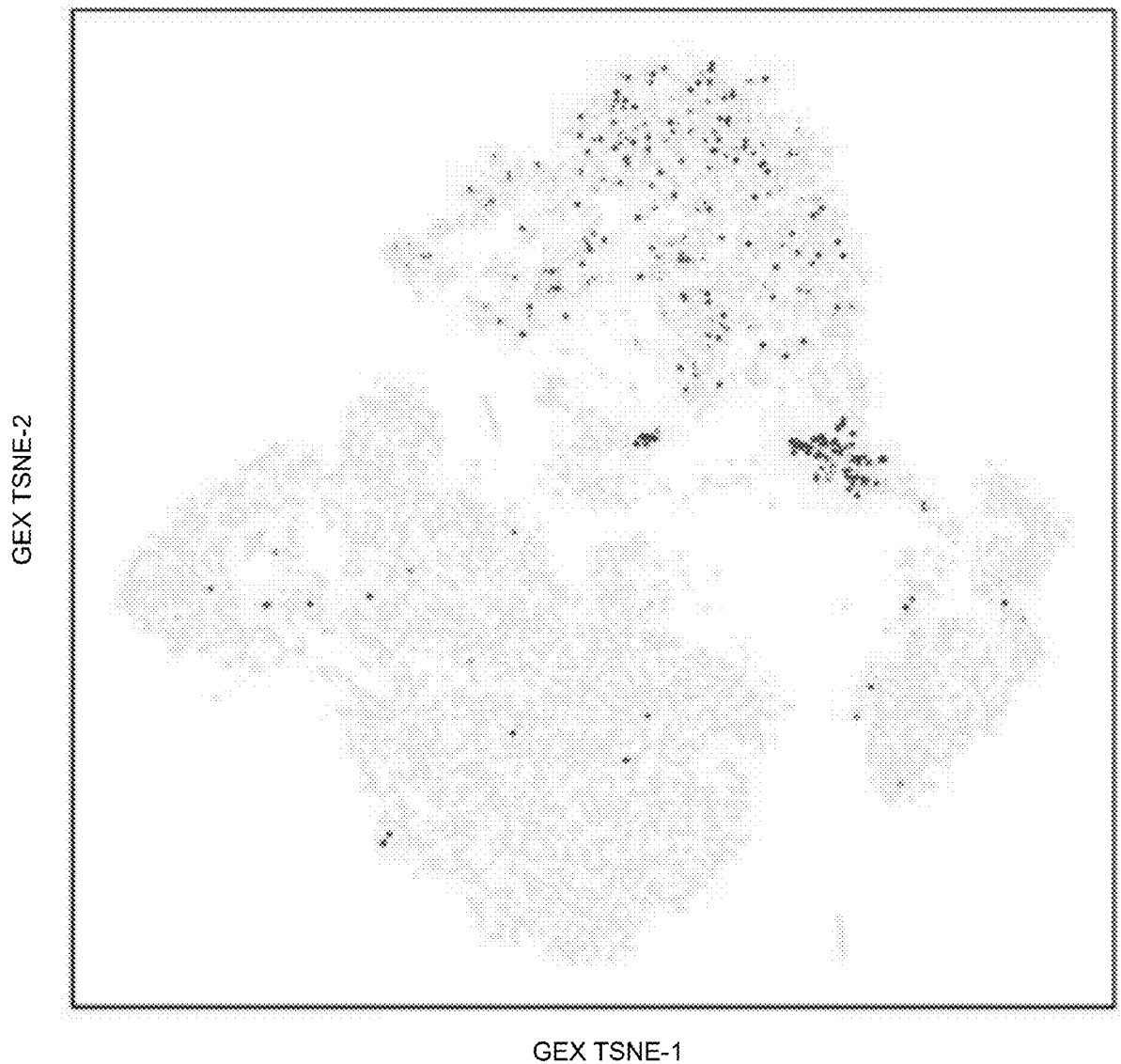
Figure 31C:
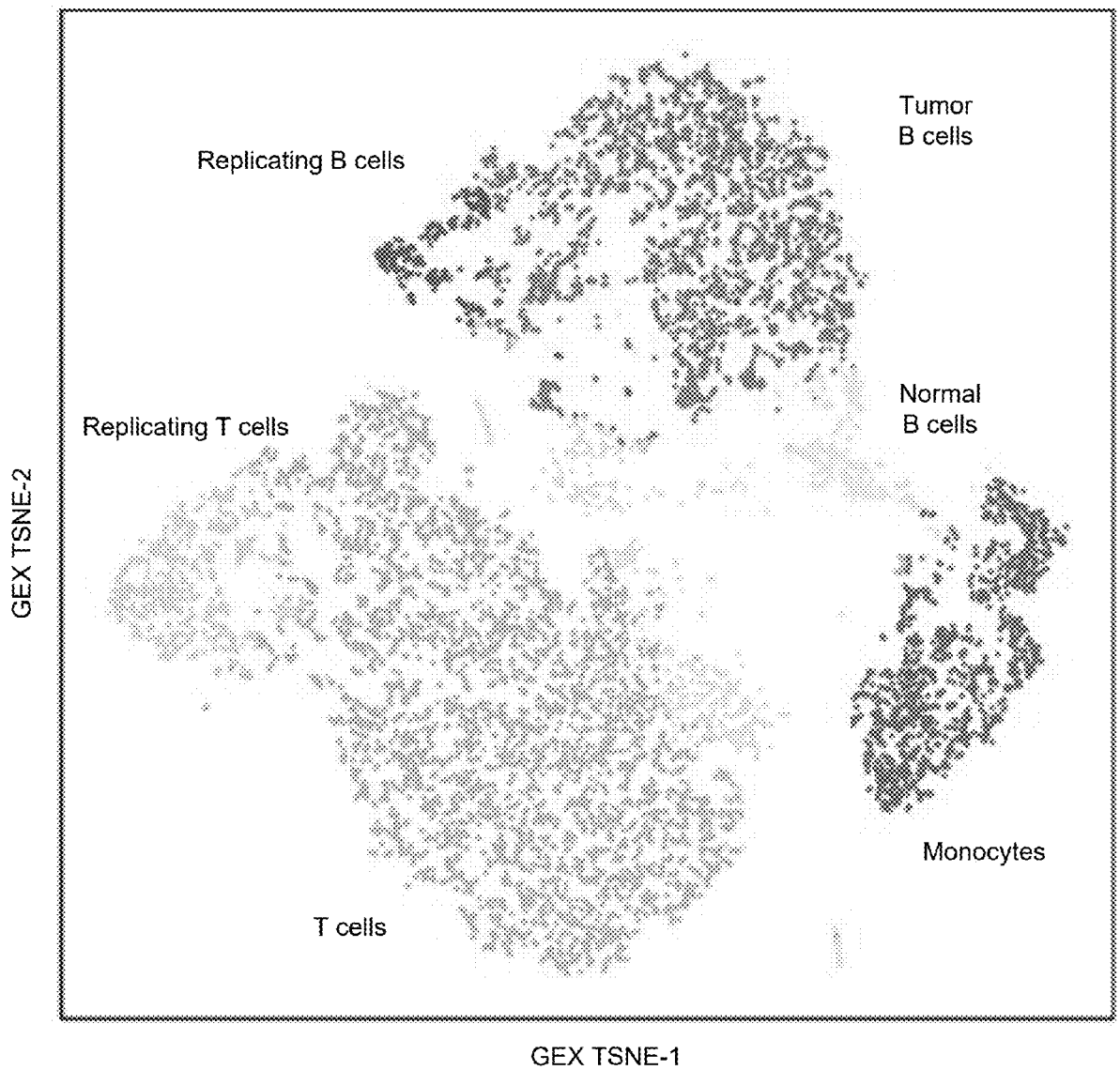

Using mutational load (SNVs) and gene expression markers for the BANK1 pathway (markers of B cell hyperactivation), tumor B cells were distinguished from normal B cells. Cells expressing differential levels of SNVs consistent with tumor cells are indicated in black in FIG. 31A, while cells expressing differential levels of BANK1 pathway genes consistent with tumor cells are indicated in black in FIG. 31B. Application of differential tumor and normal gene expression data allowed the identification of two sub-populations of B cells (tumor B cells and normal B cells) in cell populations clustered by gene expression profiling, as illustrated in FIG. 31C.

Figure 32A:
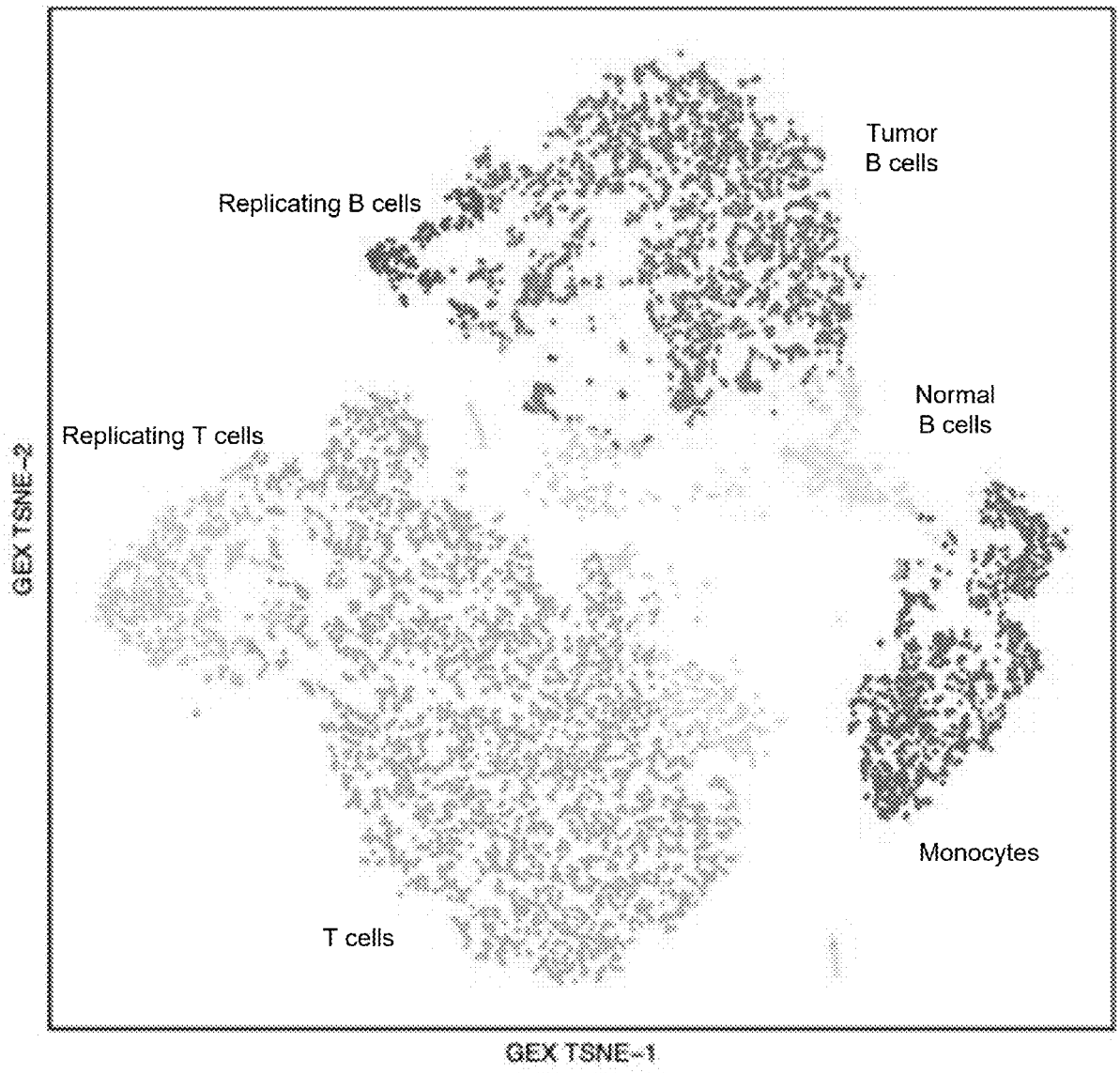
FIGS. 32A, 32B, and 32C collectively illustrate gene expression annotation of tumor cells to annotate and identify open chromatin cell populations, in accordance with an embodiment of the present disclosure.
Figure 32B:
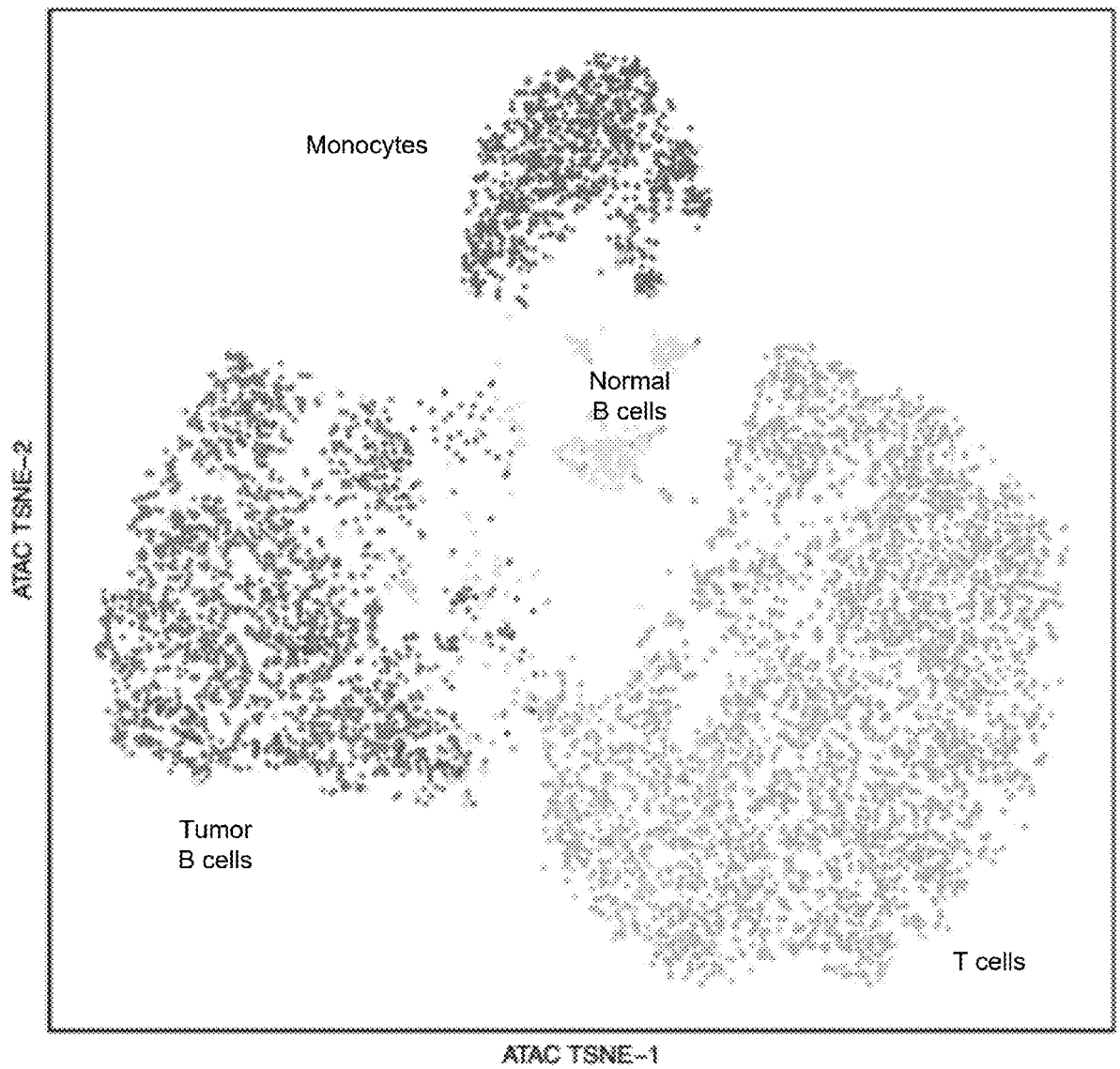
Figure 32C:
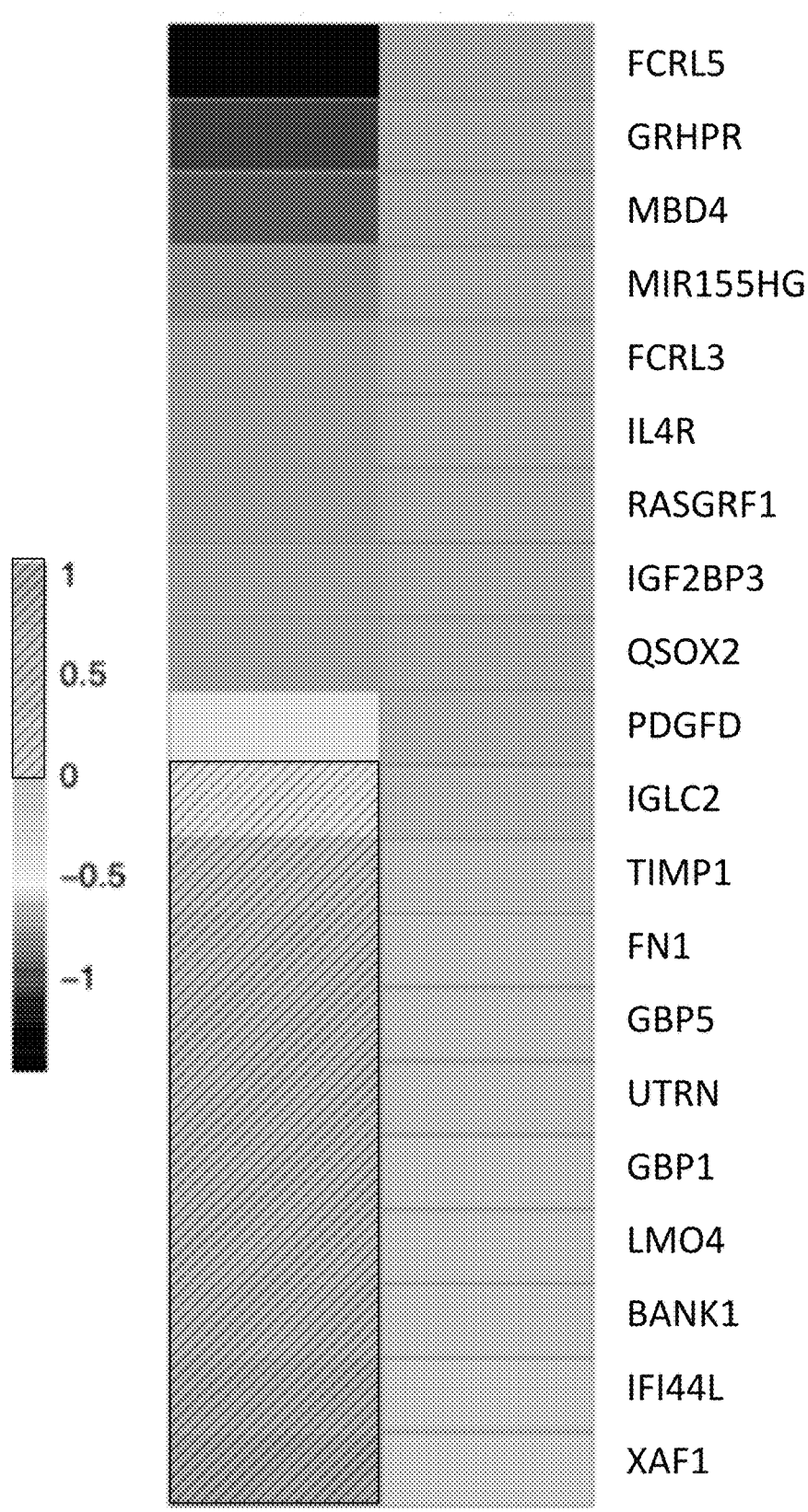

The stratification of clusters is visualized in dimension reduced projections of gene expression clustering and ATAC-seq clustering of lymph node tumor cells in FIGS. 32A and 32B. In both instances, application of differential tumor and normal gene expression data allowed the identification of two sub-populations of B cells (tumor B cells and normal B cells) in cell populations clustered by gene expression profiling (FIG. 32A) and open chromatin analysis (FIG. 32B). FIG. 32C illustrates differential gene expression for representative gene markers compared between normal B cells (left panel) and tumor (right panel) B cells. FCRL5/FCRL3 encode members of the immunoglobulin receptor superfamily and the Fc-receptor like family. These genes are implicated in B cell development and lymphomagenesis. MIR155HG represents a microRNA host gene. The long RNA transcribed from this gene is expressed at high levels in lymphoma and may function as an oncogene. RASGRF1 is a guanine nucleotide exchange factor (GEF) and is involved in MAP-Erk pathway. IL4R is a receptor to a key inflammatory signaling factor, pro-growth and pro-metastatic. XAF1 encodes a protein which binds to and counteracts the inhibitory effect of a member of the IAP (inhibitor of apoptosis) protein family. BANK1 is a tumor suppressor in B cell lymphoma.

Figure 33A:
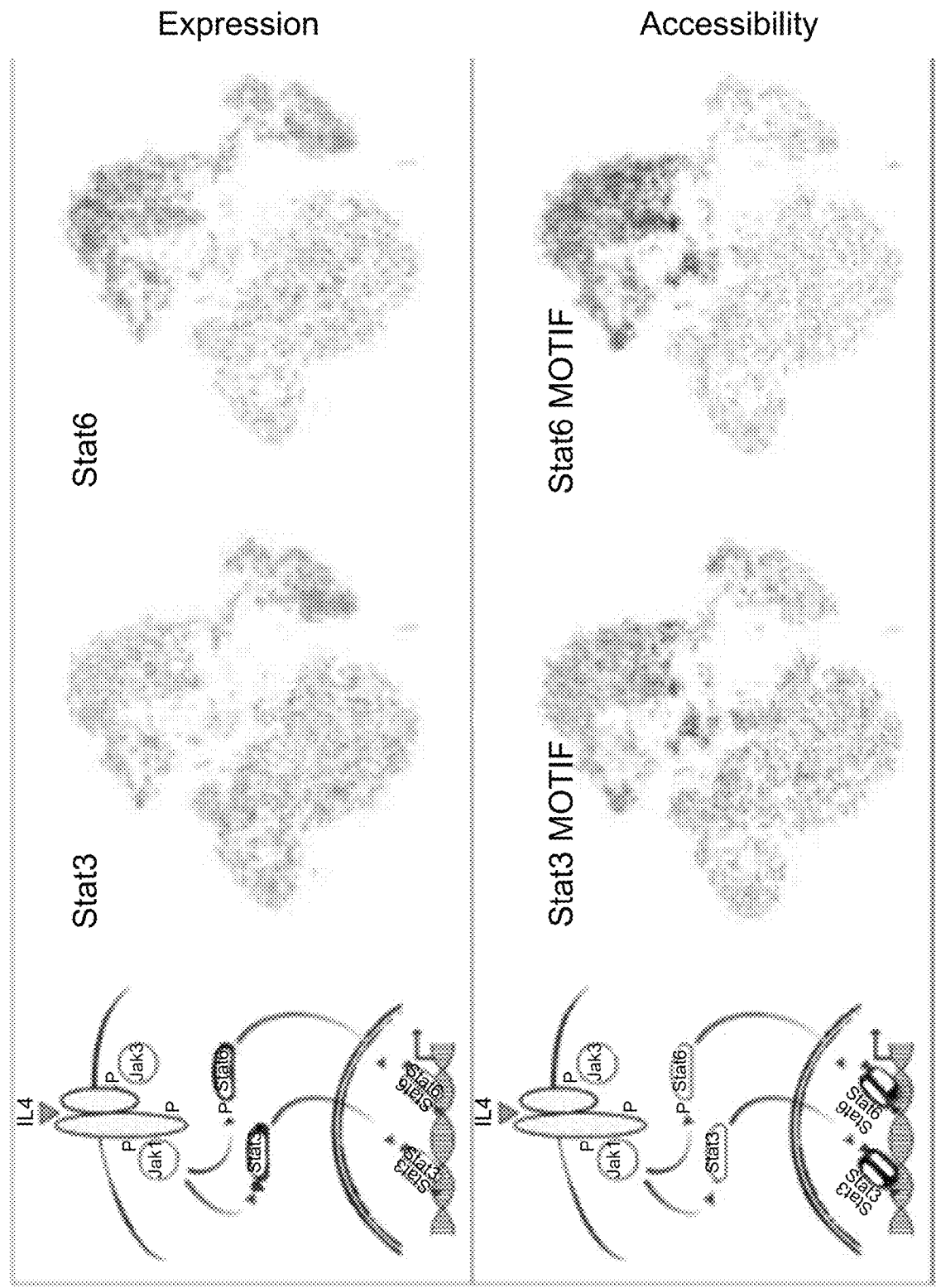
FIGS. 33A, 33B, 33C and 33D collectively illustrate, on the basis of covariance of open chromatin and gene expression, the identification of a candidate enhancer region that regulates the expression of the IL4R specifically in the tumor B cells, in accordance with an embodiment of the present disclosure.
Figure 33B:
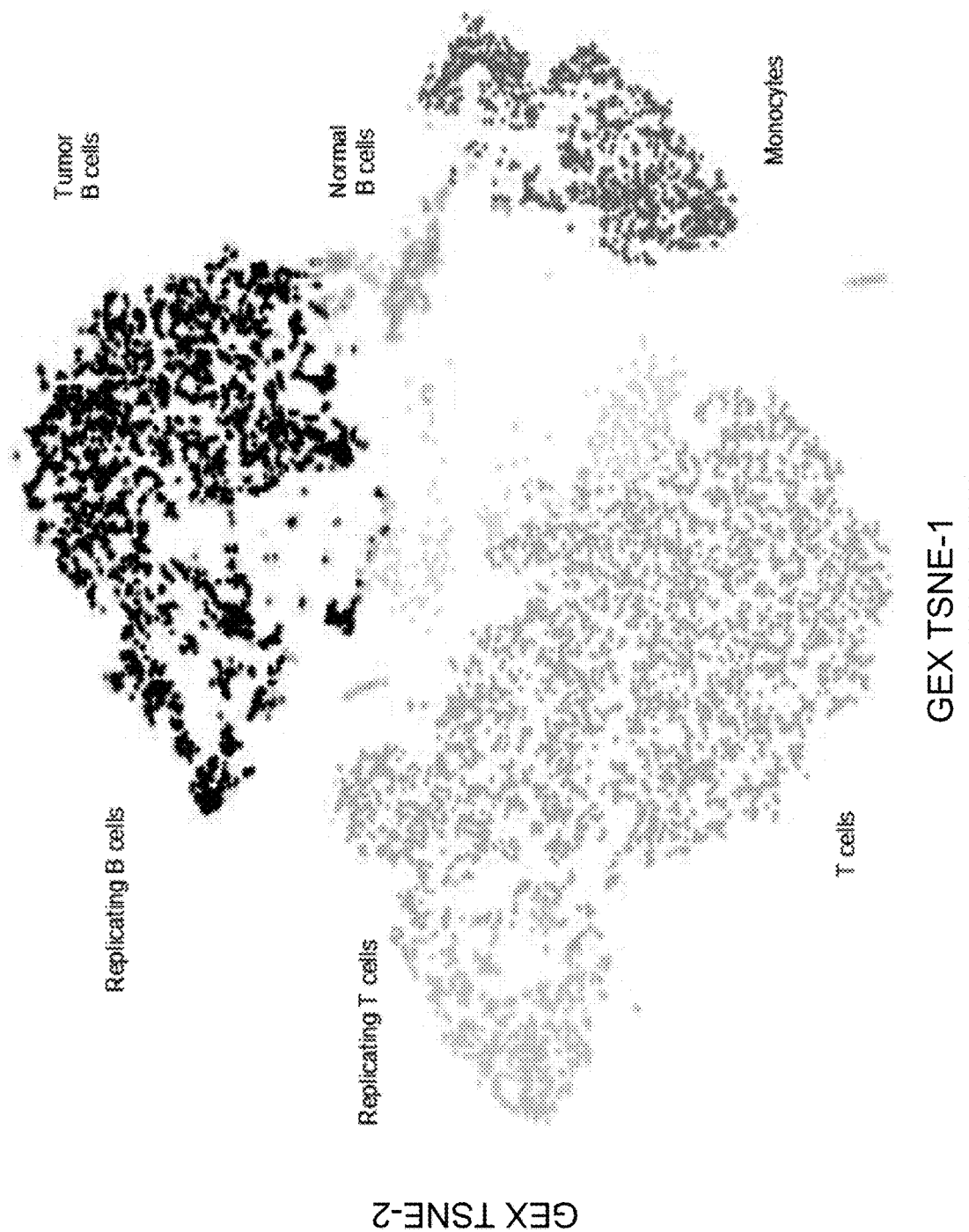
Figure 33C:
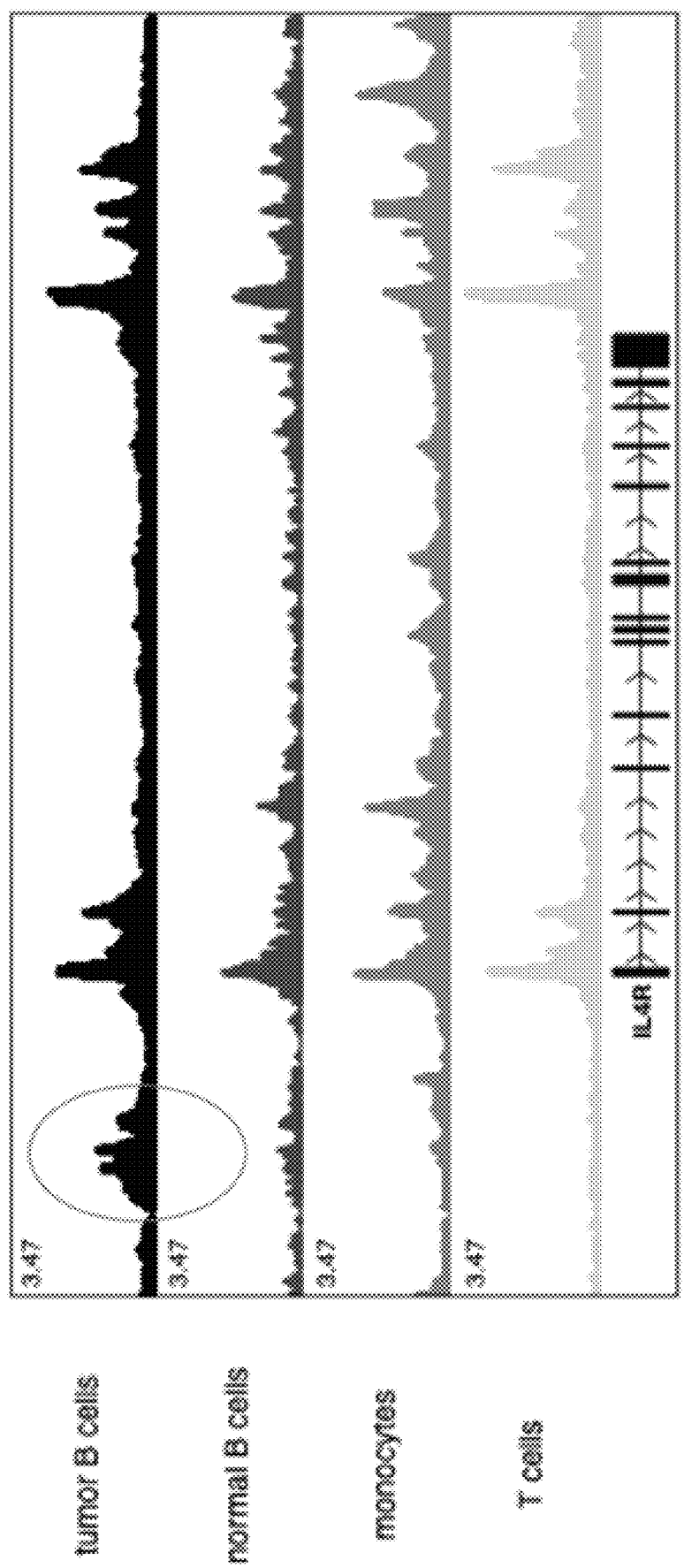
Figure 33D:
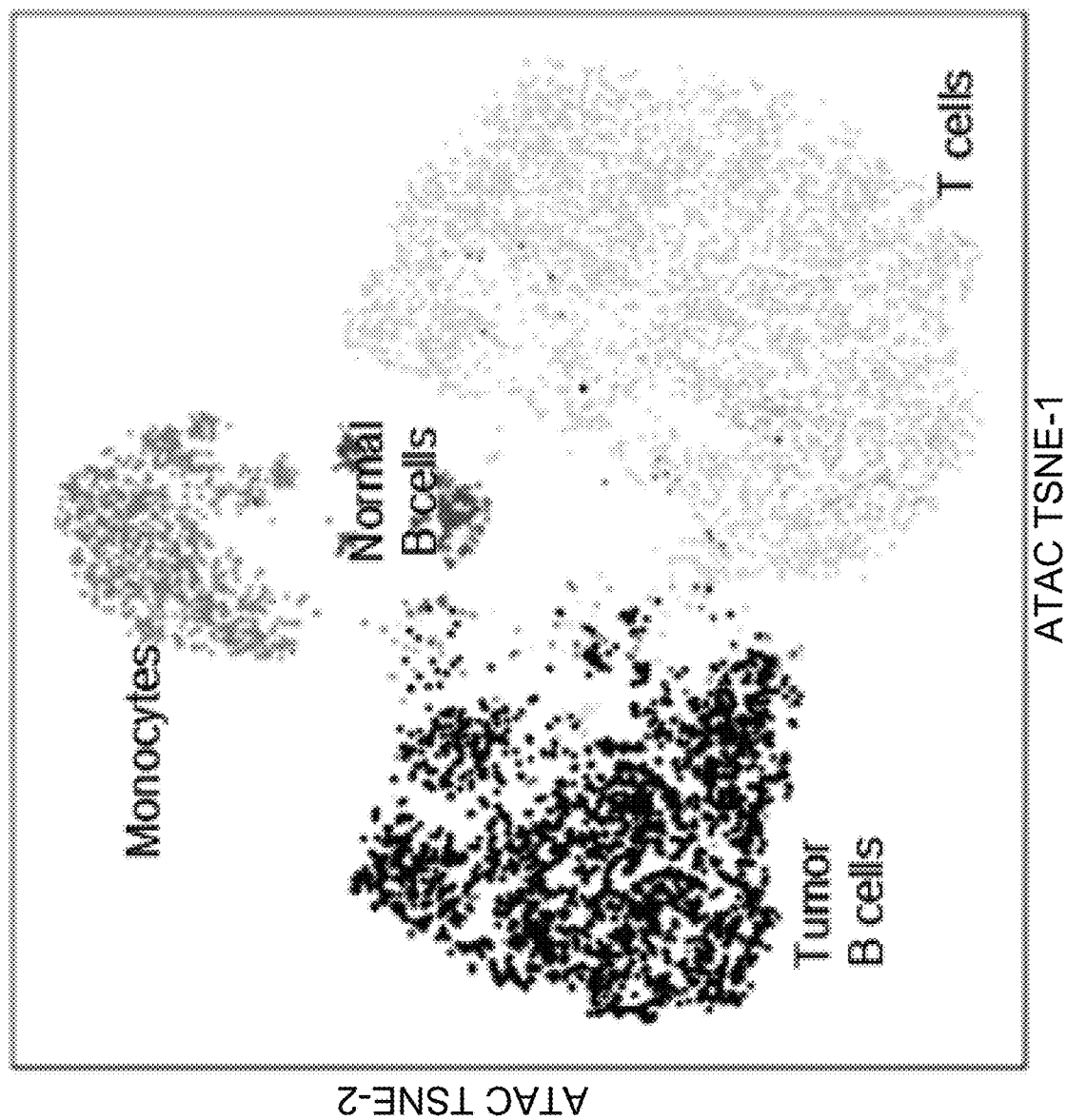

The covariance of open chromatin and gene expression was further used to identify a candidate enhancer region that regulates the expression of the IL4R specifically in the tumor B cells, as illustrated in FIGS. 33A-D. Signal transducer and activator of transcription (STAT) proteins are critical mediators of cytokine signaling. Among the seven STAT proteins, STAT6 is activated by IL-4 and IL-13 and plays a predominant role in the immune system. Gene expression characterization (FIG. 33A; top panel) and accessible chromatin characterization (FIG. 33A; bottom panel) of Stat3 and Stat6 was performed, using a dimension reduced visualization of gene expression clustering analysis (compare, for example, with FIG. 33B). The data indicate that the IL4R-mediated STAT6 signaling pathway is activated in the lymph node tumor sample. FIG. 33C further illustrates the activation of STAT proteins only in clusters of tumor B cells identified using a dimension reduced visualization of open chromatin analysis (ATAC) (compare, for example, with FIG. 33D), indicating that STAT proteins accumulate in the cytoplasm of cells but are only active upon nuclear translocations.

Figure 34:
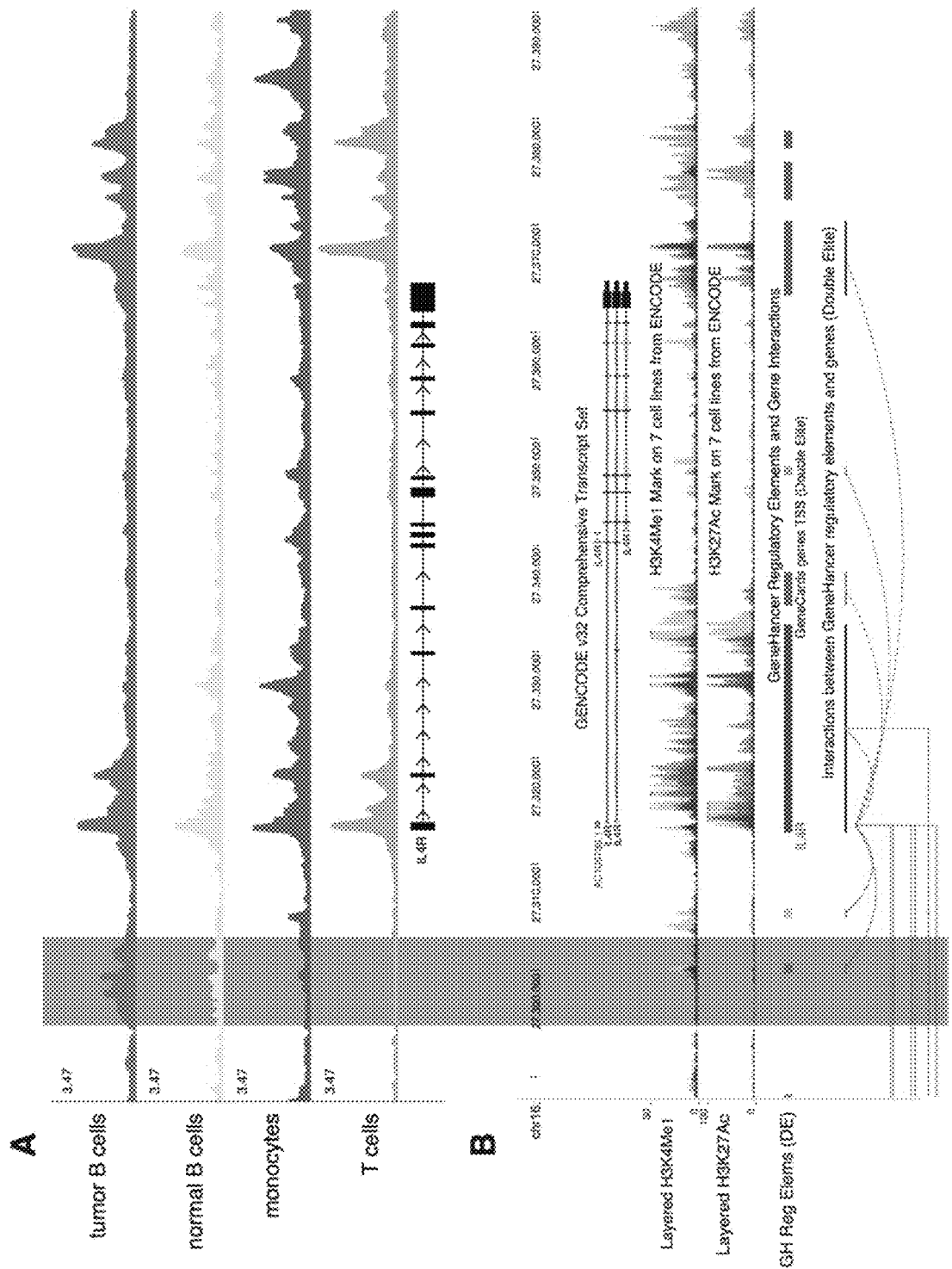
FIGS. 34A, 34B, and 34C illustrate further comparative analysis of STAT protein activation across multiple cell populations identified by open chromatin clustering (FIG. 34A), including epigenetic modifications (FIG. 34B) and quantification (FIG. 34C), in accordance with an embodiment of the present disclosure.
Figure 34C:
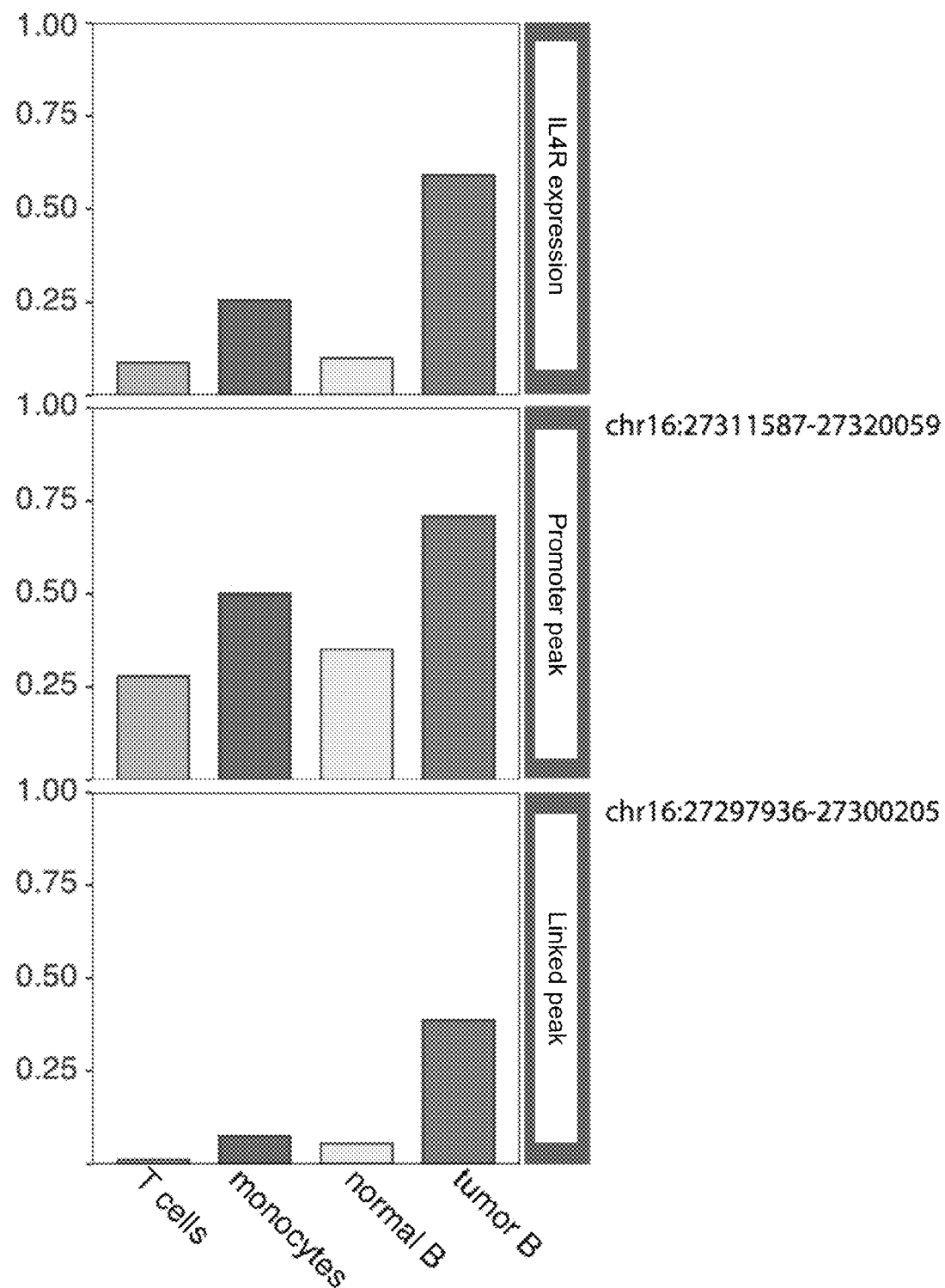

Further comparative analysis of STAT protein activation across multiple cell populations is illustrated in FIGS. 34A-C. For example, enhancer regions identified by open chromatin clustering (FIG. 34A) were assessed for the presence of epigenetic modifications, as illustrated in FIG. 34B (gray shaded column). Quantification of IL4R expression, promoter peaks, and linked peaks revealed increased levels of each consistent in the tumor B cell population but not in the T cell, monocyte, or normal B cell populations (FIG. 34C). Thus, the data indicate that the combination of gene expression annotations and open chromatin clustering can uncover tumor-specific differentially accessible chromatin regions that are not revealed when analyzing gene expression data alone and can be used to discover novel open chromatin regions associated with specific cell states.

CONCLUSION

All references cited herein are incorporated herein by reference in their entirety and for all purposes to the same extent as if each individual publication or patent or patent application was specifically and individually indicated to be incorporated by reference in its entirety for all purposes.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the present disclosure. As used in the description of the present disclosure and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event (" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed:

1. A method for identifying linkages to a first gene or a first ATAC peak in a discrete attribute value dataset, the method comprising:
   at a computer system comprising one or more processing cores, a display, and a memory:
   storing the discrete attribute value dataset in the memory, wherein the discrete attribute value dataset comprises:
      a respective discrete attribute value for each corresponding gene in a plurality of genes, for each respective cell in a plurality of cells,
      a respective assay of transposase-accessible chromatin (ATAC) fragment count for each corresponding ATAC peak in a plurality of ATAC peaks, for each respective cell in the plurality of cells,
      a feature-linkage matrix comprising:
         (i) a correlation array, in the form of a first compressed-sparse row format, that stores, for each respective gene in the plurality of genes and for each respective ATAC peak in the plurality of ATAC peaks, a correlation between the discrete attribute value of the respective gene and the ATAC fragment count of the respective ATAC peak across the plurality of cells, wherein the correlation ranges between −1 and 1,
         (ii) an index array, in the form of a second compressed-sparse row format, that stores, for each respective gene in the plurality of genes, an identity of each respective ATAC peak in the plurality of ATAC peaks across the plurality of cells that is linked to the respective gene in the correlation array and stores, for each respective ATAC peak in the plurality of ATAC peaks, an identity of each respective gene in the plurality of genes across the plurality of cells that is linked to the respective ATAC peak in the correlation array, and
         (iii) a pointer array that defines a minimum index and a maximum index in both the correlation array and the index array to retrieve, for each respective gene in the plurality of genes, an identity of a subset of ATAC peaks in the plurality of ATAC peaks that are linked with the respective gene in the correlation array, and for each respective ATAC peak in the plurality of ATAC peaks, an identity of a subset of genes in the plurality of genes that are linked with the respective ATAC peak in the correlation array;
   for each respective cell in the plurality of cells, an assignment of the respective cell to a respective cluster group in a first plurality of cluster groups wherein the first plurality of cluster groups was determined based on a first clustering of discrete attribute values for the plurality of genes across the plurality of cells, and
   for each respective cell in the plurality of cells, an assignment of the respective cell to a respective cluster group in a second plurality of cluster groups wherein the second plurality of cluster groups is based on a second clustering of ATAC fragment count values for the plurality of ATAC peaks across the plurality of cells,
   wherein:
      the plurality of cells comprises 100 cells,
      the plurality of genes comprises 200 genes, and
      the plurality of ATAC peaks comprises 5000 ATAC peaks;
   displaying, in a first panel on the display, a two-dimensional projection of the plurality of cells based on assignment of the plurality of cells to one of (i) the first plurality of cluster groups or (ii) the second plurality of cluster groups, wherein membership of each respective cell in the plurality of cells in the other of (i) the first plurality of cluster groups or (ii) the second plurality of cluster groups is indicated by coloring the respective cell in the two-dimensional projection a color that is uniquely associated with a cluster group to which the respective cell has been assigned in the other of (i) the first plurality of cluster groups or (ii) the second plurality of cluster groups;
   receiving a selection of the first gene in the plurality of genes or the first ATAC peak in the plurality of ATAC peaks;
   obtaining a first minimum index and a first maximum index for the respective first gene or the first ATAC peak from the pointer array;
   using the first minimum index and the first maximum index to retrieve, from the correlation array, a correlation of each ATAC peak in a first subset of ATAC peaks in the plurality of ATAC peaks that are linked with the first gene in the correlation array or a correlation of each gene in a first subset of genes in the plurality of genes that are linked with the first ATAC peak in the correlation array, using the first minimum index and the first maximum index to retrieve from the index array, an identity of each ATAC peak in the first subset of ATAC peaks or an identity of each gene in the first subset of genes, forming, on the display, a first plot comprising an indicator for each gene in the first subset of genes or each ATAC peak in the first subset of ATAC peaks, by order of distance apart from the first gene or the first ATAC peak in the reference genome; and forming, on the display, a second plot showing direction and the magnitude and the sign of the correlation between (i the discrete attribute values of the first gene or the ATAC fragment counts of the first ATAC peak and ii each respective gene in the first subset of genes or the ATAC fragment count of each respective ATAC peak in the first subset of ATAC peaks that has a magnitude of correlation exceeding a threshold value.

2. The method of claim 1, the method further comprising:
computing, for each respective gene in the plurality of genes for each respective cluster in the first plurality of cluster groups or the second plurality of cluster groups, a difference in the discrete attribute value for the respective gene across the respective subset of cells in the respective cluster group relative to the discrete attribute value for the respective gene across the first plurality of cluster groups or the second plurality of cluster groups other than the respective cluster group, thereby deriving a differential value for each respective gene in the plurality of genes for each respective cluster group in the first plurality of cluster groups or the second plurality of cluster groups, and displaying in a second panel, concurrently with the first panel, on the display a heat map that comprises a representation of the differential value for each respective gene in the plurality of genes for each respective cluster group in the first plurality of cluster groups or the second plurality of cluster groups thereby visualizing the pattern in the discrete attribute value dataset.

3. The method of claim 2, wherein the differential value for each respective gene in the plurality of genes for each respective cluster group in the first plurality of cluster groups or the second plurality of cluster groups is a fold change in (i) a first measure of central tendency of the discrete attribute value for the respective gene measured in each of the cells in the plurality of cells in the respective cluster group and (ii) a second measure of central tendency of the discrete attribute value for the respective gene measured in each of the cells of all cluster groups in the first plurality of cluster groups or all cluster groups in the second plurality of cluster groups, other than the first respective cluster group.

4. The method of claim 2, wherein the method further comprises normalizing the discrete attribute value for each respective gene in the plurality of genes for each cell in the plurality of cells prior to computing the differential value for each respective gene in the plurality of genes for each respective cluster group in the first plurality of cluster groups or the second plurality of cluster groups.

5. The method of claim 4, wherein the normalizing comprises modeling the discrete attribute value of each gene associated with each cell in the plurality of cells with a negative binomial distribution having a consensus estimate of dispersion.

6. The method of claim 1, further comprising performing the first clustering of discrete attribute values and the second clustering of ATAC fragment values, wherein:
the first clustering of discrete attribute values for the plurality of genes across the plurality of cells is a clustering of a first plurality of dimension reduction values for each respective cell in the plurality of cells, across the plurality of cells, wherein each respective dimensional reduction value in the first plurality of dimension reduction values for each respective cell in the plurality of cells is derived, using principal component analysis, from the discrete attribute values of each gene in the respective cell, and the second clustering of ATAC fragment counts for the plurality of ATAC peaks across the plurality of cells is a clustering of a second plurality of dimension reduction values for each respective cell in the plurality of cells, across the plurality of cells, wherein each respective dimensional reduction value in the second plurality of dimension reduction values for each respective cell in the plurality of cells is derived, using principal component analysis, from the ATAC fragment counts of each ATAC peak in the respective cell.

7. The method of claim 6, wherein
the two-dimensional projection of the plurality of cells is based on the assignment of the plurality of cells to the first plurality of cluster groups, and the two-dimensional projection of the plurality of cells is obtained from t-distributed stochastic neighbor or UMAP embedding of the first plurality of dimension reduction values for each respective cell in the plurality of cells, across the plurality of cells.

8. The method of claim 6, wherein
the two-dimensional projection of the plurality of cells is based on the assignment of the plurality of cells to the second plurality of cluster groups, and the two-dimensional projection of the plurality of cells is obtained from t-distributed stochastic neighbor or UMAP embedding of the second plurality of dimension reduction values for each respective cell in the plurality of cells, across the plurality of cells.

9. The method of claim 1, further comprising performing the first clustering of discrete attribute values and the second clustering of ATAC fragment values, wherein:
the first clustering of discrete attribute values for the plurality of genes across the plurality of cells comprises application of a Louvain modularity algorithm, and the second clustering of ATAC fragment count values for the plurality of ATAC peaks across the plurality of cells comprises application of a Louvain modularity algorithm.

10. The method of claim 1, the method further comprises performing the first clustering of discrete attribute values and the second clustering of ATAC fragment values, wherein
the first clustering of discrete attribute values for the plurality of genes across the plurality of cells comprises k-means clustering into a first predetermined number of clusters for each k between k=2 and k=10, or the second clustering of ATAC fragment count values for the plurality of ATAC peaks across the plurality of cells comprises k-means clustering into a second predetermined number of clusters for each k between k=2 and k=10.

11. The method of claim 1, wherein the respective discrete attribute value for each corresponding gene in the plurality of genes, for each respective cell in the plurality of cells, represents a whole transcriptome shotgun sequencing experiment that quantifies gene expression from each respective single cell in the plurality of cells in counts of transcript reads mapped to the genes.

12. The method of claim 1, wherein each gene in a particular cell in the plurality of cells is uniquely represented within the discrete attribute value dataset with a first barcode that is unique to the particular cell.

13. The method of claim 1, wherein the respective indicator for each respective gene in the plurality of genes or each respective ATAC peak in the plurality of ATAC peaks linked to the first gene or the first ATAC peak:
 is provided for each respective cluster group in the first plurality of cluster groups or each cluster group in the second plurality of cluster groups, and
 is dimensioned to represent a proportion of cells in the respective cluster group that have a non-zero value for the discrete attribute value of the respective gene or a non-zero value for the ATAC fragment count of the respective ATAC peak.

14. The method of claim 1, wherein:
 the feature-linkage matrix further comprises a significance array, in the form of a third compressed-sparse row format, that stores, for each respective ATAC peak in the plurality of ATAC peaks or each respective gene in the plurality of genes, a significance in an ATAC fragment count of the respective ATAC peak or a significance in the discrete attribute value of the respective gene to the first respective gene or respective ATAC peak across the plurality of cells, and
 the method further comprises using the significance array to limit the first plot to each gene in the plurality of genes or each ATAC peak in the plurality of ATAC peaks that has a threshold significance in an ATAC fragment count of the respective ATAC peak or discrete attribute value of the respective gene to the first ATAC fragment or first gene.

15. The method of claim 1, wherein the first plot is limited to each gene in the plurality of genes or each ATAC peak in the plurality of ATAC peaks that is within a threshold distance of the first gene or first ATAC peak in a reference genome and wherein the threshold distance is a value between 0.5 megabases and 10 megabases.

16. The method of claim 1, wherein the second plot is an arc plot.

17. The method of claim 1, the method further comprising generating a third plot showing differences in gene expression between cluster groups in the first plurality of cluster groups for genes linked to the first gene or the first ATAC peak.

18. The method of claim 1, wherein the threshold value is between 0 and 1.

19. The method of claim 1, further comprising performing the first clustering of discrete attribute values and the second clustering of ATAC fragment values, wherein:
 the first clustering of discrete attribute values for the plurality of genes across the plurality of cells comprises application of k-means clustering, a fuzzy k-means clustering algorithm, or Jarvis-Patrick clustering, and
 the second clustering of ATAC fragment count values for the plurality of ATAC peaks across the plurality of cells comprises application of k-means clustering, a fuzzy k-means clustering algorithm, or Jarvis-Patrick clustering.

20. A computer system comprising one or more processing cores, a display, and a memory, the memory storing instructions that use the one or more processing cores to perform a method for identifying linkages to a first gene or a first ATAC peak, the method comprising:
 storing a discrete attribute value dataset in the memory, wherein the discrete attribute value dataset comprises:
  a respective discrete attribute value for each corresponding gene in a plurality of genes, for each respective cell in a plurality of cells,
  a respective assay of transposase-accessible chromatin (ATAC) fragment count for each corresponding ATAC peak in a plurality of ATAC peaks, for each respective cell in the plurality of cells,
  a feature-linkage matrix comprising:
   (i) a correlation array, in the form of a first compressed-sparse row format, that stores, for each respective gene in the plurality of genes and for each respective ATAC peak in the plurality of ATAC peaks, a correlation between the discrete attribute value of the respective gene and the ATAC fragment count of the respective ATAC peak across the plurality of cells, wherein the correlation ranges between −1 and 1,
   (ii) an index array, in the form of a second compressed-sparse row format, that stores, for each respective gene in the plurality of genes, an identity of each respective ATAC peak in the plurality of ATAC peaks across the plurality of cells that is linked to the respective gene in the correlation array and stores, for each respective ATAC peak in the plurality of ATAC peaks, an identity of each respective gene in the plurality of genes across the plurality of cells that is linked to the respective ATAC peak in the correlation array, and
   (iii) a pointer array that defines a minimum index and a maximum index in both the correlation array and the index array to retrieve, for each respective gene in the plurality of genes, an identity of a subset of ATAC peaks in the plurality of ATAC peaks that are linked with the respective gene in the correlation array, and for each respective ATAC peak in the plurality of ATAC peaks, an identity of a subset of genes in the plurality of genes that are linked with the respective ATAC peak in the correlation array;
 for each respective cell in the plurality of cells, an assignment of the respective cell to a respective cluster group in a first plurality of cluster groups wherein the first plurality of cluster groups was determined based on a first clustering of discrete attribute values for the plurality of genes across the plurality of cells, and
 for each respective cell in the plurality of cells, an assignment of the respective cell to a respective cluster group in a second plurality of cluster groups wherein the second plurality of cluster groups is based on a second clustering of ATAC fragment count values for the plurality of ATAC peaks across the plurality of cells,
 wherein:
  the plurality of cells comprises 100 cells,
  the plurality of genes comprises 200 genes, and
  the plurality of ATAC peaks comprises 5000 ATAC peaks;
 displaying, in a first panel on the display, a two-dimensional projection of the plurality of cells based on assignment of the plurality of cells to one of (i) the first plurality of cluster groups or (ii) the second plurality of cluster groups, wherein membership of each respective cell in the plurality of cells in the other of (i) the first plurality of cluster groups or (ii) the second plurality of cluster groups is indicated by coloring the respective cell in the two-dimensional projection a color that is uniquely associated with a cluster group to which the respective cell has been assigned in the other of (i) the first plurality of cluster groups or (ii) the second plurality of cluster groups;

receiving a selection of the first gene in the plurality of genes or the first ATAC peak in the plurality of ATAC peaks; and obtaining a first minimum index and a first maximum index for the respective first gene or the first ATAC peak from the pointer array;

using the first minimum index and the first maximum index to retrieve, from the correlation array, a correlation of each ATAC peak in a first subset of ATAC peaks in the plurality of ATAC peaks that are linked with the first gene in the correlation array or a correlation of each gene in a first subset of genes in the plurality of genes that are linked with the first ATAC peak in the correlation array, using the first minimum index and the first maximum index to retrieve from the index array, an identity of each ATAC peak in the first subset of ATAC peaks or an identity of each gene in the first subset of genes, forming, on the display, a first plot comprising an indicator for each gene in the plurality of genes or each ATAC peak in the first subset of ATAC peaks by order of distance apart from the first gene or the first ATAC peak in the reference genome; and forming, on the display, a second plot showing the magnitude and the sign of the correlation between (i) the discrete attribute values of the first gene or the ATAC fragment counts of the first ATAC peak and (ii) each respective gene in the first subset of genes or the ATAC fragment count of each respective ATAC peak in the first subset of ATAC peaks that has a magnitude of correlation exceeding a threshold value.

* * * * *